US007736642B2

(12) United States Patent
Duke et al.

(10) Patent No.: US 7,736,642 B2
(45) Date of Patent: Jun. 15, 2010

(54) YEAST-BASED VACCINE FOR INDUCING AN IMMUNE RESPONSE

(75) Inventors: Richard C. Duke, Denver, CO (US);
Alex Franzusoff, Denver, CO (US);
Aurelia Haller, Boulder, CO (US);
Thomas H. King, Denver, CO (US);
Yingnian Lu, Denver, CO (US);
Victoria Kelley Hodson, Denver, CO (US)

(73) Assignee: GlobeImmune, Inc., Louisville, CO (US)

( * ) Notice: Subject to any disclaimer, the term of this patent is extended or adjusted under 35 U.S.C. 154(b) by 0 days.

(21) Appl. No.: 11/670,902

(22) Filed: Feb. 2, 2007

(65) Prior Publication Data

US 2008/0003239 A1   Jan. 3, 2008

Related U.S. Application Data

(60) Provisional application No. 60/765,025, filed on Feb. 2, 2006.

(51) Int. Cl.
*A01N 63/04* (2006.01)
*A61K 39/38* (2006.01)
*A61K 39/00* (2006.01)
*A61K 39/12* (2006.01)
*A61K 39/145* (2006.01)
*C12P 21/04* (2006.01)
*A61K 39/285* (2006.01)

(52) U.S. Cl. .............. 424/93.51; 424/184.1; 424/192.1; 424/204.1; 424/206.1; 424/209.1; 424/195.16; 435/69.9

(58) Field of Classification Search ........................ None
See application file for complete search history.

(56) References Cited

U.S. PATENT DOCUMENTS

| 5,691,189 | A | * | 11/1997 | Kurtz et al. | ............ 435/254.21 |
| 5,830,463 | A | | 11/1998 | Duke et al. | |
| 7,083,787 | B2 | | 8/2006 | Duke et al. | |
| 7,563,447 | B2 | | 7/2009 | Franzusoff et al. | |
| 2003/0008000 | A1 | | 1/2003 | Wong et al. | |
| 2003/0129197 | A1 | | 7/2003 | Fiers et al. | |
| 2003/0202982 | A1 | | 10/2003 | Birkett | |
| 2004/0146976 | A1 | * | 7/2004 | Wittrup et al. | ............. 435/69.1 |
| 2004/0156858 | A1 | | 8/2004 | Franzusoff et al. | |
| 2006/0083718 | A1 | | 4/2006 | Ginns et al. | |
| 2006/0110755 | A1 | * | 5/2006 | Duke et al. | ..................... 435/6 |

FOREIGN PATENT DOCUMENTS

| WO | WO 95/18861 | 7/1995 |
| WO | WO 96/14876 | 5/1996 |
| WO | WO 02/39951 | 5/2002 |
| WO | WO 2004/058157 | 7/2004 |
| WO | WO 2005/116270 | * 12/2005 |

OTHER PUBLICATIONS

Girard et al., A review of vaccine research and development: The human immunodeficiency virus (HIV), 2006, Vaccine, vol. 24, pp. 4062-4081.*
Meyer et al., Antibody-Dependent Enhancement of Hepatitis C Virus Infection, 2008, Journal of Virology, vol. 82, No. 5, pp. 2140-2149.*
Kitikoon et al., The antibody responses to swine influenza virus (SIV) recombinant matrix 1 (rM1), matrix 2 (M2), and hemagglutinin (HA) proteins in pigs with different SIV exposure, 2008, Veterinary Microbiology, vol. 126, pp. 51-62.*
Cho et al., A yeast surface display system for the discovery of ligands that trigger cell activation, 1998, Journal of Immunological Methods, vol. 220, pp. 179-188.*
Gillian, Sequence relationships among the hemagglutinin genes of 12 subtypes of influenza A virus, 1981, PNAS, vol. 78, No. 12, pp. 7639-7643.*
Genbank Accession AAW80717, published Feb. 9, 2005.*
Genbank Accession CAA96733, published Aug. 11, 1997.*
Genbank Accession MFIV, published Jul. 16, 1999.*
De Filette et al., Universal influenza A vaccine: Optimization of M2-based constructs, 2005, Virology, vol. 337, pp. 149-161.*
Ward et al., Expression and analysis of the NS2 protein of influenza A virus, 1995, Archives of Virology, vol. 140, pp. 2067-2073.*
Ilyinskii et al., Inhibition of Influenza M2-Induced Cell Death Alleviates Its Negative Contribution to Vaccination Efficiency, 2008, PLoS ONE, vol. 3, No. 1, pp. 1-4.*
A. Haller. "Targeting Influenza with Yeast-Based Immunotherapy". Keystone Symposia: Advances in Influenza Research: From Birds to Bench to Bedside. Poster Presentation, Mar. 29, 2006, Steamboat CO.
Andreansky et al., "Consequences of Immunodominant Epitope Deletion for Minor Influenza Virus-Specific CD8 +-T-Cell Responses", Journal of Virology, Apr. 2005, p. 4329-4339.
Epstein et al., "Protection against multiple influenza A subtypes by vaccination with highly conserved nucleoprotein", Vaccine 23 (2005), pp. 5404-5410.
Ernst et al., "Protection against H1, H5, H6 and H9 influenza A infection with liposomal matrix 2 epitope vaccines", Vaccine 24 (2006), pp. 5158-5168.
Fan et al., "Preclinical study of influenza virus A M2 peptide conjugate vaccines in mice, ferrets, and rhesus monkeys", Vaccine 22 (2004), pp. 2993-3003.

(Continued)

*Primary Examiner*—Patrick J. Nolan
*Assistant Examiner*—Benjamin P Blumel
(74) *Attorney, Agent, or Firm*—Sheridan Ross P.C.; Angela Dallas Sebor

(57) ABSTRACT

The invention provided herein relates to vaccines that can be tailored to achieve a desired immune response. Some compositions provided herein are used for preferentially eliciting a humoral immune response while other compositions are useful for preferentially eliciting a cell-mediated response. Combinations of vaccine compositions are also useful for eliciting both types of responses and/or for modulating the type of immune response elicited. The invention also provides methods for eliciting an immune response in an individual by administering the compositions disclosed herein. These immune responses are useful for protecting an individual from various types of diseases, infections, and undesirable conditions.

23 Claims, 19 Drawing Sheets

OTHER PUBLICATIONS

Filette et al., "The universal influenza vaccine M2e-HBc administered intranasally in combination with the adjuvant CTA 1-DD provides complete protection", Vaccine 2005, 8 pages.

G. Everson. "Interim Results from a Randomized, Double-Blind, Placebo-Controlled Phase 1b Study in Subjects with Chronic HCV After Treatment with GI-5005, a Yeast-based HCV Immunotherapy Targeting NS3 and Core Proteins." American Association for the Study of Liver Disease (AASLD) 2006. Poster Presentation, Oct. 30, 2006, Boston MA.

Gao et al., "Protection of Mice and Poultry from Lethal H5N1 Avian Influenza Virus through Adenovirus-Based Immunization", Journal of Virology, Feb. 2006, p. 1959-1964.

Hoelscher et al., "Development of adenoviral-vector-based pandemic influenza vaccine against antigenically distinct human H5N1 strains in mice", Lancet 2006, vol. 367, pp. 475-481.

Kreijtz et al., "Primary influenza A virus infection induces cross-protective immunity against a lethal infection with a heterosubypic virus strain in mice", Vaccine 2006, 9 pages.

Lu et al., "Mutation-Selective Tumor Remission with Ras-Targeted, Whole Yeast-Based Immunotherapy", Cancer Research 64, Aug. 1, 2004, pp. 5084-5088.

Mischo et al., "Recombinant antigen expression on yeast surface (RAYS) for the detection of serological immune responses in cancer patients", Cancer Immunity, vol. 3, Jun. 27, 2003, available at http://ww.cancerimmunity.org/v3p5/030605.htm, 11 pages.

Mozdzanowska et al., "Induction of influenza type A virus-specific resistance by immunization of mice with a synthetic multiple antigenic peptide vaccine that contains ectodomains of matrix protein 2", Vaccine 21 (2003), pp. 2616-2626.

Plotnicky et al., "The immunodominant influenza matrix T cell epitope recognized in human induces influenza protection in HLA-A2/Kb transgenic mice", Virology 309 (2003), pp. 320-329.

Saelens et al., "Protection of mice against a lethal influenza virus challenge after immunization with yeast-derived secreted influenza virus hemagglutinin", Eur. J. Biochem., vol. 260, 1999, pp. 166-175.

Saiki et al., "Induction of humoral responses specific for paraneoplastic cerebellar degeneration-associated antigen by whole recombinant yeast immunization", Journal of Autoimmunity 24 (2005), pp. 203-208.

Sato et al., "Long anchor using Flo1 protein enhances reactivity of cell surface-displayed glucoamylase to polymer substrates", Appl Microbiol Biotechnol (2002) 60, pp. 469-474.

Schreuder et al., "Immobilizing proteins on the surface of yeast cells", Tibtech, Apr. 1996, vol. 14, pp. 115-120.

Shin et al., "A predictive model for the level of sIgA based on IgG levels following the oral administration of antigens expressed in *Sacchromyces cerevisiae*", J. Vet. Sci, (2005), 6(4), pp. 305-309.

Stubbs et al., "Whole recombinant yeast vaccine activates dendritic cells and elicits protective cell-mediated immunity", Nature Medicine, vol. 7, No. 5, May 2001, pp. 1-5.

Thomas et al., "Cell-mediated Protection in Influenza Infection", Emerging Infection Diseases, vol. 12, No. 1, Jan. 2006, pp. 48-54.

Townsend et al., "The Influenza A Virus Nucleoprotein Gene Controls the Induction of Both Subtype Specific and Cross-Reactive Cytotoxic T Cells", J. Exp. Med., vol. 160, Aug. 1984, pp. 552-563.

Treanor et al., "Safety and Immunogenicity of an Inactivated Subvirion Influenza A (H5N1) Vaccine", The New England Journal of Medicine, vol. 354, No. 13, pp. 1343-1351, 2006.

Van Der Vaart et al., "Comparison of Cell Wall Proteins of *Saccharomyces cerevisiae* as Anchors for Cell Surface Expression of Heterologous Proteins", Applied and Environmental Microbiology, Feb. 1997, p. 615-620.

Wadle et al., "Cross-presentation of HLA class I epitopes from influenza matrix protein produced in *Saccharomyces cerevisiae*", Vaccine 24 (2006), pp. 6272-6281.

Webster et al., "Matrix Protein from Influenza A Virus and Its Role in Cross-Protection in Mice", Infection and Immunity, Sep. 1977, pp. 561-566.

Schreuder MP, Brekelmans S, van den Ende H, Klis FM. 1993. Targeting of a heterologous protein to the cell wall of *Saccharomyces cerevisiae*. Yeast. 9:399-409.

Zou et al., "Genetically Controlled Self-Aggregation of Cell-Surface-Engineered Yeast Responding to Glucose Concentration", Applied Environmental Microbiology, May 2004, vol. 67, No. 4, pp. 2083-2087.

Frieman et al., "Multiple sequence signals determine the distribution of glycosylphosphatidylinositol proteins between the plasma membrande and cell wall in *Saccharomyces cerevisiae*", Microbiology, Oct. 2004, vol. 150, No. 10, pp. 3105-3114.

International Search Report for International (PCT) Patent Application No. PCT/US07/61572, mailed Dec. 11, 2007 (3923-18-PCT).

Written Opinion for International (PCT) Patent Application No. PCT/US07/61572, mailed Dec. 11, 2007 (3923-18-PCT).

International Preliminary Report on Patentability for International (PCT) Patent Application No. PCT/US07/61572, mailed Aug. 14, 2008.

Chen et al. "Enhanced protection against a lethal influenza virus challenge by immunization with both hemagglutinin- and neuraminidase-expressing DNAs", Vaccine, Feb. 26, 1999 Butterworth Scientific. Guildford, GB—ISSN 0264-410X, vol. 17, Nr:7-8, pp. 653-659.

Chen et al. "Identification of effective constituents of influenza vaccine by immunization with plasmid DNAs encoding viral proteins", Japanese Journal of Infectious Diseases, Jan. 1, 2000 National Institute of Infectious Diseases, Tokyo, JP—ISSN 1344-6304, vol. 53, Nr:6, pp. 219-228.

Franzusoff et al. "Yeasts encoding tumour antigens in cancer immunotherapy" Expert opinion on biological therapy, Apr. 1, 2005 Informa Healthcare, UK—ISSN 1744-7682, vol. 5, Nr:4, pp. 565-575.

Hilleman M R "Realities and enigmas of human viral influenza: pathogenesis, epidemiology and control", Vaccine, Aug. 19, 2002 Butterworth Scientific. Guildford, GB—ISSN 0264-410X, vol. 20, Nr:25-26, pp. 3068-3087.

Okuda et al., "Protective immunity against influenza A virus induced by immunization with DNA plasmid containing influenza M gene", Vaccine, Jun. 14, 2001 Butterworth Scientific. Guildford, GB—ISSN 0264-410X, vol. 19, Nr:27, pp. 3681-3691.

Tamura et al. "Mechanisms of broad cross-protection provided by influenza virus infection and their application to vaccines", Japanese Journal of Infectious Diseases, Aug. 1, 2005 National Institute of Infectious Diseases, Tokyo, JP—ISSN 1344-6304, vol. 58, Nr:4, pp. 195-207.

Supplementary European search report for European Patent Application No. 07717549.5, mailed May 13, 2009.

Pichuantes et al. "Expression of Heterologous Gene Products in Yeast", Protein Engineering: Principles and Practice, Edited by Jeffrey L. Cleland and Charles S. Craik, ISBN 0-471-10354-3, 1996 Wiley-Liss, Inc., pp. 129-161.

Office Action for European Patent Application No. 07717549.5, mailed Sep. 3, 2009.

\* cited by examiner

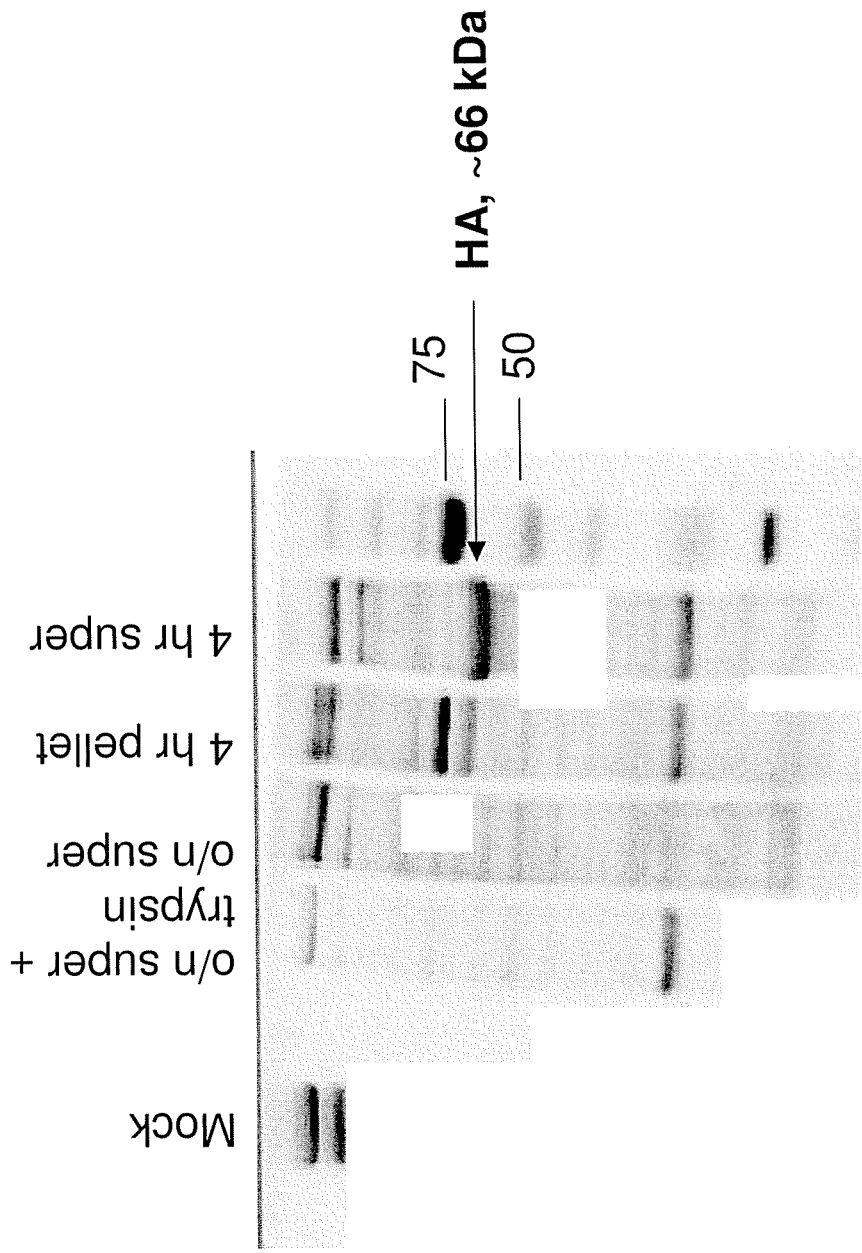

GI-8003 (prototype): A/PR/8/34 H1-HA expressed in yeast as Aga2-HA fusion protein

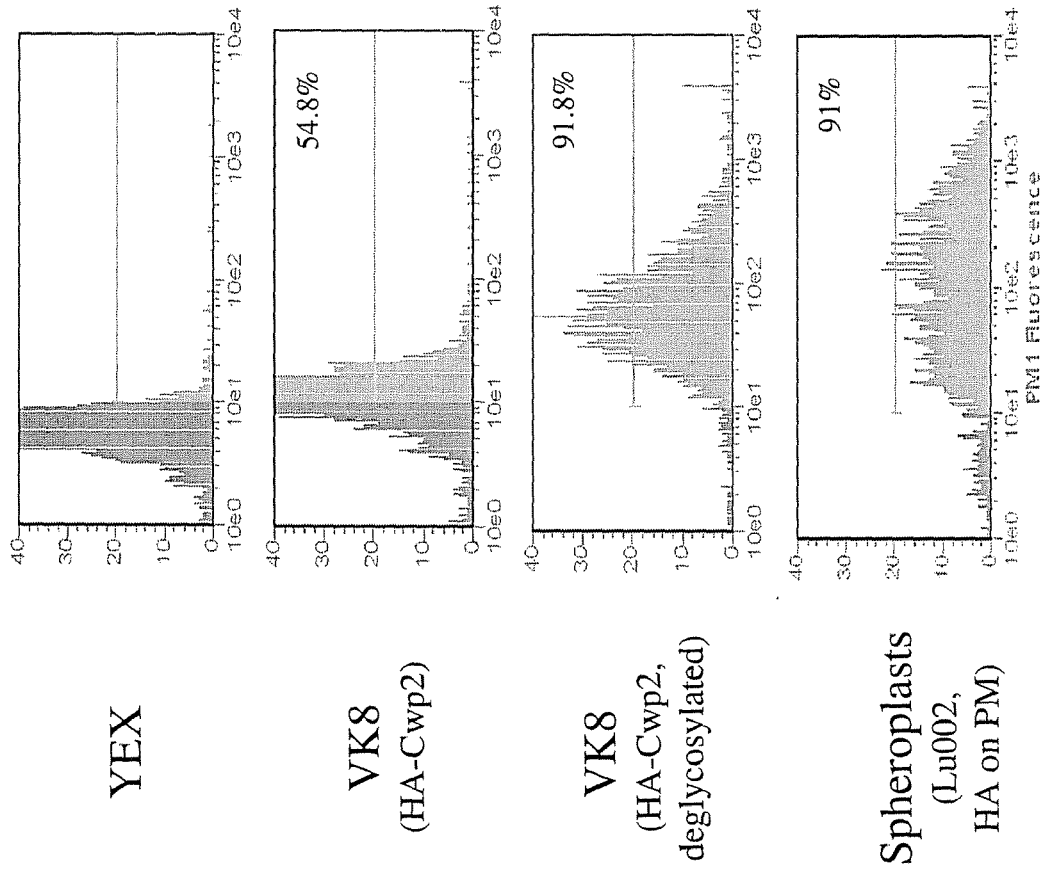

GI-8000-S

GI-8000-I

Regimen B:  PBS   PBS    OVAX   OVAX   ova
Regimen C:  PBS   OVAX   OVAX   OVAX   ova Signal 2 for Ab production Signal 1 for Ab production

YEAST-BASED VACCINE FOR INDUCING AN IMMUNE RESPONSE

CROSS-REFERENCE TO RELATED APPLICATIONS

This application claims the benefit of priority under 35 U.S.C. §119(e) from U.S. Provisional Application Ser. No. 60/765,025, filed Feb. 2, 2006. The entire disclosure of U.S. Provisional Application Ser. No. 60/765,025, filed Feb. 2, 2006 is incorporated herein by reference.

FIELD OF THE INVENTION

This invention generally relates to yeast-based vaccines that can elicit various types of protective and therapeutic immune responses, including cell-mediated and/or humoral immune responses. Compositions including such yeast-based vaccines and methods of using such vaccines, including in combination with other types of vaccines, are disclosed herein. A variety of compositions and methods for vaccinating an animal against influenza infection and for treating or preventing influenza infection in an animal are also disclosed.

BACKGROUND OF THE INVENTION

Vaccines are one of the most cost-effective measures available to the health care industry for the prevention and treatment of disease. There remains, however, an urgent need to develop safe and effective vaccines and adjuvants for a variety of diseases, including those caused by or associated with infection by pathogenic agents, cancers, genetic defects and other disorders of the immune system. Publications on vaccines, for example, Rabinovich et al., *Science* 265, 1401-1404 (1994), state that there is still a need for safe and heat-stable vaccines that can be administered orally and that need to be administered only a few times, preferably early in life. Also preferred are combination vaccines that can protect individuals from more than one disease, as well as vaccines that do not require an adjuvant and that can elicit cell-mediated, humoral, and mucosal immunity. To date very few, if any, vaccines meet all of these criteria.

Killed or attenuated pathogens are frequently used in conventional vaccines, and particularly in vaccines against viral infections. For example, two types of influenza vaccines are presently in use. The more conventional vaccine is an inactivated vaccine (containing killed virus) that is given by injection, typically into the arm. A second vaccine, called the nasal-spray flu vaccine (sometimes referred to as LAIV for Live Attenuated Influenza Vaccine), was approved in 2003 and contains attenuated (weakened) live viruses administered by nasal sprayer. As set forth by the World Health Organization (WHO), influenza virus types A and B are both common causes of acute respiratory illnesses. Although both virus types may cause epidemics of considerable morbidity and mortality, influenza B infections are often limited to localized outbreaks, whereas influenza A viruses are the principal cause of larger epidemics, including worldwide pandemics. The influenza virus is a member of the Orthomyxo virus family, and has a wide host range, including humans, horses, dogs, birds, and pigs. It is an enveloped, negative-sense RNA virus produced in 8 RNA segments encoding 10 viral proteins. The virus replicates in the nucleus of an infected host cell. The influenza virus is most dangerous for the young and the old, or immunocompromised individuals. The virus can be propagated to high titers in chicken eggs, which serve as the vehicle for generation of virus for the production of influenza vaccines.

Influenza A viruses undergo frequent changes in their surface antigens, whereas type B influenza viruses change less frequently. Immunity following infection by one strain may not protect fully against subsequent antigenic variants. As a consequence, new vaccines against influenza must be designed each year to match the circulating strains that are most likely to cause the next epidemic. Therefore, the WHO annually collects data based on the surveillance of the most prevalent influenza strains circulating among people and makes recommendations for the influenza vaccine composition. Currently, the vaccine includes two subtypes of influenza A virus and one influenza B virus in the vaccine. The vaccine typically protects approximately 50%-80% of healthy adults against clinical disease.

Subunit vaccines, the development of which was made possible by recombinant DNA technology, have been disappointing to date, as they exhibit only limited immunogenicity. One example is the recent clinical testing of several HIV (human immunodeficiency virus) subunit vaccines which has been stopped due not only to limited efficacy of the vaccines, but also because in some cases, immunized individuals showed accelerated disease progression when they were subsequently exposed to HIV; see, for example, Cohen, *Science* 264:1839 (1994); and Cohen, *Science* 264: 660 (1994). One disadvantage of subunit vaccines, as well as of killed virus and recombinant live virus vaccines, is that while they appear to stimulate a strong humoral immune response, they fail to elicit protective cell-mediated immunity. A major conclusion at the 1994 International AIDS Conference was that there remains a need for a cytotoxic T cell-mediated response to prevent, or reduce, HIV infectivity, which to date is lacking in vaccines in the clinic. In addition, HIV vaccines tested to date have failed to elicit immunity at the mucosal surfaces where primary HIV infection occurs.

Furthermore, the only adjuvants approved for use in the United States are the aluminum salts aluminum hydroxide and aluminum phosphate, neither of which stimulates cell-mediated immunity. In addition, aluminum salt formulations cannot be frozen or lyophilized, and such adjuvants are not effective with all antigens.

Yeast cells have been used in the production of subunit protein vaccines, including some of those tested in the aforementioned HIV vaccine trials. Yeast have also been fed to animals prior to immunization to try to prime the immune response in a non-specific manner (i.e., to stimulate phagocytosis as well as the production of complement and interferon). The results have been ambiguous, and such protocols have not generated protective cell-mediated immunity; see, for example, Fattal-German et al., *Dev. Biol. Stand.* 77: 115-120 (1992) and Bizzini et al., *FEMS Microbiol. Immunol.* 2: 155-167 (1990).

Previous studies have shown the potential for using recombinant *S. cerevisiae* yeast as a vaccine and immunotherapy vector. See, e.g., U.S. Pat. Nos. 5,830,463 and 7,083,787, as well as U.S. Patent Publication Nos. 2004-0156858 A1 and 2006-0110755 A1. These yeast-based immunotherapeutic products have been shown to elicit immune responses that are capable of killing target cells expressing a variety of viral and cancer antigens in vivo, in a variety of animal species, and to do so in an antigen-specific, $CD8^+$ CTL-mediated fashion. See also Stubbs et al., *Nat. Med.* 7:625-629 (2001) and Lu et al., *Cancer Research* 64:5084-5088 (2004). More specifically, other studies have shown that *Saccharomyces cerevisiae* are avidly phagocytosed by and directly activate dendritic cells which then present yeast-associated proteins to CD4+ and CD8+ T cells in a highly efficient manner. See, e.g., Stubbs et al. *Nature Med.* 5:625-629 (2001) and U.S. Pat. No. 7,083,787.

In addition to being able to interact directly with dendritic cells, yeast have a variety of other characteristics that make them an ideal platform for immunotherapy. First, multiple antigens may be engineered for expression within a single yeast strain (see, e.g., Pichuantes et al., "*Expression of heterologous gene products in yeast.*" In Protein Engineering— Principles and Practice, pp. 129-162, J. L. Cleland and C. S. Craik, eds., Wiley-Liss, New York (1996). These formulations share many advantages with DNA vaccines, including ease of construction and the ability to target multiple antigens. Unlike DNA vaccines, yeast-based immunotherapeutic formulations do not require extensive purification to remove potentially toxic contaminants. The U.S. Food and Drug Administration (FDA) has designated yeast as GRAS (Generally Recognized as Safe). As such, the concern over toxicity and safety that exists with other vaccine vectors does not apply to yeast-based delivery vehicles.

Despite all the existing efforts to produce efficacious vaccines, there still remains a need for vaccine compositions that are efficient at stimulating a variety of immune responses. With respect to influenza vaccines, rates of illness among children, the elderly and certain high-risk groups is still significant, and in developing countries, vaccination may be sporadic or non-existent. In industrialized countries, production of sufficient influenza vaccine to accommodate the recipient population is hampered by production problems, high expenses and the time required to produce the vaccine using current technologies. In addition, threats of new viral strains and the possibility of future pandemics have raised interest in more effective and efficiently produced influenza vaccines. Therefore, there is a need in the art for improved vaccines that provide long-lasting and effective protection against a variety of strains of influenza, and that can be produced rapidly and safely for use in humans and other animals. However, these concerns and needs are not unique to influenza vaccines, but extend to other types of vaccines, including vaccines directed to other viruses and other infectious agents.

Indeed, many pathogens, including bacteria and parasites, infect individuals in stages, presenting a different subset of antigens for the immune system to address at each stage. In addition, many pathogens have evolved a series of strategies that allow the pathogen to "hide" from or otherwise evade the immune system. Finally, as with the viruses described above, many pathogens evolve and mutate antigens, particularly those expressed or localized on their surface, and it is also possible to be infected by multiple species or strains of pathogens at the same time, all of which complicate vaccination strategies. By way of example, infection with the parasite that causes malaria, (e.g., *Plasmodium falciparum* or *Plasmodium vivax*) initially enters the body as a sporozoite through the blood stream as a result of a bite by an infected mosquito, but then quickly infects liver cells where the sporozoite undergoes radical changes to become a merozoite. The merozoite is released from the liver cell and rapidly infects red blood cells, where the parasite multiplies, differentiates, and continues to infect other cells. Accordingly, an ideal vaccine would be able to prime the immune system to recognize and destroy all stages of the parasite, whether in the blood, in the liver, or in red blood cells. However, most vaccines are unable to prevent or eradicate all infection, but instead are focused on limiting the ability of the pathogen to cause disease or be toxic to an individual, while other stages of the life cycle and quiescent infection remain unaddressed.

Therefore, for combating pandemics of infectious disease or disease caused by other agents, it is desirable to have the ability to control or influence the type of immune response elicited, such as by preferentially eliciting a cell-mediated immune response (e.g., generation of cytotoxic T cells (CTLs)), preferentially eliciting a humoral response (e.g., an antibody response), or eliciting both types of immune responses, depending on the disease or condition being prevented or treated, and/or the immune status of an individual with respect to a particular antigen or pathogen at a given time point. In addition, it would be useful to provide compositions that can stimulate an efficacious immune response with a few administrations, and that also are effective at stimulating immune responses with exposure to low levels of antigen (dose-sparing).

SUMMARY OF THE INVENTION

The invention disclosed herein provides compositions and methods to address the above-described needs. Immunotherapeutic products (e.g., vaccines) based on a yeast-based vaccine platform technology are straightforward to produce, are not neutralized by host immune responses, can be administered repeatedly to boost antigen-specific immune responses, and do not require a patient-specific approach for manufacturing.

One embodiment of the invention relates to a vaccine. In one aspect, the vaccine includes: (a) a first yeast vehicle comprising at least one heterologous intracellular antigen; and (b) a second yeast vehicle comprising at least one heterologous extracellular antigen. In one aspect, the vaccine includes: (a) a first yeast vehicle comprising at least one heterologous intracellular antigen and at least one heterologous extracellular antigen; and (b) a second yeast vehicle comprising at least one heterologous intracellular antigen or at least one heterologous extracellular antigen. In another aspect, the vaccine includes: (a) a yeast vehicle comprising at least one heterologous intracellular antigen and at least one heterologous extracellular antigen; and (b) a non-yeast-based composition comprising at least one antigen comprised by the yeast vehicle of (a) or an antigen from the same pathogen or disease, wherein the non-yeast-based composition is selected from a DNA vaccine, a protein subunit vaccine, and a killed or inactivated pathogen.

In the above embodiment of the invention, the yeast vehicle of (a) can be formulated for delivery by the same or a different route of administration than the non-yeast-based composition of (b). In one aspect, the intracellular antigen is an antigen that is expressed internally by a pathogen. In one aspect, the extracellular antigen is an antigen that is structurally conserved among pathogens of the same type. In one aspect, the extracellular antigen is an antigen that is expressed on the surface of a pathogen. In one aspect, the extracellular antigen is an antigen that is structurally variable among pathogens of the same type. In one aspect, the antigen is from an infectious pathogen.

Another embodiment of the invention relates to a vaccine containing at least one influenza antigen. In one aspect, the vaccine includes (a) a yeast vehicle; and (b) an influenza virus fusion protein that is expressed by or provided by the yeast vehicle, the influenza virus fusion protein comprising at least a portion of an influenza protein selected from: an influenza matrix (M1) protein and an influenza ion channel protein (M2). In one aspect, the vaccine includes (a) a first yeast vehicle that expresses an influenza virus fusion protein comprising at least a portion of an influenza protein selected from: an influenza matrix (M1) protein, an influenza ion channel protein (M2) and a nucleocapsid (NP) protein; and (b) at least one additional yeast vehicle that expresses an influenza virus fusion protein comprising at least a portion of an influenza protein selected from: a hemagglutinin (HA) protein and a neuraminidase (NA) protein. In one aspect, the vaccine includes (a) a yeast vehicle; and (b) an influenza virus fusion protein that is expressed by or provided by the yeast vehicle, the influenza virus fusion protein comprising at least a portion of at least one first influenza protein selected from: an influenza matrix (M1) protein, an influenza ion channel protein (M2) and a nucleocapsid (NP) protein; and at least a portion of at least one second influenza protein selected from: a hemagglutinin (HA) protein and a neuraminidase (NA) protein. In another aspect, the vaccine includes (a) a yeast vehicle; (b) a first influenza virus fusion protein that is expressed by or provided by the yeast vehicle, the first influenza virus fusion protein comprising at least a portion of at least one influenza protein selected from: an influenza matrix (M1) protein, an influenza ion channel protein (M2) and a nucleocapsid (NP) protein; and (c) a second influenza virus fusion protein that is expressed by the yeast vehicle, the second influenza virus fusion protein comprising at least a portion of at least one influenza protein selected from: a hemagglutinin (HA) protein and a neuraminidase (NA) protein. In yet another aspect, the vaccine includes (a) a yeast vehicle; and (b) at least a portion of a least one first influenza virus protein selected from: an influenza matrix (M1) protein, an influenza ion channel protein (M2) and a nucleocapsid (NP) protein; and (c) at least a portion of at least one second influenza protein selected from: a hemagglutinin (HA) protein and a neuraminidase (NA) protein.

In the above-embodiment, in one aspect, the HA protein is selected from: H1, H2, H3, H4, H5, H6, H7, H8, H9, H10, H11, H12, H13, H14, H15 and H16. In one aspect, the HA protein is selected from: H1, H2, and H3. In one aspect, the HA protein is H5. In one aspect, the NA protein is selected from: N1, N2, N3, N4, N5, N6, N7, N8 and N9. In one aspect, the NA protein is selected from: N1 and N2. In one aspect, the M1 protein is intracellular with respect to the yeast vehicle. In one aspect, the M2 protein is intracellular, extracellular, or both with respect to the yeast vehicle. In one aspect, the M2 protein is M2e. In one aspect, the NP protein is intracellular with respect to the yeast vehicle. In one aspect, the HA protein or the NA protein are extracellular with respect to the yeast vehicle. In this aspect, the NA protein can also be intracellular with respect to the yeast vehicle.

In the above-embodiment, in one aspect, the influenza virus fusion protein comprises at its N-terminus the amino acid sequence represented by SEQ ID NO:1 (MADEAP). In one aspect, the influenza virus fusion protein comprises at its N-terminus or C-terminus at least a portion of an Aga2 protein or a Cwp2 protein sufficient to target the fusion protein to the cell wall of the yeast vehicle.

Another embodiment of the invention includes a vaccine including: (a) a yeast vehicle; and (b) an influenza virus fusion protein comprising an M1 antigen that is expressed as a single intracellular fusion protein by the yeast vehicle, the fusion protein consisting of SEQ ID NO:4.

Another embodiment of the invention includes a vaccine including: (a) a yeast vehicle; and (b) an influenza virus fusion protein comprising an H1 antigen that is expressed as a single intracellular fusion protein by the yeast vehicle, the fusion protein consisting of an amino acid sequence selected from: SEQ ID NO:6 and SEQ ID NO:20.

Yet another embodiment of the invention includes a vaccine including (a) a yeast vehicle; and (b) an influenza virus fusion protein comprising an H1 antigen that is expressed as a single extracellular fusion protein by the yeast vehicle, the fusion protein consisting of an amino acid sequence selected from: SEQ ID NO:10, SEQ ID NO:26, SEQ ID NO:28 and SEQ ID NO:36.

Another embodiment of the invention relates to a vaccine including (a) a yeast vehicle; and (b) an influenza virus fusion protein comprising an H5 antigen that is expressed as a single extracellular fusion protein by the yeast vehicle, the fusion protein consisting of an amino acid sequence selected from: SEQ ID NO:14, SEQ ID NO:22 and SEQ ID NO:24.

Yet another embodiment of the invention relates to a vaccine comprising (a) a yeast vehicle; and (b) an influenza virus fusion protein comprising an M1 antigen, an N1 antigen and four M2e antigens that are expressed as a single intracellular fusion protein by the yeast vehicle, the fusion protein consisting of SEQ ID NO:16.

Another embodiment of the invention relates to a vaccine comprising (a) a yeast vehicle; and (b) an influenza virus fusion protein comprising an N1 antigen and two M2e antigens that are expressed as a single intracellular fusion protein by the yeast vehicle, the fusion protein consisting of SEQ ID NO:18.

Another embodiment of the invention relates to a vaccine comprising (a) a yeast vehicle; and (b) an influenza virus fusion protein comprising an H3 antigen and an N2 antigen that are expressed as a single extracellular fusion protein by the yeast vehicle.

In any of the above-embodiments, in one aspect, the expression of the fusion protein is under the control of an inducible promoter. In one aspect of any of the above-embodiments, the promoter is selected from CUP1 and TEF2.

In one aspect of any of the above-embodiments, the yeast vehicle is selected from a whole yeast, a yeast spheroplast, a yeast cytoplast, a yeast ghost, a yeast cell wall preparation, and a subcellular yeast membrane extract or fraction thereof. In one aspect of any of the above-embodiments, a yeast cell or yeast spheroplast used to prepare the yeast vehicle was transformed with a recombinant nucleic acid molecule encoding the fusion protein such that the fusion protein is expressed by the yeast cell or yeast spheroplast. In one aspect of any of the above-embodiments, the yeast cell or yeast spheroplast that expresses the fusion protein is used to produce a yeast vehicle comprising a yeast cytoplast, a yeast ghost, a yeast cell wall preparation or a subcellular yeast membrane extract or fraction thereof. In one aspect of any of the above-embodiments, the yeast vehicle is from a non-pathogenic yeast. In one aspect of any of the above-embodiments, the yeast vehicle is from a yeast selected from: *Saccharomyces, Schizosaccharomyces, Kluveromyces, Hansenula, Candida* and *Pichia*. In one aspect of any of the above-embodiments, *Saccharomyces* is *S. cerevisiae.*

In one aspect of any of the above-embodiments, the vaccine further comprises a dendritic cell, wherein the dendritic cell has been loaded intracellularly with the yeast vehicle.

In one aspect of any of the above-embodiments, the vaccine further comprises at least one biological response modifier.

Another embodiment of the invention relates to the use of any of the vaccines described herein in the preparation of a formulation for eliciting an antigen-specific immune response.

Yet another embodiment of the invention relates to the use of any of the vaccines described herein in the preparation of a formulation for protecting an animal against influenza infection.

Another embodiment of the invention relates to the use of any of the vaccines described herein in the preparation of a formulation for eliciting an antigen-specific, cell-mediated immune response against an influenza antigen.

Yet another embodiment of the invention relates to the use of any of the vaccines described herein in the preparation of a formulation for treating or preventing a disease or condition.

Another embodiment of the invention relates to the use of any of the vaccines described herein in the preparation of a formulation for immunizing a population of individuals at risk for becoming infected with influenza.

Another embodiment of the invention relates to the use of any of the vaccines described herein in the preparation of a formulation for treating a population of individuals that are infected with influenza.

Another embodiment of the invention relates to a method to produce any of the yeast-based vaccines (vaccines comprising a yeast vehicle) described herein, comprising culturing the yeast vehicle in the vaccine at a pH of greater than pH 5.5.

Yet another embodiment of the invention relates to a method produce an influenza vaccine, including producing a yeast vehicle comprising at least one intracellular influenza antigen and at least one extracellular influenza antigen, wherein the intracellular influenza antigen comprises at least a portion of an influenza virus protein selected from: an influenza matrix (M1) protein, an influenza ion channel protein (M2), and an influenza virus nucleocapsid (NP) protein; and wherein the extracellular influenza antigen comprises at least a portion of an influenza protein selected from: a hemagglutinin (HA) protein and a neuraminidase (NA) protein. In one aspect, the method includes culturing the yeast vehicle at a pH of greater than pH 5.5. In one aspect, the yeast vehicle recombinantly expresses the intracellular antigen, the extracellular antigen, or both. In other aspects, the yeast vehicle is loaded with the intracellular antigen, the extracellular antigen, or both. In another aspect, the yeast vehicle is mixed together with the intracellular antigen, the extracellular antigen, or both. In another embodiment, the yeast vehicle is physically attached to the intracellular antigen, the extracellular antigen, or both. Combinations of the above methods to provide the antigen(s) and yeast vehicle are also contemplated. In one aspect, the yeast vehicle is formulated for administration to an individual by injection, and in another aspect, the yeast vehicle is formulated for administration to an individual by intranasal administration.

Another embodiment of the invention relates to a method to protect an animal against influenza infection. The method includes administering to an animal that has been infected with influenza or is at risk of being infected with influenza, any of the vaccines described herein comprising an influenza antigen, wherein administration of the vaccine to the animal reduces or prevents influenza infection or at least one symptom resulting from influenza infection in the animal.

Yet another embodiment of the invention relates to a method to elicit an antigen-specific immune response against an influenza antigen, comprising administering to an animal any of the vaccines described herein comprising an influenza antigen.

Another embodiment of the invention relates to a method to elicit an antigen-specific immune response against an influenza antigen in a population of individuals who have been infected with influenza, comprising administering to the population of individuals any of the vaccines described herein comprising an influenza antigen.

Another embodiment of the invention relates to a method to immunize against influenza a population of individuals that is at risk of becoming infected with influenza, comprising administering to the population of individuals any of the vaccines described herein comprising an influenza antigen. In one aspect, the vaccine is administered to prime the immune system prior to boosting with a different influenza vaccine.

Yet another embodiment of the invention relates to a method to immunize an individual against a disease or condition, comprising: (a) administering a first vaccine to an individual, wherein the vaccine comprises a yeast vehicle comprising at least one heterologous intracellular antigen, wherein the antigen is associated with the disease or condition; and (b) administering a second vaccine to the individual at least 2 weeks after the administration of (a), wherein the second vaccine comprises a yeast vehicle comprising an extracellular heterologous antigen, or an antigen that is both extracellular and intracellular. In one aspect, the yeast vehicle in the first vaccine also comprises at least one extracellular antigen. In this aspect, the antigen can be the same or a different antigen than the intracellular antigen.

Another embodiment of the invention relates to a method to immunize an individual against a disease or condition, comprising: (a) administering a first vaccine to an individual, wherein the vaccine comprises a yeast vehicle comprising at least one heterologous intracellular antigen intracellularly and at least one heterologous extracellular antigen, wherein the antigens are associated with the disease or condition; and (b) administering a second vaccine to the individual together with or subsequent to the administration of (a), wherein the second vaccine is selected from: (i) a yeast vehicle that expresses or provides at least one of the heterologous antigens used in step (a) or an antigen from the same pathogen or disease, wherein the antigen is extracellular with respect to the yeast, or both intracellular and extracellular; (ii) a yeast membrane or cell wall particle containing at least one of the heterologous antigens used in step (a) or an antigen from the same pathogen or disease; (iii) a yeast vehicle in admixture with at least one of the heterologous antigens used in step (a) or an antigen from the same pathogen or disease; (iv) a DNA vaccine encoding at least one of the antigens used in step (a) or an antigen from the same pathogen or disease; (v) a protein subunit vaccine comprising at least one of the antigens used in step (a) or an antigen from the same pathogen or disease or an antigen from the same pathogen or disease; and (vi) a killed or inactivated pathogen comprising at least one of the heterologous antigens used in step (a). In one aspect, the intracellular antigen is the same antigen as the extracellular antigen. In one aspect, the intracellular antigen is different than the extracellular antigen. In one aspect, the intracellular antigen is an antigen that is expressed internally by a pathogen. In one aspect, the extracellular antigen is an antigen that is structurally conserved among pathogens of the same type. In one aspect, the extracellular antigen is an antigen that is expressed on the surface of a pathogen. In one aspect, the extracellular antigen is an antigen that is structurally variable among pathogens of the same type. In one aspect, the antigen is from an infectious pathogen.

Another embodiment of the invention relates to a kit for the preparation of a formulation for eliciting a cell-mediated immune response, a humoral immune response, or a combination thereof in an individual, the kit comprising a plurality of yeast vehicles, wherein each of the yeast vehicles comprises at least one intracellular heterologous antigen or at least one extracellular heterologous antigen, and instructions for use of the yeast vehicles to prepare the formulation. In one aspect, the yeast vehicles express the antigens. In one aspect, the kit also includes at least one additional composition selected from: (a) a yeast membrane or cell wall particle containing at least one of the heterologous antigens or an antigen from the same pathogen or disease; (b) a yeast vehicle in admixture with at least one of the heterologous antigens or an antigen from the same pathogen or disease; (c) a DNA vaccine encoding at least one of the antigens or an antigen from the same pathogen or disease; (d) a protein subunit vaccine comprising at least one of the antigens or an antigen from the same pathogen or disease or an antigen from the same pathogen or disease; and/or (e) a killed or inactivated pathogen comprising at least one of the heterologous antigens. In one aspect, the intracellular antigen is an antigen that is expressed internally by a pathogen. In one aspect, the extracellular antigen is an antigen that is structurally conserved among pathogens of the same type. In one aspect, the extracellular antigen is an antigen that is expressed on the surface of a pathogen. In one aspect, the extracellular antigen is an antigen that is structurally variable among pathogens of the same type.

BRIEF DESCRIPTION OF THE FIGURES OF THE INVENTION

FIG. 4 is a digital image of a Western blot of lysates from P815 cells infected with influenza A/PR/8/34, illustrating that P815 cells can be infected with influenza virus and used as target cells in the CTL assays.

Figure 10A:
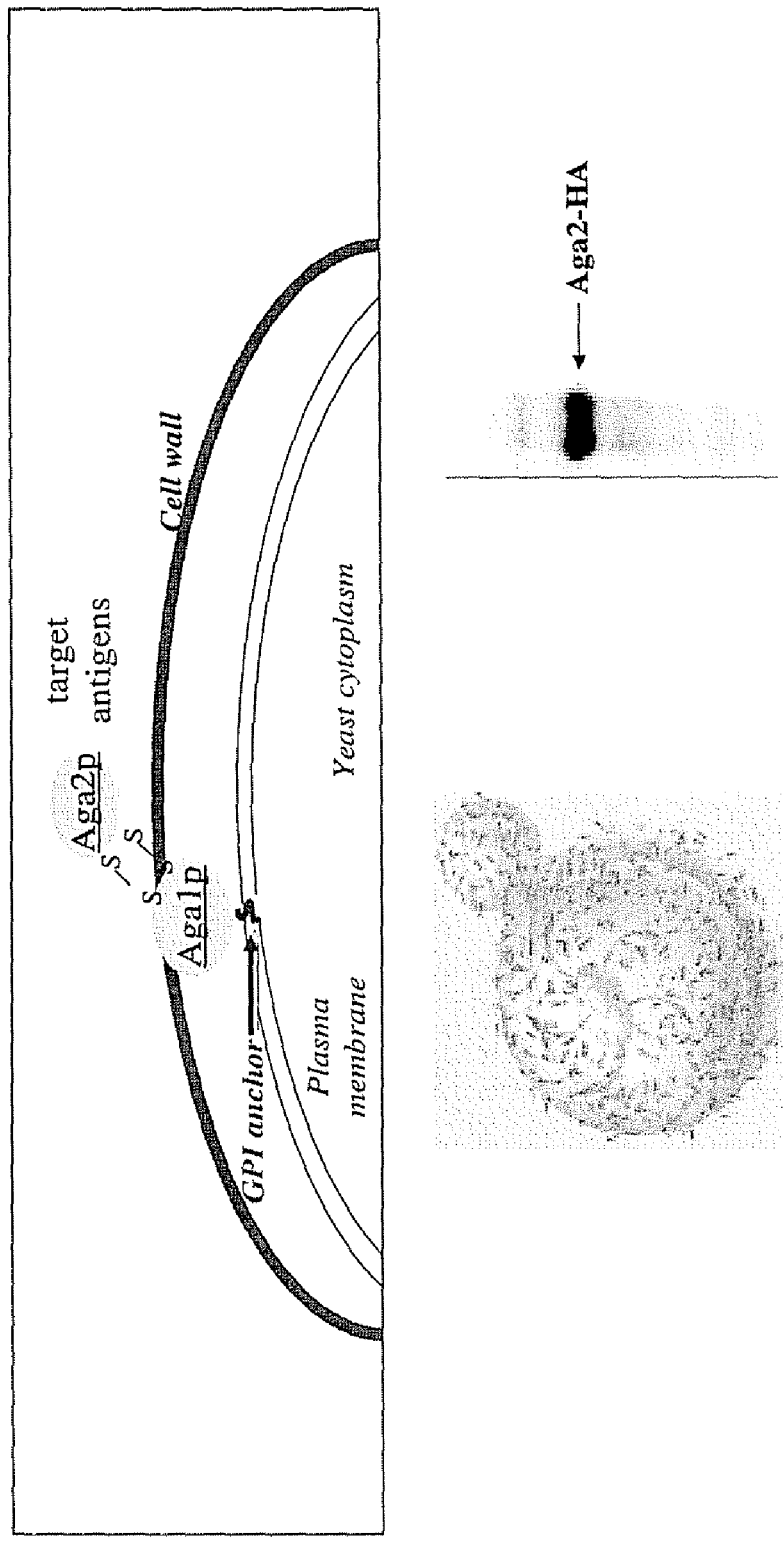

FIG. 10A depicts a Tarmogen construction scheme that allows for expression and localization of any target antigen of interest on the surface of the yeast vehicle (upper panel). The lower panels show a specific Tarmogen, also known as GI-8003, which is a yeast vehicle engineered to extracellularly display (display on its surface) influenza A/PR/8/34 HA (H1) as an Aga2-HA fusion protein. A digitized image of a Western blot is shown that indicates the expression of Aga2-HA protein.

Figure 10B:
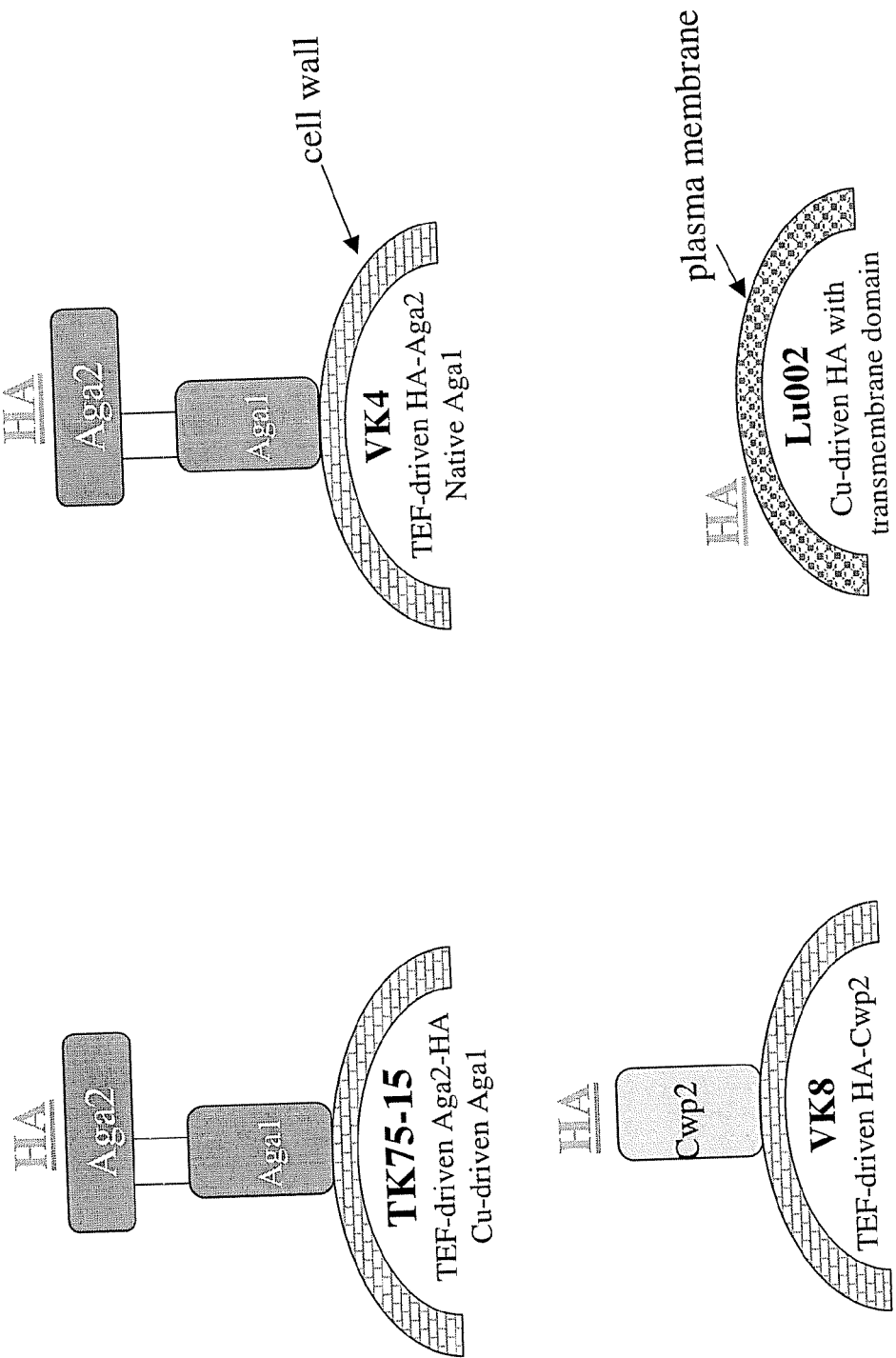

FIG. 10B depicts exemplary constructs where antigens have been engineered to be displayed on the yeast surface. This figure is a schematic illustrating examples of how various yeast proteins can be used as spacer arms.

Figure 11:
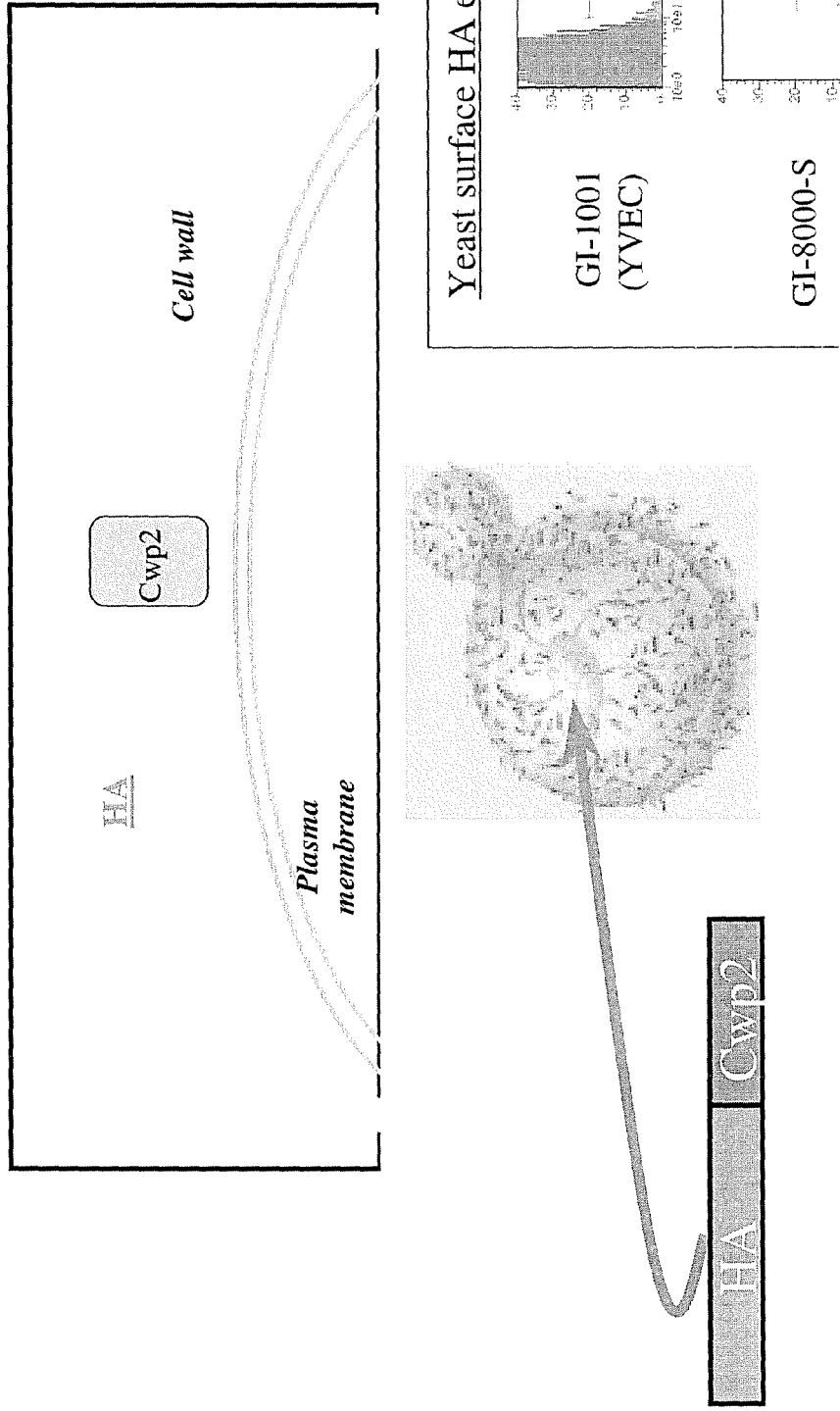

FIG. 11 depicts the Tarmogen expressing the fusion protein referred to in FIG. 10B as VK8, that expresses influenza HA protein on the surface of the yeast via the cell wall protein 2 (cwp2), and shows histograms of yeast surface HA (Tarmogen also known as GI-8000-S) expression from flow cytometric analysis of intact cells as compared to the yeast vehicle alone (GI-1001 or YVEC).

Figure 12A:
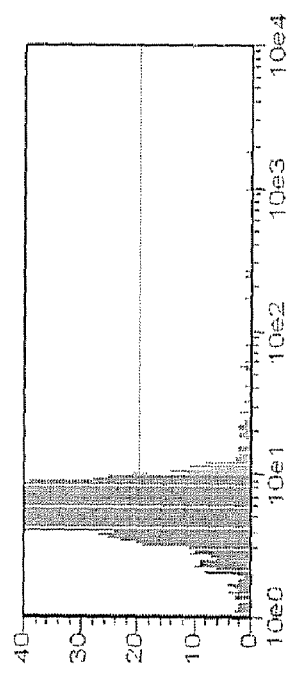
Figure 12B:
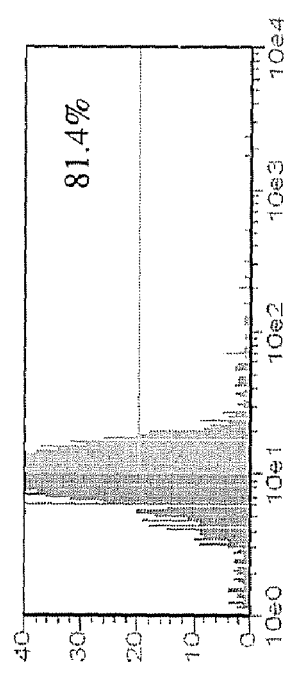
Figure 12C:
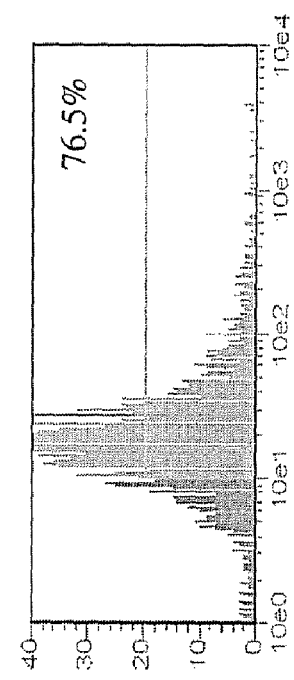

FIGS. 12A-12G shows histograms where various approaches (described above and illustrated in FIG. 10B) have been utilized to localize influenza HA protein on the surface. FIG. 12A shows the yeast control (YEX) for FIGS. 12B and 12C. FIGS. 12B-12C illustrate expression by the VK4 (FIG. 12B) and TK75-15 (FIG. 12C) expressing Tarmogens. FIG. 12D shows the yeast control (YEX) for FIGS. 12E-12G. FIGS. 12E and 12F show expression of HA VK8 by a yeast, when the yeast is glycosylated (FIG. 12E) and deglycosylated (FIG. 12F). FIG. 12G shows expression of HA on plasma membrane of the Lu002-expressing spheroplast preparations.

Figure 13B:
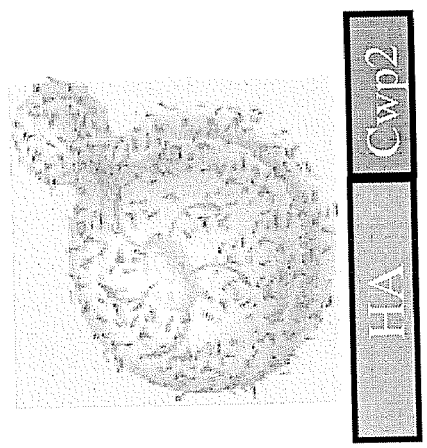
Figure 13A:
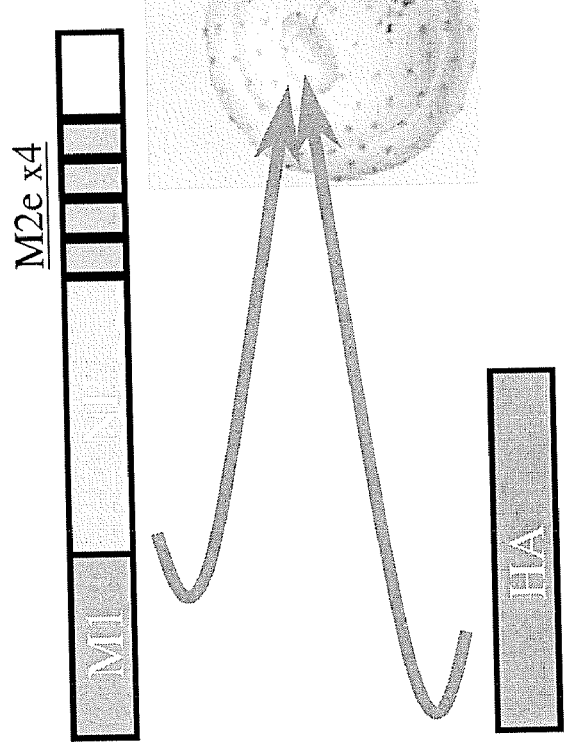

FIGS. 13A and 13B are schematics of constructs for expression of extracellular (FIG. 13B) and intracellular (FIG. 13A) influenza hemagglutinin (HA), which may be combined with the intracellular expression of conserved influenza antigens M1, NP and M2 (FIG. 13A).

Figure 14B:
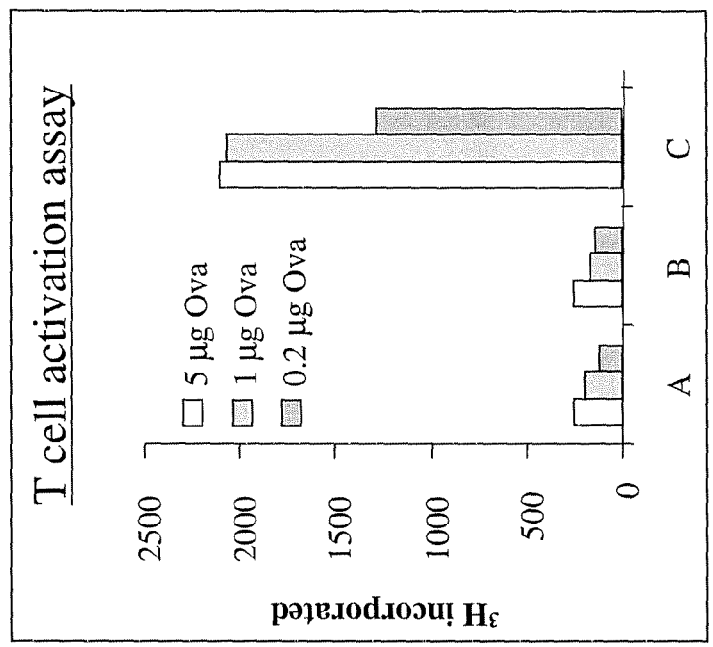
Figure 14A:
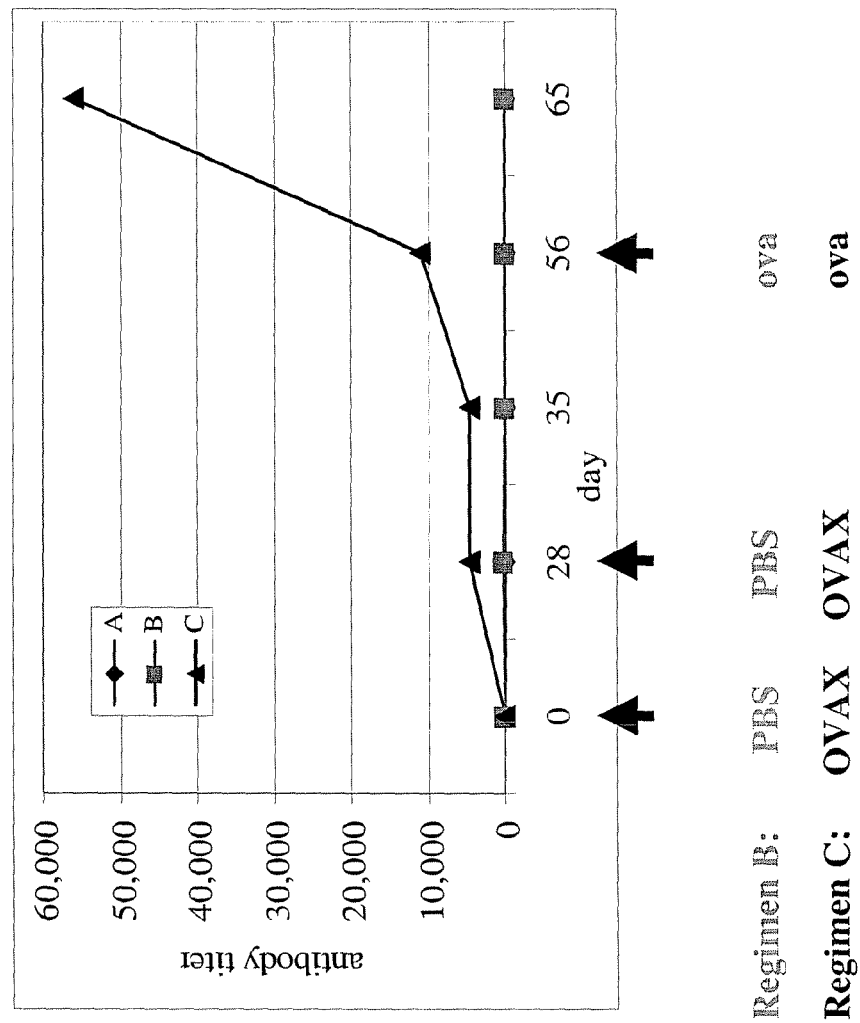

FIGS. 14A and 14B show T cell priming (FIG. 14B) and antibody production (FIG. 14A) for three regimens used (FIG. 14A). Regimen A uses only PBS (control). Regimen B uses PBS on days 0 and 28 for priming and soluble ovalbumin protein (ova) was used to boost on day 56. Regimen C used the yeast vehicle expressing ovalbumin (OVAX) for priming and soluble ovalbumin protein was used to boost. FIG. 14B shows the results of a T cell activation assay using various amounts of soluble ovalbumin protein for the in vitro restimulation of T cells harvested from mice immunized by each of the three regimens described above.

Figure 15:
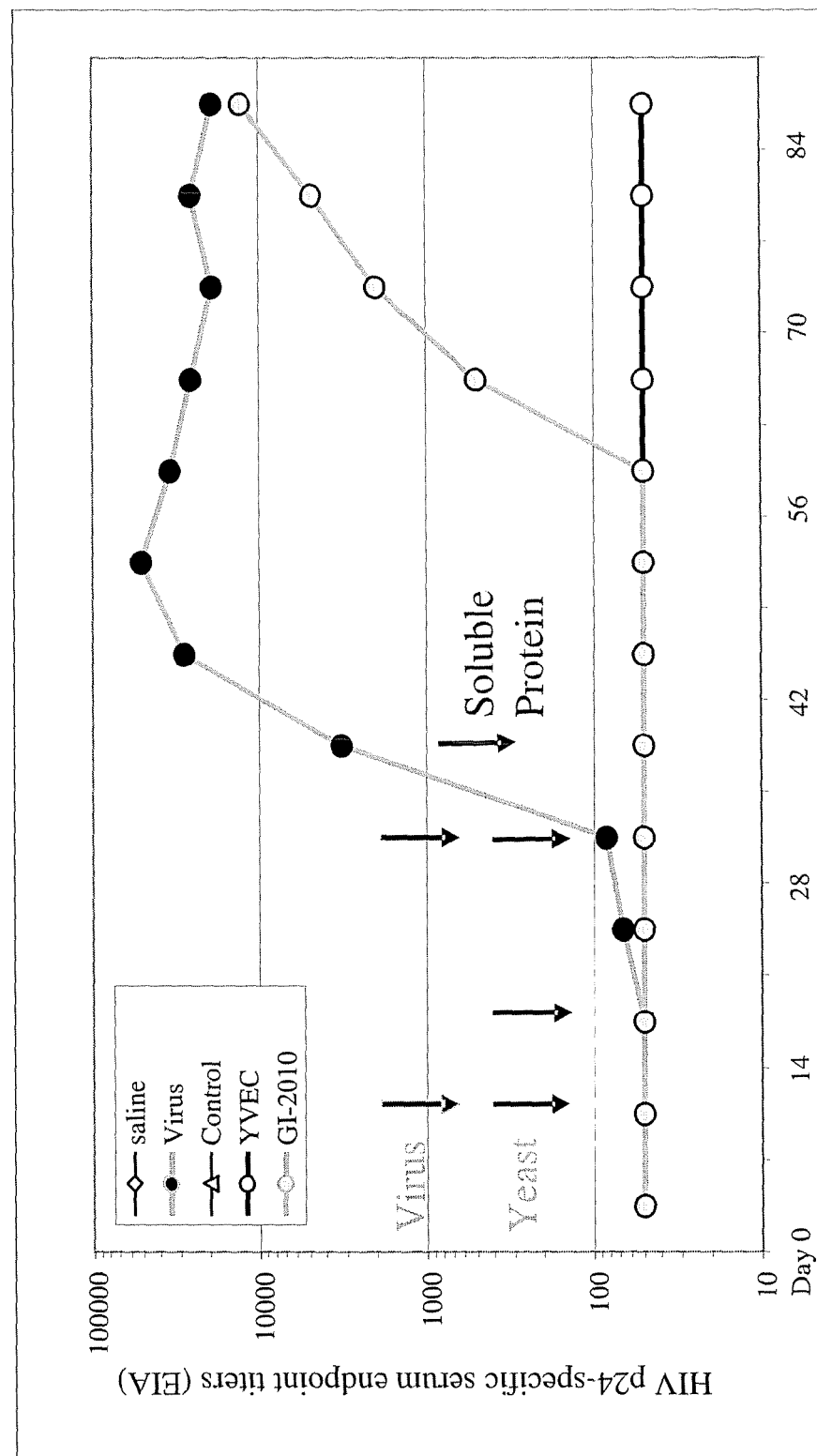

FIG. 15 shows the results of experiments where GI-2010, a Tarmogen expressing HIV Gag protein, was tested for its ability to prime an antibody response, compared to the humoral response observed following infection with live vaccinia virus encoding nothing (control) or HIV-Gag protein (virus). The saline and control curves are under the GI-2010 and YVEC lines (i.e, the GI-2010 and YVEC lines are superimposed on the saline and control lines)

Figure 16B:
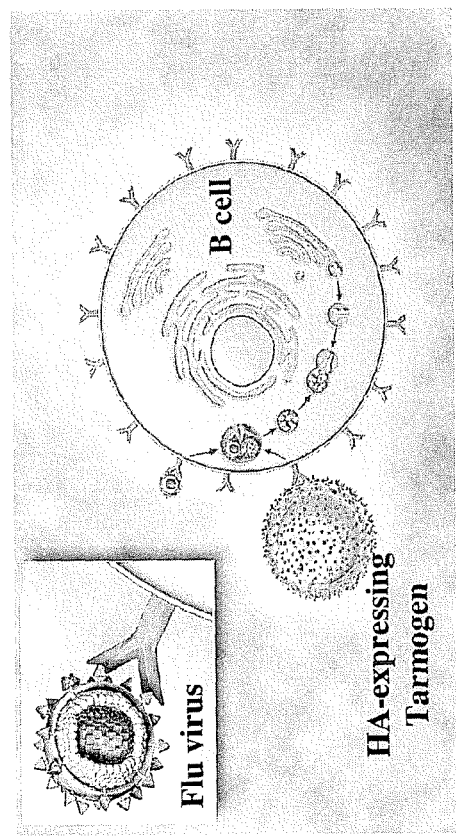
Figure 16A:
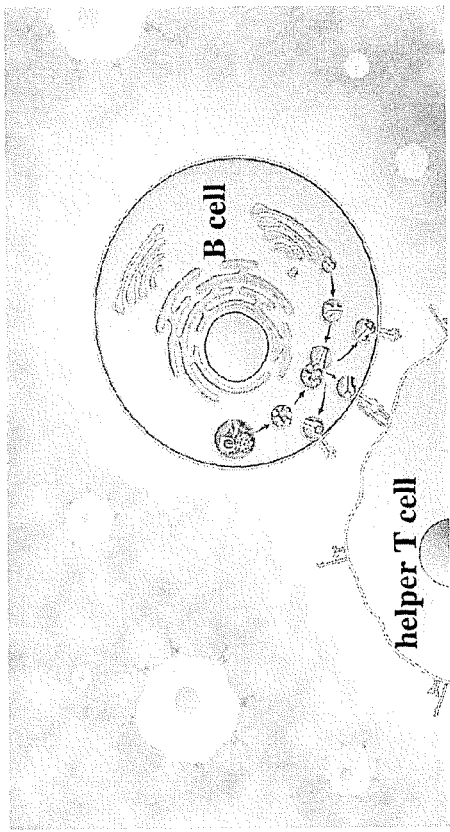

FIGS. 16A and 16B are schematic drawings showing the requirements for combining B cell activation and signals derived from helper T cell responses to peptides derived from the antigen to which antibody responses are sought (Signal 1 is shown in FIG. 16A and Signal 2 is shown in FIG. 16B).

Figure 17:
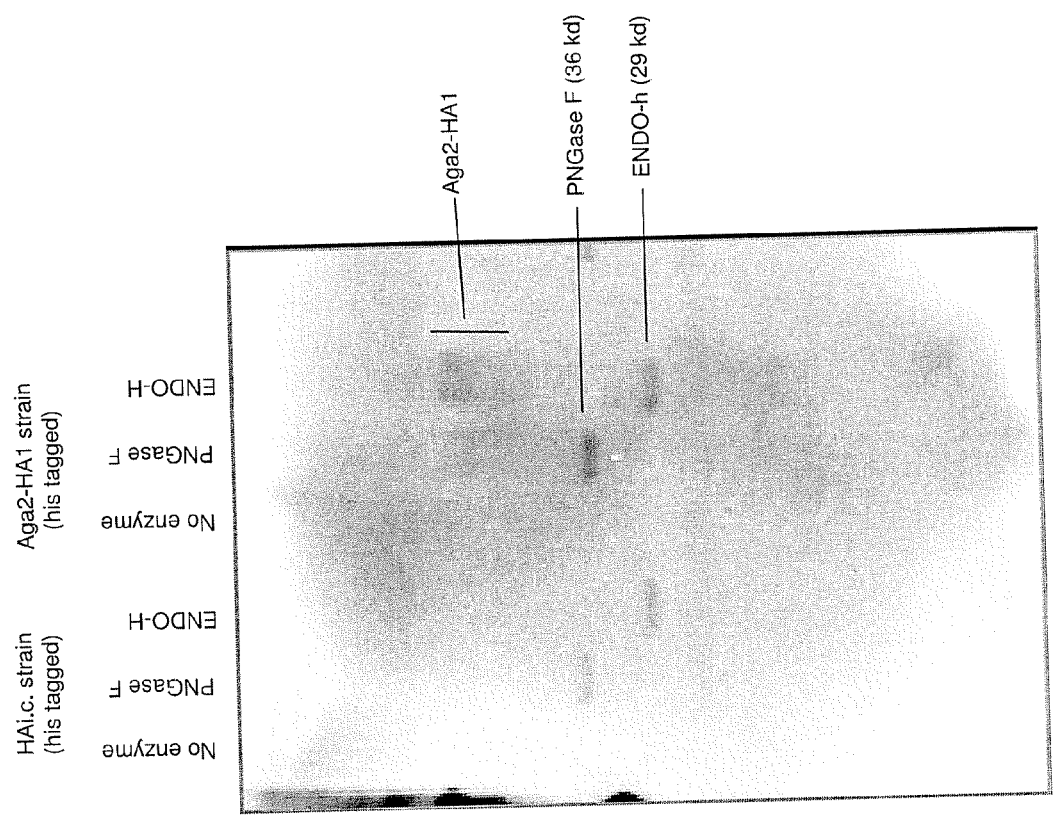

FIG. 17 is a digitized image of a Western blot showing cell surface expression of Influenza HA1 domain fused to Aga2 (Aga2-HA1).

DETAILED DESCRIPTION OF THE INVENTION

The invention generally relates to compositions and methods for efficiently eliciting various types of immune responses, including cell-mediated immune responses, humoral immune responses, and combinations thereof. The invention is useful for eliciting protective and/or therapeutic immune responses against a wide variety of antigens (including pathogens), and the responses can be optimized to preferentially elicit (or ensure the elicitation of) a cell-mediated immune response, a humoral immune response, or both a cell-mediated and humoral immune response. In addition, the immune responses elicited by vaccines and vaccine strategies of the invention can be optimized to provide an efficacious response against: pathogens that frequently mutate and/or infect an individual with multiple species or strains at the same time, pathogens that infect or exist in individuals in different life cycle stages, and pathogens that evade the immune system by various actions, including by infection of target cells. The immune responses elicited by the present invention are particularly efficacious in scenarios where humoral immune responses may be at least somewhat effective in limiting the pathogen's ability to cause disease, but where the immune system nonetheless fails to prevent or detect alternate forms of the pathogen (mutants or life cycle forms) and/or infection or occupation of a host cell by the pathogen, which may then evade or misdirect the immune response. The immune response elicited by vaccines and vaccine strategies of the invention can also be optimized to protect or treat an individual with a disease or condition, depending on the type of immune response that would be most beneficial for a particular disease or condition, and depending on the immune status of the patient with respect to a given antigen or pathogen at a given time point. Finally, the vaccines and vaccine strategies of the invention can stimulate an efficacious immune response with a few administrations, and also are effective at stimulating immune responses with exposure to low levels of antigen (dose-sparing).

The invention provides both compositions and methods for eliciting immune responses to a variety of antigens that are useful for protective or therapeutic immunity and/or for vaccination purposes. In one aspect, the invention provides compositions that can elicit both a humoral immune response and a cell-mediated immune response, and in additional aspects, provides compositions and vaccine strategies for preferentially eliciting or priming a humoral immune response, including priming for an antigen-specific antibody production directed to one or more antigen(s) of interest, or for preferentially eliciting or priming a cell-mediated (cellular) immune response, including cytotoxic T cell responses. By preferentially eliciting, it is meant that an immune response can be pushed or directed toward a particular type of immune response, primarily based on how the antigen is made available to the immune system using the yeast-based vaccines of the invention. The compositions and immunization strategies are particularly designed to provide the optimization of the immune response as described above. The invention also provides for compositions and methods which can enhance or complement the immunogenicity of or successful immunization using non-yeast-based vaccines, such as DNA vaccines.

More particularly, the present invention is directed to improvements on the platform technology related to yeast-based immunotherapeutic products as described in U.S. Pat. Nos. 5,830,463 and 7,083,787, and in U.S. Patent Publication Nos. 2004-0156858 A1 and 2006-0110755 A1, and provides novel yeast-based vaccines for use in eliciting protective and/or therapeutic immune responses against a wide variety of antigens (including pathogens). In one aspect, the present invention takes advantage of the ability to selectively design yeast-based vaccine compositions to express or provide antigens intracellularly, extracellularly (i.e., yeast surface expression), or both, and to select different antigens and combinations of antigens for intracellular and/or extracellular expression/location, in order to manipulate the type of immune response that is preferentially induced against specified antigen(s), and also to manipulate the ability of the immune response(s) to most effectively immunize an individual against a particular antigen or antigens, and to most effectively prevent or treat a disease or condition associated with an antigen or antigen.

For example, in one embodiment, using the invention disclosed herein, compositions and methods are disclosed that provide a cross-protective, "universal" vaccine approach to provide long-lasting immunity, and importantly, cell-mediated immunity, against an antigen or antigens. This element of the invention takes advantage of the fact that with respect to pathogens, for example, certain antigens are highly conserved among different strains or species of pathogens. In addition, certain cells against which an immune response could be targeted, e.g., tumor cells, may also share particular conserved antigens. Such antigens are frequently expressed internally by the pathogen or cell (i.e., the antigens displayed on the surface of a pathogen or cell are more likely to be readily varied or mutated to evade immune detection and clearance, whereas antigens that are internal to the pathogen or cell are more likely to be conserved from strain to strain, species to species, or cell to cell). Such conserved antigens (which if expressed internally by a pathogen, such as a virus, can also be generally referred to as internal antigens) provide a basis for a yeast-based vaccine that is cross-protective and able to elicit an effective cell-mediated immune response (cellular) against the antigen (and thus against a cell that is infected with or occupied by the pathogen). In this aspect, the conserved antigens or internal antigens are typically expressed or provided intracellularly by the yeast vehicles of the invention. However, expression of these types of antigens is not limited to intracellular expression; conserved or internal antigens can also or alternatively be expressed or provided extracellularly (on the surface of the yeast) by the yeast vehicles of the invention, as discussed below.

Intracellular expression or location of antigen by a yeast vehicle according to the present invention (e.g., by expression, by intracellular loading, or any other method of providing an antigen that is contained within the intracellular milieu of the yeast) is generally useful for preferentially eliciting a cell-mediated immune response against any antigen, or more particularly, provides antigen in a context in which a cell-mediated immune response is readily elicited, although humoral immune responses will also be primed or induced by this approach, particularly if the antigen in its naturally occurring form is or has been available to the extracellular milieu (i.e., by prior infection, disease, or immunization). Intracellular expression or provision of antigen by a yeast vehicle is particularly useful for priming or initial vaccinations with an antigen, since providing a strong cell-mediated immune response and preferably immunological memory will enhance the ability of both the cell-mediated and humoral arms of the immune response to respond to future encounters with the antigen (e.g., through boosting immunizations, infection, or disease). Intracellular expression or provision of antigens is useful for the elicitation of an immune response against any antigens, including the conserved or internal antigens described above, and the variable or external antigens described below.

In another embodiment, compositions and methods are provided that are designed to induce a strain, species, or antigen variant-specific immune response. For example, this approach immunizes a host against more specific antigens that may be associated with a particular mutant, strain, species or life cycle stage of a pathogen, or a particular antigen variant, as is done, for example, in conventional killed virus vaccines that usually include three selected viral strains representing three viral groups based on surface antigens. In other words, this aspect of the invention takes further advantage of the fact that many pathogens and cells express variations of proteins (variable antigens), particularly on the surface of such pathogens or cells (surface antigens can also generally be referred to herein as external antigens) that can be used to create a yeast-based vaccine that provides a very directed immunization, or even a seasonal immunization, against the antigen or pathogen. In one aspect of the invention, such antigens are typically expressed extracellularly (on the surface) by the yeast vehicles of the invention. Expression of variable or external antigens is not limited to extracellular expression or extracellular provision of antigens on the yeast vehicle; such antigens can also or alternatively be expressed or provided intracellularly by the yeast vehicles of the invention, as discussed below.

Extracellular or surface expression or provision of antigen by a yeast vehicle according to the present invention (e.g., by expression that results in surface expression or translocation of the antigen to the outer surface of the yeast vehicle, by attaching an antigen to the outer surface or by secreting the antigen from the yeast) preferentially elicits a humoral immune response against the antigen, or more particularly, enhances the elicitation of a humoral immune response as compared to when the antigen is expressed intracellularly by the yeast vehicle, although cell-mediated immune responses will also be primed or induced by this approach. Indeed, one advantage of such a vaccine is that, in contrast to a conventional killed virus vaccine mentioned above, for example, which primarily elicits a neutralizing antibody response against the virus, the vaccine of the present invention can elicit both a cell-mediated and a humoral immune response against these surface antigens. Extracellular expression or provision of antigens by the yeast vehicle is useful for the elicitation of an immune response against any antigens, including the conserved or internal antigens and the variable or external antigens described above. However, extracellular expression or provision of the antigen on the yeast vehicle is particularly useful for the elicitation of an immune response against antigens that the immune system is expected to encounter in the extracellular milieu, such as soluble antigens, cell surface-expressed antigens, or pathogen surface-expressed antigens, since development of a humoral immune response against such antigens is desirable.

In one aspect, the present invention also combines the two vaccine approaches described above (intracellular and extracellular expression or provision of the antigen by the yeast vehicle) to provide powerful new vaccines that effectively elicit both cell-mediated and humoral immunity, which can be designed to provide both cross-protective immunity and more specific immunity against a particular antigen variant or pathogen species, strain or mutant. For example, referring to a viral infection such as influenza infection, the combination vaccine approach elicits a powerful immune response against influenza viral infection in a cross-protective, "universal" manner, together with a viral strain-specific antigen approach. This approach will elicit both a cell-mediated and a humoral immune response against influenza virus and in a preferred embodiment of the invention, does so in both a cross-protective and viral strain-specific manner.

In this embodiment of the invention, the vaccines can be designed in any of a number of ways. For example, in one aspect, conserved antigen(s) from a pathogen (e.g., a viral internal antigen) can be expressed or provided intracellularly by a yeast vehicle, and variable antigens from the pathogen (e.g., a viral surface antigen) can be expressed or provided extracellularly by the yeast vehicle. Immunization using such yeast vehicles will elicit both a cell-mediated and a humoral immune response against the virus, and does so in both a cross-protective and viral strain-specific manner. The individual immunized with a vaccine containing such a yeast vehicle will have strong cell-mediated immunity against the conserved antigen(s) and strong humoral immunity against the variable antigens, although both types of immune responses will be primed against both types of antigens. It will be apparent to those of skill in the art how this first example can be modified to improve or modify the immune response against the virus. For example, both the conserved antigens and the variable antigens can be expressed or provided intracellularly by the yeast, and the variable antigens can be expressed or provided extracellularly by the yeast, to ensure a better cell-mediated immune response (which is important for the priming of future cell-mediated and humoral immune responses) against both types of antigens, and to provide more effective humoral immunity immediately against the variable antigens (e.g., see FIG. 16 and the discussion herein).

In the combination embodiments described herein, the yeast vehicle that expresses or provides the antigens extracellularly (on the yeast vehicle surface) can be the same or a different yeast vehicle than the yeast vehicle that expresses or provides antigen(s) intracellularly. In addition, different combinations of intracellular antigens and/or extracellular antigens can be expressed on different yeast vehicles, and the vehicles can be used separately or together, depending on the vaccination that is desired. In general, when the antigens are provided by two or more different yeast vehicles (i.e., as opposed to expressing or providing all antigens in one yeast vehicle), the yeast vehicles can be combined (mixed) for administration as a single vaccine (e.g., a single injection or other type of dosage) or the different yeast vehicles can be administered sequentially. The sequential administration can be separated by any suitable period of time, including small increments of time (seconds or minutes) and longer increments of time (days, weeks, months, or even years). The invention contemplates that in these embodiments, any combination of antigens that in a preferred embodiment, includes at least one intracellular antigen and at least one extracellular antigen can be used, and these antigens can be provided using any combination of yeast vehicles (including a single yeast vehicle) that express or provide such antigens.

The vaccine approaches described above can accordingly be modified by combination or sequential administration (e.g., a prime/boost strategy) of different yeast-based vaccines where different combinations of antigens, including different combinations of extracellular antigens and/or intracellular antigens, and in some aspects, different combinations of conserved and/or variable antigens, are provided. In addition, yeast vehicles described herein can be combined with other types of vaccines, either concurrently or sequentially (e.g., in a priming and boosting protocol) to further direct the immune response and to provide enhanced protection against infection and disease. In one embodiment, a yeast-based vaccine of the invention that provides at least cell-mediated immunity, and in one aspect, both cell-mediated and humoral immunity, such as by expressing or providing antigens both intracellularly and extracellularly, is used to prime an immune response against a particular antigen, set of antigens, or pathogen. Immunization boosts are then provided by delivery of a conventional vaccine, such as a DNA vaccine, a protein subunit vaccine, or a killed or inactivated pathogen, or by another yeast-based vaccine (including a membrane or cell wall particle vaccine) or a combination of a yeast and conventional antigen preparations or even yeast alone (e.g., in these latter two scenarios, where the yeast is serving primarily as an adjuvant). In such "prime-boost" strategies, a strong cell-mediated response elicited as a result of the first immunization (priming) improves the efficacy of subsequent boosts and in some embodiments, can actually provide synergistic effects, particularly when the boosting vaccine is a different type of vaccine than the priming vaccine and/or contains different antigens as compared to the priming vaccine.

By priming the immune response using the yeast-based vaccines and methods of the invention, both cell-mediated and humoral immunological memory is generated (i.e., memory B cells and T cells that selectively recognize the antigens of interest are generated). As a result, upon subsequent exposure to the antigen, e.g., through vaccination boosts, disease, or infection, the immune system will respond more quickly and more efficaciously, and importantly with respect to vaccination boosts, lower antigen doses can be used in boosters of non-yeast-based vaccines (see, for example, Example 2 and FIGS. 14 and 16). In addition, the yeast vehicles may work in synergy with non-yeast-based vaccines, such that immune responses are optimized by the combinatorial approach, such as by combining DNA vaccines with yeast-based vaccines. As such, the vaccines may need to be administered only once and/or in a lower amount for efficacy. These dose-sparing qualities are desirable when non-yeast-based vaccines are in short supply or when combating an agent that threatens public health, since it becomes difficult to immunize individual more than once, especially in circumstances of mass immunization.

The compositions and methods of the invention also include vaccines where a yeast vehicle does not necessarily recombinantly express or otherwise provide the antigen(s) of interest but rather, is used as an adjuvant to enhance the immune response of an antigen that is provided separately (e.g., as any conventional vaccine, including DNA vaccines, subunit protein vaccines, killed or inactivated pathogens, dendritic cell vaccines, etc.) or in the context of an individual that already carries the antigen in sufficient quantities to elicit an immune response upon administration of the non-antigen-carrying yeast vehicle, such as an individual that is currently infected with a pathogen, an individual who has experienced a mutation in a cellular protein or otherwise expresses or carries an antigen to which the immune system is not tolerant or against which tolerance can be broken. This approach may be combined with a prior or subsequent immunization with a yeast vehicle that expresses or provides intracellular and/or extracellular heterologous antigens, as discussed above.

Indeed, there is great flexibility in how the vaccine of the present invention is designed and used. For example, a "universal" vaccine comprising a yeast vehicle that expresses or is complexed with (i.e., associated with, mixed with, containing, providing) certain antigens, such as conserved antigens can be administered to an individual on a periodic basis, in order to develop a cross-protective immunity in an individual. This vaccine can then be combined, for example, on a one-time or periodic basis with additional yeast vehicles expressing or complexed with other antigens, such as variable antigens, for example, to address a particular strain of virus that is known to be circulating in a population of individuals. The yeast vehicles expressing or complexed with such variable antigens can be rotated, alternated or selected annually or on any other preferred basis (e.g., emergency or anticipated epidemic or pandemic, or as otherwise needed) to target pathogens of interest and/or the most prevalent pathogen strain(s) during a given period of time or for a particular geographic region. Other embodiments of the invention will be apparent in view of the disclosure provided herein.

As discussed above, manipulation of the type of expression or association of an antigen with a yeast vehicle achieves a particular immunological result, which can be exploited as desired to "tailor" or "design" vaccines for populations, individuals, or particular diseases, conditions, or pathogenic infections. In the case of extracellular expression or provision of an antigen by a yeast vehicle, both humoral and cell-mediated immunity are elicited, although this type of expression or provision is particularly efficacious for the elicitation of humoral immunity, as compared to intracellular expression or provision of antigens by the yeast. This is primarily because the antigen is exposed directly to B cells in this embodiment, allowing B cell activation, proliferation, maturation and antibody production to occur more effectively.

More specifically, an antigen expressed or provided on the yeast surface (or secreted by the yeast) can be recognized by a B cell antigen receptor (BCR) expressed by a B cell (B lymphocytes). Upon binding of this surface antigen to the BCR, the B cell then internalizes the bound antigen-expressing yeast vehicle, and the antigens are processed and returned to the surface of the B cell in the form of peptides from the antigen(s) in complex with major histocompatibility complex (MHC) class II receptors. These MHC-peptide complexes are bound by "helper" T cells (e.g., $CD4^+$ T cells) that have T cell receptors (TCR) that specifically recognize the particular MHC-peptide complexes. Activated, antigen-specific T cells that recognize the MHC-peptide complex presented by a B cell in turn provide to such B cell "help" in the form of signals (e.g., cytokines) that cause the B cell to proliferate and its progeny to differentiate and mature into antibody-secreting cells. Helper T cells may be activated by contact of the T cell with such a B cell that is presenting the MHC-antigen complex, as well as by contact with the MHC-peptide complex presented by other antigen-presenting cells, including dendritic cells and macrophages. In addition, because the yeast vehicles of the invention are avidly phagocytosed by and directly activate the MHC class I pathway of antigen presenting cells such as dendritic cells (in addition to the MHC class II pathway), a $CD8^+$ cell-mediated immune response can also be elicited by extracellular expression or provision of the antigen, in addition to a $CD4^+$ cell-mediated response. In this manner, both humoral and cell-mediated immune responses are elicited by extracellular expression or provision of the antigen by the yeast, and this type of expression is believed to be more efficacious for eliciting humoral immune responses than by intracellular expression or provision of the antigen. Humoral immune responses can include the generation of neutralizing antibodies, which are useful for the prevention and treatment of infectious diseases and other undesirable conditions.

Aspects of B cell activation resulting in a humoral immune response are schematically shown in FIGS. 16A and 16B. Referring to FIG. 16A, for signal 1 of B cell activation, the antigen may be provided by a non-yeast based vaccine or soluble protein, or by yeast expressing, displaying or otherwise containing the target antigen on the surface. Referring to FIG. 16B, the intracellular processing of the antigen taken up by the activated B cells is presented via MHC class 2 receptors, which is recognized by and activates antigen-specific helper T cells. The signals and cytokines transmitted by the activated antigen-specific T cells matures the B cell responses and boosts antibody production. Yeast intracellularly expressing the target antigen are very effective for activating and amplifying the number of antigen-specific helper T cells, as previously described and as discussed below. Antibody production is more effectively elicited when helper T cell activation and proliferation precede or are concomitant to B cell binding of the soluble target antigen.

When the antigen is expressed or provided intracellularly by a yeast vehicle, a cell-mediated immune response (both CD4+ and CD8+ T cell responses) is generated by the presentation of the antigens through both the MHC class I-restricted and the MHC class II-restricted pathways of antigen-presenting cells such as dendritic cells and macrophages, as described previously (See, e.g., U.S. Pat. Nos. 5,830,463 and 7,083,787, Stubbs et al., *Nat. Med.* 7:625-629 (2001) and Lu et al., *Cancer Research* 64:5084-5088 (2004)). The T cells activated by this mechanism can also contribute to antibody production by providing a signal to B cells that have encountered the target antigen by a different approach, such as a non-yeast-based vaccine, or by natural exposure to a pathogen or disease, for example. Experimental results demonstrating this concept are shown in FIGS. 14 and 15.

Various aspects of the invention will be better understood through the specific examples of influenza vaccines disclosed herein, although the invention is not limited to such vaccines. Indeed, given the information provided herein, one skilled in the art will readily be able to extrapolate the vaccine strategies described for influenza virus to other pathogens and to immunization protocols where the target antigen is a cellular protein, by making use of the manipulation of extracellular and/or intracellular antigen expression or provision by yeast vehicles according to the invention, the manipulation of expression or provision of conserved and variable antigens (or internal and external antigens), and the manipulation of priming and boosting methods described herein.

In one embodiment, the invention generally relates to novel compositions and methods for vaccinating an animal against an influenza virus and for treating or preventing influenza infection in an animal. The invention includes the use of a yeast-based vaccine or a combination of yeast-based vaccines, the vaccine including at least one yeast vehicle and at least one influenza antigen that is selected to elicit an immune response against influenza infection in an animal. In particularly preferred embodiments, the invention includes the use of a combination of influenza antigens in the yeast-based vaccine, where the combination of antigens provides cross-protection against a variety of influenza viral strains, as well as specific protection against particular viral strains. The invention specifically provides novel yeast-based vaccines for use in protecting against influenza viral infection using a cross-protective, "universal" vaccine approach, alone or together with a viral strain-specific antigen approach. This approach will elicit both a cell-mediated and a humoral immune response against influenza virus preferably does so in both a cross-protective and viral strain-specific manner.

In a first aspect of this embodiment, the present invention takes advantage of the fact that certain proteins expressed internally by influenza virus are highly conserved among viral strains. These antigens (referred to herein generally as internal viral proteins) provide a basis for a yeast-based vaccine that is cross-protective and able to elicit an effective cell-mediated immune response against the viral protein (and thus an influenza virus-infected cell). In another aspect of this embodiment, the present invention takes further advantage of the fact that influenza viral strains express variations of surface proteins (referred to herein generally as external viral proteins) that can be used to create a yeast-based vaccine that immunizes a host against more specific viral strains, as is done in conventional killed virus vaccines that typically include three selected viral strains representing three viral groups based on surface antigens. However, in contrast to these conventional killed virus vaccines, which primarily elicit a neutralizing antibody response against the virus, the vaccine of the present invention can elicit both a cell-mediated and a humoral immune response against these viral surface antigens. Moreover, the present invention combines these two vaccines in preferred aspects to provide a powerful new influenza vaccine that elicits both cross-protective and viral strain-specific immunity, including both cell-mediated and humoral immunity.

General Techniques

The practice of the present invention will employ, unless otherwise indicated, conventional techniques of molecular biology (including recombinant techniques), microbiology, cell biology, biochemistry, nucleic acid chemistry, and immunology, which are well known to those skilled in the art. Such techniques are explained fully in the literature, such as, *Methods of Enzymology*, Vol. 194, Guthrie et al., eds., Cold Spring Harbor Laboratory Press (1990); *Biology and activities of yeasts*, Skinner, et al., eds., Academic Press (1980); *Methods in yeast genetics: a laboratory course manual*, Rose et al., Cold Spring Harbor Laboratory Press (1990); *The Yeast Saccharomyces: Cell Cycle and Cell Biology*, Pringle et al., eds., Cold Spring Harbor Laboratory Press (1997); *The Yeast Saccharomyces: Gene Expression*, Jones et al., eds., Cold Spring Harbor Laboratory Press (1993); *The Yeast Saccharomyces: Genome Dynamics, Protein Synthesis, and Energetics*, Broach et al., eds., Cold Spring Harbor Laboratory Press (1992); *Molecular Cloning: A Laboratory Manual*, second edition (Sambrook et al., 1989) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2001); *PCR: The Polymerase Chain Reaction*, (Mullis et al., eds., 1994); Harlow and Lane (1988) *Antibodies, A Laboratory Manual*, Cold Spring Harbor Publications, New York; Harlow and Lane (1999) *Using Antibodies: A Laboratory Manual* Cold Spring Harbor Laboratory Press, Cold Spring Harbor, N.Y. (jointly referred to herein as "Harlow and Lane"), Beaucage et al. eds., *Current Protocols in Nucleic Acid Chemistry* John Wiley & Sons, Inc., New York, 2000); *Casarett and Doull's Toxicology The Basic Science of Poisons*, C. Klaassen, ed., 6th edition (2001), and *Vaccines*, S. Plotkin and W. Orenstein, eds., $3^{rd}$ edition (1999).

General Definitions

A "humoral immune response" refers generally to antibody production, and to all of the processes that accompany antibody production, including, but not limited to, B lymphocyte (B cell) activation, affinitiy maturation, differentiation into plasma cells, and memory B cell generation, germinal center formation and isotype switching, and T helper cell activation, signaling, and cytokine production, as well as effector functions of antibodies, which include neutralization, classical complement activation, and opsonization.

A "cell-mediated" immune response (which may be used interchangeably anywhere herein with the term "cellular" immune response) refers generally to the response to an antigen of immune cells including T lymphocytes (including cytotoxic T lymphocytes (CTL)), dendritic cells, macrophages, and natural killer cells, and to all of the processes that accompany such responses, including, but not limited to, activation and proliferation of these cells, CTL effector functions, cytokine production that influences the function of other cells involved in adaptive immune responses and innate immune responses, and memory T cell generation.

According to the present invention, the term "extracellular" as it is applied herein to the provision of an antigen extracellularly (or the provision of an extracellular antigen) with respect to a yeast vehicle, means that the antigen is extracellular to (on the surface of or outside of) the yeast vehicle, which can be achieved by any of a number of methods. For example, an antigen is extracellular with respect to the yeast vehicle if the antigen is expressed by the yeast vehicle (e.g., by recombinant production) such that the antigen, or a portion thereof, is displayed on (located on, contained on, localized to) the outer surface of the yeast vehicle (e.g., the cell wall for whole, intact yeast, or the plasma membrane for yeast spheroplasts, cytoplasts and ghosts). The antigen may, for example, be expressed in the ER of the yeast and then translocated to the surface of the yeast, although, in general, with respect to recombinant antigen production, reference to "expression" on the surface of a yeast vehicle or extracellular to the yeast vehicle is intended to encompass the entire process of antigen production, from transcription, through translation, through targeting and delivery or translocation of the antigen to its final destination in the yeast vehicle. The term "expression" can also be generically used interchangeably with the term "provision" and can most generically encompass any way of providing an antigen on the surface of a yeast vehicle (i.e., association by other methods is encompassed). For example, an antigen is also extracellular with respect to the yeast vehicle if it is attached to the outer surface of the yeast, such as by a covalent or non-covalent linkage (i.e., not necessarily recombinantly expressed by the yeast). An antigen is also extracellular with respect to the yeast vehicle if it is simply in a mixture with the yeast (an admixture, combined, a composition). An antigen is also extracellular with respect to the yeast vehicle if it is secreted by the yeast.

According to the present invention, the term "intracellular" as it is applied herein to the provision of an antigen intracellularly (or the provision of an intracellular antigen) with respect to a yeast vehicle, means that the antigen is contained within the intracellular milieu of the yeast vehicle, which can be achieved by any number of methods. For example, an antigen is intracellular with respect to the yeast vehicle if the antigen is expressed by the yeast vehicle (e.g., by recombinant production) and at least some of the antigen that is produced remains inside the yeast (i.e., is not translocated to or delivered to the surface of the yeast vehicle, or has not yet been delivered to or translocated to the surface of the yeast vehicle). The intracellular milieu of the yeast vehicle can include, but is not limited to, the cytosol, the ER, internal membranes, and secretory vesicles that have not yet traversed to the cell surface. An antigen is also intracellular with respect to the yeast vehicle if it is loaded into the yeast (e.g., by any suitable method of transport, including electroporation, particle bombardment, microinjection, lipofection, adsorption, infection and protoplast fusion).

According to the present invention, the general use herein of the term "antigen" refers: to any portion of a protein (peptide, partial protein, full-length protein), wherein the protein is naturally occurring or synthetically derived, to a cellular composition (whole cell, cell lysate or disrupted cells), to an organism (whole organism, lysate or disrupted cells) or to a carbohydrate (such as those expressed on cancer cells), or other molecule, or a portion thereof. An antigen elicits an antigen-specific immune response (e.g., a humoral and/or a cell-mediated immune response) against the same or similar antigens that are encountered within the cells and tissues of an individual to which the antigen is administered. Alternatively, an antigen can act as a toleragen.

When referring to stimulation of an immune response, the term "antigen" can be used interchangeably with the term "immunogen". An immunogen, as used herein, describes an antigen which elicits a humoral and/or cell-mediated immune response (i.e., is antigenic), such that administration of the immunogen to an animal (e.g., via a vaccine of the present invention) mounts an antigen-specific immune response against the same or similar antigens that are encountered within the tissues of the animal.

A "toleragen" is used to describe an antigen that is provided in a form, amount, or route of administration such that there is a reduced or changed immune response to the antigen, and preferably substantial non-responsiveness, anergy, other inactivation, or deletion of immune system cells in response to contact with the toleragen or a cell expressing or presenting such toleragen.

A "vaccinating antigen" can be an immunogen or a toleragen, but is an antigen used in a vaccine, where a biological response (elicitation of an immune response, tolerance) is to be elicited against the vaccinating antigen.

An "immunogenic domain" of a given antigen can be any portion, fragment or epitope of an antigen (e.g., a peptide fragment or subunit or an antibody epitope or other conformational epitope) that contains at least one epitope that acts as an immunogen when administered to an animal. For example, a single protein can contain multiple different immunogenic domains. Immunogenic domains need not be linear sequences within a protein, such as in the case of a humoral immune response.

An epitope is defined herein as a single immunogenic site within a given antigen that is sufficient to elicit an immune response, or a single toleragenic site within a given antigen that is sufficient to suppress, delete or render inactive an immune response. Those of skill in the art will recognize that T cell epitopes are different in size and composition from B cell epitopes, and that epitopes presented through the Class I MHC pathway differ from epitopes presented through the Class II MHC pathway. Epitopes can be linear sequence or conformational epitopes (conserved binding regions). An antigen can be as small as a single epitope, or larger, and can include multiple epitopes. As such, the size of an antigen can be as small as about 5-12 amino acids (e.g., a peptide) and as large as: a full length protein, including a multimer and fusion proteins, chimeric proteins, whole cells, whole microorganisms, or portions thereof (e.g., lysates of whole cells or extracts of microorganisms). In addition, antigens can include carbohydrates, which can be loaded into a yeast vehicle or into a composition of the invention. It will be appreciated that in some embodiments (i.e., when the antigen is expressed by the yeast vehicle from a recombinant nucleic acid molecule), the antigen is a protein, fusion protein, chimeric protein, or fragment thereof, rather than an entire cell or microorganism. Preferred influenza fusion proteins of the invention are described herein.

"Vaccination" or "immunization" refers to the elicitation (induction) of an immune response against an antigen or immunogenic or toleragenic portion thereof, as a result of administration of the antigen, alone or together with an adjuvant. Vaccination preferably results in a protective or therapeutic effect, wherein subsequent exposure to the antigen (or a source of the antigen) elicits an immune response against the antigen (or source) that reduces or prevents a disease or condition in the animal. The concept of vaccination is well known in the art. The immune response that is elicited by administration of a composition (vaccine) of the present invention can be any detectable change in any facet of the immune response (e.g., cell-mediated response, humoral response, cytokine production), as compared to in the absence of the administration of the composition.

A Tarmogen (targeted molecular antigen) generally refers to a yeast vehicle expressing one or more heterologous antigens extracellularly (on its surface), intracellularly (internally or cytosolically) or both extracellularly and intracellularly. Tarmogens have been generally described in the art. See, e.g., U.S. Pat. No. 5,830,463.

In one embodiment of the present invention, any of the amino acid sequences described herein can be produced with from at least one, and up to about 20, additional heterologous amino acids flanking each of the C- and/or N-terminal ends of the specified amino acid sequence. The resulting protein or polypeptide can be referred to as "consisting essentially of" the specified amino acid sequence. As discussed above, according to the present invention, the heterologous amino acids are a sequence of amino acids that are not naturally found (i.e., not found in nature, in vivo) flanking the specified amino acid sequence, or that are not related to the function of the specified amino acid sequence, or that would not be encoded by the nucleotides that flank the naturally occurring nucleic acid sequence encoding the specified amino acid sequence as it occurs in the gene, if such nucleotides in the naturally occurring sequence were translated using standard codon usage for the organism from which the given amino acid sequence is derived. Similarly, the phrase "consisting essentially of", when used with reference to a nucleic acid sequence herein, refers to a nucleic acid sequence encoding a specified amino acid sequence that can be flanked by from at least one, and up to as many as about 60, additional heterologous nucleotides at each of the 5' and/or the 3' end of the nucleic acid sequence encoding the specified amino acid sequence. The heterologous nucleotides are not naturally found (i.e., not found in nature, in vivo) flanking the nucleic acid sequence encoding the specified amino acid sequence as it occurs in the natural gene or do not encode a protein that imparts any additional function to the protein or changes the function of the protein having the specified amino acid sequence.

According to the present invention, "heterologous amino acids" are a sequence of amino acids that are not naturally found (i.e., not found in nature, in vivo) flanking the specified amino acid sequence, or that are not related to the function of the specified amino acid sequence, or that would not be encoded by the nucleotides that flank the naturally occurring nucleic acid sequence encoding the specified amino acid sequence as it occurs in the gene, if such nucleotides in the naturally occurring sequence were translated using standard codon usage for the organism from which the given amino acid sequence is derived. Therefore, at least two amino acid residues that are heterologous to the influenza antigen are any two amino acid residues that are not naturally found flanking the influenza antigen.

According to the present invention, reference to a "heterologous" protein or "heterologous" antigen, including a heterologous fusion protein, in connection with a yeast vehicle of the invention means that the protein or antigen is not a protein or antigen that is naturally expressed by the yeast, although a fusion protein may include yeast sequences or proteins or portions thereof that are naturally expressed by yeast (e.g., an Aga protein as described herein). For example, a fusion protein of an influenza hemagglutinin protein and a yeast Aga protein is considered to be a heterologous protein with respect to the yeast vehicle for the purposes of the present invention, since such a fusion protein is not naturally expressed by a yeast.

According to the present invention, the phrase "selectively binds to" refers to the ability of an antibody, antigen-binding fragment or binding partner of the present invention to preferentially bind to specified proteins. More specifically, the phrase "selectively binds" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen-binding fragment thereof in the absence of the antigen is considered to be background. Binding can be measured using a variety of methods standard in the art including enzyme immunoassays (e.g., ELISA), immunoblot assays, etc.).

An "individual" is a vertebrate, preferably a mammal, more preferably a human. Mammals include, but are not limited to, farm animals, sport animals, pets, primates, mice and rats. The term "individual" can be used interchangeably with the term "animal", "subject" or "patient".

Reference to an isolated protein or polypeptide in the present invention includes full-length proteins, fusion proteins, or any fragment, domain, conformational epitope, or homologue of such proteins. More specifically, an isolated protein, according to the present invention, is a protein (including a polypeptide or peptide) that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. Preferably, an isolated protein of the present invention is produced recombinantly. According to the present invention, the terms "modification" and "mutation" can be used interchangeably, particularly with regard to the modifications/mutations to the amino acid sequence of proteins or portions thereof (or nucleic acid sequences) described herein.

As used herein, the term "homologue" is used to refer to a protein or peptide which differs from a naturally occurring protein or peptide (i.e., the "prototype" or "wild-type" protein) by minor modifications to the naturally occurring protein or peptide, but which maintains the basic protein and side chain structure of the naturally occurring form. Such changes include, but are not limited to: changes in one or a few amino acid side chains; changes one or a few amino acids, including deletions (e.g., a truncated version of the protein or peptide) insertions and/or substitutions; changes in stereochemistry of one or a few atoms; and/or minor derivatizations, including but not limited to: methylation, glycosylation, phosphorylation, acetylation, myristoylation, prenylation, palmitation, amidation and/or addition of glycosylphosphatidyl inositol. A homologue can have either enhanced, decreased, or substantially similar properties as compared to the naturally occurring protein or peptide. A homologue can include an agonist of a protein or an antagonist of a protein. Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

A homologue of a given protein may comprise, consist essentially of, or consist of, an amino acid sequence that is at least about 45%, or at least about 50%, or at least about 55%, or at least about 60%, or at least about 65%, or at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical (or any percent identity between 45% and 99%, in whole integer increments), to the amino acid sequence of the reference protein. In one embodiment, the homologue comprises, consists essentially of, or consists of, an amino acid sequence that is less than 100% identical, less than about 99% identical, less than about 98% identical, less than about 97% identical, less than about 96% identical, less than about 95% identical, and so on, in increments of 1%, to less than about 70% identical to the naturally occurring amino acid sequence of the reference protein.

As used herein, unless otherwise specified, reference to a percent (%) identity refers to an evaluation of homology which is performed using: (1) a BLAST 2.0 Basic BLAST homology search using blastp for amino acid searches and blastn for nucleic acid searches with standard default parameters, wherein the query sequence is filtered for low complexity regions by default (described in Altschul, S. F., Madden, T. L., Schäffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety); (2) a BLAST 2 alignment (using the parameters described below); (3) and/or PSI-BLAST with the standard default parameters (Position-Specific Iterated BLAST. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described in Tatusova and Madden, (1999), "Blast 2 sequences—a new tool for comparing protein and nucleotide sequences", *FEMS Microbiol Lett.* 174: 247-250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:

Reward for match=1

Penalty for mismatch=−2

Open gap (5) and extension gap (2) penalties gap x_dropoff (50) expect (10) word size (11) filter (on)

For blastp, using 0 BLOSUM62 matrix:

Open gap (11) and extension gap (1) penalties gap x_dropoff (50) expect (10) word size (3) filter (on).

An isolated nucleic acid molecule is a nucleic acid molecule that has been removed from its natural milieu (i.e., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome in which the nucleic acid molecule is found in nature. An isolated nucleic acid molecule can include a gene. An isolated nucleic acid molecule that includes a gene is not a fragment of a chromosome that includes such gene, but rather includes the coding region and regulatory regions associated with the gene, but no additional genes that are naturally found on the same chromosome. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences). Isolated nucleic acid molecule can include DNA, RNA (e.g., mRNA), or derivatives of either DNA or RNA (e.g., cDNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein or domain of a protein.

A recombinant nucleic acid molecule is a molecule that can include at least one of any nucleic acid sequence encoding any one or more proteins described herein operatively linked to at least one of any transcription control sequence capable of effectively regulating expression of the nucleic acid molecule(s) in the cell to be transfected. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. In addition, the phrase "recombinant molecule" primarily refers to a nucleic acid molecule operatively linked to a transcription control sequence, but can be used interchangeably with the phrase "nucleic acid molecule" which is administered to an animal.

A recombinant nucleic acid molecule includes a recombinant vector, which is any nucleic acid sequence, typically a heterologous sequence, which is operatively linked to the isolated nucleic acid molecule encoding a fusion protein of the present invention, which is capable of enabling recombinant production of the fusion protein, and which is capable of delivering the nucleic acid molecule into a host cell according to the present invention. Such a vector can contain nucleic acid sequences that are not naturally found adjacent to the isolated nucleic acid molecules to be inserted into the vector. The vector can be either RNA or DNA, either prokaryotic or eukaryotic, and preferably in the present invention, is a virus or a plasmid. Recombinant vectors can be used in the cloning, sequencing, and/or otherwise manipulating of nucleic acid molecules, and can be used in delivery of such molecules (e.g., as in a DNA vaccine or a viral vector-based vaccine).

Recombinant vectors are preferably used in the expression of nucleic acid molecules, and can also be referred to as expression vectors. Preferred recombinant vectors are capable of being expressed in a transfected host cell.

In a recombinant molecule of the present invention, nucleic acid molecules are operatively linked to expression vectors containing regulatory sequences such as transcription control sequences, translation control sequences, origins of replication, and other regulatory sequences that are compatible with the host cell and that control the expression of nucleic acid molecules of the present invention. In particular, recombinant molecules of the present invention include nucleic acid molecules that are operatively linked to one or more expression control sequences. The phrase "operatively linked" refers to linking a nucleic acid molecule to an expression control sequence in a manner such that the molecule is expressed when transfected (i.e., transformed, transduced or transfected) into a host cell.

According to the present invention, the term "transfection" is used to refer to any method by which an exogenous nucleic acid molecule (i.e., a recombinant nucleic acid molecule) can be inserted into a cell. The term "transformation" can be used interchangeably with the term "transfection" when such term is used to refer to the introduction of nucleic acid molecules into microbial cells, such as algae, bacteria and yeast. In microbial systems, the term "transformation" is used to describe an inherited change due to the acquisition of exogenous nucleic acids by the microorganism and is essentially synonymous with the term "transfection." Therefore, transfection techniques include, but are not limited to, transformation, chemical treatment of cells, particle bombardment, electroporation, microinjection, lipofection, adsorption, infection and protoplast fusion.

Vaccines and Compositions of the Invention

Embodiments of the present invention relate to a composition (vaccine) which can be used in a method to elicit a cell-mediated and/or a humoral immune response against an antigen or antigens, and in a preferred embodiment, to protect an animal from a disease or condition (including an infection by a pathogen) or to alleviate at least one symptom resulting from the disease or condition. The compositions generally include: (a) a yeast vehicle; and (b) a heterologous antigen expressed by, associated with, or combined with the yeast vehicle. Other compositions may include a yeast vehicle combined with a heterologous antigen provided in the form of another vaccine composition, such as a DNA vaccine, a protein subunit vaccine, or a killed or inactivated pathogen. When the yeast vehicle express one or more antigens, antigens are expressed or provided intracellularly, extracellularly, or both, in any combination. In certain embodiments, the antigens are provided as fusion proteins which are designed to stabilize the expression of the heterologous protein in the yeast vehicle, prevent posttranslational modification of the expressed heterologous protein, and/or can, in some embodiments, cause the fusion protein to be expressed on (including translocated to) the surface of the yeast vehicle (extracellular expression). The fusion proteins also provide a broad cell-mediated immune response and in some embodiments, a humoral immune response, and preferably express more than one different antigen, and/or are combined with other yeast vehicles expressing different antigen(s). These fusion proteins are most typically expressed as recombinant proteins by the yeast vehicle (e.g., by an intact yeast or yeast spheroplast, which can optionally be further processed to a yeast cytoplast, yeast ghost, or yeast membrane or cell wall extract or fraction or particle thereof), although it is an embodiment of the invention that one or much such fusion proteins could be loaded into a yeast vehicle (e.g., as proteins) or otherwise complexed or mixed with a yeast vehicle as described herein to form a vaccine of the present invention.

Yeast Vehicles

In any of the compositions (e.g., vaccines) of the present invention, the following aspects related to the yeast vehicle are included in the invention. According to the present invention, a yeast vehicle is any yeast cell (e.g., a whole or intact cell) or a derivative thereof (see below) that can be used in conjunction with one or more antigens in a vaccine or therapeutic composition of the invention, or as an adjuvant. The yeast vehicle can therefore include, but is not limited to, a live intact yeast microorganism (i.e., a yeast cell having all its components including a cell wall), a killed (dead) intact yeast microorganism, or derivatives thereof including: a yeast spheroplast (i.e., a yeast cell lacking a cell wall), a yeast cytoplast (i.e., a yeast cell lacking a cell wall and nucleus), a yeast ghost (i.e., a yeast cell lacking a cell wall, nucleus and cytoplasm), a subcellular yeast membrane extract or fraction thereof (also referred to as a yeast membrane particle and previously as a subcellular yeast particle), or a yeast cell wall preparation.

Yeast spheroplasts are typically produced by enzymatic digestion of the yeast cell wall. Such a method is described, for example, in Franzusoff et al., 1991, *Meth. Enzymol.* 194, 662-674., incorporated herein by reference in its entirety.

Yeast cytoplasts are typically produced by enucleation of yeast cells. Such a method is described, for example, in Coon, 1978, *Natl. Cancer Inst. Monogr.* 48, 45-55 incorporated herein by reference in its entirety.

Yeast ghosts are typically produced by resealing a permeabilized or lysed cell and can, but need not, contain at least some of the organelles of that cell. Such a method is described, for example, in Franzusoff et al., 1983, *J. Biol. Chem.* 258, 3608-3614 and Bussey et al., 1979, *Biochim. Biophys. Acta* 553, 185-196, each of which is incorporated herein by reference in its entirety.

A yeast membrane particle (subcellular yeast membrane extract or fraction thereof) refers to a yeast membrane that lacks a natural nucleus or cytoplasm. The particle can be of any size, including sizes ranging from the size of a natural yeast membrane to microparticles produced by sonication or other membrane disruption methods known to those skilled in the art, followed by resealing. A method for producing subcellular yeast membrane extracts is described, for example, in Franzusoff et al., 1991, *Meth. Enzymol.* 194, 662-674. One may also use fractions of yeast membrane particles that contain yeast membrane portions and, when the antigen was expressed recombinantly by the yeast prior to preparation of the yeast membrane particles, the antigen of interest. Antigens can be carried inside the membrane, on either surface of the membrane, or combinations thereof (i.e., the antigen can be both inside and outside the membrane and/or spanning the membrane of the yeast membrane particle). In one embodiment, a yeast membrane particle is a recombinant yeast membrane particle that can be an intact, disrupted, or disrupted and resealed yeast membrane that includes at least one desired antigen on the surface of the membrane or at least partially embedded within the membrane.

An example of a yeast cell wall preparation is isolated yeast cell walls carrying an antigen on its surface or at least partially embedded within the cell wall such that the yeast cell wall preparation, when administered to an animal, stimulates a desired (e.g., protective) immune response against the infectious agent.

Any yeast strain can be used to produce a yeast vehicle of the present invention. Yeast are unicellular microorganisms that belong to one of three classes: Ascomycetes, Basidiomycetes and Fungi Imperfecti. One major consideration for the selection of a type of yeast for use as an immune modulator is the pathogenicity of the yeast. In one embodiment, the yeast is a non-pathogenic strain such as *Saccharomyces cerevisiae*. The selection of a non-pathogenic yeast strain is done to minimize any adverse effects to the individual to whom the yeast vehicle is administered. However, pathogenic yeast may be used if the pathogenicity of the yeast can be negated by any means known to one of skill in the art (e.g., mutant strains). While pathogenic yeast strains, or nonpathogenic mutants thereof, have been used in the past as adjuvants or as biological response modifiers, and can be used in accordance with the present invention, nonpathogenic yeast strains are preferred.

Preferred genera of yeast strains include *Saccharomyces, Candida* (which can be pathogenic), *Cryptococcus, Hansenula, Kluyveromyces, Pichia, Rhodotorula, Schizosaccharomyces* and *Yarrowia*, with *Saccharomyces, Candida, Hansenula, Pichia* and *Schizosaccharomyces* being more preferred, and with *Saccharomyces* being particularly preferred. Preferred species of yeast strains include *Saccharomyces cerevisiae, Saccharomyces carlsbergensis, Candida albicans, Candida kefyr, Candida tropicalis, Cryptococcus laurentii, Cryptococcus neoformans, Hansenula anomala, Hansenula polymorpha, Kluyveromyces fragilis, Kluyveromyces lactis, Kluyveromyces marxianus* var. *lactis, Pichia pastoris, Rhodotorula rubra, Schizosaccharomyces pombe,* and *Yarrowia lipolytica*. It is to be appreciated that a number of these species include a variety of subspecies, types, subtypes, etc. that are meant to be included within the aforementioned species. More preferred yeast species include *S. cerevisiae, C. albicans, H. polymorpha, P. pastoris* and *S. pombe*. *S. cerevisiae* is particularly preferred due to it being relatively easy to manipulate and being "Generally Recognized As Safe" or "GRAS" for use as food additives (GRAS, FDA proposed Rule 62FR18938, Apr. 17, 1997). One embodiment of the present invention is a yeast strain that is capable of replicating plasmids to a particularly high copy number, such as a *S. cerevisiae* cir$^o$ strain. The *S. cerevisiae* strain is one such strain that is capable of supporting expression vectors that allow one or more target antigen(s) and/or antigen fusion protein(s) to be expressed at high levels. In addition, any mutant yeast strains can be used in the present invention, including those that exhibit reduced post-translational modifications of expressed target antigens, such as mutations in the enzymes that extend N-linked glycosylation.

In one embodiment, a preferred yeast vehicle of the present invention is capable of fusing with the cell type to which the yeast vehicle and antigen is being delivered, such as a dendritic cell or macrophage, thereby effecting particularly efficient delivery of the yeast vehicle, and in many embodiments, the antigen(s), to the cell type. As used herein, fusion of a yeast vehicle with a targeted cell type refers to the ability of the yeast cell membrane, or particle thereof, to fuse with the membrane of the targeted cell type (e.g., dendritic cell or macrophage), leading to syncytia formation. As used herein, a syncytium is a multinucleate mass of protoplasm produced by the merging of cells. A number of viral surface proteins (including those of immunodeficiency viruses such as HIV, influenza virus, poliovirus and adenovirus) and other fusogens (such as those involved in fusions between eggs and sperm) have been shown to be able to effect fusion between two membranes (i.e., between viral and mammalian cell membranes or between mammalian cell membranes). For example, a yeast vehicle that produces an HIV gp120/gp41 heterologous antigen on its surface is capable of fusing with a CD4+ T-lymphocyte. It is noted, however, that incorporation of a targeting moiety into the yeast vehicle, while it may be desirable under some circumstances, is not necessary. In the case of yeast vehicles that express the antigens extracellularly, this can be a further advantage of the yeast vehicles of the present invention. It has been previously shown that yeast vehicles of the present invention are readily taken up by dendritic cells (as well as other cells, such as macrophages).

Methods of producing yeast vehicles and expressing, combining or associating yeast vehicles with antigens are described below.

Antigens

The antigens contemplated for use in this invention include any antigen against which it is desired to elicit an immune response. For example, the antigens can include, but are not limited to, any antigens associated with a pathogen, including viral antigens, fungal antigens, bacterial antigens, helminth antigens, parasitic antigens, ectoparasite antigens, protozoan antigens, or antigens from any other infectious agent. Antigens can also include any antigens associated with a particular disease or condition, whether from pathogenic or cellular sources, including, but not limited to, cancer antigens, antigens associated with an autoimmune disease (e.g., diabetes antigens), allergy antigens (allergens), mammalian cell molecules harboring one or more mutated amino acids, proteins normally expressed pre- or neo-natally by mammalian cells, proteins whose expression is induced by insertion of an epidemiologic agent (e.g. virus), proteins whose expression is induced by gene translocation, and proteins whose expression is induced by mutation of regulatory sequences. These antigens can be native antigens or genetically engineered antigens which have been modified in some manner (e.g., sequence change or generation of a fusion protein). It will be appreciated that in some embodiments (i.e., when the antigen is expressed by the yeast vehicle from a recombinant nucleic acid molecule), the antigen can be a protein or any epitope of immunogenic domain thereof, a fusion protein, or a chimeric protein, rather than an entire cell or microorganism.

Other preferred antigens to include in compositions (vaccines) of the present invention include antigens that are capable of suppressing an undesired, or harmful, immune response, such as is caused, for example, by allergens, autoimmune antigens, inflammatory agents, antigens involved in GVHD, certain cancers, septic shock antigens, and antigens involved in transplantation rejection. Such compounds include, but are not limited to, antihistamines, cyclosporin, corticosteroids, FK506, peptides corresponding to T cell receptors involved in the production of a harmful immune response, Fas ligands (i.e., compounds that bind to the extracellular or the cytosolic domain of cellular Fas receptors, thereby inducing apoptosis), suitable MHC complexes presented in such a way as to effect tolerization or anergy, T cell receptors, and autoimmune antigens, preferably in combination with a biological response modifier capable of enhancing or suppressing cell-mediated and/or humoral immunity.

Tumor antigens (cancer antigens) useful in the present invention can include a tumor antigen such as a protein, glycoprotein or surface carbohydrates from a tumor cell, an epitope from a tumor antigen, an entire tumor cell, mixtures of tumor cells, and portions thereof (e.g., lysates).

In one aspect, the antigen is from virus, including, but not limited to, adenoviruses, arena viruses, bunyaviruses, coronaviruses, coxsackie viruses, cytomegaloviruses, Epstein- Barr viruses, flaviviruses, hepadnaviruses, hepatitis viruses, herpes viruses, influenza viruses, lentiviruses, measles viruses, mumps viruses, myxoviruses, oncogenic viruses, orthomyxoviruses, papilloma viruses, papovaviruses, parainfluenza viruses, paramyxoviruses, parvoviruses, picornaviruses, pox viruses, rabies viruses, respiratory syncytial viruses, reoviruses, rhabdoviruses, rubella viruses, togaviruses, and varicella viruses. Other viruses include T-lymphotrophic viruses, such as human T-cell lymphotrophic viruses (HTLVs, such as HTLV-I and HTLV-II), bovine leukemia viruses (BLVS) and feline leukemia viruses (FLVs). The lentiviruses would include, but are not limited to, human (HIV, including HIV-1 or HIV-2), simian (SIV), feline (FIV) and canine (CIV) immunodeficiency viruses.

In another aspect, the antigen is from an infectious agent from a genus selected from: *Aspergillus, Bordatella, Brugia, Candida, Chlamydia, Coccidia, Cryptococcus, Dirofilaria, Escherichia, Francisella, Gonococcus, Histoplasma, Leishmania, Mycobacterium, Mycoplasma, Paramecium, Pertussis, Plasmodium, Pneumococcus, Pneumocystis, Rickettsia, Salmonella, Shigella, Staphylococcus, Streptococcus, Toxoplasma, Vibriocholerae Yersinia*. In one aspect, the infectious agent is selected from *Plasmodium falciparum* or *Plasmodium vivax*.

In one aspect, the antigen is from a bacterium from a family selected from: Enterobacteriaceae, Micrococcaceae, Vibrionaceae, Pasteurellaceae, Mycoplasmataceae, and Rickettsiaceae. In one aspect, the bacterium is of a genus selected from: *Pseudomonas, Bordetella, Mycobacterium, Vibrio, Bacillus, Salmonella, Francisella, Staphylococcus, Streptococcus, Escherichia, Enterococcus, Pasteurella*, and *Yersinia*. In one aspect, the bacterium is from a species selected from: *Pseudomonas aeruginosa, Pseudomonas mallei, Pseudomonas pseudomallei, Bordetella pertussis, Mycobacterium tuberculosis, Mycobacterium leprae, Francisella tularensis, Vibrio cholerae, Bacillus anthracis, Salmonella enteric, Yersinia pestis, Escherichia coli* and *Bordetella bronchiseptica*.

According to the present invention, an antigen suitable for use in the present composition or vaccine can include two or more immunogenic domains or epitopes from the same antigen, two or more antigens immunogenic domains, or epitopes from the same cell, tissue or organism, or two or more different antigens, immunogenic domains, or epitopes from different cells, tissues or organisms.

As discussed above, the fusion proteins used in the vaccines and compositions of the invention include at least one influenza antigen for vaccinating an animal. The composition or vaccine can include, one, two, a few, several or a plurality of influenza antigens, including one or more immunogenic domains of one or more influenza antigens, as desired.

When antigens from pathogens are used, such as the influenza virus, one of skill in the art can maximize long term efficacy of the vaccine comprising the yeast vehicle expressing the pathogen antigens by selecting antigens from regions of the pathogen genome that are highly conserved over different strains of the pathogen. In addition, by selecting antigens from regions of the pathogen that are variable, such as antigens that differ from strain to strain or may be mutated each season or in a geographic region, for example, the ability of the vaccine to address specific epidemics is maximized. This aspect of the invention has been discussed in detail above.

In one aspect, the pathogen is an influenza virus. In this aspect, conserved or internally expressed antigens include: the matrix protein (M1), ion channel (M2) antigen, nucleocapsid (NP) antigen, polymerase PB1 (PB1) antigen, polymerase (PB2) antigen, and polymerase PA (PA) antigen. Variable or externally expressed antigens include hemagglutinin (HA) antigens (any one or more subtypes) and neuraminidase (NA) antigens (any one or more subtypes), as well as the extracellular portion of M2, called M2e. These antigens can be selected as described above for use in a novel vaccine strategy according to the invention.

In one aspect, the pathogen is a hepatitis virus, such as hepatitis virus C(HCV). In this aspect, conserved or internally expressed antigens include HCV Core protein, HCV NS2, NS3, NS4, NS5. Variable or externally expressed antigens include HCV E1 and E2 (envelope proteins). These antigens can be selected as described above for use in a novel vaccine strategy according to the invention.

In one aspect, the pathogen is a hepatitis virus, such as hepatitis virus B (HBV). In this aspect, conserved or internally expressed antigens include: core antigen HbcAg and e antigen HbeAg. Variable or externally expressed antigens include HbsAg (42 nM virion and 22 nM particle). These antigens can be selected as described above for use in a novel vaccine strategy according to the invention.

In one aspect, the pathogen is an immunodeficiency virus, such as human immunodeficiency virus (HIV). In this aspect, conserved or internally expressed antigens include: Vif, Vpr, Nef, p7, nucleocapsid. Variable or externally expressed antigens include gp120 and gp41. These antigens can be selected as described above for use in a novel vaccine strategy according to the invention.

In some embodiments, the antigen is a fusion protein. In one aspect of the invention, fusion protein can include two or more antigens. In one aspect, the fusion protein can include two or more immunogenic domains or two or more epitopes of one or more antigens (e.g., an influenza M1 sequence and an influenza HA sequence). Such a vaccine may provide antigen-specific immunization in a broad range of patients. For example, a multiple domain fusion protein useful in the present invention may have multiple domains, wherein each domain consists of a peptide from a particular protein, the peptide consisting of at least 4 amino acid residues flanking either side of and including a mutated amino acid that is found in the protein, wherein the mutation is associated with a particular disease or condition (e.g., influenza infection by a particular strain).

In one embodiment, fusion proteins that are used as a component of the yeast-based vaccine of the present invention are produced using constructs that are particularly useful for the expression of heterologous antigens in yeast. Typically, the desired antigenic protein(s) or peptide(s) are fused at their amino-terminal end to: (a) a specific synthetic peptide that stabilizes the expression of the fusion protein in the yeast vehicle or prevents posttranslational modification of the expressed fusion protein (such peptides are described in detail, for example, in U.S. Patent Publication No. 2004-0156858 A1, published Aug. 12, 2004, incorporated herein by reference in its entirety); (b) at least a portion of an endogenous yeast protein, wherein either fusion partner provides significantly enhanced stability of expression of the protein in the yeast and/or a prevents post-translational modification of the proteins by the yeast cells (such proteins are also described in detail, for example, in U.S. Patent Publication No. 2004-0156858 A1, supra); and/or (c) at least a portion of a yeast protein that causes the fusion protein to be expressed on the surface of the yeast (e.g., an Aga protein, described in more detail herein).

Also, the fusion peptides or proteins may provide an epitope that can be designed to be recognized by a selection agent, such as an antibody, and do not appear to negatively impact the immune response against the vaccinating antigen in the construct. Such agents are useful for the identification, selection and purification of proteins useful in the invention.

In addition, the present invention includes the use of peptides that are fused to the C-terminus of the antigen-encoding construct, particularly for use in the selection and identification of the protein. Such peptides include, but are not limited to, any synthetic or natural peptide, such as a peptide tag (e.g., 6×His) or any other short epitope tag. Peptides attached to the C-terminus of an antigen according to the invention can be used with or without the addition of the N-terminal peptides discussed above.

One fusion construct useful in the present invention is a fusion protein that includes: (a) at least one antigen (including immunogenic domains and epitopes of a full-length antigen, as well as various fusion proteins and multiple antigen constructs as described elsewhere herein); and (b) a synthetic peptide.

In one embodiment, the synthetic peptide is linked to the N-terminus of the influenza antigen, the peptide consisting of at least two amino acid residues that are heterologous to the influenza antigen, wherein the peptide stabilizes the expression of the fusion protein in the yeast vehicle or prevents posttranslational modification of the expressed fusion protein. The synthetic peptide and N-terminal portion of the antigen together form a fusion protein that has the following requirements: (1) the amino acid residue at position one of the fusion protein is a methionine (i.e., the first amino acid in the synthetic peptide is a methionine); (2) the amino acid residue at position two of the fusion protein is not a glycine or a proline (i.e., the second amino acid in the synthetic peptide is not a glycine or a proline); (3) none of the amino acid residues at positions 2-6 of the fusion protein is a methionine (i.e., the amino acids at positions 2-6, whether part of the synthetic peptide or the protein, if the synthetic peptide is shorter than 6 amino acids, do not include a methionine); and (4) none of the amino acids at positions 2-6 of the fusion protein is a lysine or an arginine (i.e., the amino acids at positions 2-6, whether part of the synthetic peptide or the protein, if the synthetic peptide is shorter than 5 amino acids, do not include a lysine or an arginine). The synthetic peptide can be as short as two amino acids, but is more preferably at least 2-6 amino acids (including 3, 4, 5 amino acids), and can be longer than 6 amino acids, in whole integers, up to about 200 amino acids, 300 amino acids, 400 amino acids, 500 amino acids, or more.

In one embodiment, a fusion protein comprises an amino acid sequence of $M-X_2-X_3-X_4-X_5-X_6$, wherein M is methionine; wherein $X_2$ is any amino acid except glycine, proline, lysine or arginine; wherein $X_3$ is any amino acid except methionine, lysine or arginine; wherein $X_4$ is any amino acid except methionine, lysine or arginine; wherein $X_5$ is any amino acid except methionine, lysine or arginine; and wherein $X_6$ is any amino acid except methionine, lysine or arginine. In one embodiment, the $X_6$ residue is a proline. An exemplary synthetic sequence that enhances the stability of expression of an influenza antigen in a yeast cell and/or prevents post-translational modification of the protein in the yeast includes the sequence M-A-D-E-A-P (SEQ ID NO:1). The MADEAP sequence can be used with other antigens in addition to the influenza antigen. In addition to the enhanced stability of the expression product, this fusion partner does not appear to negatively impact the immune response against the vaccinating antigen in the construct. In addition, the synthetic fusion peptides can be designed to provide an epitope that can be recognized by a selection agent, such as an antibody.

In another embodiment of the invention, the nucleic acids that encode the translation start site of a synthetic peptide used in the invention are A-C-C-A-T-G-G, in accordance with Kozak translation sequence rules, where the ATG in this sequence is the initial translation start site and encodes the methionine of M-A-D-E-A-P (SEQ ID NO:1). It is to be understood that various embodiments of the invention as described herein may also be combined. For example, in one aspect of the invention, when the synthetic peptide is MA-D-E-A-P (SEQ ID NO:1), the nucleic acids encoding the start site for this peptide can be A-C-C-A-T-G-G. Various other combinations of embodiments of the invention will be apparent to those of skill in the art.

In one aspect of the invention, the yeast vehicle is manipulated such that the antigen is expressed or provided by delivery or translocation of an expressed antigen product, partially or wholly, on the surface of the yeast vehicle (extracellular expression). One method for accomplishing this aspect of the invention is to use a spacer arm for positioning one or more antigen(s) on the surface of the yeast vehicle. One way to use a spacer arm is to create a fusion protein of the antigen(s) of interest with a protein that targets the antigen(s) of interest to the yeast cell wall. For example, one protein that can be used is a yeast protein (e.g., cell wall protein 2 (cwp2), Aga2, Pir4 or Flo1 protein) that enables the antigen(s) to be targeted to the yeast cell wall such that the antigen is located on the surface of the yeast. Proteins other than yeast proteins may be used for the spacer arm; however, for any spacer arm protein, it is most desirable to have the immunogenic response be directed against the target antigen rather than the spacer arm protein. As such, if other proteins are used for the spacer arm, then the spacer arm protein that is used should not generate such a large immune response to the spacer arm protein itself such that the immune response to the target antigen(s) is overwhelmed. One of skill in the art should aim for a small immune response to the spacer arm protein relative to the immune response for the target antigen(s). Any known method of determining the magnitude of immune responses can be used (e.g., antibody production, lytic assays, etc.) and are readily known to one of skill in the art.

Another method for positioning the target antigen(s) to be exposed on the yeast surface is to use signal sequences such as glycosylphosphatidyl inositol (GPI) to anchor the target to the yeast cell wall. Alternatively, positioning can be accomplished by appending signal sequences that target the antigen(s) of interest into the secretory pathway via translocation into the endoplasmic reticulum (ER) such that the antigen binds to a protein which is bound to the cell wall (e.g., cwp).

In one aspect, the spacer arm protein is a yeast protein. The yeast protein can consist of between about two and about 800 amino acids of a yeast protein. In one embodiment, the yeast protein is about 10 to 700 amino acids. In another embodiment, the yeast protein is about 40 to 600 amino acids. Other embodiments of the invention include the yeast protein being at least 250 amino acids, at least 300 amino acids, at least 350 amino acids, at least 400 amino acids, at least 450 amino acids, at least 500 amino acids, at least 550 amino acids, at least 600 amino acids, or at least 650 amino acids. In one embodiment, the yeast protein is at least 450 amino acids in length.

In another embodiment, the yeast protein stabilizes the expression of the fusion protein in the yeast vehicle, prevents posttranslational modification of the expressed fusion protein, and/or targets the fusion protein to a particular compartment in the yeast (e.g., to be expressed on the yeast cell surface). For delivery into the yeast secretory pathway, exemplary yeast proteins to use include, but are not limited to: Aga (including, but not limited to, Aga1 and/or Aga2); SUC2 (yeast invertase); alpha factor signal leader sequence; CPY; Cwp2p for its localization and retention in the cell wall; BUD genes for localization at the yeast cell bud during the initial phase of daughter cell formation; Flo1p; Pir2p; and Pir4p.

In another aspect of the invention, other sequences can be used to target, retain and/or stabilize the protein to other parts of the yeast vehicle, for example, in the cytosol or the mitochondria. Examples of suitable yeast protein that can be used for any of the embodiments above include, but are not limited to, SEC7; phosphoenolpyruvate carboxykinase PCK1, phosphoglycerokinase PGK and triose phosphate isomerase TPI gene products for their repressible expression in glucose and cytosolic localization; the heat shock proteins SSA1, SSA3, SSA4, SSC1, whose expression is induced and whose proteins are more thermostable upon exposure of cells to heat treatment; the mitochondrial protein CYC1 for import into mitochondria; ACT1.

For priming an effective humoral immune response, the target antigen should be expressed or provided in some part on the yeast surface (or secreted by the yeast). As shown in FIGS. 10A and 10B, FIG. 11, and FIG. 13B, and the Examples, multiple variations are possible for expressing or providing an antigen on the yeast cell surface. One of skill in the art will appreciate that other combinations of yeast proteins can be used to position one or more antigens of interest on the surface.

One of skill in the art can optimize the expression or provision of an antigen on the surface of a yeast vehicle in several ways. One such way is to monitor and/or control the antigen surface expression. One possible method to achieve this is to optimize expression levels of the antigen as to render maximal impact. With some antigens, too much expression of the antigen is toxic for the yeast or alternatively, for the immune cells and immune system of the individual. In other cases, too little surface expression can cause priming of the immune system to be suboptimal due to the lack of antigen interaction with the B cells. One of skill in the art can monitor the expression of the antigen by using well-known techniques, such a flow cytometry (e.g., FACS) and correlating the expression level with cell viability.

Another method of optimizing antigen surface expression or provision is to carefully select the spacer arms from the cell wall fusion partner. Although examples of yeast proteins that can be used as spacer arms are given infra and also shown in FIG. 10B, the size of the spacer arm(s) can affect how much of the antigen is exposed for binding on the surface of the yeast. Thus, depending on which antigen(s) are being used, one of skill in the art will select a spacer arm that effectuates appropriate spacing for the antigen on the yeast surface. In one embodiment, the spacer arm is a yeast protein of at least 450 amino acids.

Another consideration for optimizing antigen surface expression is whether the antigen and spacer arm combination should be expressed as a monomer (e.g., HA-cwp2 as shown in FIG. 11) or as dimer or as a trimer (e.g., trimeric HA-aga2p plus soluble secreted HA), or even more units connected together. This use of monomers, dimers, trimers, etc. allows for appropriate spacing or folding of the antigen such that some part, if not all, of the antigen is displayed on the surface of the yeast vehicle in a manner that makes it more immunogenic, if for example the multimeric form adopts a conformation required for eliciting a specific class of antibodies, e.g. neutralizing antibodies.

One of skill in the art can optimize the performance of the yeast vehicle (with and without heterologous antigen expression), both on the surface of the yeast vehicle and in the cytosol, by growing the yeast cells at a pH level which is higher than 5.5 (i.e., neutral pH). The use of neutral pH helps to optimize the antigen accessibility and surface presentation, allows the yeast cell wall to be in a more pliable state, and trigger the immune cells binding the yeast to generate an optimized immune response including secreting beneficial cytokines (e.g., INF-gamma) and optimized activation responses.

Another method that one of skill in the art can use to optimize yeast vehicles for priming for antibody responses is to control the amount of yeast glycosylation. The amount of yeast glycosylation can affects the immunogenicity and antigenicity of the antigen expressed on the surface, since sugar moieties tend to be bulky. As such, when practicing the invention, the existence of sugar moieties on the surface of yeast and its impact on the three-dimensional space around the target antigen(s) should be considered. Any method can be used to reduce the amount of glycosylation of the yeast. For example, one could use a yeast mutant strain that has been selected to have low glycosylation (e.g. mnn1, och1 and mnn9 mutants), or one could eliminate by mutation the glycosylation acceptor sequences on the target antigen. Alternatively, one could use a yeast with abbreviated glycosylation patterns, e.g. *Pichia*. An example of the effects of glycosylation on surface antigen is provided in Example 5.

Another consideration with respect to the provision of antigen on the surface of a yeast is how the yeast is inactivated and its potential effects on how this affects the antigenicity of the antigen expressed on the surface. Heat inactivation of yeast is a standard way of inactivating yeast, however, heat inactivation has the potential to alter the secondary, tertiary or quaternary structure of the target antigen. If heat inactivation is used, then one of skill in the art should take care to monitor the structural changes of the target antigen by standard methods known in the art. Alternatively, other methods of inactivating the yeast can be used, such as chemical, electrical, radioactive or UV methods. See, for example, the methodology disclosed in standard yeast culturing textbooks such as *Methods of Enzymology*, Vol. 194, Cold Spring Harbor Publishing (1990). Any of the optimization strategies used should take the secondary, tertiary or quaternary structure of the target antigen into consideration and preserve such structure as to optimize its immunogenicity.

Another specific aspect of the fusion protein constructs of the present invention that is similar to the embodiments above, and that can include the limitations of the embodiments above (although this is not required), includes a vaccine comprising a peptide linked to the C-terminus of the influenza antigen, the peptide consisting of at least two amino acid residues that are heterologous to the influenza antigen, wherein the peptide stabilizes the expression of the fusion protein in the yeast vehicle or prevents posttranslational modification of the expressed fusion protein. In one exemplary aspect of the invention, the peptide comprises an amino acid sequence of E-D (Glu-Asp). Such a sequence works to counteract hydrophobicity.

In one embodiment, a vaccine of the present invention can comprise a peptide linked to the C-terminus of the influenza antigen, wherein the peptide allows for recognition of the fusion protein by an antibody directed against the peptide. In one aspect, the peptide comprises an amino acid sequence of G-G-G-H-H-H-H-H-H (SEQ ID NO:2). This embodiment can be used alone or in conjunction with other aspects of the fusion proteins described above.

In one embodiment, the yeast protein/peptides, spacer arms, or the synthetic peptide used in fusion proteins herein comprise an antibody epitope for identification and purification of the fusion protein. Antibodies may already be available that selectively bind to an endogenous antigen or can be readily generated. Finally, if it is desired to direct a protein to a particular cellular location (e.g., into the secretory pathway, into mitochondria, into the nucleus), then the construct can use the endogenous signals for the yeast protein to be sure that the cellular machinery is optimized for that delivery system. Such signals have been described in some detail above. Preferably, an antibody is available or produced that selectively binds to the fusion partner.

Production of Yeast Vehicles, Tarmogens, and Compositions (Vaccines) of the Invention According to the present invention, the term "yeast vehicle-antigen complex" or "yeast-antigen complex" is used generically to describe any association of a yeast vehicle with an antigen. Such association includes expression of the antigen by the yeast (a recombinant yeast), introduction of an antigen into a yeast, physical attachment of the antigen to the yeast, and mixing of the yeast and antigen together, such as in a buffer or other solution or formulation. These types of complexes are described in detail below.

In one embodiment, a yeast cell used to prepare the yeast vehicle is transfected with a heterologous nucleic acid molecule encoding the antigen such that the antigen is expressed by the yeast cell. Such a yeast is also referred to herein as a recombinant yeast or a recombinant yeast vehicle. The yeast cell can then be loaded into the dendritic cell as an intact cell, or the yeast cell can be killed, or it can be derivatized such as by formation of yeast spheroplasts, cytoplasts, ghosts, or subcellular particles, any of which is followed by loading of the derivative into the dendritic cell. Yeast spheroplasts can also be directly transfected with a recombinant nucleic acid molecule (e.g., the spheroplast is produced from a whole yeast, and then transfected) in order to produce a recombinant spheroplast that expresses an antigen.

In one aspect, a yeast cell or yeast spheroplast used to prepare the yeast vehicle is transfected with a recombinant nucleic acid molecule encoding the antigen(s) such that the antigen is recombinantly expressed by the yeast cell or yeast spheroplast. In this aspect, the yeast cell or yeast spheroplast that recombinantly expresses the antigen(s) is used to produce a yeast vehicle comprising a yeast cytoplast, a yeast ghost, or a yeast membrane particle or yeast cell wall particle, or fraction thereof.

In general, the yeast vehicle and antigen(s) can be associated by any technique described herein. In one aspect, the yeast vehicle was loaded intracellularly with the antigen(s). In another aspect, the antigen(s) was covalently or non-covalently attached to the yeast vehicle. In yet another aspect, the yeast vehicle and the antigen(s) were associated by mixing. In another aspect, and in the preferred embodiment, the antigen(s) is expressed recombinantly by the yeast vehicle or by the yeast cell or yeast spheroplast from which the yeast vehicle was derived.

A preferred number of antigens to be produced by a yeast vehicle of the present invention is any number of antigens that can be reasonably produced by a yeast vehicle, and typically ranges from at least one to at least about 6 or more, with from about 2 to about 6 heterologous antigens being more preferred.

Expression of an antigen in a yeast vehicle of the present invention is accomplished using techniques known to those skilled in the art. Briefly, a nucleic acid molecule encoding at least one desired antigen is inserted into an expression vector in such a manner that the nucleic acid molecule is operatively linked to a transcription control sequence in order to be capable of effecting either constitutive or regulated expression of the nucleic acid molecule when transformed into a host yeast cell. Nucleic acid molecules encoding one or more antigens can be on one or more expression vectors operatively linked to one or more expression control sequences. Particularly important expression control sequences are those which control transcription initiation, such as promoter and upstream activation sequences. Any suitable yeast promoter can be used in the present invention and a variety of such promoters are known to those skilled in the art. Preferred promoters for expression in *Saccharomyces cerevisiae* include, but are not limited to, promoters of genes encoding the following yeast proteins: alcohol dehydrogenase I (ADH1) or II (ADH2), CUP1, phosphoglycerate kinase (PGK), triose phosphate isomerase (TPI), translational elongation factor EF-1 alpha (TEF2), glyceraldehyde-3-phosphate dehydrogenase (GAPDH; also referred to as TDH3, for triose phosphate dehydrogenase), galactokinase (GAL1), galactose-1-phosphate uridyl-transferase (GAL7), UDP-galactose epimerase (GAL10), cytochrome $c_1$ (CYC1), Sec7 protein (SEC7) and acid phosphatase (PHO5), with hybrid promoters such as ADH2/GAPDH and CYC1/GAL10 promoters being more preferred, and the ADH2/GAPDH promoter, which is induced when glucose concentrations in the cell are low (e.g., about 0.1 to about 0.2 percent), as well as the CUP1 promoter and the TEF2 promoter, being even more preferred. Likewise, a number of upstream activation sequences (UASs), also referred to as enhancers, are known. Preferred upstream activation sequences for expression in *Saccharomyces cerevisiae* include, but are not limited to, the UASs of genes encoding the following proteins: PCK1, TPI, TDH3, CYC1, ADH1, ADH2, SUC2, GAL1, GAL7 and GAL10, as well as other UASs activated by the GAL4 gene product, with the ADH2 UAS being particularly preferred. Since the ADH2 UAS is activated by the ADR1 gene product, it is preferable to overexpress the ADR1 gene when a heterologous gene is operatively linked to the ADH2 UAS. Preferred transcription termination sequences for expression in *Saccharomyces cerevisiae* include the termination sequences of the α-factor, GAPDH, and CYC1 genes.

Preferred transcription control sequences to express genes in methyltrophic yeast include the transcription control regions of the genes encoding alcohol oxidase and formate dehydrogenase.

Optimization concerns and methods for extracellular expression of antigens by yeast have been discussed in detail previously herein.

Transfection of a nucleic acid molecule into a yeast cell according to the present invention can be accomplished by any method by which a nucleic acid molecule administered into the cell and includes, but is not limited to, diffusion, active transport, bath sonication, electroporation, microinjection, lipofection, adsorption, and protoplast fusion. Transfected nucleic acid molecules can be integrated into a yeast chromosome or maintained on extrachromosomal vectors using techniques known to those skilled in the art. Examples of yeast vehicles carrying such nucleic acid molecules are disclosed in detail herein. As discussed above, yeast cytoplast, yeast ghost, and yeast membrane particles or cell wall preparations can also be produced recombinantly by transfecting intact yeast microorganisms or yeast spheroplasts with desired nucleic acid molecules, producing the antigen therein, and then further manipulating the microorganisms or spheroplasts using techniques known to those skilled in the art to produce cytoplast, ghost or subcellular yeast membrane extract or fractions thereof containing desired antigens.

Effective conditions for the production of recombinant yeast vehicles and expression of the antigen by the yeast vehicle include an effective medium in which a yeast strain can be cultured. An effective medium is typically an aqueous medium comprising assimilable carbohydrate, nitrogen and phosphate sources, as well as appropriate salts, minerals, metals and other nutrients, such as vitamins and growth factors. The medium may comprise complex nutrients or may be a defined minimal medium. Yeast strains of the present invention can be cultured in a variety of containers, including, but not limited to, bioreactors, Erlenmeyer flasks, test tubes, microtiter dishes, and petri plates. Culturing is carried out at a temperature, pH and oxygen content appropriate for the yeast strain. Such culturing conditions are well within the expertise of one of ordinary skill in the art (see, for example, Guthrie et al. (eds.), 1991, *Methods in Enzymology*, vol. 194, Academic Press, San Diego).

In some aspects of the invention, and particularly when it is desired to have sufficient surface expression or provision of an antigen in embodiments where induction of a humoral immune response is desired, the yeast are grown in a media maintained at a pH level of at least 5.5, namely the pH of the culture media is not allowed to drop below pH 5.5. In other aspects, the yeast is grown at a pH level maintained at about 5.5. In other aspects, the yeast is grown at a pH level maintained at about 5.6, 5.7, 5.8 or 5.9. In another aspect, the yeast is grown at a pH level maintained at about 6. In another aspect, the yeast is grown at a pH level maintained at about 6.5. In other aspects, the yeast is grown at a pH level maintained at about 6, 6.1, 6.2, 6.3, 6.4, 6.5, 6.6, 6.7, 6.8, 6.9 or 7.0. In other aspects, the yeast is grown at a pH level maintained at about 7, 7.1, 7.2, 7.3, 7.4, 7.5, 7.6, 7.7, 7.8, 7.9, or 8.0. The pH level is important in the culturing of yeast. One of skill in the art will appreciate that the culturing process includes not only the start of the yeast culture but the maintenance of the culture as well. As yeast culturing is known to turn acidic (i.e., lowering the pH) over time, care must be taken to monitor the pH level during the culturing process. Yeast cell cultures whereby the pH level of the medium drops below 6 are still contemplated within the scope of the invention provided that the pH of the media is brought up to at least 5.5 at some point during the culturing process. As such, the longer time the yeast are grown in a medium that is at least pH 5.5 or above, the better the results will be in terms of obtaining yeast with desirable characteristics.

The use of a neutral pH in culturing yeast promotes several biological effects that are desirable characteristics for using the yeast as vehicles for immunomodulation. In one aspect, culturing the yeast in neutral pH allows for good growth of the yeast without any negative effect on the cell generation time (e.g., slowing down the doubling time). The yeast can continue to grow to high densities without losing their cell wall pliability. In another aspect, the use of a neutral pH allows for the production of yeast with pliable cell walls and/or yeast that are sensitive to cell wall digesting enzymes (e.g., glucanase) at all harvest densities. This trait is desirable because yeast with flexible cell walls can exhibit unique immune responses, such as by promoting the secretion of cytokines (e.g., interferon-γ (IFN-γ)) in the cells hosting the yeast. In addition, greater accessibility to the antigens located in the cell wall is afforded by such culture methods. In another aspect, the use of neutral pH for some antigens, such as the influenza HA antigen, allows for release of the di-sulfide bonded HA by treatment with dithiothreitol (DTT) that is not possible when the HA-expressing yeast is cultured in media at lower pH (e.g., pH 5). Finally, in another aspect, cells that produce Th1-type cytokines, when exposed to (e.g., by phagocytosis or other loading) yeast cultured using the neutral pH methodologies, express increased production of such Th1-type cytokines including, but not limited to, IFN-γ, interleukin-12 (IL-12), and IL-2.

As used herein, the general use of the term "neutral pH" refers to a pH range between about pH 5.5 and about pH 8, preferably between about pH 6 and about 8. One of skill the art will appreciate that minor fluctuations (e.g., tenths or hundredths) can occur when measuring with a pH meter. As such, the use of neutral pH to grow yeast cells means that the yeast cells are grown in neutral pH for the majority of the time that they are in culture.

In one embodiment of the present invention, as an alternative to expression of an antigen recombinantly in the yeast vehicle, a yeast vehicle is loaded intracellularly with the protein or peptide antigen, or with carbohydrates or other molecules that serve as an antigen. Subsequently, the yeast vehicle, which now contains the antigen intracellularly, can be administered to the patient or loaded into a carrier such as a dendritic cell (described below). As used herein, a peptide comprises an amino acid sequence of less than or equal to about 30-50 amino acids, while a protein comprises an amino acid sequence of more than about 30-50 amino acids; proteins can be multimeric. A protein or peptide useful as an antigen can be as small as a T cell epitope (i.e., greater than 5 amino acids in length) and any suitable size greater than that which comprises multiple epitopes, protein fragments, full-length proteins, chimeric proteins or fusion proteins. Peptides and proteins can be derivatized either naturally or synthetically; such modifications can include, but are not limited to, glycosylation, phosphorylation, acetylation, myristylation, prenylation, palmitoylation, amidation and/or addition of glycerophosphatidyl inositol. Peptides and proteins can be inserted directly into yeast vehicles of the present invention by techniques known to those skilled in the art, such as by diffusion, active transport, liposome fusion, electroporation, phagocytosis, freeze-thaw cycles and bath sonication. Yeast vehicles that can be directly loaded with peptides, proteins, carbohydrates, or other molecules include intact yeast, as well as spheroplasts, ghosts or cytoplasts, which can be loaded with antigens after production, but before loading into dendritic cells. Alternatively, intact yeast can be loaded with the antigen, and then spheroplasts, ghosts, cytoplasts, or subcellular particles can be prepared therefrom. Any number of antigens can be loaded into a yeast vehicle in this embodiment, from at least 1, 2, 3, 4 or any whole integer up to hundreds or thousands of antigens, such as would be provided by the loading of a microorganism, by the loading of a mammalian tumor cell, or portions thereof, for example.

In another embodiment of the present invention, an antigen is physically attached to the yeast vehicle. Physical attachment of the antigen to the yeast vehicle can be accomplished by any method suitable in the art, including covalent and non-covalent association methods which include, but are not limited to, chemically crosslinking the antigen to the outer surface of the yeast vehicle or biologically linking the antigen to the outer surface of the yeast vehicle, such as by using an antibody or other binding partner. Chemical cross-linking can be achieved, for example, by methods including glutaraldehyde linkage, photoaffinity labeling, treatment with carbodiimides, treatment with chemicals capable of linking di-sulfide bonds, and treatment with other cross-linking chemicals standard in the art. Alternatively, a chemical can be contacted with the yeast vehicle that alters the charge of the lipid bilayer of yeast membrane or the composition of the cell wall so that the outer surface of the yeast is more likely to fuse or bind to antigens having particular charge characteristics. Targeting agents such as antibodies, binding peptides, soluble receptors, and other ligands may also be incorporated into an antigen as a fusion protein or otherwise associated with an antigen for binding of the antigen to the yeast vehicle.

In yet another embodiment, the yeast vehicle and the antigen are associated with each other by a more passive, non-specific or non-covalent binding mechanism, such as by gently mixing the yeast vehicle and the antigen together in a buffer or other suitable formulation (e.g., admixture).

In one embodiment of the invention, the yeast vehicle and the antigen are both loaded intracellularly into a carrier such as a dendritic cell or macrophage to form the therapeutic composition or vaccine of the present invention. Alternatively, an antigen of the invention (i.e., an influenza fusion protein of the invention) can be loaded into a dendritic cell in the absence of the yeast vehicle.

Various forms in which the loading of both components can be accomplished are discussed in detail below. As used herein, the term "loaded" and derivatives thereof refer to the insertion, introduction, or entry of a component (e.g., the yeast vehicle and/or antigen) into a cell (e.g., a dendritic cell). To load a component intracellularly refers to the insertion or introduction of the component to an intracellular compartment of the cell (e.g., through the plasma membrane and at a minimum, into the cytoplasm, a phagosome, a lysosome, or some intracellular space of the cell). To load a component into a cell references any technique by which the component is either forced to enter the cell (e.g., by electroporation) or is placed in an environment (e.g., in contact with or near to a cell) where the component will be substantially likely to enter the cell by some process (e.g., phagocytosis). Loading techniques include, but are not limited to: diffusion, active transport, liposome fusion, electroporation, phagocytosis, and bath sonication. In a preferred embodiment, passive mechanisms for loading a dendritic cell with the yeast vehicle and/or antigen are used, such passive mechanisms including phagocytosis of the yeast vehicle and/or antigen by a dendritic cell.

In one embodiment, intact yeast (with or without expression of heterologous antigens) can be ground up or processed in a manner to produce yeast cell wall preparations, yeast membrane particles or yeast fragments (i.e., not intact) and the yeast fragments can, in some embodiments, be provided with or administered with other compositions that include antigens (e.g., DNA vaccines, protein subunit vaccines, killed or inactivated pathogens) to enhance immune response. For example, enzymatic treatment, chemical treatment or physical force (e.g., mechanical shearing or sonication) can be used to break up the yeast into parts that are used as an adjuvant.

In one embodiment of the present invention, a composition or vaccine can also include biological response modifier compounds, or the ability to produce such modifiers (i.e., by transfection of the yeast vehicle with nucleic acid molecules encoding such modifiers), although such modifiers are not necessary to achieve a robust immune response according to the invention. For example, a yeast vehicle can be transfected with or loaded with at least one antigen and at least one biological response modifier compound, or a vaccine or composition of the invention can be administered in conjunction with at least one biological response modifier. Biological response modifiers include compounds that can modulate immune responses, which may be referred to as immunomodulatory compounds. Certain biological response modifiers can stimulate a protective immune response whereas others can suppress a harmful immune response. Certain biological response modifiers preferentially enhance a cell-mediated immune response whereas others preferentially enhance a humoral immune response (i.e., can stimulate an immune response in which there is an increased level of cell-mediated compared to humoral immunity, or vice versa.). There are a number of techniques known to those skilled in the art to measure stimulation or suppression of immune responses, as well as to differentiate cell-mediated immune responses from humoral immune responses.

Suitable biological response modifiers include cytokines, hormones, lipidic derivatives, small molecule drugs and other growth modulators, such as, but not limited to, interleukin 2 (IL-2), interleukin 4 (IL-4), interleukin 10 (IL-10), interleukin 12 (IL-12), interferon gamma (IFN-gamma) insulin-like growth factor I (IGF-I), transforming growth factor beta (TGF-β) steroids, prostaglandins and leukotrienes. The ability of a yeast vehicle to express (i.e., produce), and possibly secrete, IL-2, IL-12 and/or IFN-gamma preferentially enhances cell-mediated immunity, whereas the ability of a yeast vehicle to express, and possibly secrete, IL-4, IL-5 and/or IL-10 preferentially enhances humoral immunity. Other suitable biological response modifiers include, but are not limited to, anti-CTLA-4 antibody (e.g., to release anergic T cells); T cell co-stimulators (e.g., anti-CD137, anti-CD28, anti-CD40); alemtuzumab (e.g., CamPath®), denileukin diftitox (e.g., ONTAK®), anti-CD4, anti-CD25, anti-PD-1, anti-PD-L1, anti-PD-L2 or agents that block FOXP3 (e.g., to abrogate the activity/kill CD4+/CD25+T regulatory cells); Flt3 ligand, imiquimod (Aldara™), GM-CSF, sargramostim (Leukine®), Toll-like receptor (TLR)-7 agonists, or TLR-9 agonists (e.g., agents that increase the number of, or increase the activation state, of dendritic cells, macrophages and other professional antigen-presenting cells). Such biological response modifiers are well known in the art and are publicly available.

Compositions and therapeutic vaccines of the invention can further include any other compounds that are useful for protecting a subject from a particular disease or condition, I including an infection by a pathogen, or any compounds that treat or ameliorate any symptom of such an infection.

As used herein, a pharmaceutically acceptable carrier refers to any substance or vehicle suitable for delivering a yeast vaccine of the present invention to a suitable in vivo or ex vivo site. Such a carrier can include, but is not limited to, an adjuvant, an excipient, or any other type of delivery vehicle or carrier.

According to the present invention, adjuvants are typically substances that generally enhance the immune response of an animal to a specific antigen. Suitable adjuvants include, but are not limited to, Freund's adjuvant; other bacterial cell wall components; aluminum-based salts; calcium-based salts; silica; polynucleotides; toxoids; serum proteins; viral coat proteins; other bacterial-derived preparations; gamma interferon; block copolymer adjuvants, such as Hunter's Titermax adjuvant (CytRx™, Inc. Norcross, Ga.); Ribi adjuvants (available from Ribi ImmunoChem Research, Inc., Hamilton, Mont.); and saponins and their derivatives, such as Quil A (available from Superfos Biosector A/S, Denmark). Adjuvants are not required in the yeast vaccine of the present invention, but their use is not excluded.

Carriers are typically compounds that increase the half-life of a therapeutic composition in the treated animal. Suitable carriers include, but are not limited to, polymeric controlled release formulations, biodegradable implants, liposomes, oils, esters, and glycols.

Compositions and vaccines of the present invention can also contain one or more pharmaceutically acceptable excipients. As used herein, a pharmaceutically acceptable excipient refers to any substance suitable for delivering a composition useful in a method of the present invention to a suitable in vivo or ex vivo site. Preferred pharmaceutically acceptable excipients are capable of maintaining a composition (e.g., a yeast vehicle or dendritic cell comprising the yeast vehicle) in a form that, upon arrival of the composition at a target cell, tissue, or site in the body, the composition is capable of eliciting an immune response at the target site (noting that the target site can be systemic). Suitable excipients of the present invention include excipients or formularies that transport, but do not specifically target the vaccine to a site (also referred to herein as non-targeting carriers). Examples of pharmaceutically acceptable excipients include, but are not limited to water, saline, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity. Auxiliary substances can also include preservatives. Stabilizers, such as trehalose, glycine, sorbitol, lactose or monosodium glutamate (MSG), can be added to stabilize the vaccine formulation against a variety of conditions, such as temperature variations or a freeze-drying process. Compositions may also include a suspending fluid such as sterile water or saline (preferably buffered).

Yeast vehicles can be formulated into compositions of the present invention, including preparations to be administered to a patient directly or first loaded into a carrier such as a dendritic cell, using a number of techniques known to those skilled in the art. For example, yeast vehicles can be dried by lyophilization, which is one preferred embodiment. Prior to administration or loading into a dendritic cell, or other type of administration with an antigen, yeast vehicles can also be mixed with a pharmaceutically acceptable excipient. For example, formulations may be re-suspended or diluted in a suitable diluent such as sterile water, saline, isotonic buffered saline (e.g. phosphate buffered to physiological pH), or other suitable diluent. Lyophilization (freeze-drying) is a favored option. Formulations comprising yeast vehicles can also be prepared by packing yeast in a cake or a tablet, such as is done for yeast used in baking or brewing operations.

Kits of the Invention

The invention contemplates kits comprising any one or more of the vaccines of the invention, and/or any one or more of the Tarmogens or yeast vehicles of the invention, alone or in combination with antigens and antigen preparations described herein. Included in the kits of the invention are any combination of intracellular and extracellular antigens for use in any type of vaccine and particularly, in a yeast vehicle-based vaccine or vaccine strategy of the invention. For example, any of the fusion proteins described herein, or protein preparations that provide intracellular and extracellular antigens as described herein may be provided in the kit. The antigens can be provided in any form, including expressed by or otherwise provided with a yeast vehicle (as a Tarmogen), in a DNA vaccine, as a protein preparation, including a fusion protein preparation, or as a killed or inactivated pathogen. Any suitable form of antigens are encompassed. Also included are multiple antigen or antigen preparations, wherein each antigen is expressed by or otherwise provided (e.g., in complex with) a different yeast vehicle. For example, each yeast vehicle can express or otherwise provide a different antigen from a particular pathogen, so that one can select a preferred combination of antigens (e.g., conserved or internal and/or variable or external) and a preferred vaccine strategy (e.g., priming with conserved or internal antigens and boosting with variable or external antigens) for administration to an individual or population of individuals. In one aspect, this kit can additionally include antigen preparations to be used in a priming or boosting vaccine strategy, alone or in combination with a Tarmogen included in the kit (to be administered concurrently or sequentially, in prime/boost strategies, and the like, as described herein). Kits may also include yeast vehicles that do not express or provide antigens, for use as an adjuvant as described herein. A set of instructions for use can be included with any kit of the invention. Culture reagents for the yeast vehicles may also be included. The yeast cells can be frozen for starting a culture, or previously cultured to express antigens, and then frozen for packaging as part of the kit, or provided lyophilized.

Methods of the Invention

One embodiment of the present invention relates to a method to elicit an immune response, including a cell-mediated immune response, a humoral immune response, and/or combinations thereof. Another embodiment of the invention relates to a method to protect an animal against a condition or disease (including prevention and/or therapeutic treatment of the condition or disease), including an infection by a pathogen (e.g., an influenza virus infection) or a disease resulting therefrom. The method includes the step of administering to an animal that has or is at risk of developing the disease or condition (including pathogen infection), a vaccine or composition of the present invention as described herein, to reduce or prevent the disease or condition, including prevention of infection or reduction in at least one symptom resulting from the infection in the animal. The method of the present invention preferentially elicits an antigen-specific cell-mediated immune response against at least one antigen in an animal, at least in the first administration of a vaccine comprising the antigen to an individual. Detailed strategies for tailoring an immune response to a particular pathogen or disease, and the immune status of an individual to whom the vaccine is to be administered have been described above and are exemplified herein. One of skill in the art will readily be able to use different combinations of antigens, types of expression or provision of the antigens, and vaccine compositions, and vaccine protocols as described herein, to achieve the desired immune response.

In the above-embodiments, the vaccine or composition includes: (a) a first yeast vehicle; and (b) any one or more of the antigens described herein (expressed by, carried by complexed with, associated with, secreted by, and/or mixed with the yeast vehicle). The vaccine may include additional yeast vehicles that express, carry, secrete, or are mixed, associated or complexed with different antigens as described above. The preferred combinations of antigens to be expressed by, carried by, secreted by, or mixed, associated, or complexed with a yeast vehicle of the invention, and the preferred combinations of yeast vehicles to be combined or administered sequentially, have been described in detail above.

In one embodiment, the vaccine includes at least one antigen that is expressed or provided intracellularly by the yeast. In one embodiment, the vaccine includes at least one antigen that is expressed or provided intracellularly by the yeast and at least one antigen that is expressed or provided extracellularly by the yeast. In one aspect of this embodiment, the intracellular and the extracellular antigens are the same antigen, and in another aspect, they are different antigens. In one embodiment, antigens expressed or provided intracellularly by the yeast include at least one antigen that is a conserved antigen or that is expressed internally by a pathogen. In one embodiment, antigens expressed or provided extracellularly by the yeast include at least one antigen that is a variable antigen or that is expressed externally (on the surface) by a pathogen. In another embodiment, such variable or external antigens are also expressed or provided intracellularly by the yeast.

In one embodiment of the invention, the vaccine includes at least one antigen that is expressed or provided intracellularly by the yeast and at least one antigen that is expressed or provided extracellularly by the yeast, and the vaccine is used to prime the immune system against the antigen(s). By priming is meant that the vaccine is the first administration of the vaccine to an individual, such that the individual has not been previously immunized using the antigen or antigen combination. Thus, the immune system is "primed" to respond more rapidly and efficiently to subsequent encounters with the antigen (e.g., by boosting vaccines or by encounter with the natural antigen, for example, as a result of infection with the pathogen).

In one embodiment, the vaccine includes at least one antigen that is expressed or provided intracellularly by the yeast, or at least one antigen that is expressed or provided extracellularly by the yeast, or both an antigen(s) that is expressed or provided intracellularly by the yeast and an antigen(s) that is expressed or provided extracellularly by the yeast, and the vaccine is administered as a booster vaccine (i.e., subsequent to an initial priming immunization of first immunization with the antigen or antigens).

In one embodiment, the expression of a single antigen may be desirable in cases where the antigen is highly conserved and not likely to mutate. In other embodiments, expression or provision of multiple antigens is desirable for cross-protective responses of a broader scope than achievable by targeting a single antigen. Such cross-protective responses are useful for the generation of universal vaccines, which may be combined with antibody-generating vaccines, as discussed above, to provide a broad spectrum of protective immune responses. The targeting of universal antigens may be applied in a dose-sparing regimen because the mechanism of protection is different than that being elicited with antibody-generating vaccines.

In other embodiments, the booster vaccine is of a different type (e.g., a non-yeast based vaccine (e.g., protein subunit, DNA, killed/inactivated pathogen) or a yeast-based vaccine which uses a different type of yeast vehicle, such as yeast membrane or cell wall particles or yeast that are used as an adjuvant with protein, DNA or inactivated/killed pathogen vaccines. More particularly, in one embodiment of the present invention, the vaccine or composition of the invention as described herein can be administered in a protocol that includes the administration of one or more other vaccine or immunotherapy compositions, including any conventional, non-yeast-based vaccine or composition. For example, such other vaccines or immunotherapy compositions can include any other antigen-containing, antigen-encoding, or antigen-expressing composition, such as a DNA vaccine, killed or inactivated pathogen vaccine or a protein subunit vaccine (e.g., a purified antigen preparation). The yeast-based vaccine of the invention is preferably used to prime an antigen-specific immune response, including at least a strong cell-mediated, and in on embodiment, both a cell-mediated and a humoral immune response, and the non-yeast-based vaccine or alternate form of the yeast-based vaccine is preferably used to boost the immune response (cell-mediated and/or humoral). Alternatively, there may be instances when the yeast-based vaccine of the present invention is administered to boost the immune response of an individual to an antigen or antigens that have been administered previously in a non-based yeast vaccine.

In one aspect, yeast which do not express or otherwise contain or provide heterologous antigens can be used as an adjuvant in conjunction with one more antigen(s) of interest. In one embodiment, yeast which do not express or otherwise contain or provide heterologous antigen are used contemporaneously with non-yeast-based vaccines (e.g., DNA vaccines) to enhance the immune response of the DNA vaccine. In one alternative, yeast expressing or providing heterologous antigens (either on the surface or internally or both) are used in conjunction with other types of vaccines to enhance the immune response. In another alternative, yeast which do not express or otherwise contain or provide heterologous antigen are administered to an individual alone (i.e., exogenous antigen is not administered). In this aspect of the invention, the individual already carries the antigen in sufficient quantities to elicit an immune response upon administration of the non-antigen-carrying yeast vehicle, such as an individual that is currently infected with a pathogen, an individual who has experienced a mutation in a cellular protein or otherwise expresses or carries an antigen to which the immune system is not tolerant or against which tolerance can be broken.

It is not necessary for the heterologous antigens on the yeast vehicle to be identical to the antigen used in the non-yeast-based vaccine in order to elicit a protective immune response. The selection of antigens can be such that the two antigens share sequence similarity, have shared epitopes, or may be different antigens in a target pathogen. In one aspect, antigens are selected for the yeast-based and non-yeast-based vaccines to elicit supplementary or complementary immune responses. This is obviously preferable over a situation where the immune response to the heterologous antigen of the yeast vehicle is antagonistic to the immune response to the antigen in the non-yeast-based vaccine.

The method of use of the therapeutic composition or vaccine of the present invention preferably elicits an immune response in an animal such that the animal is protected from the disease or condition (including infection), or from symptoms resulting from the disease or condition (including infection). As used herein, the phrase "protected from a disease" refers to reducing the symptoms of the disease; reducing the occurrence of the disease, and/or reducing the severity of the disease. Protecting an animal can refer to the ability of a composition of the present invention, when administered to an animal, to prevent a disease from occurring and/or to cure or to alleviate disease symptoms, signs or causes. As such, to protect an animal from a disease includes both preventing disease occurrence (prophylactic treatment or prophylactic vaccine) and treating an animal that has a disease or that is experiencing initial symptoms of a disease (therapeutic treatment or a therapeutic vaccine). In particular, protecting an animal from a disease is accomplished by eliciting an immune response in the animal by inducing a beneficial or protective immune response which may, in some instances, additionally suppress (e.g., reduce, inhibit or block) an over-active or harmful immune response. The term, "disease" refers to any deviation from the normal health of an animal and includes a state when disease symptoms are present, as well as conditions in which a deviation (e.g., infection) has occurred, but symptoms are not yet manifested.

In one embodiment, any of the vaccines of the present invention is administered to an individual, or to a population of individuals, who have been infected with a pathogen, such as an influenza virus. In another embodiment, any of the vaccines of the present invention is administered to an individual, or to a population of individuals, who are at risk of being infected with such a pathogen. Such individuals can include populations identified as higher-risk for influenza infection than, for example, the normal or entire population of individuals. Such individuals can also include populations that are selected for a particular vaccine of the present invention due to expected pathogen strains (e.g., viral strains) in the geographical location of the population. Such populations can be defined by any suitable parameter. In another embodiment, any of the vaccines of the present invention is administered to any individual, or to any population of individuals, regardless of their known or predicted infection status or susceptibility to becoming infected with a particular pathogen.

More specifically, a vaccine as described herein, when administered to an animal by the method of the present invention, preferably produces a result which can include alleviation of the pathogen infection (e.g., reduction of at least one symptom or clinical manifestation of the infection), elimination of the infection or reduction in the time to eliminate the infection, prevention of the infection and/or symptoms related thereto, and stimulation of effector cell immunity against the infection, as well as humoral immunity. In addition, the vaccine preferably primes the immune system to prevent or reduce all infection by the pathogen, including all life cycle forms, strains, or mutants of the pathogen, whether free in the circulation or in the cells or tissues of an individual. The vaccine also preferably confers long-lasting immunity against the pathogen, or at least a universal or cross-protective immunity, so that future infections by new strains or mutants are more readily prevented and/or eliminated.

The present invention includes the delivery of a composition or vaccine of the invention to an animal. The administration process can be performed ex vivo or in vivo. Ex vivo administration refers to performing part of the regulatory step outside of the patient, such as administering a composition of the present invention to a population of cells (dendritic cells) removed from a patient under conditions such that a yeast vehicle and antigen are loaded into the cell, and returning the cells to the patient. The therapeutic composition of the present invention can be returned to a patient, or administered to a patient, by any suitable mode of administration.

Administration of a vaccine or composition, alone or in combination with a carrier according to the present invention, is typically systemic or mucosal. The preferred routes of administration will be apparent to those of skill in the art. Preferred methods of administration include, but are not limited to, intravenous administration, intraperitoneal administration, intramuscular administration, intranodal administration, intracoronary administration, intraarterial administration (e.g., into a carotid artery), subcutaneous administration, transdermal delivery, intratracheal administration, subcutaneous administration, intraarticular administration, intraventricular administration, inhalation (e.g., aerosol), intracranial, intraspinal, intraocular, aural, intranasal, oral, pulmonary administration, impregnation of a catheter, and direct injection into a tissue.

Particularly preferred routes of administration include: intravenous, intraperitoneal, subcutaneous, intradermal, intranodal, intramuscular, transdermal, inhaled, intranasal, oral, intraocular, intraarticular, intracranial, and intraspinal. Parenteral delivery can include intradermal, intramuscular, intraperitoneal, intrapleural, intrapulmonary, intravenous, subcutaneous, atrial catheter and venal catheter routes. Aural delivery can include ear drops, intranasal delivery can include nose drops or intranasal injection, and intraocular delivery can include eye drops. Aerosol (inhalation) delivery can also be performed using methods standard in the art (see, for example, Stribling et al., *Proc. Natl. Acad. Sci. USA* 189: 11277-11281, 1992, which is incorporated herein by reference in its entirety). For example, in one embodiment, a composition or vaccine of the invention can be formulated into a composition suitable for nebulized delivery using a suitable inhalation device or nebulizer. Oral delivery can include solids and liquids that can be taken through the mouth, and is useful in the development of mucosal immunity and since compositions comprising yeast vehicles can be easily prepared for oral delivery, for example, as tablets or capsules, as well as being formulated into food and beverage products.

Other routes of administration that modulate mucosal immunity are particularly useful in the treatment of viral infections and infections by other pathogens. Such routes include bronchial, intradermal, intramuscular, intranasal, other inhalatory, rectal, subcutaneous, topical, transdermal, vaginal and urethral routes.

In one embodiment of any of the above-identified methods, the vaccine is administered to the respiratory tract. In another embodiment, the vaccine is administered by a parenteral route of administration. In yet another embodiment, the vaccine further comprises dendritic cells or macrophages, wherein a yeast vehicle or vehicles (referring to the preferred combinations described above) expressing the fusion protein(s) is delivered to dendritic cells or macrophages ex vivo and wherein the dendritic cell or macrophage containing the yeast vehicle(s) expressing the antigen(s) is administered to the animal. In one aspect of this embodiment, the dendritic cell or the yeast vehicle has been additionally loaded with free antigen. In one aspect, a yeast-based vaccine is administered to the same location in an individual as another yeast-based vaccine or a non-yeast-based vaccine. In another aspect, a yeast-based vaccine is administered to a different location in an individual as another yeast-based vaccine or a non-yeast-based vaccine. In one aspect, the vaccine is administered as a therapeutic vaccine. In another aspect, the vaccine is administered as a prophylactic vaccine.

According to the present invention, an effective administration protocol (i.e., administering a vaccine or therapeutic composition in an effective manner) comprises suitable dose parameters and modes of administration that result in elicitation of an immune response in an animal that has a disease or condition, or that is at risk of contracting a disease or condition, preferably so that the animal is protected from the disease. Effective dose parameters can be determined using methods standard in the art for a particular disease. Such methods include, for example, determination of survival rates, side effects (i.e., toxicity) and progression or regression of disease.

In accordance with the present invention, a suitable single dose size is a dose that is capable of eliciting an antigen-specific immune response in an animal when administered one or more times over a suitable time period. Doses can vary depending upon the disease or condition being treated. For example, in one embodiment, a single dose of a yeast vehicle of the present invention is from about $1 \times 10^5$ to about $5 \times 10^7$ yeast cell equivalents per kilogram body weight of the organism being administered the composition. In a preferred embodiment, the yeast cells per dose are not adjusted for weight of the organism. In this embodiment, a single dose of a yeast vehicle of the present invention is from about $1 \times 10^4$ to about $1 \times 10^9$ yeast cells per dose. The amount of yeast vehicle that is used in a single dose can be between about 0.0001 yeast units (YU) to about 10,000 YU (1 YU=$10^7$ yeast). In one embodiment, the amount of yeast vehicle used is about 0.001 YU to about 1000 YU. In other embodiments, the amount of yeast vehicle used is about 0.01 YU to about 100 YU. In other embodiments, the amount of yeast vehicle used is about 0.1

YU to about 10 YU. In one embodiment, a single dose of a yeast vehicle of the present invention is from about 0.1 YU ($1\times10^6$ cells) to about 100 YU ($1\times10^9$ cells) per dose (i.e., per organism), including any interim dose, in increments of $0.1\times10^6$ cells (i.e., $1.1\times10^6$, $1.2\times10^6$, $1.3\times10^6$ . . . ). This range of doses can be effectively used in any organism of any size, including mice, monkeys, humans, etc.

When the vaccine is administered by loading the yeast vehicle and antigen into dendritic cells, a preferred single dose of a vaccine of the present invention is from about $0.5\times10^6$ to about $40\times10^6$ dendritic cells per individual per administration. Preferably, a single dose is from about $1\times10^6$ to about $20\times10^6$ dendritic cells per individual, and more preferably from about $1\times10^6$ to about $10\times10^6$ dendritic cells per individual.

"Boosters" or "boosts" of a therapeutic composition are preferably administered when the immune response against the antigen has waned or as needed to provide an immune response or induce a memory response against a particular antigen or antigen(s). Boosters can be administered from about 2 weeks to several years after the original administration. In one embodiment, an administration schedule is one in which from about $1\times10^5$ to about $5\times10^7$ yeast cell equivalents of a composition per kg body weight of the organism is administered from about one to about 4 times over a time period of from about 1 month to about 6 months.

In one embodiment of the present invention, a first vaccine, comprising a dose of yeast vehicle or vehicles and one or more antigens as described in detail above, and in one aspect, preferably comprising a dose of yeast vehicle or vehicles and one or more intracellular antigens, alone or in combination with one or more extracellular antigens, is administered to an individual or population of individuals. In the case of influenza, the vaccine preferably comprises at least one or more internal influenza antigens. This vaccine can be administered on any suitable periodic basis to the individual(s) as needed to maintain or elicit cell-mediated immunity against the antigens and, when an antigen is extracellular, to maintain or elicit humoral immunity against the antigens. In the case of a pathogen, such as influenza, the vaccine preferably maintains or elicits at least cell-mediated immunity against one or more influenza viral strains. For example, the vaccine can be administered with boosters, or on an annual or biannual basis, every several years, or as otherwise needed. As discussed above, this embodiment of the invention can be used as a universal, cross-protective vaccine, and may provide longer lasting immunity against various types of pathogen infections than conventional vaccines.

In a further embodiment, a second vaccine, comprising a dose of yeast vehicle or vehicles and one or more antigens (the same or different than is included in the first vaccine above), and preferably comprising a dose of yeast vehicle or vehicles and one or more extracellular antigens alone or together with one or more intracellular antigens, is administered to the same individual or population of individuals as received the first vaccine above. This second vaccine can be administered together with the first vaccine (e.g., as a single vaccine comprising a combination of different yeast vehicles) or separately from the first vaccine. In the latter scenario, the second vaccine can be administered sequentially with, but contemporaneously with, the first vaccine (e.g., where administration separated by seconds, minutes, or hours) or on a different schedule than the first vaccine, in order to manipulate the immune response elicited by the various vaccines. For example, the first vaccine could be administered once a year or in longer increments, if possible, with the goal of eliciting a universal, cross-protective cell-mediated immune response and if applicable based on the vaccine design, a humoral immune response. The second vaccine could also be administered once a year or as needed (i.e., on a one time basis, more than once per year, or as relevant to an immunization strategy) to timely immunize a population against the most prevalent pathogen strain(s) in the population at that time, or as needed to control or prevent an epidemic or a pandemic of infection by the pathogen. This strategy as it applies to influenza vaccines is described in particular detail herein, but the invention is not limited to influenza vaccines. As discussed above, the vaccine strategy of the present invention can be designed to provide both cross-protective and pathogen strain/mutant-specific immunity, including both cell-mediated and humoral immunity, which is believed to provide a more flexible and efficacious immunization against pathogens than has been previously described. This strategy is readily adapted to cellular antigens, such as antigens expressed by tumor cells, for example.

In the method of the present invention, vaccines and therapeutic compositions can be administered to animal (subject, individual, patient), including any vertebrate, and particularly to any member of the Vertebrate class, Mammalia, including, without limitation, primates, rodents, livestock and domestic pets. Livestock include mammals to be consumed or that produce useful products (e.g., sheep for wool production). Preferred mammals to protect include humans, dogs, cats, mice, rats, goats, sheep, cattle, horses and pigs, with humans being particularly preferred.

First and Second Medical Uses

The invention also contemplates the use of any of the yeast vehicles expressing or providing extracellular and/or intracellular antigen(s) (Tarmogens), combinations of extracellular and intracellular antigens, fusion proteins, yeast vehicles as adjuvants, and/or antigen preparations described herein, and/or any combinations thereof for the preparation of a formulation or medicament for any use, and particularly, for the treatment or prevention of a disease or condition, including infection by a pathogen, cancer, autoimmune disease, etc. The formulations or medicaments may be formulated for any type of administration, including combinations of routes of administration (e.g., intranasal and/or parenteral). The formulations or medicaments may be prepared for any type of administration protocol as described herein. In one aspect, the formulations or medicaments are for eliciting an antigen-specific immune response (cell-mediated and/or humoral), for protecting an animal against influenza infection, for treating or preventing a disease or condition, for immunizing a population of individuals at risk for becoming infected with a pathogen, such as influenza virus, for treating a population of individuals that are infected with a pathogen, such as influenza virus, or for protecting an animal against pathogen infection, including influenza virus.

Influenza Compositions and Vaccines

Various aspects of the invention as directed to any antigen and described above will be illustrated and exemplified by a detailed discussion of the application of the concepts and embodiments of the invention to the influenza virus and composition and methods for eliciting an immune response against influenza virus. The invention is not limited to influenza virus as an antigen or source of antigens.

The present inventors have developed yeast-based vaccines and methods of use thereof that comprises yeast vehicles and one or more influenza virus fusion proteins. Such yeast vehicles that express or are otherwise complexed with one or more influenza antigens can be used alone or combined with one or more additional yeast vehicles that express or are otherwise complexed with one or more additional influenza virus fusion proteins, or the yeast vehicle can be combined with other forms of influenza antigen, including any non-yeast-based vaccine (e.g., DNA vaccine, protein subunit vaccine, or killed or inactivated influenza virus).

In one embodiment, the vaccine includes a yeast vehicle that expresses or provides one or more internal influenza antigens selected from the matrix protein (M1), ion channel (M2) antigen, nucleocapsid (NP) antigen, polymerase PB1 (PB1) antigen, polymerase (PB2) antigen, and polymerase PA (PA) antigen. In another embodiment, the vaccine includes a yeast vehicle that expresses one or more external influenza antigens selected from hemagglutinin (HA) antigens (any one or more subtypes) and neuraminidase (NA) antigens (any one or more subtypes). The internal antigens are typically expressed intracellularly by the yeast. The external influenza antigens are typically expressed or provided on the surface of the yeast (extracellular antigens) and may also be expressed or provided intracellularly by the yeast. In some embodiments, both types of provision of the antigen(s) (intracellular and extracellular) are preferred. In a particularly preferred embodiment, the external influenza protein(s) are selected to represent the types or groups of viruses most prominently circulating among a species of animal (e.g., humans) in a given period of time (e.g., in a year), or are selected to respond to a potential, suspected, or anticipated influenza outbreak of a particular type, including an influenza epidemic or pandemic.

Further and particularly preferred embodiments of the invention relate to vaccines that take advantage of the combination of the use of both external and internal influenza antigens. In this embodiment, the vaccine includes a yeast vehicle that expresses or provides at least one internal influenza antigen selected from the matrix protein (M1), ion channel (M2), nucleocapsid (NP) antigen, polymerase PB1 (PB1) antigen, polymerase (PB2) antigen, and polymerase PA (PA) antigen. The use of combinations of these proteins is also encompassed by the present invention. The internal influenza antigen is preferably expressed intracellularly by the yeast, although the antigen may also be provided extracellularly. The vaccine also includes expression or provision by a yeast vehicle of at least one external influenza antigen selected from hemagglutinin (HA) antigens (any one or more subtypes) and neuraminidase (NA) antigens (any one or more subtypes). The external influenza antigens are expressed or provided on the surface of the yeast (extracellular) and may also be expressed or provided intracellularly by the yeast. In some embodiments, both types of expression or antigen provision are preferred for the external influenza antigens.

The nucleic acid and amino acid sequences for proteins from various strains of influenza virus are known. For example, sequences for H1N1 of influenza virus strain A/PR/8/34 are published under NCBI Database Accession Nos. M38279 (nucleotide sequence represented herein as SEQ ID NO: 29, which encodes SEQ ID NO:30) and NC_002019 (nucleotide sequence represented herein as SEQ ID NO:31 which encodes SEQ ID NO:32). Sequences for avian influenza strain A/Vietnam/1203/04, for example, are also known. For example, the nucleotide encoding H5N1 from A/Vietnam/1203/04 (e.g., NCBI Database Accession No. AY818135) is represented herein as SEQ ID NO:33, which encodes SEQ ID NO:34. It will be understood that although particular sequences described herein are derived from the known or reported sequences for these strains, one of skill in the art can readily choose a different strain or reported sequence for the same strain and use it in the present invention in the same manner as described for the disclosed sequences.

One can readily align sequences using any of a variety of sequence software programs and identify corresponding sequences for the proteins described herein in other strains or reported viral sequences. It is further noted that nucleotide and amino acid sequences may differ slightly among various strains or reports of sequences in the public databases. Such minor differences are not expected to significantly impact the ability to elicit an immune response according to the invention. The invention is not limited to the sequences described herein. In this embodiment, the yeast vehicle that expresses or provides the external influenza antigen(s) can be the same or a different yeast vehicle than the yeast vehicle that expresses or provides the internal influenza antigen(s). In addition, different combinations of internal influenza antigens and/or external influenza antigens can be expressed or provided on different yeast vehicles, and the vehicles can be used separately or together, depending on the vaccination that is desired. In general, when the influenza antigens are provided by two or more different yeast vehicles (i.e., as opposed to providing all influenza antigens in one yeast vehicle), the yeast vehicles can be combined (mixed) for administration as a single vaccine (e.g., a single injection or other type of dosage) or the different yeast vehicles can be administered sequentially. The sequential administration can be separated by any suitable period of time, including small increments of time (seconds or minutes) and longer increments of time (days, weeks, months, or even years). The invention contemplates that in these embodiments, any combination of influenza proteins that includes at least one internal influenza protein and at least one external influenza protein can be used, and these proteins can be provided using any combination of yeast vehicles (including a single yeast vehicle) that express or are otherwise complexed with such proteins.

There is great flexibility in how the vaccine of the present invention is designed and used. For example, a "universal" vaccine comprising a yeast vehicle that provides internal influenza antigens can be administered to an individual on a periodic basis, in order to develop a cross-protective immunity in an individual that is cell-mediated. This vaccine can then be combined, for example, on a one-time or periodic basis with additional yeast vehicles providing external influenza antigens. The yeast vehicles providing external influenza antigens can be rotated, alternated or selected annually or on any other preferred basis (e.g., emergency or anticipated epidemic or pandemic, or as otherwise needed) to target virus strains of interest and/or the most prevalent viral strain(s) during a given period of time or for a particular geographic region. Other embodiments of the invention will be apparent in view of the disclosure provided herein.

In yet another embodiment of the invention, a yeast vehicle expressing or providing one or more internal antigens (alone or in combination with one or more external antigens) can be administered as a priming vaccine, to be followed by boosters of additional yeast-based vaccines or by boosters of other internal and/or external antigen preparations, including, but not limited to, partially purified or purified influenza protein preparations, lysates of yeast vehicles that express the influenza proteins, DNA influenza vaccines, killed (or inactivated) virus, or combinations of yeast vehicles (providing or not providing heterologous antigens) and non-yeast-based vaccines. It is noted that because the yeast-based vaccines of the present invention are extremely efficacious at eliciting an immune response, booster vaccines are not likely to be needed, although they are included in one embodiment of the present invention.

The influenza M1, M2 and NP proteins are internal proteins expressed by influenza and exhibit a high degree of sequence conservation among influenza virus strains, making them excellent targets for immunotherapy. Administration of the vaccine of the present invention augments the influenza-specific CD4+ and CD8+ T cell response, and is expected to result in a reduction of viral load, and ultimately enhance viral clearance in influenza-infected individuals. When combined with the external influenza antigens (e.g., HA, M2e (the external peptide of the M2 protein) and/or NA antigens) in the yeast-based format, the vaccine further augments influenza-specific cell-mediated and humoral immunity to provide a vaccination platform that includes a cross-protective vaccination approach (via the internal antigens), with potential long-lasting effects, as well as a strain-specific approach (via the external antigens), which can be tailored to address current vaccine needs. Moreover, the vaccine of the present invention is not egg-based, allowing the vaccine to be used in a broader range of recipients than conventional influenza vaccine. The vaccine is also expected to be more efficiently and quickly produced as compared to current influenza vaccines. Finally, as discussed above, the flexibility in vaccine design that is provided by the present invention, in terms of the ability to establish universal immunity while also targeting virus subtypes according to need, is a significant improvement over conventional influenza vaccines.

One embodiment of the present invention relates to a composition (vaccine) which can be used in a method to protect an animal against influenza infection or to alleviate at least one symptom resulting from the influenza infection. The vaccine comprises: (a) a yeast vehicle; and (b) a heterologous influenza fusion protein expressed or provided by the yeast vehicle. As discussed above, the invention includes several different influenza fusion proteins for use as antigens in the vaccines of the invention. These fusion proteins are designed to stabilize the expression of the heterologous protein in the yeast vehicle, prevent posttranslational modification of the expressed heterologous protein, and/or can, in some embodiments, cause the fusion protein to be expressed on the surface of the yeast vehicle. The fusion proteins also provide a broad cell-mediated immune response and in some embodiments, a humoral immune response, and preferably express or provide more than one different influenza antigen, and/or are combined with other yeast vehicles expressing or providing different influenza antigen(s). Preferably, the combination of antigens includes at least one internal influenza antigen and at least one external influenza antigen. These fusion proteins are most typically expressed or provided as recombinant proteins by the yeast vehicle (e.g., by an intact yeast or yeast spheroplast, which can optionally be further processed to a yeast cytoplast, yeast ghost, or yeast membrane extract or fraction thereof), although it is an embodiment of the invention that one or much such fusion proteins could be loaded into a yeast vehicle (e.g., as proteins) or otherwise complexed or mixed with a yeast vehicle as described herein to form a vaccine of the present invention.

As discussed above, the fusion proteins used in the vaccines and compositions of the invention include at least one influenza antigen for vaccinating an animal. The composition or vaccine can include, one, two, a few, several or a plurality of influenza antigens, including one or more immunogenic domains of one or more influenza antigens, as desired. For example, any fusion protein described herein can include at least a portion of any one or more internal influenza proteins selected from: influenza matrix protein (M1), influenza ion channel protein (M2), or influenza nucleocapsid protein (NP), polymerase PB1 (PB1) antigen, polymerase (PB2) antigen, and polymerase PA (PA) antigen and/or one or more external influenza proteins selected from: influenza hemagglutinin (HA) or influenza neuraminidase (NA).

According to the present invention, the phrase "internal influenza protein" refers to a protein expressed by an influenza virus (any type or strain) that is entirely, or mostly, contained inside the virus particle in the core of the virus or the matrix protein membrane. Such proteins are typically highly conserved among viral types and strains, and may be abundantly produced by the virus. An "external influenza protein" as described herein refers to a protein expressed by an influenza virus (any type or strain) that extends through the lipid membrane and is mostly expressed on the surface of the virus particle (e.g., is a viral surface protein). Such proteins can be recognized by antibodies and are therefore useful for eliciting a humoral immune response against a virus. It is noted that the influenza ion channel protein (M2), while primarily being contained within the influenza virus, does have a small extracellular domain (known in the art as M2e) that is expressed on the surface of the influenza virus. Therefore, for the purposes of this invention, the M2 protein, although it is generally considered to be an internal influenza protein, to the extent that it is capable of being recognized by an antibody when expressed by an influenza virus or by a cell that expresses or displays at least the extracellular domain on its surface, can also be considered to be an external influenza protein.

In one embodiment of the invention, the influenza antigen portion of the vaccine is produced as a fusion protein comprising two or more antigens. In one aspect, the fusion protein can include two or more immunogenic domains or two or more epitopes of one or more antigens (e.g., an influenza M1 sequence and an influenza HA sequence). Such a vaccine may provide antigen-specific immunization in a broad range of patients. For example, a multiple domain fusion protein useful in the present invention may have multiple domains, wherein each domain consists of a peptide from a particular protein, the peptide consisting of at least 4 amino acid residues flanking either side of and including a mutated amino acid that is found in the protein, wherein the mutation is associated with a particular disease or condition (e.g., influenza infection by a particular strain).

The nucleic acid and amino acid sequence for influenza genes and the polyproteins encoded thereby from a variety of influenza types, subtypes, and strains are known in the art. Therefore, using the guidance provided herein and the reference to particular exemplary influenza antigens, one of skill in the art will readily be able to produce and use a variety of influenza-based fusion proteins from any influenza strain in the compositions and vaccines of the present invention.

In the present invention, the present inventors have generated novel recombinant yeast immunotherapeutics for use in the prevention or inhibition of influenza virus infection. One of the yeast immunotherapeutics expresses the influenza matrix protein (M1) as a fusion protein under the control of an inducible promoter. Immunoblot analysis of yeast vaccine cell lysates using antibodies against a histidine tag showed that recombinant yeast expressed the protein. Injection of the M1-expressing yeast vaccine in BALB/c mice resulted in induction of potent M1 antigen-specific helper and cytotoxic T cell immune responses as shown by lymphocyte proliferation and cytotoxicity assays. Another yeast immunotherapeutic expresses the hemagglutinin antigen (HA) protein intracellularly and another yeast immunotherapeutic provide the hemagglutinin antigen (HA) protein extracellularly. Some immunotherapeutics provide antigens under control of constitutive promoters. Other yeast vaccines encompassed by the present invention will be discussed in detail below.

Figure 1:
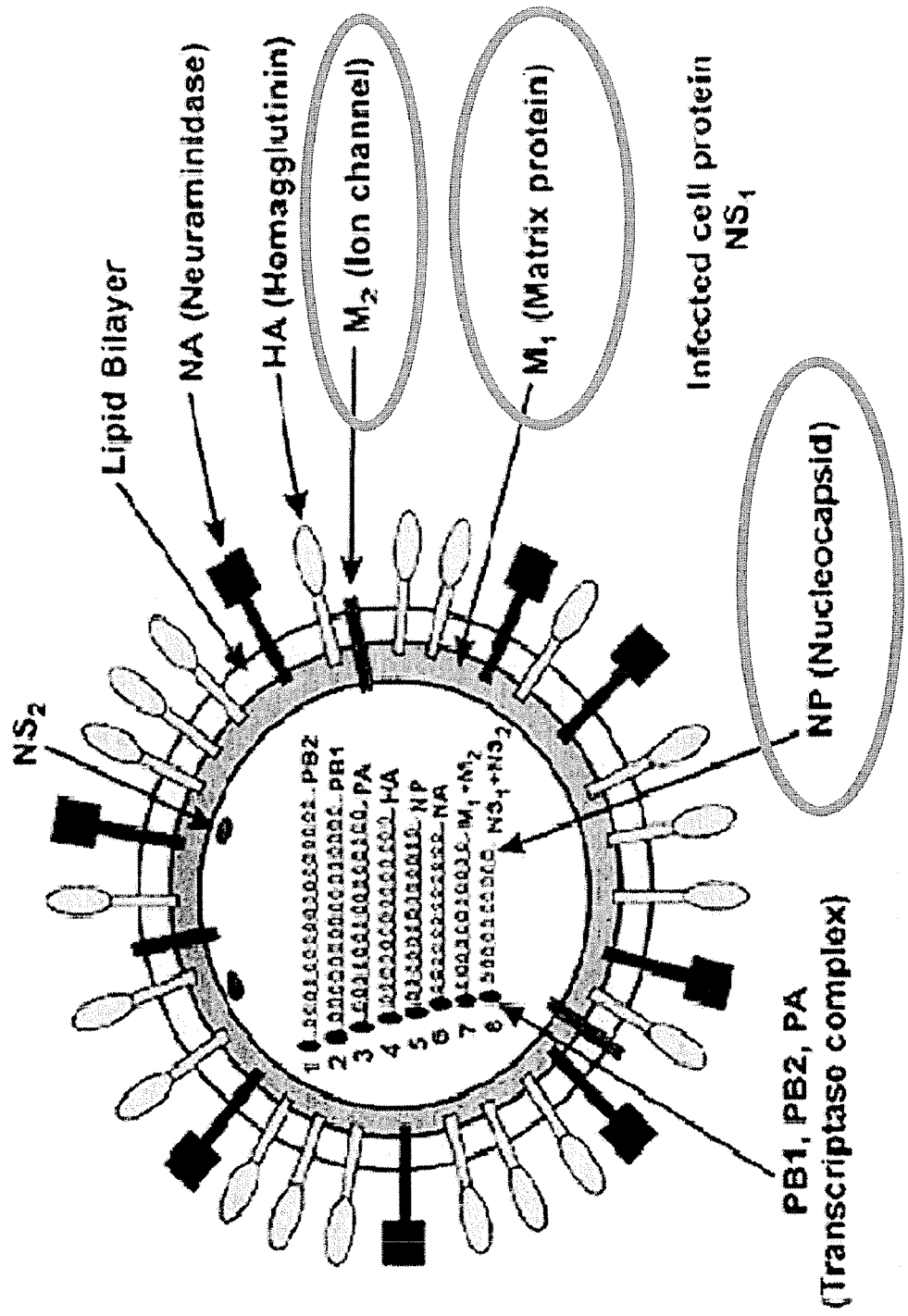
FIG. 1 is a schematic drawing illustrating an influenza virus and several of its components. Some of the more highly conserved antigens are circled.

In one aspect of the invention, the influenza antigen is the internal influenza protein, matrix protein (M1). In one aspect of the invention, the influenza antigen consists essentially of amino acids 2 to 252 of influenza M1 protein. M1 is an approximately 27 kD influenza protein that forms the matrix protein membrane in influenza virus (see FIG. 1). M1 is a structural protein, and is involved in viral assembly and nuclear export of ribonucleoprotein (RNP) to the cytoplasm. M1 is a highly conserved protein among influenza viruses and is an abundant viral protein, comprising approximately 47% of total virus protein. Any M1 protein or portion thereof is contemplated for use in the present invention, as well as any mutants or variants of any of such M1 proteins.

Example 1 describes the use of the matrix protein (M1 or MP) internal influenza protein to produce an exemplary vaccine or component of a vaccine of the present invention (i.e., the reference to a component being to the extent that the yeast vehicle is combined with other yeast vehicles expressing different proteins or further transformed to express additional influenza proteins as described herein). In this embodiment, a yeast (e.g., *Saccharomyces cerevisiae* W303α) was engineered to express an influenza M1 fusion protein derived from A/PR/8/34 influenza virus under the control of the copper-inducible promoter, CUP1. The fusion protein is a single polypeptide having the amino acid sequence of SEQ ID NO:4, which is encoded by a nucleic acid sequence represented by SEQ ID NO:3.

In another aspect of the invention, the influenza antigen is the external influenza protein, hemagglutinin (HA). In one aspect of the invention, the influenza antigen consists essentially of amino acids 2 to 530 of influenza HA protein, which includes the N-terminal ER-targeting signal sequence of HA, but excludes 36 C-terminal residues of HA, thus eliminating its C-terminal membrane anchor and cytoplasmic tail. In another aspect, the influenza antigen consists essentially of amino acids 17 to 342 of influenza HA protein, which excludes the 16 amino acid N-terminal ER-targeting signal sequence of HA and excludes the 36 C-terminal residues of HA comprising its C-terminal membrane anchor and cytoplasmic tail. HA is an integral membrane protein that is expressed on the surface of the influenza viral particle (see FIG. 1). Hemagglutinin is responsible for host cell binding via sialic acid residues of glycosylated receptor proteins on target cell surfaces, as well as subsequent fusion of viral and host membranes in the endosome after the virus has been taken up by endocytosis. HA contains at least four major antigenic sites, and just a single amino acid substitution within one of these four regions can result in the ability of the virus to escape immune surveillance and to spread worldwide every year. Three distinct HA proteins have been found in human infections, referred to as H1, H2 and H3; 13 others have been found in animal influenza viruses, including H5, found in avian influenza virus. Any HA protein or portion thereof is contemplated for use in the present invention, as well as any mutants or variants of any of such HA proteins. In one embodiment, a yeast vehicle of the invention expressing an HA protein expresses more than one HA protein (e.g., H1, H2, etc.) or is combined in a vaccine with a yeast vehicle that expresses a different HA protein (e.g., one vehicle expresses H1 and one vehicle expresses H2 or another HA protein).

Example 2 describes the use of a hemagglutinin (HA) external influenza protein to produce another exemplary vaccine or component of a vaccine of the present invention. In this embodiment, a yeast (e.g., *Saccharomyces cerevisiae* W303α) was engineered to express a fusion protein under the control of the TEF2 promoter. The fusion protein comprising the influenza HA antigen (H1) derived from A/PR/8/34 influenza virus is a single polypeptide comprising the amino acid sequence of SEQ ID NO:6, which is encoded by a nucleic acid sequence represented herein by SEQ ID NO:5.

Example 2 also describes the use of another hemagglutinin (HA) external influenza protein, in this case, the H5 HA from the avian influenza strain, to produce another exemplary vaccine or component of a vaccine of the present invention. In this embodiment, a yeast (e.g., *Saccharomyces cerevisiae* W303α) was engineered to express a fusion protein. The fusion protein comprising the influenza HA antigen (H5) derived from A/Vietnam/1203/04 influenza virus is a single polypeptide comprising the amino acid sequence of SEQ ID NO:20, which is encoded by a nucleic acid sequence represented herein by SEQ ID NO:19.

Both of the above-described fusion proteins were designed to provide intracellular expression of the HA fusion protein by the yeast. Briefly, these fusion proteins contains the N-terminal signal sequences for both Aga2 and HA. The signal sequence of Aga2 targets the fusion for translocation into the ER, but the signal sequence of HA acts as a stop transfer. Because of this, the fusion protein does not make it through the secretory pathway. It becomes an integral membrane protein whose HA portion remains on the cytosolic side of the plasma membrane.

Example 3 describes the use of a hemagglutinin (HA) external influenza protein to produce yet another exemplary vaccine or component of a vaccine of the present invention. In this embodiment, a yeast (e.g., *Saccharomyces cerevisiae* W303α) was engineered to express a fusion protein under the control of the TEF2 promoter. This fusion protein was designed to provide extracellular expression of the N-terminal portion of HA (H1) antigen, referenced as HA1, derived from A/PR/8/34 influenza virus by the yeast. This protein, when expressed in cells that also express Aga1p, localizes to the outer cell wall of the yeast cell, but is also contained intracellularly. The fusion protein comprises an amino acid sequence of SEQ ID NO:10, which is encoded by the nucleic acid sequence represented herein by SEQ ID NO:9.

In another aspect of the invention, the influenza antigen is the external influenza protein, neuraminidase (NA), and in another embodiment, an immunogenic portion of NA is contemplated. NA is an integral membrane protein that is expressed on the surface of the influenza viral particle (see FIG. 1). Neuraminidase digests sialic acid (neuraminic acid), which most cells have on their surface. Since sialic acid is part of the virus receptor, when the virus binds to the cell, it will be internalized (endocytosed). By late in infection, the sialic acid will have been removed from the infected cell surface by the neuraminidase, making it is easier for the progeny virions to diffuse away once they exit the cell. Neuraminidase is also involved in penetration of the mucus layer in the respiratory tract. Two distinct NA proteins have been found in human infections, referred to as N1 and N2; 7 others have been found in animal influenza viruses. Any NA protein or portion thereof is contemplated for use in the present invention, as well as any mutants or variants of any of such NA proteins. In a preferred embodiment, a yeast vehicle of the invention expressing an NA protein expresses more than one NA protein (e.g., N1, N2, etc.) or is combined in a vaccine with a yeast vehicle that expresses a different NA protein (e.g., one vehicle expresses NA and one vehicle expresses NA or another NA protein).

In yet another aspect of the invention, the influenza antigen used in a vaccine of the invention is the internal or external influenza protein, ion channel protein (M2). In one aspect of the invention, the influenza antigen consists essentially of the extracellular portion of the influenza M2 protein, also known as M2e. In one aspect, M2e is fused to the C-terminus of an NP influenza protein, or a portion thereof. This protein (M2e) can be designed for intracellular (cytosolic) expression. In another embodiment, M2e is fused to a cell wall protein (e.g., Aga2) for expression on the extracellular surface of yeast. M2 is a matrix protein and is an integral membrane protein that spans the matrix protein membrane and lipid bilayer and is expressed on the surface of the viral particle (see FIG. 1). M2 is an ion channel that permits protons to enter virus particles during the uncoating of virions in endosomes, and it also modulates the pH of the trans-Golgi network in virus-infected cells. M2 is a homo-oligomer of 97 residues with a single transmembrane (TM) domain whose residues encompass the pore region of the channel. The biologically active form of the channel is a homotetramer. According to the present invention, the portion of the M2 protein that expressed externally on the virus (i.e., also known as the extracellular domain of M2) can be referred to herein as M2e. M2e is known to be highly conserved among influenza viruses of the A type. As discussed above, in one embodiment of the invention, a portion of the M2 protein comprising primarily or exclusively M2e is expressed by a yeast vehicle. In this embodiment, the M2 protein is considered to be an external influenza protein. In other embodiments, when matrix protein membrane portions of the M2 protein are expressed, the M2 protein can be considered to be an internal influenza protein. Any M2 protein or portion thereof is contemplated for use in the present invention, as well as any mutants or variants of any of such M2 proteins.

In another aspect of the invention, the influenza antigen used in a vaccine of the invention is the internal influenza protein, nucleocapsid protein (NP), also referred to as nucleoprotein. In one aspect of the invention, the influenza antigen consists essentially a portion of the influenza NP protein that expresses in the cytosol of yeast and that is immunogenic. NP is a protein that is located inside the shell formed by the matrix protein membrane (see FIG. 1). The primary function of NP is to encapsidate the virus genome to form a ribonucleoprotein (RNP) for the purposes of RNA transcription, replication and packaging, but NP also performs other essential functions throughout the viral life cycle. NP is responsible for the classification of influenza into types A, B and C, but is still highly conserved even between viral types, and particularly between types A and B. Any NP protein or portion thereof is contemplated for use in the present invention, as well as any mutants or variants of any of such NP proteins. In a preferred embodiment, a yeast vehicle of the invention expressing an NP protein expresses more than one NP protein (e.g., NP from type A influenza and NP from type B influenza) or is combined in a vaccine with a yeast vehicle that expresses a different NP protein (e.g., one vehicle expresses NP from influenza type A and one vehicle expresses NP from influenza type B).

Example 4 describes the use of a hemagglutinin (HA) external influenza protein to produce yet another exemplary vaccine or component of a vaccine of the present invention. In this embodiment, a yeast (e.g., *Saccharomyces cerevisiae*) was engineered to express a fusion protein under the control of the TEF2 promoter. This fusion protein was designed to provide extracellular expression of the HA (H5) antigen derived from A/Vietnam/1203/04 influenza virus strain by the yeast. This protein, when expressed in cells that also express Aga1p, localizes to the outer cell wall of the yeast cell. The fusion protein comprises an amino acid sequence of SEQ ID NO:14, which is encoded by the nucleic acid sequence represented herein by SEQ ID NO:13.

Example 5 describes the engineering of several HA-containing fusion proteins that have been expressed by yeast vehicles of the invention, and that illustrate various constructs for surface expression, including on a yeast spheroplast, and that further illustrate the effect of glycosylation on surface expression.

One fusion protein, denoted TK75-15, is the fusion protein referenced herein by SEQ ID NO:36, which is encoded by SEQ ID NO:35, and illustrates construction of a fusion protein with the HA sequence placed C-terminal to the Aga2 sequence. This protein, when expressed in yeast cells that also express Aga1p (in this case, driven by the CUP1 promoter), localizes to the outer cell wall of the yeast cell, as well as to the cytosol, as shown in FIG. 10B (upper left).

Example 5 also describes a fusion protein denoted VK4, shown schematically in FIG. 10B (upper right), was engineered to localize the influenza HA protein (H1) to the cell wall using the Aga2 sequence, driven by the TEF2 promoter. In this construct the protein was constructed with the HA sequence placed N-terminal to the Aga2 sequence. This protein, when expressed in Mat a yeast that also expresses native Aga1p (in this case, its native promoter), localizes to the outer cell wall of the yeast cell, and is also present intracellularly. The fusion protein comprises an amino acid sequence of SEQ ID NO:26, which is encoded by the nucleic acid sequence represented herein by SEQ ID NO:25.

Example 5 also describes a fusion protein denoted VK11, which is analogous to VK4 above, except that the fusion protein was engineered to localize the influenza H5 HA protein to the cell wall using the Aga2 sequence, driven by the TEF2 promoter. In this construct the protein was also constructed with the HA sequence placed N-terminal to the Aga2 sequence. The fusion protein comprises an amino acid sequence of SEQ ID NO:22, which is encoded by the nucleic acid sequence represented herein by SEQ ID NO:21.

Example 5 also describes a fusion protein denoted VK8, shown schematically in FIG. 10B (lower left), was engineered to localize influenza HA (H1) protein to the cell wall using the Cwp2 sequence, driven by the TEF2 promoter. In this construct the protein was also constructed with the HA sequence placed N-terminal to the Cwp2 sequence. This protein localizes to the outer cell wall of the yeast cell, and is also present intracellularly. The fusion protein comprises an amino acid sequence of SEQ ID NO:28, which is encoded by the nucleic acid sequence represented herein by SEQ ID NO:27.

Example 5 also describes a fusion protein denoted VK12, which is analogous to VK8 above, except that the fusion protein was engineered to localize the influenza H5 HA protein to the cell wall using the Cwp2 sequence, driven by the TEF2 promoter. In this construct the protein was also constructed with the HA sequence placed N-terminal to the Cwp2 sequence. The fusion protein comprises an amino acid sequence of SEQ ID NO:24, which is encoded by the nucleic acid sequence represented herein by SEQ ID NO:23.

Example 5 also describes a fusion protein denoted Lu002, shown schematically in FIG. 10B (lower right), was engineered with the endogenous α-factor signal and leader sequence to express influenza HA protein with the transmembrane domain intact on the plasma membrane of a yeast spheroplast, driven by the TEF2 promoter. This protein, from which the α-factor signal and leader sequence is naturally cleaved off in the Golgi, localizes to the plasma membrane of the yeast spheroplast, and is also present intracellularly. The use of the endogenous α-factor signal and leader sequence to direct foreign proteins into the yeast secretory pathway was previously described (e.g., see U.S. Pat. No. 5,413,914; or Franzusoff et al *J. Biol. Chem.* 270, 3154-3159 (1995)).

Example 6 describes the use of several internal influenza proteins to produce yet another exemplary Tarmogen or component of a Tarmogen of the present invention. In this embodiment, a yeast (e.g., *Saccharomyces cerevisiae*) was engineered to express a fusion protein under the control of the TEF2 promoter. This fusion protein was designed to provide intracellular expression of the M1 antigen and the NP antigen derived from the A/PR/8/34 influenza virus and the M2e antigen, including M2e antigens derived from both the A/PR/8/34 influenza virus strain and the A/Vietnam/1203/04 influenza virus strain by the yeast. This yeast-based vaccine of the invention is useful for the induction of cross-protective immunity against antigens that are conserved across influenza strains. The fusion protein comprises an amino acid sequence of SEQ ID NO:16, which is encoded by the nucleic acid sequence represented herein by SEQ ID NO:15.

Example 7 describes the use of several internal influenza proteins to produce yet another exemplary Tarmogen or component of a Tarmogen of the present invention. In this embodiment, a yeast (e.g., *Saccharomyces cerevisiae*) was engineered to express a fusion protein under the control of the TEF2 promoter. This fusion protein was designed to provide intracellular expression of the NP antigen derived from the A/PR/8/34 influenza virus and the M2e antigen derived from the A/PR/8/34 influenza virus. This yeast-based vaccine of the invention is useful for the induction of cross-protective immunity against antigens that are conserved across influenza strains. The fusion protein comprises an amino acid sequence of SEQ ID NO:18, which is encoded by the nucleic acid sequence represented herein by SEQ ID NO:17.

In one embodiment of the present invention, any of the above-described influenza virus antigens are expressed in a yeast vehicle of the invention with at least one other influenza virus antigen. Preferably, both an internal influenza antigen (e.g., M1, M2 or NP) is expressed together with an external influenza antigen (e.g., HA, NA, or M2e). The influenza antigens can be expressed using the same or different constructs. The external influenza antigens can be provided extracellularly by the yeast and/or intracellularly. Preferred combinations of antigens to be expressed by the yeast vehicle include, but are not limited to: M1 and HA; M1 and NA; M1, HA and NA; NP and HA; NP and NA; NP, HA and NA; M2 and HA; M2 and NA; M2 and M1; M2, HA and NA; and M1, M2 and NA. In any of these combinations that include M2, the M2 can be full-length M2 or M2e, or any portion of M2 that can be expressed or provided in yeast and is immunogenic. Similarly, the other proteins can be expressed as any form, portion, or variant described herein. In these combinations, any one or more subtypes of the proteins can be expressed or provided, and particularly, any one or more subtypes of HA or NA.

In another embodiment of the invention, any of the above-described yeast vehicles expressing or providing one or more influenza antigens or combinations of such antigens is combined with a yeast vehicle expressing or providing one or more different antigens or combinations of antigens to form the yeast vaccine. Alternatively, any of the above-described yeast vehicles expressing or providing one or more influenza antigens can be administered sequentially with a yeast vehicle expressing one or more different antigens or combinations of antigens. Preferably, a yeast vehicle expressing or providing one or more internal influenza antigens is combined with or administered sequentially with a yeast vehicle expressing or providing one or more external influenza antigens. Preferred combinations of yeast vehicles include, but are not limited to, yeast vehicles expressing or providing M1 administered together or sequentially with yeast vehicles expressing or providing HA, NA, or combinations thereof (including one or more subtypes of these antigens); yeast vehicles expressing or providing NP administered together or sequentially with yeast vehicles expressing or providing HA, NA, or combinations thereof (including one or more subtypes of these antigens); and yeast vehicles expressing or providing M2 administered together or sequentially with yeast vehicles expressing or providing HA, NA, or combinations thereof (including one or more subtypes of these antigens). In another embodiment, yeast vehicles expressing or providing any two or more of M1, NP and/or M2 can be administered together or sequentially with yeast vehicles expressing or providing HA, NA, or combinations thereof (including one or more subtypes of these antigens).

Isolated Fusion Proteins, Nucleic Acid Molecules, and Cells

Another embodiment of the present invention includes an isolated protein, comprising any of the isolated fusion protein comprising an influenza antigen(s) as described herein. Also included in the present invention are isolated nucleic acid molecules encoding any of such proteins, recombinant nucleic acid molecules comprising nucleic acid sequences encoding such proteins, and cells and vectors, including viral vectors, that contain or are transfected/transformed with such nucleic acid molecules or recombinant nucleic acid molecules.

Preferred fusion proteins according to the present invention include any of the fusion proteins described herein. Exemplary fusion proteins encompassed by the present invention include those fusion proteins comprising, consisting essentially of, or consisting of, and amino acid sequence selected from SEQ ID NO:4, SEQ ID NO:6, SEQ ID NO:10, SEQ ID NO:14, SEQ ID NO:16, SEQ ID NO:18, SEQ ID NO:20, SEQ ID NO:22, SEQ ID NO:24, SEQ ID NO:26, SEQ ID NO:28, and SEQ ID NO:36. Other fusion protein sequences will be apparent to those of skill in the art given the guidance provided herein, since various influenza protein sequences are well-known in the art.

The present invention also includes any nucleic acid molecules comprising, consisting essentially of, or consisting of, a nucleic acid sequence encoding any of the fusion proteins described herein.

Suitable host cells to transfect with a recombinant nucleic acid molecule according to the present invention include any cell that can be transfected or transformed, including any animal, insect, bacterial, fungal (including yeast) cell. In one embodiment, the host cell is an animal cell that has been transfected with and expresses a fusion protein of the present invention. Such a cell is exemplified in the Examples section and is useful, for example, for assessing antigen-specific T cell responses that are induced by a vaccine or composition of the present invention. Other vaccines or compositions directed against an influenza antigen can also be tested such transfected cells.

The following experimental results are provided for purposes of illustration and are not intended to limit the scope of the invention.

EXAMPLES

Example 1

The following example describes the engineering of GI-8001 (also generally referred to in some of the figures as GI-8000), an influenza M1 fusion protein yeast vaccine of the present invention.

*Saccharomyces cerevisiae* was engineered to express an influenza M1 fusion protein under the control of the copper-inducible promoter, CUP1. The fusion protein is a single polypeptide with the following sequence elements fused in frame from N- to C-terminus (the amino acid sequence of the fusion protein being represented herein by SEQ ID NO:4): 1) the sequence MADEAP (SEQ ID NO:1) to impart resistance to proteasomal degradation (positions 1 to 6 of SEQ ID NO:4); 2) amino acids 2 through 252 of the M1 protein (positions 7 to 257 of SEQ ID NO:4); 3) a triglycine spacer introduced to separate the M1 protein from a histidine tag (positions 258 to 260 of SEQ ID NO:4); and 4) a C-terminal hexahistidine tag (positions 261 to 266 of SEQ ID NO:4). A nucleic acid sequence encoding the fusion protein of SEQ ID NO:2 is represented herein by SEQ ID NO:1. In this exemplary yeast-based vaccine, the M1 gene was cloned from influenza A/PR/8/34/H1N1-infected culture cells by RT-PCR, and the encoded amino acid sequence is an exact match to the theoretical M1 amino acid sequence from this strain/genotype.

Figure 2:
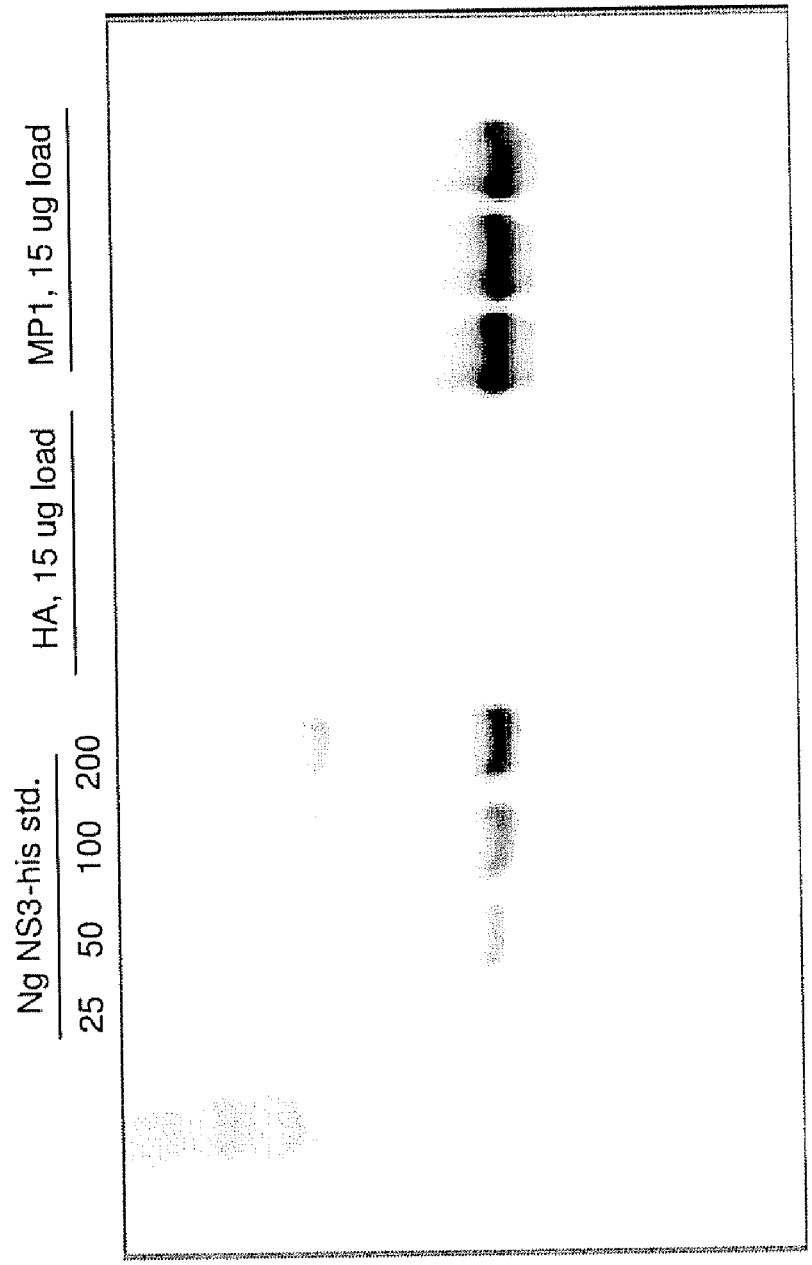
FIG. 2 is a digital image of a Western blot showing the intracellular expression of influenza matrix protein 1 (M1, also referred to as MP or MP1) in yeast.

Growth and induction of the yeast (*Saccharomyces cerevisiae* W303) expressing the influenza M1 fusion protein was performed in ULDM medium. The pH of this medium was not adjusted to neutral pH conditions as described herein (i.e., regular yeast growth conditions were used). Expression of the influenza M1 fusion protein was induced at 0.2 YU/ml with 0.375 mM copper sulfate. The yeast were harvested in mid-exponential phase and heat killed. The expression of the M1 fusion protein was confirmed by Western blot analysis of lysates from copper-induced, heat-inactivated GI-8001 yeast (see FIG. 2). Monoclonal antibodies specific the histidine tag were used for protein detection.

A standard recipe for ULDM media follows:

| Component | g/L | 20 L | Source |
|---|---|---|---|
| YNB w/o ammonium sulfate and amino acids | 1.7 | 34.0 | Difco 233520 |
| Ammonium sulfate OR | 5.0 | 100.0 | EMD AX13853 |
| YNB w/o amino acids | 6.7 | 134.0 | Difco |
| Adenine | 0.02 | 0.4 | Sigma A9795 |
| Tryptophan | 0.02 | 0.4 | JTBaker 2092 |
| Histidine | 0.02 | 0.4 | JTBaker N327 |
| Glucose monohydrate | 25.0 | 500.0 | EMD 1.08342.2500 |

Figure 3B:
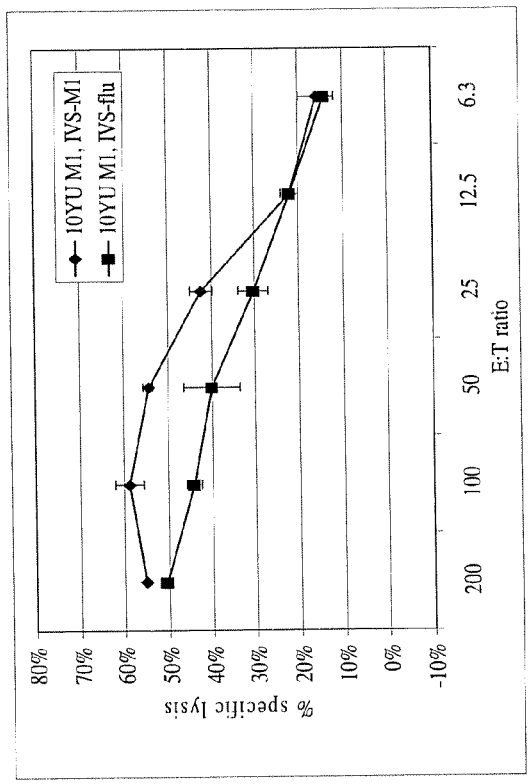
FIGS. 3A and 3B show the results of a CTL assay in which immunization of mice with a yeast vehicle expressing the influenza matrix protein (M1) intracellularly elicited both M1-specific (FIG. 3A) and influenza virus-specific (FIG. 3B) cytotoxic T cell (CTL) killing of influenza-infected target cells.
Figure 3A:
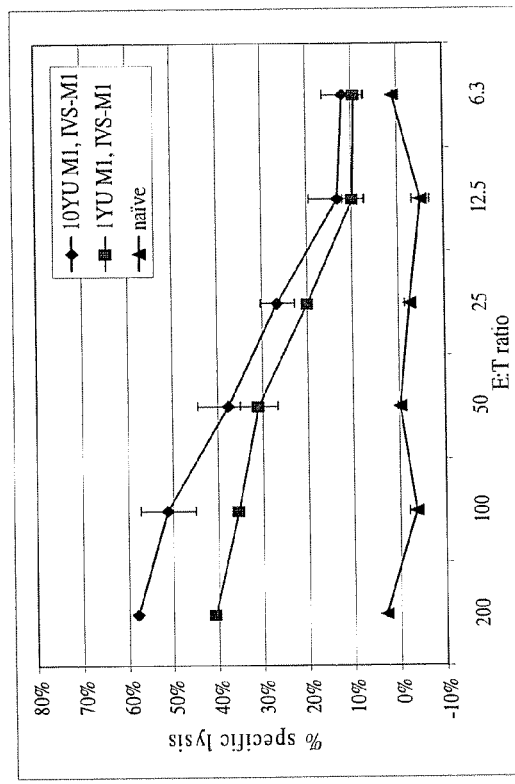

Female BALB/c mice were injected with 3 weekly doses of PBS alone, or 1 YU or 10 YU of the GI-8001 yeast-based vaccine expressing M1 (denoted "1YU M1" and "10YU M1", respectively, in FIGS. 3A and 3B). The mice were sacrificed 16 days after receiving the last dose. In vitro stimulation assays were conducted using the M1-expressing yeast as a target (IVS-M1) or using attenuated flu virus as a target (IVS-flu) to evaluate CTL responses and lymphocyte proliferation, and supernatants were collected for cytokine analysis. P815 tumor cells were transfected with the influenza M1 fusion proteins or infected with influenza as target cells in these assays. The results of CTL assays are shown in FIG. 3. The results show that vaccination of mice with the GI-8001 vaccine induces antigen-specific (M1 and influenza virus) CTL responses.

FIG. 4 shows a Western blot of lysates from P815 cells infected with influenza A/PR/8/34. HA is identified in the supernate, illustrating that P815 cells can be infected with influenza virus and used as target cells in the assays described herein.

Figure 5:
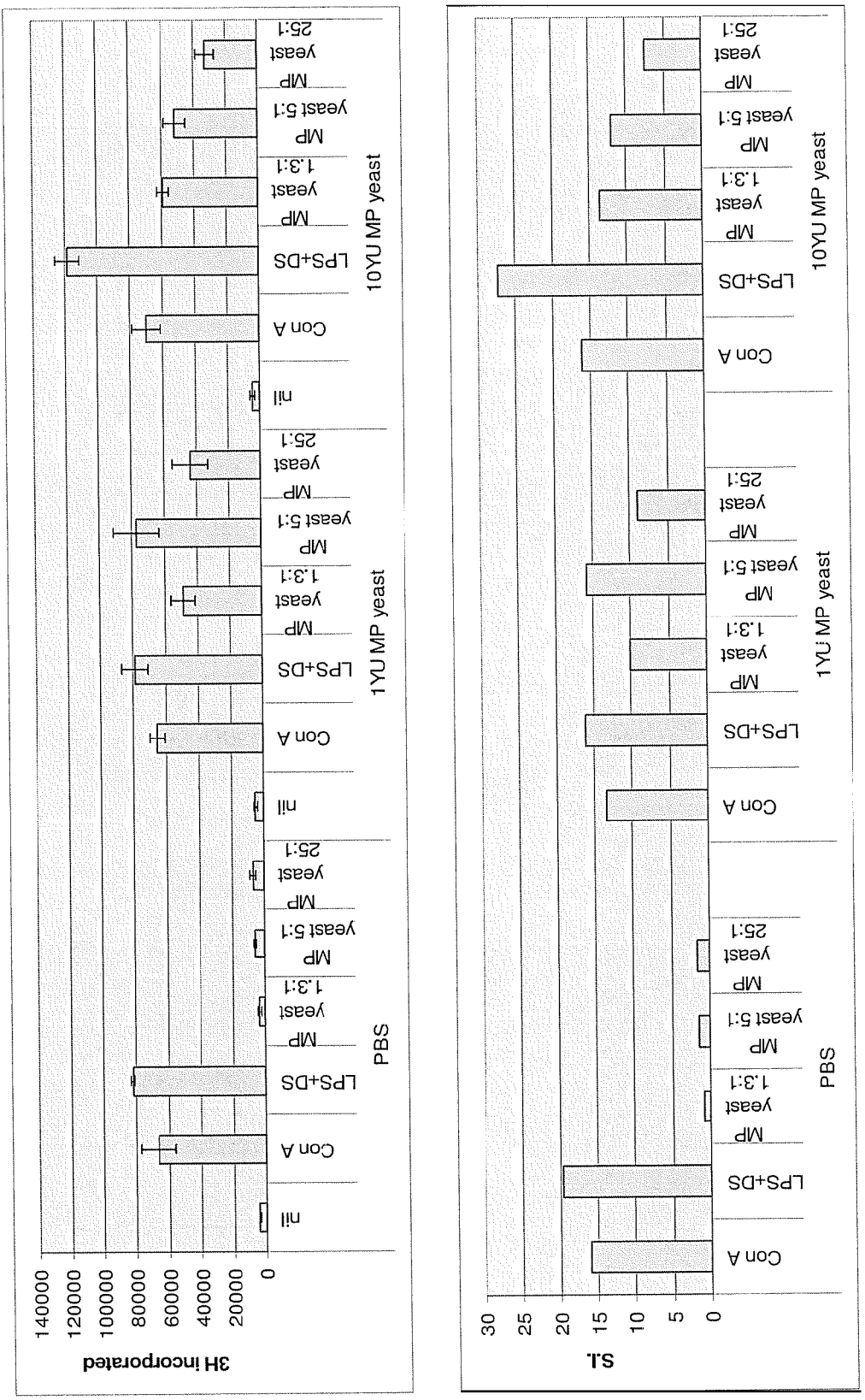
FIG. 5 shows the results of a T lymphocyte proliferation assay in which immunization of mice with a yeast vehicle expressing the influenza matrix protein (M1 or MP) intracellularly elicited M1-specific T cell responses.
Figure 6:
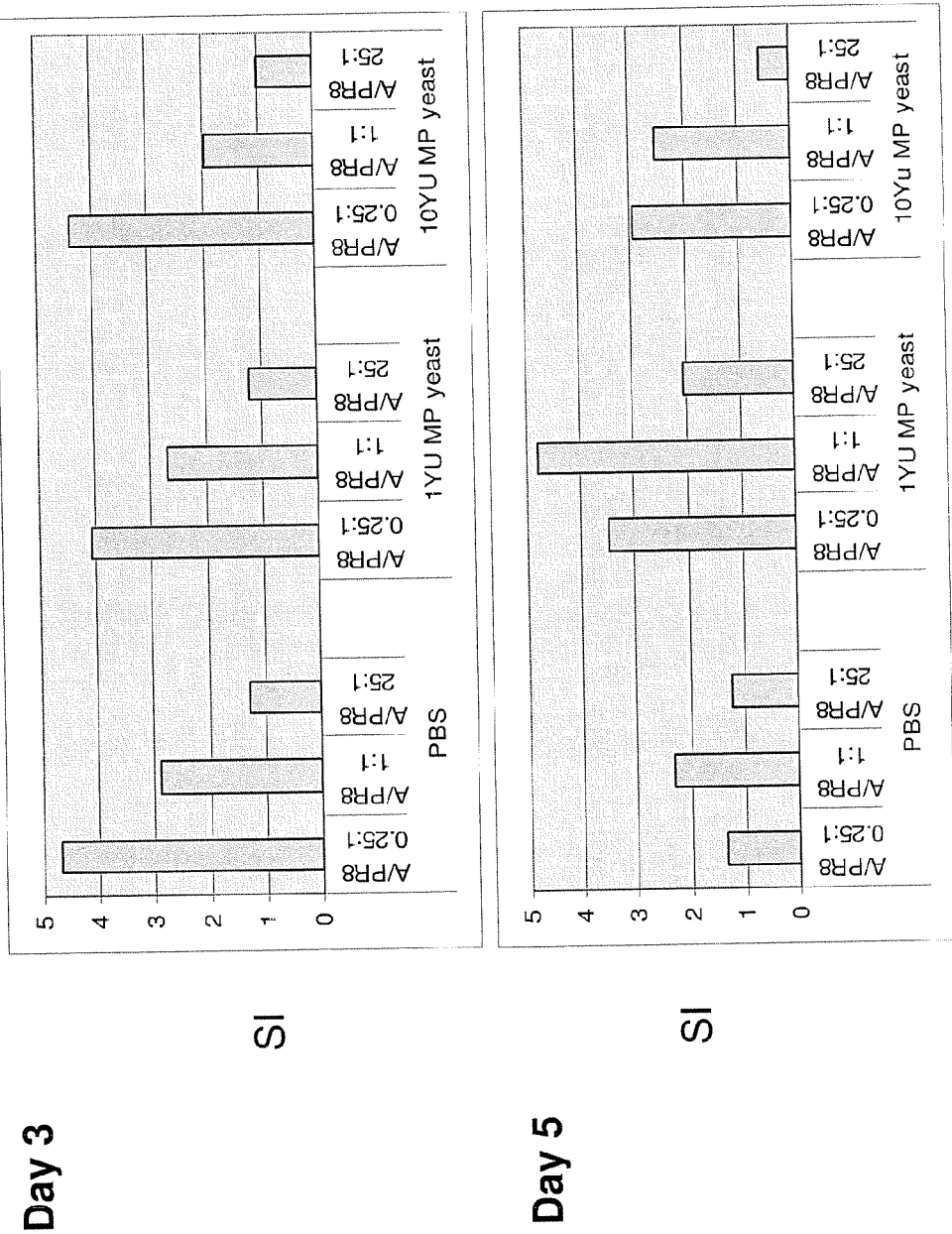
FIG. 6 shows the results of a T lymphocyte proliferation assay in which immunization of mice with a yeast vehicle expressing the influenza matrix protein (M1) intracellularly elicited influenza-specific T cell responses.

FIGS. 5 and 6 show the results of lymphocyte proliferation assays. In FIG. 5, the stimulating antigen was lysates of yeast expressing the M1 fusion protein (MP yeast). In FIG. 6, the stimulating antigen was killed influenza (A/PR8). The results show that GI-8001 (GI-8000, M1-expressing yeast) induces yeast-specific proliferation responses.

Example 2

The following example describes the engineering of two yeast-based vaccines of the present invention that expresses hemagglutinin (HA) intracellularly, using H1 HA (also referred to elsewhere herein as GI-8002 or GI-8000-I), and a second using H5 HA (also referred to as GI-8102).

H1-HA for Intracellular Expression

Figure 7:
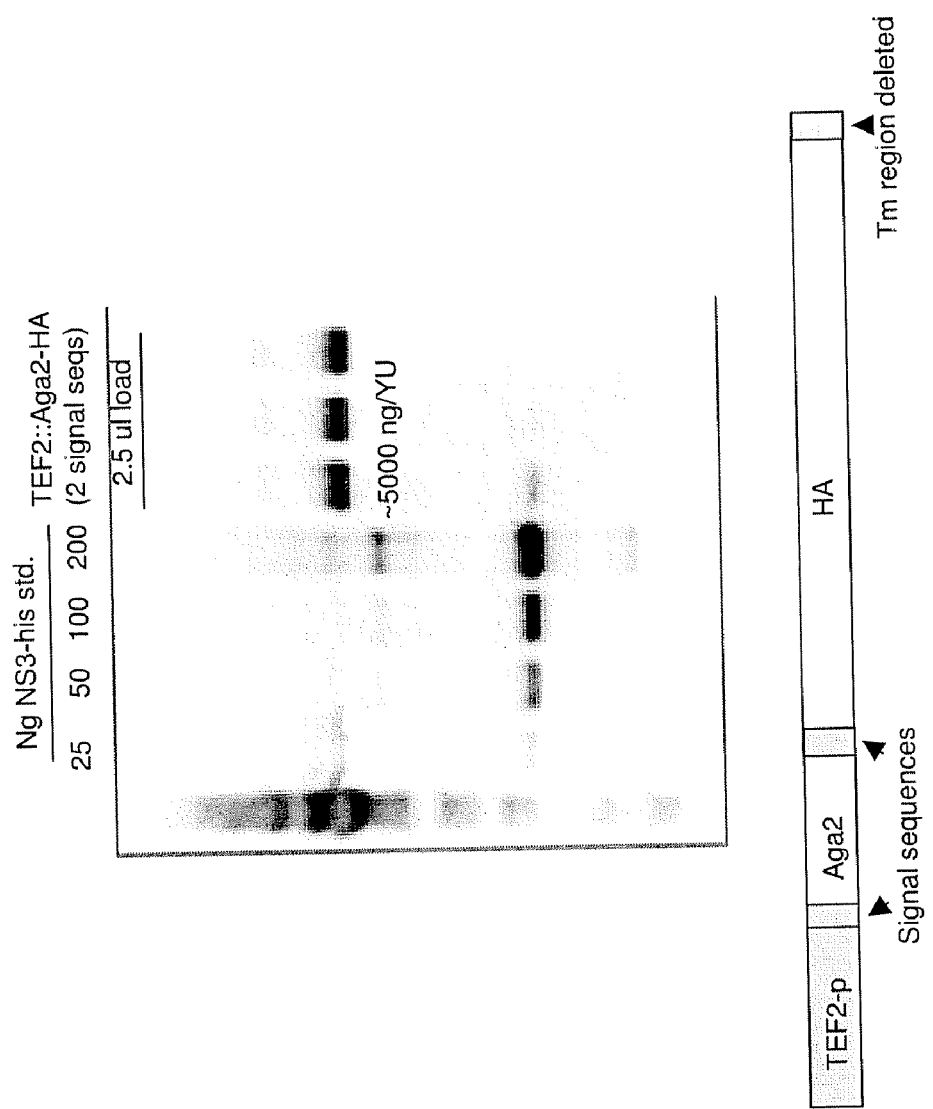
FIG. 7 is a digitized image of a Western blot (top) and schematic drawing of a fusion construct (bottom), illustrating intracellular expression of influenza hemagglutinin (HA) fused to Aga2 (Aga2-HA) in yeast.

A *Saccharomyces cerevisiae* was engineered to express an HA (H1 or HA1) fusion protein intracellularly under the control of the transcription elongation factor 2 promoter, TEF2 (see FIG. 7, bottom). The fusion protein comprising the influenza HA antigen is a single polypeptide with the following sequence elements fused in frame from N- to C-terminus (the amino acid sequence of the fusion protein being represented herein by SEQ ID NO:6): 1) the full length *S. cerevisiae* Aga2 protein sequence (positions 1 to 87 of SEQ ID NO:6), including its natural 18 amino acid ER-targeting signal sequence (positions 1 to 18 of SEQ ID NO:6); 2) amino acids 2 to 530 of influenza HA protein (positions 88 to 616 of SEQ ID NO:6), which includes the N-terminal ER-targeting signal sequence of HA (positions 88 to 105 of SEQ ID NO:6) but excludes 36 C-terminal residues of HA, thus eliminating its C-terminal membrane anchor and cytoplasmic tail; 3) a triglycine spacer to separate the body of HA protein from the histidine tag (positions 617 to 619 of SEQ ID NO:6); and 4) a C-terminal hexahistidine tag (positions 620 to 625 of SEQ ID NO:6). A nucleic acid sequence encoding the fusion protein of SEQ ID NO:6 is represented herein by SEQ ID NO:5. This fusion protein and the Tarmogen expressing it can be called GI-8000 Aga2-HA or GI-8002.

In this exemplary yeast-based vaccine, the HA gene was cloned from influenza A/PR/8/34/H1N1-infected culture cells, and the encoded amino acid sequence is not an exact match to the theoretical HA amino acid sequence from this strain/genotype. An alignment of the actual and theoretical sequences is shown in Table 1 (see Example 2).

TABLE 1

Alignment of Theoretical HA protein from A/PR/8/34/H1N1
(SEQ ID NO:7) with the actual HA protein region cloned herein
(HA signal sequence excluded) (SEQ ID NO:8).

```
theoretical_HA   DTICIGYHANNSTDTVDTVLEKNVTVTHSVNLLEDSHNGKLCRLKGIAPLQLGKCNIAGW   60
actual_HA        DTICIGYHANNSTDTVDTVLEKNVTVTHSVNLLEDSHNGKLCRLKGIAPLQLGKCNIAGW   60
                 ************************************************************
```

TABLE 1-continued

Alignment of Theoretical HA protein from A/PR/8/34/H1N1
(SEQ ID NO:7) with the actual HA protein region cloned herein
(HA signal sequence excluded) (SEQ ID NO:8).

```
theoretical_HA  LLGNPECDPLLPVRSWSYIVETPNSENGICYPGDFIDYEELREQLSSVSSFERFEIFPKE  120
actual_HA       LLGNPECDPLLPVRSWSYIVETPNSENGICYPGDFIDYEELREQLSSVSSFERFEIFPKE  120
                ************************************************************ theoretical_HA  SSWPNHNTTKGVTAACSHAGKSSFYRNLLWLTEKEGSYPKLKNSYVNKKGKEVLVLWGIH  180
actual_HA       SSWPNHN-TNGVTAACSHEGKSSFYRNLLWLTEKEGSYPKLKNSYVNKKGKEVLVLWGIH  179
                *******.*.******.*************************************** theoretical_HA  HPSNSKDQQNIYQNENAYVSVVTSNYNRRFTPEIAERPKVRDQAGRMNYYWTLLKPGDTI  240
actual_HA       HPSNSKEQQNLYQNENAYVSVVTSNYNRRFTPEIAERPKVRDQAGRMNYYWTLLKPGDTI  239
                ******.***.*************************************************
```

Yeast harboring the TEF2::Aga2-HA plasmid were grown to mid-exponential phase in UDM. The growth conditions using this medium were not adjusted for neutral pH conditions. Cells were washed and heat-killed, and total protein was extracted from the cells. Expression of the HA fusion protein was confirmed by Western blot analysis of lysates from heat-inactivated yeast expressing the protein (FIG. 7). Western blots of total protein probed with his tag mAb (FIG. 7, right) or an HA-specific mAb (not shown) indicate that the Aga2-HA protein accumulates to high levels in the yeast.

A standard recipe for UDM medium follows:

| Component | g/L | 20 L | Source |
|---|---|---|---|
| YNB w/o ammonium sulfate and amino acids | 1.7 | 34.0 | Difco 233520 |
| Ammonium sulfate OR | 5.0 | 100.0 | EMD AX13853 |
| YNB w/o amino acids | 6.7 | 134.0 | Difco |
| Adenine | 0.02 | 0.4 | Sigma A9795 |
| Tryptophan | 0.02 | 0.4 | JTBaker 2092 |
| Histidine | 0.02 | 0.4 | JTBaker N327 |
| Leucine | 0.03 | 0.6 | JTBaker 2083 |
| Glucose monohydrate | 25.0 | 500.0 | EMD 1.08342.2500 |

BALB/c female mice, aged 5-10 weeks old, were administered PBS, 0.5 YU GI-8000 Aga2-HA (GI-8002) or 5 YU GI-8000 Aga2-HA (GI-8002), by either subcutaneous (100μ) or intranasal (50 μL) administration, once per week for three weeks. The mice were sacrificed two weeks after the third dose. Serum was collected for analysis and in vitro stimulation assays were performed on splenocytes to evaluate CTL responses (using $^{51}$Cr-labeled syngeneic P815 tumor cells that had been infected overnight with A/PR/8/34 flu virus) and lymphocyte proliferation. For the proliferation assays, splenocytes were cultured for five days with GI-8000 Aga2-HA (GI-8002) or UV-inactivated A/PR8 influenza virus. Serum was also collected for antibody analysis.

Figure 8:
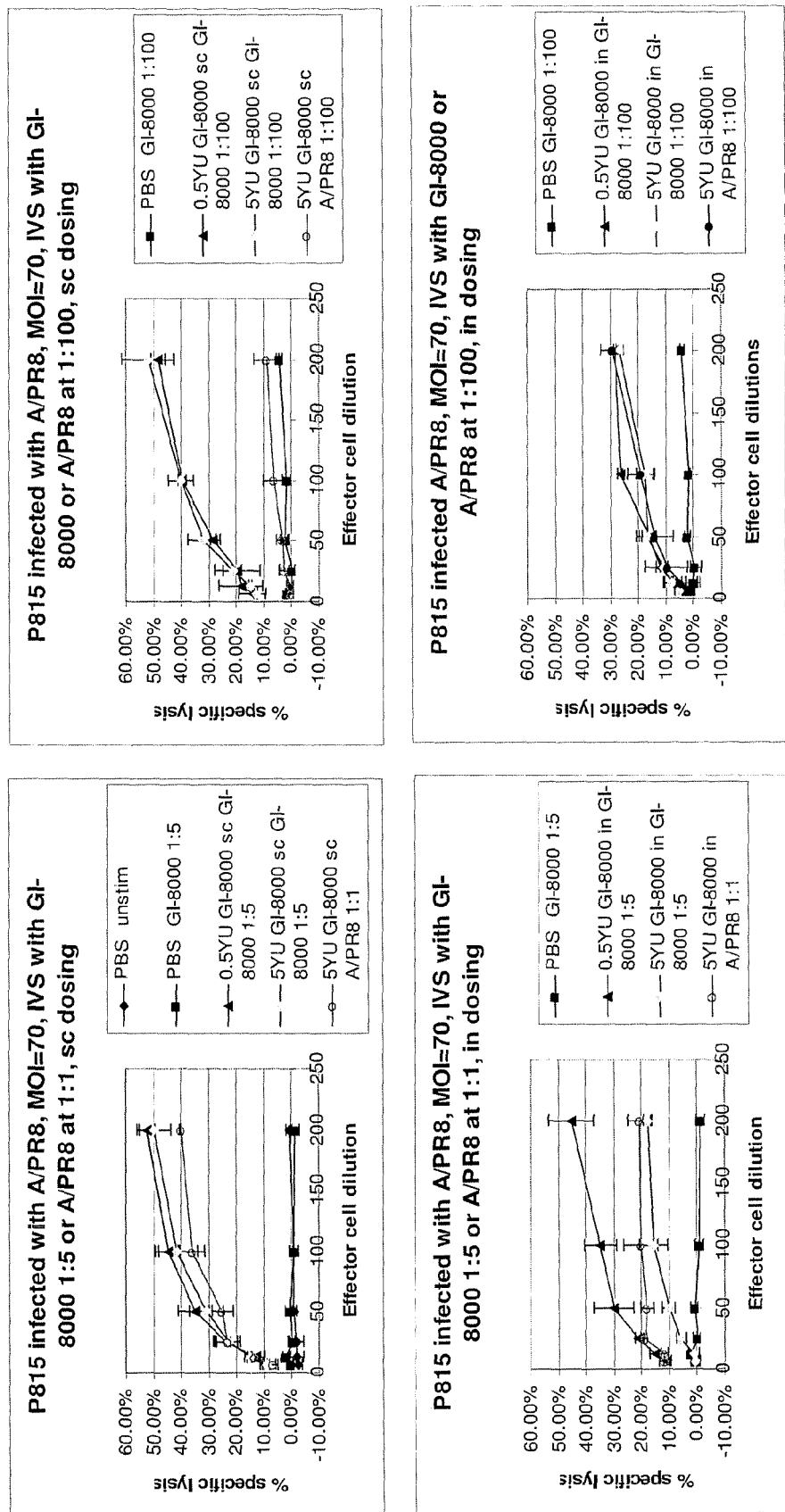
FIG. 8 shows the results of CTL assays in which immunization of mice by two different routes of administration with a yeast vehicle expressing the influenza hemagglutinin (HA) fused to Aga2 (Aga2-HA) intracellularly elicited influenza virus-specific CTL responses.
Figure 9:
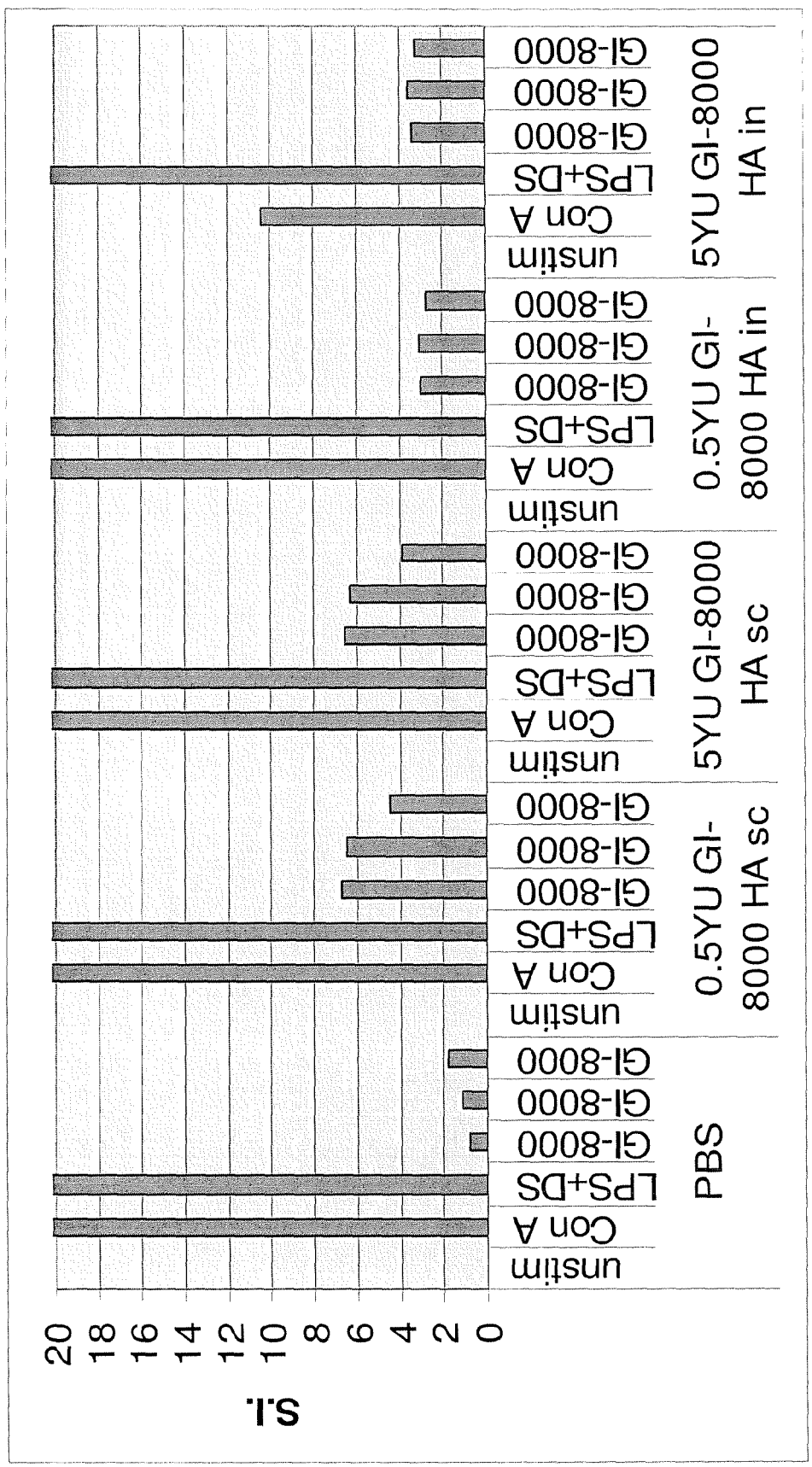
FIG. 9 shows the results of T lymphocyte proliferation assays in which immunization mice by two different routes of administration with a yeast vehicle expressing the influenza hemagluttinin (HA) fused to Aga2 (Aga2-HA) intracellularly elicited influenza virus-specific T lymphocyte proliferation responses.

FIG. 8 shows the results of the CTL assays, and FIG. 9 shows the results of the lymphocyte proliferation assays. The results show that GI-8000 Aga2-HA induces influenza virus-specific CTL responses. Administration by the subcutaneous route induced a more robust CTL response than intranasal administration as a whole. However, the low dose intranasal administration did induce high levels of CTL responses. The proliferation assays showed that both routes of administration induced influenza virus-specific lymphocyte proliferation, although the intranasal route of administration produced lower levels of proliferation responses as compared to the subcutaneous administration.

The Tarmogen expressing HA as an intracellular antigen described above was also evaluated for its ability to induce a humoral response as an adjuvant. Specifically, two doses of antigen (HA from A/PR/8/34) were given on day 0 and day 21 with or without adjuvant (adjuvant being the GI-8000-I Tarmogen described in this example) or Alum. The HA neutralizing antibody titer was measured for 3 weeks after the second dose of the antigen. Table 2 shows the results of this experiment. The data showed that GI-8000-I has excellent ability to serve as an adjuvant for B cell responses. In fact, it works just as well or better than purified protein without or with added alum as an adjuvant. As such, a lower dosage of non-yeast-based vaccine can be used to attain the same efficacy in generating antibody response (i.e., dose-sparing).

TABLE 2

GI-8000 as adjuvant for dose sparing

Treatment

| Adjuvant | Antigen (μg HA from A/PR/8/34 i.a.) | HI titer (# animals responding) | HI titer (Geometric mean) |
|---|---|---|---|
| GI-8000-I | — | (0/5) | 0 |
| — | 1 μg | 16, 8, 8, 4, 0 (4/5) | 8 |
| Alum | 1 μg | 16, 4, 4, 0, 0 (3/5) | 6.3 |
| GI-8000-I | 1 μg | 32, 32, 32, 32, 16 (5/5) | 27.9 |

The Tarmogen expressing HA as an intracellular antigen described above was also evaluated for its ability to prime an immune response against influenza. The priming was performed with enough virions of inactivated A/PR/8/34 to give 10 μg HA. Five YU of GI-8000-I was used. A boost was given about 1 month later. The HI (HA-neutralizing inhibition) titers were measured another month later. The challenge was done at the same time that HI titers were measured. The virus titer was measured 5 days later. Table 3 shows the results when GI-8000-I was used to prime against flu.

TABLE 3

GI-8000-I priming protects against flu

| Prime | Boost | HI titers (each animal, post-boost) | Virus titer in lungs ($\log_{10}$ pfu/g lung) | Mean virus titer $\log_{10}$ pfu/g lung (+/− S.E.) |
|---|---|---|---|---|
| None | None | nd | 7.14<br>7.41<br>7.18<br>7.06<br>7.32 | 7.22<br>(+/−0.14) |
| Inactivated A/PR/8/34 (SC) | Low dose live A/PR/8/34 - IN | 64<br>16<br>16<br>0 | 0<br>0<br>0<br>5.09 | 1.27<br>(+/−2.55) |
| GI-8000-I (HA) (4 doses SC) | Low dose live A/PR/8/34 - IN | 256<br>64<br>32<br>32 | 0<br>0<br>0<br>0 | 0 |

Using this type of Tarmogen, T cells against multiple antigens were generated in flu-infected cells. The benefit of eliciting an immune response against multiple antigens is that it allows for cross-protective responses and allows the Tarmogen expression of multiple antigens to act as a universal vaccine. By generating an effective immune response, this type of vaccine can be dose-sparing (i.e., less dosage needed for efficacy) as compared to conventional vaccines for avian or seasonal flu.

H5 HA for Intracellular Expression

A *Saccharomyces cerevisiae* was engineered to express an HA (H5) fusion protein intracellularly (also referred to herein as GI8102). The fusion protein comprising the influenza H5 antigen is a single polypeptide with the following sequence elements fused in frame from N- to C-terminus (the amino acid sequence of the fusion protein being represented herein by SEQ ID NO:20): 1) the full length *S. cerevisiae* Aga2 protein sequence (positions 1 to 87 of SEQ ID NO:20), including its natural 18 amino acid ER-targeting signal sequence (positions 1 to 18 of SEQ ID NO:20); 2) the N-terminal ER-targeting signal sequence corresponding to residues 1 to 16 of H1 HA (positions 88 to 105 of SEQ ID NO:20), 3) H5 HA from avian flu strain A/Vietnam/1203/2004 (positions 106 to 620 of SEQ ID NO:20); which excludes 36 C-terminal residues of HA, thus eliminating its C-terminal membrane anchor and cytoplasmic tail; and; 4) a C-terminal hexahistidine tag (positions 621 to 626 of SEQ ID NO:20). A nucleic acid sequence encoding the fusion protein of SEQ ID NO:20 is represented herein by SEQ ID NO:19.

Example 3

The following example describes the engineering of another HA fusion protein, referred to herein as HA1 in a yeast vaccine (which can be generically referenced herein as GI-8000-S) of the present invention.

This fusion protein was designed to provide extracellular expression, as well as intracellular expression, of the HA fusion protein by the yeast. The fusion protein comprising the N-terminal portion of the influenza HA antigen (HA1) is a single polypeptide with the following sequence elements fused in frame from N- to C-terminus (the amino acid sequence of the fusion protein being represented herein by SEQ ID NO:10): 1) the full length *S. cerevisiae* Aga2 protein sequence (positions 1 to 89 of SEQ ID NO:10) including its natural 18 amino acid ER-targeting signal sequence (positions 1 to 18 of SEQ ID NO:10), 2) amino acids 17 to 342 of influenza HA protein (positions 90 to 415 of SEQ ID NO:10), which excludes the 16 amino acid N-terminal ER-targeting signal sequence of HA and excludes the 36 C-terminal residues of HA comprising its C-terminal membrane anchor and cytoplasmic tail; 3) a triglycine spacer (positions 416 to 418 of SEQ ID NO:10) to separate the body of HA1 protein from the histidine tag; and 4) a C-terminal hexahistidine tag (positions 419 to 424 of SEQ ID NO:10). This protein, when expressed in cells that also express Aga1p, localizes to the outer cell wall of the yeast cell (See FIG. 10A for a schematic depiction of extracellular expression using this technique). The protein will also be expressed intracellularly. A nucleic acid sequence encoding the fusion protein of SEQ ID NO:10 is represented herein by SEQ ID NO:9.

In this exemplary yeast-based vaccine, the HA gene was cloned from influenza A/PR/8/34/H1N1 egg stock and the encoded amino acid sequence is not an exact match to the theoretical HA amino acid sequence from this strain/genotype. An alignment of the actual and theoretical sequences is shown in Table 4. There are 10 amino acid mismatches between the two sequences.

TABLE 4

Alignment of theoretical HA1 region (SEQ ID NO:11) with actual HA1 sequence that was cloned herein (SEQ ID NO:12).

```
theoretical_HA   ------------------------------DTICIGYHANNSTDTVDTVLEKNVTVTHSVN   31
actual_HA        SVTFVSNCGSHPSTTSKGSPINTQYVFTSDTICIGYHANNSTDTVDTVLEKNVTATHSVN  120
                                               **********************:*** theoretical_HA   LLEDSHNGKLCRLKGIAPLQLGKCNIAGWLLGNPECDPLLPVRSWSYIVETPNSENGICY   91
actual_HA        LLEDSHNGKLCRLKGIAPLQLGKCNIAGWLLGNPECDPLLPVRSWSYIVETPNSENGICY  180
                 ************************************************************ theoretical_HA   PGDFIDYEELREQLSSVSSFERFEIFPKESSWPNHNTTKGVTAACSHAGKSSFYRNLLWL  151
actual_HA        PGDFIDYEELREQLSSVSSFERFEIFPKESSWPNHN-TNGVTAACSHEGKSSFYRNLLWL  239
                 *********************************  :********:****** theoretical_HA   TEKEGSYPKLKNSYVNKKGKEVLVLWGIHHPSNSKDQQNIYQNENAYVSVVTSNYNRRFT  211
actual_HA        TEKEGSYPKLKNSYVNKKGKEVLVLWGIHHPSNSKEQQNLYQNENAYVSVVTSNYNRRFT  299
                 *********************************:*:******************* theoretical_HA   PEIAERPKVRDQAGRMNYYWTLLKPGDTIIFEANGNLIAPRYAFALSRGFGSGIITSNAS  271
actual_HA        PEIAERPKVRDQAGRMNYYWTLLKPGDTIIFEANGNLIAPMSAFALSRGFGSGIITSNAS  359
                 ****************************************  *****************
```

TABLE 4-continued

Alignment of theoretical HA1 region (SEQ ID NO:11) with actual HA1 sequence that was cloned herein (SEQ ID NO:12).

```
theoretical_HA  MHECNTKCQTPLGAINSSLPFQNIHPVTIGECPKYVRSAKLRMVTGLRNIPSIQSRGLFG  331
actual_HA       MHECNTKCQTPLGAINSSLPYQNIHPVTIGERPKYVRSAKLRMVTGLRNIPSIQSRG---  416
                ********************:*************** ********************  .
```

Expression of the fusion protein was confirmed by Western blot analysis of lysates from copper-induced, heat-inactivated yeast (see FIG. 17). After copper induction in UDM, under regular (not neutral pH) conditions to induce Aga1 synthesis, constitutively expressed Aga2-HA1 was released from Aga1 at the cell surface of live cells with 50 mM DTT and the DTT eluate was treated with glycosidase enzymes PNGase F or ENDO-h for 1 h. The reactions were analyzed for Aga-HA1 content by Western blot (FIG. 17). Both intracellular and cell surface HA1 expression were observed.

Example 4

The following example describes the engineering of another HA fusion protein yeast vaccine of the present invention.

Another yeast vehicle was engineered to express the hemagglutinin (HA) protein, H5, from avian flu strain A/Vietnam/1203/2004 (H5-N1), as a yeast cell surface (extracellular) protein, also referred to as TK88 (Aga2-H5 HA), which will also be located intracellularly. Referring again to the top panel of FIG. 10A, the construction for surface expression is exemplified. The fusion protein comprising the influenza HA antigen (H5) is a single polypeptide with the following sequence elements fused in frame from N- to C-terminus (the amino acid sequence of the fusion protein being represented herein by SEQ ID NO:14): 1) the full length *S. cerevisiae* Aga2 protein sequence (amino acids 1 to 87 of SEQ ID NO:14), including its natural 18 amino acid ER-targeting signal sequence; 2) amino acids 2 to 530 of influenza H5 HA protein (positions 88 to 616 of SEQ ID NO:14), which lacked the N-terminal ER-targeting signal sequence of HA and also excluded the 36 C-terminal residues of HA, thus eliminating its C-terminal membrane anchor and cytoplasmic tail; 3) a triglycine spacer to separate the body of HA protein from the histidine tag (positions 617 to 619 of SEQ ID NO:14); and 4) a C-terminal hexahistidine tag (positions 620 to 625 of SEQ ID NO:14). This protein, when expressed in cells that also express Aga1p, localizes to the outer cell wall of the yeast cell, as well as to the cytosol and ER. A nucleic acid sequence encoding the fusion protein of SEQ ID NO:14 is represented herein by SEQ ID NO:13.

This Tarmogen has been expressed using both neutral pH conditions described herein and under normal yeast growth conditions. When expressed using neutral pH conditions, the fusion protein is detected on the cell wall (surface). Neutral pH conditions increase the efficiency of expression of the proteins and improve the ability to detect the presence of the protein on the surface due to the pH effects on the cell wall and the ability of HA-specific antibodies to detect the surface expressed protein.

Example 5

The following example describes the production of additional constructs where antigens have been engineered to be targeted to the yeast surface (extracellular constructs).

Additional Tarmogens have been engineered to express the hemagglutinin (HA) protein, from influenza as a yeast cell surface (extracellular) protein. The proteins are also expressed intracellularly in the yeast. Referring again to the top panel of FIG. 10A, the construction for surface expression is exemplified.

FIG. 10B schematically illustrates several specific constructs for surface expression of antigen and shows how various yeast proteins can be used as spacer arms. While the constructs were used to express influenza HA, any protein could be expressed using these methods and constructs.

Aga2-HA H1Fusion Protein (Surface)

A fusion protein denoted TK75-15, shown schematically in FIG. 10B (upper left), was engineered to express influenza HA protein on the cell wall using the Aga2 sequence, driven by the TEF2 promoter. In this construct the protein was constructed with the HA sequence C-terminal to the Aga2 sequence. This protein, when expressed in cells that also express Aga1p (in this case, driven by the CUP1 promoter), localizes to the outer cell wall of the yeast cell, as well as to the cytosol, as shown in FIG. 10B (upper left). The fusion protein comprising the influenza HA antigen is a single polypeptide with the following sequence elements fused in frame from N- to C-terminus (the amino acid sequence of the fusion protein being represented herein by SEQ ID NO:36): 1) the full length *S. cerevisiae* Aga2 protein sequence (positions 1 to 87 of SEQ ID NO:36), including its natural 18 amino acid ER-targeting signal sequence (positions 1 to 18 of SEQ ID NO:36; 2) a spacer to separate the Aga2 from the HA body (positions 88 and 89); 3) influenza HA protein lacking its signal sequence (positions 90 to 600 of SEQ ID NO:36), and lacking 36 C-terminal residues of HA, thus eliminating its C-terminal membrane anchor and cytoplasmic tail; 4) a triglycine spacer to separate the body of HA protein from the histidine tag (positions 601-603 of SEQ ID NO:36); and 5) a C-terminal hexahistidine tag (positions 604-609 of SEQ ID NO:36). A nucleic acid sequence encoding the fusion protein of SEQ ID NO:36 is represented herein by SEQ ID NO 35. This fusion protein and the Tarmogen expressing it can be called 75-15.

HA H1-Aga2 Fusion Protein (Surface)

A fusion protein denoted VK4, shown schematically in FIG. 10B (upper right), was engineered to express influenza HA protein on the cell wall using the Aga2 sequence, driven by the TEF2 promoter. In this construct the protein was constructed with the HA sequence N-terminal to the Aga2 sequence. This protein, when expressed in yeast that also express native Aga1p (in this case, its native promoter), localizes to the outer cell wall of the yeast cell, and is also present intracellularly. The fusion protein comprising the influenza HA antigen (H1) is a single polypeptide with the following sequence elements fused in frame from N- to C-terminus (the amino acid sequence of the fusion protein being represented herein by SEQ ID NO:26): 1) the Aga2 ER-targeting signal sequence (amino acids 1 to 19 of SEQ ID NO:26); 2) H1 HA from A/PR/8/34, lacking its signal sequence and C-terminal transmembrane domain (positions 20 to 533 of SEQ ID NO:26); 3) a spacer to separate the body of HA protein from the histidine tag (positions 534 to 535 of SEQ ID NO:26); 4) a hexahistidine tag (positions 536 to 541 of SEQ ID NO:26); 5) an enterokinase cleavage site (positions 542 to 548 of SEQ ID NO:26; 6) Aga2 lacking its signal sequence (positions 549 to 614 of SEQ ID NO:26. A nucleic acid sequence encoding the fusion protein of SEQ ID NO:26 is represented herein by SEQ ID NO:25. HA H5-Aga2 Fusion Protein (Surface)

A fusion protein denoted VK11, similar to VK4 described above, except that it includes the H5 HA protein from avian influenza (A/Vietnam/1203/04), was engineered to express influenza HA H5 protein on the cell wall using the Aga2 sequence. In this construct the protein was constructed with the HA sequence N-terminal to the Aga2 sequence. This protein, when expressed in yeast, localizes to the outer cell wall of the yeast cell, and is also present intracellularly. The fusion protein comprising the influenza HA antigen (H5) is a single polypeptide with the following sequence elements fused in frame from N- to C-terminus (the amino acid sequence of the fusion protein being represented herein by SEQ ID NO:22): 1) the Aga2 ER-targeting signal sequence (amino acids 1 to 19 of SEQ ID NO:22); 2) H5 HA from A/Vietnam/1203/04, lacking its signal sequence and C-terminal transmembrane domain (positions 20 to 536 of SEQ ID NO:22); 3) a hexahistidine tag (positions 537 to 542 of SEQ ID NO:22); 4) an enterokinase cleavage site (positions 543 to 548 of SEQ ID NO:22; 5) Aga2 lacking its signal sequence (positions 549 to 616 of SEQ ID NO:22. A nucleic acid sequence encoding the fusion protein of SEQ ID NO:22 is represented herein by SEQ ID NO:21.

HA H1-Cwp2 Fusion Protein (Surface)

A fusion protein denoted VK8, shown schematically in FIG. 10B (lower left), was engineered to express influenza HA protein on the cell wall using the Cwp2 sequence, driven by the TEF2 promoter. This protein localizes to the outer cell wall of the yeast cell, and is also present intracellularly. The fusion protein comprising the influenza HA antigen (H1) is a single polypeptide with the following sequence elements fused in frame from N- to C-terminus (the amino acid sequence of the fusion protein being represented herein by SEQ ID NO:28): 1) the Suc2 invertase signal sequence (amino acids 1 to 21 of SEQ ID NO:28); 2) H1 HA from A/PR/8/34, lacking its signal sequence and C-terminal transmembrane domain (positions 22 to 535 of SEQ ID NO:28); 3) a spacer to separate the body of HA protein from the histidine tag (positions 536 to 537 of SEQ ID NO:28); 4) a hexahistidine tag (positions 538 to 543 of SEQ ID NO:28); 5) an enterokinase cleavage site (positions 544 to 549 of SEQ ID NO:28; 6) Cwp2 lacking its signal sequence (positions 550 to 617 of SEQ ID NO:28. A nucleic acid sequence encoding the fusion protein of SEQ ID NO:28 is represented herein by SEQ ID NO:27.

HA H5-Cwp2 Fusion Protein (Surface)

A fusion protein denoted VK12, similar to VK8 described above, except that it includes the H5 HA protein from avian influenza (A/Vietnam/1203/04), was engineered to express influenza HA H5 protein on the cell wall using the Cwp2 sequence. This protein localizes to the outer cell wall of the yeast cell, and is also present intracellularly. The fusion protein comprising the influenza HA antigen (H5) is a single polypeptide with the following sequence elements fused in frame from N- to C-terminus (the amino acid sequence of the fusion protein being represented herein by SEQ ID NO:24): 1) the Suc2 invertase signal sequence (amino acids 1 to 21 of SEQ ID NO:24); 2) H5 HA from A/Vietnam/1203/04, lacking its signal sequence and C-terminal transmembrane domain (positions 22 to 536 of SEQ ID NO:24); 3) a spacer to separate the body of HA protein from the histidine tag (positions 537 to 538 of SEQ ID NO:24); 4) a hexahistidine tag (positions 539 to 544 of SEQ ID NO:24); 5) an enterokinase cleavage site (positions 545 to 550 of SEQ ID NO:24); 6) Cwp2 lacking its signal sequence (positions 551 to 618 of SEQ ID NO:24. A nucleic acid sequence encoding the fusion protein of SEQ ID NO:24 is represented herein by SEQ ID NO:23.

HA-Fusion Protein for Spheroplast Expression (Surface)

A fusion protein denoted Lu002, shown schematically in FIG. 10B (lower right), was engineered to express influenza HA protein with the transmembrane domain intact on the plasma membrane of a yeast spheroplast, driven by the TEF2 promoter. This protein localizes to the plasma membrane of the yeast spheroplast, and is also present intracellularly.

FIG. 11 depicts another the Tarmogen expressing the fusion protein referred to above as VK8 that expresses influenza HA protein on the surface of the yeast via the cell wall protein 2 (cwp2). Histograms of yeast surface HA expression from flow cytometric analysis are shown in the lower right corner. The histograms indicate that this particular construct expresses HA very well on its cell surface as compared to the yeast vehicle alone (GI-1001 or YVEC).

FIGS. 12A-12G show histograms where various approaches (described above and illustrated in FIG. 10B) have been utilized to express influenza HA protein on the surface of yeast vehicles. These experiments were all conducted under normal yeast growth conditions (i.e., neutral pH conditions were not used). FIGS. 12A-12C illustrate expression by the Tarmogens expressing VK4 and TK75-15, which use the Aga2 spacer arm or linker, fused in two different orientations as discussed above. FIG. 12A shows expression by the control (non-transformed) yeast (YEX). FIG. 12B shows expression of VK4, and FIG. 12C shows expression of TK75-15. FIGS. 12D-12G show other possible configurations for surface expression of HA. FIG. 12D is again the yeast control (YEX). FIGS. 12E and 12F show the Tarmogen expressing VK8, which uses Cwp2 as a spacer arm for expression of HA. These figures also illustrates the effects of modulating glycosylation of the yeast on expression of the protein. The deglycosylated VK8-expressing Tarmogen (FIG. 12F) has improved surface expression of HA as compared to the glycosylated VK8-expressing Tarmogen (FIG. 12E). Finally, FIG. 12G shows expression of HA by the Lu002-expressing Tarmogen, which is a spheroplast expressing HA on the plasma membrane.

These results demonstrate that a variety of constructs can be used to successfully express antigens on the surface (extracellularly) of yeast vehicles of the invention.

Example 6

The following example describes the engineering of another influenza fusion protein yeast vaccine of the present invention, where combinations of influenza proteins are expressed intracellularly by the yeast vehicle.

A Tarmogen was engineered to express the matrix protein (M1) nucleocapsid protein (NP) and ion channel protein extracellular sequences (M2e) as an intracellular fusion protein under the control of the TEF2 promoter (see FIG. 13A, in which expression of this fusion protein is illustrated together with expression of a second, HA construct on the same plasmid). The M1 and NP (N1) sequences were derived from the A/PR/8/34 influenza strain. The 4xM2e represents two copies of M2e sequence from the A/PR/8/34 influenza strain and two copies of M2e sequence from the A/Viet Nam/1203/2004 influenza strain. The fusion protein comprising the M1-N1-4xM2e protein is a single polypeptide with the following sequence elements fused in frame from N- to C-terminus (the amino acid sequence of the fusion protein being represented herein by SEQ ID NO:16): 1) the sequence MADEAP (SEQ ID NO:1) to impart resistance to proteasomal degradation (positions 1 to 6 of SEQ ID NO:16); 2) influenza A/PR/8/34 M1 protein (positions 7 to 260 of SEQ ID NO:16); 3) a spacer to separate the M1 protein from the NP protein (positions 261 to 262 of SEQ ID NO:16); 4) influenza A/PR/8/34 NP protein (positions 263 to 760 of SEQ ID NO:16; 5) a spacer to separate the NP protein from the M2e proteins (positions 761 to 762 of SEQ ID NO:16); 6) a first M2e (extracellular) protein from influenza A/PR/8/34 M2 protein (positions 763 to 787 of SEQ ID NO:16); 7) a second M2e (extracellular) protein from influenza A/Viet Nam/1203/2004 M2 protein (positions 788 to 811 of SEQ ID NO:16); 8) a spacer to separate the second M2e protein from the third M2e protein (positions 812 to 813 of SEQ ID NO:16); 9) a third M2e (extracellular) protein from influenza A/PR/8/34 M2 protein (positions 814 to 838 of SEQ ID NO:16); 10) a fourth M2e protein consisting of (extracellular) protein from influenza A/Viet Nam/1203/2004 M2 protein (positions 839 to 862 of SEQ ID NO:16); and 11) a C-terminal hexahistidine tag (positions 864 to 869 of SEQ ID NO:16). A nucleic acid sequence encoding the fusion protein of SEQ ID NO:16 is represented herein by SEQ ID NO:15.

Referring to FIG. 13A and FIG. 13B, a schematic illustration of the use of a Tarmogen expressing the M1-NP-4xM2e fusion protein (SEQ ID NO:16) in conjunction with an additional construct is shown. Specifically, the fusion protein represented by SEQ ID NO:16 has also been produced in a single plasmid that also contains a second construct encoding an HA protein under the control of the CUP1 promoter. The expression of this plasmid results in the intracellular expression of the M1-NP-4xM2e fusion protein and the HA protein. The expression of HA can also be achieved via the use of a second independent construct. Additional Tarmogens to be produced include the use of the construct depicted in FIG. 13B (corresponding to the VK8 construct described above), which causes extracellular (surface) expression of the HA protein. This fusion protein can be expressed in the same Tarmogen with the M1-N1-4xM2e fusion protein described above, alone or in combination with the internally expressed HA construct described above. A separate Tarmogen expressing the VK8 (surface HA) fusion protein could also be provided in a vaccine together with the Tarmogen expressing the M1-N1-4xM2e fusion protein described above, alone or in combination with the internally expressed HA. One advantage of providing separate fusion proteins for intracellular and extracellular expression is to ensure that sufficient antigen is available for both B cell responses and uptake by antigen presenting cells such as dendritic cells for cell-mediated immune responses.

Example 7

The following example describes the engineering of another influenza fusion protein yeast vaccine of the present invention, where combinations of influenza proteins are expressed intracellularly by the yeast vehicle.

A Tarmogen has been produced that expresses an NP-2xM2e fusion protein and a Tarmogen has been produced that expresses an NP-4xM2e fusion protein.

The NP-4xM2e fusion protein is constructed in the same manner as the M1-N1-4xM2e fusion protein described in Example 6 and represented by SEQ ID NO:16, except that the M1 portion of the construct is not included.

In the NP-2xM2e fusion protein, the NP (N1) and 2 copies of M2e sequence are all from the A/PR/8/34 influenza strain. The fusion protein comprising the N1-2xM2e protein is a single polypeptide with the following sequence elements fused in frame from N- to C-terminus (the amino acid sequence of the fusion protein being represented herein by SEQ ID NO:18): 1) the sequence MADEAP (SEQ ID NO:1) to impart resistance to proteasomal degradation (positions 1 to 6 of SEQ ID NO:18); 2) influenza A/PR/8/34 NP protein (positions 7 to 503 of SEQ ID NO:18; 3) a spacer to separate the NP protein from the M2e proteins (positions 504 to 505 of SEQ ID NO:18); 4) a first M2e (extracellular) protein from influenza A/PR/8/34 M2 protein (positions 506 to 530 of SEQ ID NO:18); 5) a spacer to separate the first M2e protein from the second M2e protein (position 531 of SEQ ID NO:18); 6) a second M2e (extracellular) protein from influenza A/PR/8/34 M2 protein (positions 532 to 555 of SEQ ID NO:18); and 7) a triglycine spacer immediately followed by a C-terminal hexahistidine tag (positions 556 to 564 of SEQ ID NO:18). A nucleic acid sequence encoding the fusion protein of SEQ ID NO:18 is represented herein by SEQ ID NO:17.

This fusion protein, expressed in a yeast vehicle to produce a Tarmogen, is expressed intracellularly, and can be combined with the expression of other constructs (e.g., an HA-surface or HA-internal expression strategy as discussed in Example 6 above.

Example 8

The following example demonstrates that immunization of a Tarmogen expressing influenza HA as an extracellular protein primes a humoral immune response.

In this example, a single dose of GI-8000-S, which expresses HA on the yeast cell surface as a fusion protein with Cwp2 (see FIG. 10B, VK8), was administered to mice subcutaneously, or the mice were infected with a low dose of live flu virus intravenously. One week after the immunization, the HI titers were measured. Another group of mice received 5 YU of GI-8000-S. One week after the immunization, the HI titers were measured. The results of this study are shown in Table 5. The data shows that a single dose of GI-8000-S vaccine is capable of eliciting HA neutralizing antibody response without the addition of soluble purified protein, or without the addition of a non-yeast-based vaccine.

TABLE 5

GI-8000-S elicits HA antibody

| Immunization | HI Titers per animal (# animals responding) |
|---|---|
| Infection w/ low dose live flu virus (IN) | 8, 8, 4, 0, 0 (3/5) |
| GI-8000-S (single dose, SC) | 16, 8, 8, 0, 0 (3/5) |

Example 9

Tarmogens expressing various antigens of interest were used to prime for antibody production. As discussed infra, the invention disclosed herein provides methods to induce humoral immune responses, which include antibody responses.

One study was performed with GI-2001 (HIVAX-1), which produces the HIV-1 gp160 envelope protein as an integral yeast cell membrane protein (Franzusoff et al *J. Biol. Chem.* 270, 3154-3159 (1995)). Western blot analysis of serum from mice that had been injected weekly for three weeks with $2\times10^7$ (2 YU) of either YVEC or HIVAX-1 strains administered as live, intact yeast cells or as spheroplasts was carried out against whole lysates of intact yeast or spheroplasts. The Western blot showed that mice made antibodies to a variety of yeast-derived proteins and that the pattern of antibodies obtained was dependent on whether the mice were injected with intact yeast or spheroplasts. Sera from mice immunized with HIVAX-1 spheroplasts but not intact HIVAX-1 yeast or YVEC yeast or spheroplasts, appeared to contain antibodies specific for gp160. Without being bound by theory, this finding was likely due to the expression of gp160 in HIVAX-1 as an integral membrane protein such that it would not be exposed to B cells on the surface of intact yeast but would be exposed on the external surface of spheroplasts.

In contrast to the results obtained with HIVAX-1, sera from mice vaccinated with OVAX, a Tarmogen producing chicken ovalbumin demonstrated titers of anti-OVA antibody. This result appeared to be due to the fact that chicken ovalbumin is secreted predominantly in the periplasmic space in the OVAX yeast strain and that some soluble protein is released through the cell walls from intact yeast. Thus, the localization of a heterologous antigen within the recombinant yeast-based vaccine appeared to determine whether antibody was produced.

To further investigate the ability of OVAX yeast to induce anti-OVA antibodies, BALB/c mice were vaccinated once a month for two months with the antigens shown in the table below. One month after the second vaccination, the mice were vaccinated with soluble chicken ovalbumin (without added adjuvant). Mice that were mock vaccinated with PBS did not mount an anti-OVA antibody response following the single challenge with soluble OVA on day 56. In contrast, mice that were vaccinated twice with $2\times10^7$ (2 YU) OVAX yeast mounted a high-titer anti-OVA antibody response after boosting with soluble OVA without added adjuvant. This study shows that an antigen-sparing effect is achieved with Tarmogens in that high titers of anti-OVA antibodies were observed in mice that were immunized with OVAX followed prior to boosting with soluble OVA (an example of a non-yeast-based vaccine) or co-administered OVAX and OVA-Alum prior to boosting with soluble OVA, especially after a single dose of OVAX plus OVA-Alum. FIGS. 14A and 14B also illustrate the results for similar experiments.

TABLE 6

OVAX primes an antibody response

| Vaccinations | | | Serum anti-OVA antibody measurements | | | |
|---|---|---|---|---|---|---|
| Day 0 | Day 28 | Day 56 | Day 0 | Day 28 | Day 56 | Day 65 |
| PBS | PBS | Soluble OVA | <1:50 | 1:50 | <1:50 | 1:50 |
| OVA-Alum | OVA-Alum | Soluble OVA | <1:50 | 1:40000 | 1:93000 | 1:220000 |
| OVAX | OVAX | Soluble OVA | 1:50 | 1:4600 | 1:11000 | 1:56000 |
| OVAX + OVA-Al | OVAX + OVA-Al | Soluble OVA | <1:50 | 1:86000 | 1:128000 | 1:274000 |

Referring to FIGS. 14A and 14B, results of T cell priming (FIG. 14B) and antibody production (FIG. 14A) for three regimens used are shown. In FIG. 14A, Regimen A (control), in which only PBS was administered, shows that no ovalbumin-specific antibody titer was detected when PBS was used to boost. In Regimen B, PBS was administered on days 0 and 28 for priming, and when soluble ovalbumin protein (ova) was used to boost on day 56, no ovalbumin-specific antibody titer was detected by day 65. In Regimen C, a yeast vehicle expressing ovalbumin (OVAX) was used for priming, and when soluble ovalbumin protein was used to boost, a rapid generation of high antibody titers was observed. FIG. 14B shows the results of a T cell activation assay using various amounts of soluble ovalbumin protein for the in vitro restimulation of T cells harvested from mice immunized by each of the three regimens described above. Regimen C was effective for inducing cell-mediated immune responses.

Example 10

The following example demonstrates that a Gag-producing Tarmogen primes antigen-specific helper T cells.

The purpose of the following example was to ascertain the ability of GI-2010, a Tarmogen producing HIV-1 Gag protein as a cytoplasmic protein, to prime antigen-specific helper T cells for antibody production. Groups of 5 BALB/c mice were injected with either saline, 2 YU YVEC or 2 YU GI-2010 (subcutaneously on days 0, 7, and 21) or with either $1\times10^7$ pfu MVA-control or $1\times10^7$ MVA-UGD (recombinant Modified Vaccinia Ankara virus encoding HIV-1 Gag; intraperitoneally on days 0 and 21). Mice immunized with saline or yeast were subsequently injected with 5 µg recombinant p24 Gag protein in saline (without adjuvant) on day 28. Anti-p24 Gag antibody titers were determined by ELISA from mouse serum samples isolated throughout the study. The results, shown in FIG. 15, show that mice that were immunized with GI-2010 did not develop detectable p24 Gag-specific antibody unless they were boosted with soluble Gag protein. As antibodies were not produced by mice injected with saline or YVEC, this data indicates that GI-2010 primes helper T cells in vaccinated mice to boost the B cell responses elicited by soluble Gag protein without adjuvant.

This example shows that Tarmogens can induce helper T cells for antibody production and that the localization of the antigen within the yeast plays an important role in the amount of antibody that is produced. For example, studies indicate that yeast expressing HBsAg as a yeast cell surface protein induce anti-HBsAg antibodies. See, e.g., M. P. Schreuder et al., *Vaccine*, 14(5):383-8 (1996).

Example 11

The following example demonstrates that a yeast-based vaccine of the invention has an adjuvant effect when admixed with a non-yeast-based antigen preparation.

In this experiment, GI-8002, a Tarmogen producing A/PR/8/34 HA as a cytoplasmic protein was used (see Example 2). In brief, BALB/c mice (5 per group) were immunized subcutaneously on days 1 and 22 with either 5 YU (5×107) GI-8002 yeast cells alone, with 1 ug or 10 ug of BPL-inactivated influenza virus (A/PR/8/34) alone, or with the 5 YU GI-8002 plus the indicated amount of BPL-inactivated influenza virus. Serum was collected 4 weeks after the second dose, and HI assays were performed to determine the presence of neutralizing antibodies. The results of this experiment show that yeast has an adjuvant effect when simply admixed with BPL-inactivated virus for induction of neutralizing antibodies.

TABLE 7

| Treatment | | | Geometric mean HI titer | Mean HI titer |
|---|---|---|---|---|
| Adjuvant | Antigen | HI titer | (reciprocal) | (reciprocal) |
| 5 YU GI-8002 | None | <4, <4, <4, <4, <4 | <4 | <4 |
| None | 1 ug A/PR/8/34 | 8, 16, 4, <4, 8 | 8 | 9 |
| 5 YU GI-8002 | 1 ug A/PR/8/34 | 32, 32, 16, 32, 32 | 27.9 | 28.8 |
| None | 10 ug A/PR/8/34 | 8, 16, 16, 16, 8 | 12.1 | 12.8 |
| 5 YU GI-8002 | 10 ug A/PR/8/34 | 8, 128, 8, N.D., N.D. | 20.2 | 48 |

* N.D. = not determined due to technical problems with retro-orbital bleeding

The disclosure of all patents, patent applications, and publications cited herein are hereby incorporated by reference in their entirety for all purposes.

REFERENCES

1. Kiyosawa et al., *Hepatology* 12 (1990):671-675.
2. Tong et al., *NEJM* 332 (1995):1463-1466.
3. Yano et al., *Hepatology* 23 (1996):1334-1340.
4. Gordon et al., *Hepatology* 28 (1998) 2:562-567.
5. Di Bisceglie et al., *Hepatology* 14 (1991):969-974.
6. Koretz et al., *Ann Intern Med* 119 (1993):110-115.
7. Mattson et al., *Liver* 13 (1993):274-276.
8. Tremolada et al., *J Hepatol* 16 (1992):273-281.
9. Fattovich et al., *Gastroenterology* 112 (1997):463-472.
10. Serfaty et al., *Hepatology* 27 (1998):1435-1440.
11. Armstrong et al., *Hepatology* 31 (2000):777-82.
12. Shiratori et al., *Annals of Internal Medicine,* 142 (2005): 105-114.
13. Yoshida et al., IHIT Study Group (Inhibition of Hepatocarcinogenesis by Interferon Therapy). *Ann. Intern. Med.* 131 (1999):174-81.
14. Okanoue et al., Viral hepatitis therapy study group. *J Hepatol* 30 (1999): 653-9.
15. Shoukry et al., *Annual Rev. Microbiol* 58 (2004):391-424.
16. Stubbs et al., *Nat Med* 7 (2001):625-629.
17. Lu et al., *Cancer Research* 64 (2004):5084-5088.
18. Haller et al., Abstract, "A novel yeast-based immunotherapeutic product for chronic hepatitis C virus infection". *AASLD Meeting*, Mar. 4-5, 2005, Chicago, Ill.
19. Mondelli et al., *Journal of Hepatology* 31 (1999):65-70.
20. Day et al., *Journal of Virology* (2002):12584-12595.
21. Lauer and Walker, *New England Journal of Medicine* 345 (2001) 1:41-52.
22. Grakoui et al., *Science Mag. Report* 342 (2003).
23. Yewdell et al., *Adv. Immunol* 73 (1999):1-77.
24. Shoukry et al., *The Journal of Experimental Medicine* 197 (2003):1645-1655.
25. Matzinger, *Science* 296 (2002):301-305.
26. Falo et al., *Nat Med* 1 (1995):649-53.
27. Kikuchi et al., *Int. Immunopharmacol,* 2 (2002):1503-1508.
28. Tada et al., *Microbiol. Immunol.* 46 (2002):503-512.
29. Pichuantes et al., "Expression of heterologous gene products in yeast. In Protein Engineering—Principles and Practice. J. L. Cleland and C. S. Craik, editors." Wiley-Liss, New York (1996):129-162.
30. Underhill, *Eur. J. Immunol.* 33 (2003):1767-1775.
31. Ozinsky et al., *Proc. Natl. Acad. Sci*. USA. 97 (2000): 13766-13771.
32. Akira et al., *Nat. Immunol.* 2 (2001):675-680.
33. Medzhitov et al., *Science* 296 (2002):298-300.
34. Gantner et al., *J. Exp. Med.* 197 (2003):1107-1117.
35. Huang et al., *Science.* 294 (2001):870-875.
36. Savolainen et al., *Allergy* 53 (1998):506-512.
37. Mari et al., *Clin. Exp. Allergy.* 33 (2003):1429-1438.
38. Kortekangas-Savolainen et al., *Clin Exp Allergy* 24 (1994):836-842.
39. Belchi-Hernandez et al., *Allergy Clin. Immunol.* 97 (1996):131-134.
40. Dentico et al., *Eur J Epidemiol.* 8 (1992):650-655.
41. Joossens et al., *Gastroenterology* 122 (2002):1242-7.
42. Sandborn et al., *Inflammatory Bowel Dis.* 7 (2001):192-201.
43. Ponton et al., *Med. Mycology* 38 (2000):225-236.
44. Wheeler et al., *Proc Natl Acad Sci* USA. 100 (2003):2766-2770.
45. Haller et al., Vaccine 25 (2007): 1452-1463

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An immunogenic composition comprising:
   a) a yeast vehicle; and
   b) an influenza virus fusion protein expressed as a single intracellular fusion protein by the yeast vehicle, the fusion protein consisting of the amino acid sequence of SEQ ID NO:16.

2. The immunogenic composition of claim 1, wherein the fusion protein is under the under the control of the TEF2 promoter.

3. The immunogenic composition of claim 1, wherein the yeast vehicle is from *Saccharomyces*.

4. The immunogenic composition of claim 1, wherein the yeast vehicle is a whole, heat-inactivated yeast.

5. The immunogenic composition of claim 4, wherein the yeast vehicle is from *Saccharomyces cerevisiae*.

6. The immunogenic composition of claim 1, wherein the immunogenic composition is formulated for intranasal delivery.

7. The immunogenic composition of claim 1, wherein the immunogenic composition is formulated for oral delivery.

8. The immunogenic composition of claim 1, further comprising at least one compound selected from the group consisting of: cytokines, hormones, and small molecule drugs.

9. An immunogenic composition, comprising:
   a) a yeast vehicle; and
   b) a fusion protein comprising influenza sequences and expressed as a single intracellular fusion protein by the yeast vehicle, the influenza sequences consisting of: an M1 protein or an immunogenic domain thereof, an NP protein or an immunogenic domain thereof, and at least one M2e protein or an immunogenic domain thereof.

10. The immunogenic composition of claim 9, wherein the influenza sequences comprise at least two M2e proteins, derived from at least two different influenza strains.

11. The immunogenic composition of claim 10, wherein the different influenza strains are A/PR/8/34 influenza virus strain and A/Vietnam/1203/04 influenza virus strain.

12. The immunogenic composition of claim 9, wherein the influenza sequences consist of an M1 protein, an NP protein, and four M2e proteins.

13. The immunogenic composition of claim 9, wherein the fusion protein consists of a single polypeptide with the following sequence elements fused in frame from N- to C-terminus: (1) an N-terminal synthetic peptide that stabilizes the expression of the fusion protein in the yeast vehicle or prevents posttranslational modification of the expressed fusion protein; (2) an M1 protein; (3) a spacer peptide; (4) an NP protein; (5) a spacer peptide; (6) a first M2e protein; (7) a second M2e protein; (8) a spacer peptide; (9) a third M2e protein; (10) a fourth M2e protein; and (11) a C-terminal peptide tag.

14. The immunogenic composition of claim 9, wherein the expression of the fusion protein is under the control of an inducible promoter.

15. The immunogenic composition of claim 14, wherein the promoter is selected from the group consisting of CUP1 and TEF2.

16. The immunogenic composition of claim 9, wherein the yeast vehicle is from a non-pathogenic yeast.

17. The immunogenic composition of claim 9, wherein the yeast vehicle is from *Saccharomyces*.

18. The immunogenic composition of claim 9, wherein the yeast vehicle is a whole, heat-inactivated yeast.

19. The immunogenic composition of claim 18, wherein the yeast vehicle is from *Saccharomyces cerevisiae*.

20. The immunogenic composition of claim 9, further comprising at least one compound selected from the group consisting of: cytokines, hormones, and small molecule drugs.

21. An immunogenic composition comprising:
   a) a yeast vehicle; and
   b) an influenza virus fusion protein expressed as a single intracellular fusion protein by the yeast vehicle, the fusion protein consisting of the amino acid sequence of SEQ ID NO:6.

22. The immunogenic composition of claim 21, wherein the yeast vehicle is a whole, heat-inactivated yeast.

23. The immunogenic composition of claim 22, wherein the yeast vehicle is from *Saccharomyces cerevisiae*.

* * * * *

SEQUENCE LISTING

```
<160> NUMBER OF SEQ ID NOS: 36

<210> SEQ ID NO 1
<211> LENGTH: 6
<212> TYPE: PRT
<213> ORGANISM: Artificial
```

<220> FEATURE:
<223> OTHER INFORMATION: synthetic

<400> SEQUENCE: 1

Met Ala Asp Glu Ala Pro
1               5

<210> SEQ ID NO 2
<211> LENGTH: 9
<212> TYPE: PRT
<213> ORGANISM: Artificial
<220> FEATURE:
<223> OTHER INFORMATION: synthetic

<400> SEQUENCE: 2

Gly Gly Gly His His His His His His
1               5

<210> SEQ ID NO 3
<211> LENGTH: 801
<212> TYPE: DNA
<213> ORGANISM: Artificial
<220> FEATURE:
<223> OTHER INFORMATION: synthetic

<400> SEQUENCE: 3

```
atggccgacg aggcaccaag tcttctaacc gaggtcgaaa cgtacgttct ctctatcatc      60
ccgtcaggcc ccctcaaagc cgagatcgca cagagacttg aagatgtctt tgcagggaag     120
aacaccgatc ttgaggttct catggaatgg ctaaagacaa gaccaatcct gtcacctctg     180
actaagggga ttttaggatt tgtgttcacg ctcaccgtgc ccagtgagcg aggactgcag     240
cgtagacgct ttgtccaaaa tgcccttaat gggaacgggg atccaaataa catggacaaa     300
gcagttaaac tgtataggaa gctcaagagg gagataacat ccatggggc caaagaaatc      360 tcactcagtt attctgctgg tgcacttgcc agttgtatgg cctcatata acaggatg        420 ggggctgtga ccactgaagt ggcatttggc ctggtatgtg caacctgtga acagattgct     480
gactcccagc atcggtctca taggcaaatg gtgacaacaa ccaacccact aatcagacat     540
gagaacagaa tggttttagc cagcactaca gctaaggcta tggagcaaat ggctggatcg     600
agtgagcaag cagcagaggc catggaggtt gctagtcagg ctaggcaaat ggtgcaagcg     660 atgagaaacca ttgggactca tcctagctcc agtgctggtc tgaaaaatga tcttcttgaa     720
aatttgcagg cctatcagaa acgaatgggg gtgcagatgc aacggttcaa gggtggcggg     780
catcaccatc accatcacta g                                                801
```

<210> SEQ ID NO 4
<211> LENGTH: 266
<212> TYPE: PRT
<213> ORGANISM: Artificial
<220> FEATURE:
<223> OTHER INFORMATION: synthetic

<400> SEQUENCE: 4

Met Ala Asp Glu Ala Pro Ser Leu Leu Thr Glu Val Glu Thr Tyr Val
1               5                   10                  15

Leu Ser Ile Ile Pro Ser Gly Pro Leu Lys Ala Glu Ile Ala Gln Arg
                20                  25                  30

Leu Glu Asp Val Phe Ala Gly Lys Asn Thr Asp Leu Glu Val Leu Met
            35                  40                  45

Glu Trp Leu Lys Thr Arg Pro Ile Leu Ser Pro Leu Thr Lys Gly Ile

```
                    50                      55                      60
Leu Gly Phe Val Phe Thr Leu Thr Val Pro Ser Glu Arg Gly Leu Gln
 65                      70                      75                      80

Arg Arg Arg Phe Val Gln Asn Ala Leu Asn Gly Asn Gly Asp Pro Asn
                     85                      90                      95

Asn Met Asp Lys Ala Val Lys Leu Tyr Arg Lys Leu Lys Arg Glu Ile
                    100                     105                     110

Thr Phe His Gly Ala Lys Glu Ile Ser Leu Ser Tyr Ser Ala Gly Ala
                    115                     120                     125

Leu Ala Ser Cys Met Gly Leu Ile Tyr Asn Arg Met Gly Ala Val Thr
                130                     135                     140

Thr Glu Val Ala Phe Gly Leu Val Cys Ala Thr Cys Glu Gln Ile Ala
145                     150                     155                     160

Asp Ser Gln His Arg Ser His Arg Gln Met Val Thr Thr Thr Asn Pro
                    165                     170                     175

Leu Ile Arg His Glu Asn Arg Met Val Leu Ala Ser Thr Thr Ala Lys
                180                     185                     190

Ala Met Glu Gln Met Ala Gly Ser Ser Glu Gln Ala Ala Glu Ala Met
            195                     200                     205

Glu Val Ala Ser Gln Ala Arg Gln Met Val Gln Ala Met Arg Thr Ile
                210                     215                     220

Gly Thr His Pro Ser Ser Ser Ala Gly Leu Lys Asn Asp Leu Leu Glu
225                     230                     235                     240

Asn Leu Gln Ala Tyr Gln Lys Arg Met Gly Val Gln Met Gln Arg Phe
                    245                     250                     255

Lys Gly Gly Gly His His His His His His
                260                     265

<210> SEQ ID NO 5
<211> LENGTH: 1878
<212> TYPE: DNA
<213> ORGANISM: Artificial
<220> FEATURE:
<223> OTHER INFORMATION: synthetic

<400> SEQUENCE: 5
atgcagttac ttcgctgttt ttcaatattt tctgttattg cttcagtttt agcacaggaa      60
ctgacaacta tatgcgagca atcccctca ccaactttag aatcgacgcc gtactctttg     120
tcaacgacta ctattttggc caacgggaag gcaatgcaag gagttttga atattacaaa     180 tcagtaacgt tgtcagtaa ttgcggttct caccctcaa caactagcaa aggcagcccc     240
ataaacacac agtatgtttt tactagtaag gcaaacctac tggtcctgtt atgtgcactt     300
gcagctgcag atgcagacac aatatgtata ggctaccatg cgaacaattc aaccgacact     360
gttgacacag tactcgagaa gaatgtgaca gtgacacact tgttaaacct gctcgaagac     420
agccacaacg gaaaactatg tagattaaaa ggaatagccc cactacaatt ggggaaatgt     480
aacatcgccg gatggctctt ggggaatcca gaatgcgacc cactgcttcc agtgagatca     540
tggtcctaca ttgtagaaac accaaactct gagaatggaa tatgttatcc aggagatttc     600
atcgactatg aggagctgag ggagcaattg agctcagtgt catcattcga agattcgaa     660 atatttccca agaaagctc atggcccaac acaacacaa cggagtaac ggcagcatgc     720 tcccatgagg ggaaaagcag tttttacaga aatttgctat ggctgacgga aaggagggc     780 tcatacccaa agctgaaaaa ttcttatgtg aacaaaaaag ggaagaagt ccttgtactg     840
```

-continued

```
tggggtattc atcacccgtc taacagtaag gaacaacaga atctctatca gaatgaaaat    900
gcttatgtct ctgtagtgac ttcaaattat aacaggagat ttaccccgga aatagcagaa    960
agacccaaag taagagatca agctgggagg atgaactatt actggacctt gctaaaaccc   1020
ggagacacaa taatatttga ggcaaatgga atctaatag caccaatgta tgctttcgca    1080
ctgagtagag gctttgggtc cggcatcatc acctcaaacg catcaatgca tgagtgtaac   1140
acgaagtgtc aaacacccct gggagctata acagcagtc tcccttacca gaatatacac    1200
ccagtcacaa taggagagcg cccaaaatac gtcaggagtg ccaaattgag gatggttaca   1260
ggactaagga acattccgtc cattcaatcc agaggtctat ttggagccat tgccggtttt   1320
attgaagggg gatggactgg aatgatagat ggatggtatg gttatcatca tcagaatgaa   1380
cagggatcag gctatgcagc ggatcaaaaa agcacacaaa atgccattaa cgggattaca   1440
aacaaggtga acactgttat cgagaaaatg aacattcaat tcacagctgt gggtaaagaa   1500
ttcaacaaat tagaaaaaag gatggaaaat ttaataaaaa agttgatgat ggatttctg   1560
gacatttgga catataatgc agaattgtta gttctactgg aaaatgaaag gactctggac   1620
ttccatgact caaatatgaa gaatctgtat gagaaagtaa aaagccaatt aaagaataat   1680
gccaaagaaa tcggaaatgg atgttttgag ttctaccaca agtgtgacaa tgaatgcatg   1740
gaaagtgtaa aaatgggac ttatgattat cccaaatatt cagaagagtc aaagttgaac   1800
agggaaaagg tagatggagt gaaattggaa tcaatgggga tctatcaggg tggcgggcat   1860
caccatcacc atcactag                                                 1878
```

<210> SEQ ID NO 6
<211> LENGTH: 625
<212> TYPE: PRT
<213> ORGANISM: Artificial
<220> FEATURE:
<223> OTHER INFORMATION: synthetic

<400> SEQUENCE: 6

```
Met Gln Leu Leu Arg Cys Phe Ser Ile Phe Ser Val Ile Ala Ser Val
 1               5                  10                  15

Leu Ala Gln Glu Leu Thr Thr Ile Cys Glu Gln Ile Pro Ser Pro Thr
            20                  25                  30

Leu Glu Ser Thr Pro Tyr Ser Leu Ser Thr Thr Thr Ile Leu Ala Asn
        35                  40                  45

Gly Lys Ala Met Gln Gly Val Phe Glu Tyr Tyr Lys Ser Val Thr Phe
    50                  55                  60

Val Ser Asn Cys Gly Ser His Pro Ser Thr Thr Ser Lys Gly Ser Pro
65                  70                  75                  80

Ile Asn Thr Gln Tyr Val Phe Thr Ser Lys Ala Asn Leu Leu Val Leu
                85                  90                  95

Leu Cys Ala Leu Ala Ala Ala Asp Ala Asp Thr Ile Cys Ile Gly Tyr
            100                 105                 110

His Ala Asn Asn Ser Thr Asp Thr Val Asp Thr Val Leu Glu Lys Asn
        115                 120                 125

Val Thr Val Thr His Ser Val Asn Leu Leu Glu Asp Ser His Asn Gly
    130                 135                 140

Lys Leu Cys Arg Leu Lys Gly Ile Ala Pro Leu Gln Leu Gly Lys Cys
145                 150                 155                 160

Asn Ile Ala Gly Trp Leu Leu Gly Asn Pro Glu Cys Asp Pro Leu Leu
                165                 170                 175
```

-continued

```
Pro Val Arg Ser Trp Ser Tyr Ile Val Glu Thr Pro Asn Ser Glu Asn
        180                 185                 190

Gly Ile Cys Tyr Pro Gly Asp Phe Ile Asp Tyr Glu Glu Leu Arg Glu
        195                 200                 205

Gln Leu Ser Ser Val Ser Ser Phe Glu Arg Phe Glu Ile Phe Pro Lys
        210                 215                 220

Glu Ser Ser Trp Pro Asn His Asn Thr Asn Gly Val Thr Ala Ala Cys
225                 230                 235                 240

Ser His Glu Gly Lys Ser Ser Phe Tyr Arg Asn Leu Leu Trp Leu Thr
                245                 250                 255

Glu Lys Glu Gly Ser Tyr Pro Lys Leu Lys Asn Ser Tyr Val Asn Lys
                260                 265                 270

Lys Gly Lys Glu Val Leu Val Leu Trp Gly Ile His His Pro Ser Asn
            275                 280                 285

Ser Lys Glu Gln Gln Asn Leu Tyr Gln Asn Glu Asn Ala Tyr Val Ser
        290                 295                 300

Val Val Thr Ser Asn Tyr Asn Arg Arg Phe Thr Pro Glu Ile Ala Glu
305                 310                 315                 320

Arg Pro Lys Val Arg Asp Gln Ala Gly Arg Met Asn Tyr Tyr Trp Thr
                325                 330                 335

Leu Leu Lys Pro Gly Asp Thr Ile Ile Phe Glu Ala Asn Gly Asn Leu
                340                 345                 350

Ile Ala Pro Met Tyr Ala Phe Ala Leu Ser Arg Gly Phe Gly Ser Gly
            355                 360                 365

Ile Ile Thr Ser Asn Ala Ser Met His Glu Cys Asn Thr Lys Cys Gln
        370                 375                 380

Thr Pro Leu Gly Ala Ile Asn Ser Ser Leu Pro Tyr Gln Asn Ile His
385                 390                 395                 400

Pro Val Thr Ile Gly Glu Arg Pro Lys Tyr Val Arg Ser Ala Lys Leu
                405                 410                 415

Arg Met Val Thr Gly Leu Arg Asn Ile Pro Ser Ile Gln Ser Arg Gly
                420                 425                 430

Leu Phe Gly Ala Ile Ala Gly Phe Ile Glu Gly Gly Trp Thr Gly Met
            435                 440                 445

Ile Asp Gly Trp Tyr Gly Tyr His His Gln Asn Glu Gln Gly Ser Gly
        450                 455                 460

Tyr Ala Ala Asp Gln Lys Ser Thr Gln Asn Ala Ile Asn Gly Ile Thr
465                 470                 475                 480

Asn Lys Val Asn Thr Val Ile Glu Lys Met Asn Ile Gln Phe Thr Ala
                485                 490                 495

Val Gly Lys Glu Phe Asn Lys Leu Glu Lys Arg Met Glu Asn Leu Asn
                500                 505                 510

Lys Lys Val Asp Asp Gly Phe Leu Asp Ile Trp Thr Tyr Asn Ala Glu
            515                 520                 525

Leu Leu Val Leu Leu Glu Asn Glu Arg Thr Leu Asp Phe His Asp Ser
        530                 535                 540

Asn Met Lys Asn Leu Tyr Glu Lys Val Lys Ser Gln Leu Lys Asn Asn
545                 550                 555                 560

Ala Lys Glu Ile Gly Asn Gly Cys Phe Glu Phe Tyr His Lys Cys Asp
                565                 570                 575

Asn Glu Cys Met Glu Ser Val Arg Asn Gly Thr Tyr Asp Tyr Pro Lys
                580                 585                 590

Tyr Ser Glu Glu Ser Lys Leu Asn Arg Glu Lys Val Asp Gly Val Lys
```

```
                   595                 600                 605

Leu Glu Ser Met Gly Ile Tyr Gln Gly Gly His His His His
    610                 615                 620

His
625

<210> SEQ ID NO 7
<211> LENGTH: 240
<212> TYPE: PRT
<213> ORGANISM: Artificial
<220> FEATURE:
<223> OTHER INFORMATION: synthetic

<400> SEQUENCE: 7

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Ser His Asn Gly Lys Leu Cys Arg Leu Lys Gly Ile Ala
        35                  40                  45

Pro Leu Gln Leu Gly Lys Cys Asn Ile Ala Gly Trp Leu Leu Gly Asn
    50                  55                  60

Pro Glu Cys Asp Pro Leu Leu Pro Val Arg Ser Trp Ser Tyr Ile Val
65                  70                  75                  80

Glu Thr Pro Asn Ser Glu Asn Gly Ile Cys Tyr Pro Gly Asp Phe Ile
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Glu Ser Ser Trp Pro Asn His Asn Thr
        115                 120                 125

Thr Lys Gly Val Thr Ala Ala Cys Ser His Ala Gly Lys Ser Ser Phe
    130                 135                 140

Tyr Arg Asn Leu Leu Trp Leu Thr Glu Lys Glu Gly Ser Tyr Pro Lys
145                 150                 155                 160

Leu Lys Asn Ser Tyr Val Asn Lys Lys Gly Lys Glu Val Leu Val Leu
                165                 170                 175

Trp Gly Ile His His Pro Ser Asn Ser Lys Asp Gln Gln Asn Ile Tyr
            180                 185                 190

Gln Asn Glu Asn Ala Tyr Val Ser Val Val Thr Ser Asn Tyr Asn Arg
        195                 200                 205

Arg Phe Thr Pro Glu Ile Ala Glu Arg Pro Lys Val Arg Asp Gln Ala
    210                 215                 220

Gly Arg Met Asn Tyr Tyr Trp Thr Leu Leu Lys Pro Gly Asp Thr Ile
225                 230                 235                 240

<210> SEQ ID NO 8
<211> LENGTH: 239
<212> TYPE: PRT
<213> ORGANISM: Influenza A virus

<400> SEQUENCE: 8

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Ser His Asn Gly Lys Leu Cys Arg Leu Lys Gly Ile Ala
        35                  40                  45
```

```
Pro Leu Gln Leu Gly Lys Cys Asn Ile Ala Gly Trp Leu Leu Gly Asn
         50                  55                  60

Pro Glu Cys Asp Pro Leu Leu Pro Val Arg Ser Trp Ser Tyr Ile Val
 65                  70                  75                  80

Glu Thr Pro Asn Ser Glu Asn Gly Ile Cys Tyr Pro Gly Asp Phe Ile
                 85                  90                  95

Asp Tyr Glu Glu Leu Arg Glu Gln Leu Ser Ser Val Ser Ser Phe Glu
                100                 105                 110

Arg Phe Glu Ile Phe Pro Lys Glu Ser Ser Trp Pro Asn His Asn Thr
            115                 120                 125

Asn Gly Val Thr Ala Ala Cys Ser His Glu Gly Lys Ser Ser Phe Tyr
        130                 135                 140

Arg Asn Leu Leu Trp Leu Thr Glu Lys Glu Gly Ser Tyr Pro Lys Leu
145                 150                 155                 160

Lys Asn Ser Tyr Val Asn Lys Gly Lys Glu Val Leu Val Leu Trp
                165                 170                 175

Gly Ile His His Pro Ser Asn Ser Lys Glu Gln Gln Asn Leu Tyr Gln
                180                 185                 190

Asn Glu Asn Ala Tyr Val Ser Val Val Thr Ser Asn Tyr Asn Arg Arg
            195                 200                 205

Phe Thr Pro Glu Ile Ala Glu Arg Pro Lys Val Arg Asp Gln Ala Gly
        210                 215                 220

Arg Met Asn Tyr Tyr Trp Thr Leu Leu Lys Pro Gly Asp Thr Ile
225                 230                 235
```

<210> SEQ ID NO 9
<211> LENGTH: 750
<212> TYPE: DNA
<213> ORGANISM: Artificial
<220> FEATURE:
<223> OTHER INFORMATION: synthetic

<400> SEQUENCE: 9

```
atgcagttac ttcgctgttt ttcaatattt tctgttattg cttcagtttt agcacaggaa    60
ctgacaacta tatgcgagca atcccctca ccaactttag aatcgacgcc gtactctttg    120
tcaacgacta ctattttggc caacgggaag gcaatgcaag gagttttgga atattacaaa   180
tcagtaacgt tgtcagtaa ttgcggttct caccccctcaa caactagcaa aggcagcccc    240
ataaacacac agtatgtttt tactagtgac acaatatgta taggctacca tgcgaacaat   300
tcaaccgaca ctgttgacac agtactcgag aagaatgtga cagtgacaca ctctgttaac   360
ctgctcgaag acagccacaa cggaaaacta tgtagattaa aaggaatagc cccactacaa   420
ttggggaaat gtaacatcgc cggatggctc ttggggaatc cagaatgcga cccactgctt   480
ccagtgagat catggtccta cattgtagaa acaccaaact ctgagaatgg aatatgttat   540
ccaggagatt tcatcgacta tgaggagctg agggagcaat tgagctcagt gtcatcattc   600
gaaagattcg aaatatttcc caagaaagc tcatggccca accacaacac aaacggagta   660
acggcagcat gctcccatga ggggaaaagc agttttttaca gaaatttgct atggctgacg   720
gagaaggagg gctcataccc aaagctgaaa                                    750
```

<210> SEQ ID NO 10
<211> LENGTH: 424
<212> TYPE: PRT
<213> ORGANISM: Artificial
<220> FEATURE:

<223> OTHER INFORMATION: synthetic

<400> SEQUENCE: 10

```
Met Gln Leu Leu Arg Cys Phe Ser Ile Phe Ser Val Ile Ala Ser Val
1               5                   10                  15

Leu Ala Gln Glu Leu Thr Thr Ile Cys Glu Gln Ile Pro Ser Pro Thr
            20                  25                  30

Leu Glu Ser Thr Pro Tyr Ser Leu Ser Thr Thr Thr Ile Leu Ala Asn
        35                  40                  45

Gly Lys Ala Met Gln Gly Val Phe Glu Tyr Tyr Lys Ser Val Thr Phe
    50                  55                  60

Val Ser Asn Cys Gly Ser His Pro Ser Thr Thr Ser Lys Gly Ser Pro
65                  70                  75                  80

Ile Asn Thr Gln Tyr Val Phe Thr Ser Asp Thr Ile Cys Ile Gly Tyr
                85                  90                  95

His Ala Asn Asn Ser Thr Asp Thr Val Asp Thr Val Leu Glu Lys Asn
            100                 105                 110

Val Thr Val Thr His Ser Val Asn Leu Leu Glu Asp Ser His Asn Gly
        115                 120                 125

Lys Leu Cys Arg Leu Lys Gly Ile Ala Pro Leu Gln Leu Gly Lys Cys
    130                 135                 140

Asn Ile Ala Gly Trp Leu Leu Gly Asn Pro Glu Cys Asp Pro Leu Leu
145                 150                 155                 160

Pro Val Arg Ser Trp Ser Tyr Ile Val Glu Thr Pro Asn Ser Glu Asn
                165                 170                 175

Gly Ile Cys Tyr Pro Gly Asp Phe Ile Asp Tyr Glu Glu Leu Arg Glu
            180                 185                 190

Gln Leu Ser Ser Val Ser Ser Phe Glu Arg Phe Glu Ile Phe Pro Lys
        195                 200                 205

Glu Ser Ser Trp Pro Asn His Asn Thr Asn Gly Val Thr Ala Ala Cys
    210                 215                 220

Ser His Glu Gly Lys Ser Ser Phe Tyr Arg Asn Leu Leu Trp Leu Thr
225                 230                 235                 240

Glu Lys Glu Gly Ser Tyr Pro Lys Leu Lys Asn Ser Tyr Val Asn Lys
                245                 250                 255

Lys Gly Lys Glu Val Leu Val Leu Trp Gly Ile His His Pro Ser Asn
            260                 265                 270

Ser Lys Glu Gln Gln Asn Leu Tyr Gln Asn Glu Asn Ala Tyr Val Ser
        275                 280                 285

Val Val Thr Ser Asn Tyr Asn Arg Arg Phe Thr Pro Glu Ile Ala Glu
    290                 295                 300

Arg Pro Lys Val Arg Asp Gln Ala Gly Arg Met Asn Tyr Tyr Trp Thr
305                 310                 315                 320

Leu Leu Lys Pro Gly Asp Thr Ile Ile Phe Glu Ala Asn Gly Asn Leu
                325                 330                 335

Ile Ala Pro Met Tyr Ala Phe Ala Leu Ser Arg Gly Phe Gly Ser Gly
            340                 345                 350

Ile Ile Thr Ser Asn Ala Ser Met His Glu Cys Asn Thr Lys Cys Gln
        355                 360                 365

Thr Pro Leu Gly Ala Ile Asn Ser Ser Leu Pro Tyr Gln Asn Ile His
    370                 375                 380

Pro Val Thr Ile Gly Glu Arg Pro Lys Tyr Val Arg Ser Ala Lys Leu
385                 390                 395                 400
```

```
Arg Met Val Thr Gly Leu Arg Asn Ile Pro Ser Ile Gln Ser Arg Gly
                405                 410                 415

Gly Gly His His His His His His
            420

<210> SEQ ID NO 11
<211> LENGTH: 331
<212> TYPE: PRT
<213> ORGANISM: Artificial
<220> FEATURE:
<223> OTHER INFORMATION: synthetic

<400> SEQUENCE: 11

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Ser His Asn Gly Lys Leu Cys Arg Leu Lys Gly Ile Ala
        35                  40                  45

Pro Leu Gln Leu Gly Lys Cys Asn Ile Ala Gly Trp Leu Leu Gly Asn
    50                  55                  60

Pro Glu Cys Asp Pro Leu Leu Pro Val Arg Ser Trp Ser Tyr Ile Val
65                  70                  75                  80

Glu Thr Pro Asn Ser Glu Asn Gly Ile Cys Tyr Pro Gly Asp Phe Ile
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Glu Ser Ser Trp Pro Asn His Asn Thr
        115                 120                 125

Thr Lys Gly Val Thr Ala Ala Cys Ser His Ala Gly Lys Ser Ser Phe
    130                 135                 140

Tyr Arg Asn Leu Leu Trp Leu Thr Glu Lys Glu Gly Ser Tyr Pro Lys
145                 150                 155                 160

Leu Lys Asn Ser Tyr Val Asn Lys Lys Gly Lys Glu Val Leu Val Leu
                165                 170                 175

Trp Gly Ile His His Pro Ser Asn Ser Lys Asp Gln Gln Asn Ile Tyr
            180                 185                 190

Gln Asn Glu Asn Ala Tyr Val Ser Val Val Thr Ser Asn Tyr Asn Arg
        195                 200                 205

Arg Phe Thr Pro Glu Ile Ala Glu Arg Pro Lys Val Arg Asp Gln Ala
    210                 215                 220

Gly Arg Met Asn Tyr Tyr Trp Thr Leu Leu Lys Pro Gly Asp Thr Ile
225                 230                 235                 240

Ile Phe Glu Ala Asn Gly Asn Leu Ile Ala Pro Arg Tyr Ala Phe Ala
                245                 250                 255

Leu Ser Arg Gly Phe Gly Ser Gly Ile Ile Thr Ser Asn Ala Ser Met
            260                 265                 270

His Glu Cys Asn Thr Lys Cys Gln Thr Pro Leu Gly Ala Ile Asn Ser
        275                 280                 285

Ser Leu Pro Phe Gln Asn Ile His Pro Val Thr Ile Gly Glu Cys Pro
    290                 295                 300

Lys Tyr Val Arg Ser Ala Lys Leu Arg Met Val Thr Gly Leu Arg Asn
305                 310                 315                 320

Ile Pro Ser Ile Gln Ser Arg Gly Leu Phe Gly
                325                 330
```

```
<210> SEQ ID NO 12
<211> LENGTH: 356
<212> TYPE: PRT
<213> ORGANISM: Influenza A virus

<400> SEQUENCE: 12

Ser Val Thr Phe Val Ser Asn Cys Gly Ser His Pro Ser Thr Thr Ser
1               5                   10                  15

Lys Gly Ser Pro Ile Asn Thr Gln Tyr Val Phe Thr Ser Asp Thr Ile
            20                  25                  30

Cys Ile Gly Tyr His Ala Asn Asn Ser Thr Asp Thr Val Asp Thr Val
        35                  40                  45

Leu Glu Lys Asn Val Thr Ala Thr His Ser Val Asn Leu Leu Glu Asp
    50                  55                  60

Ser His Asn Gly Lys Leu Cys Arg Leu Lys Gly Ile Ala Pro Leu Gln
65                  70                  75                  80

Leu Gly Lys Cys Asn Ile Ala Gly Trp Leu Leu Gly Asn Pro Glu Cys
                85                  90                  95

Asp Pro Leu Leu Pro Val Arg Ser Trp Ser Tyr Ile Val Glu Thr Pro
            100                 105                 110

Asn Ser Glu Asn Gly Ile Cys Tyr Pro Gly Asp Phe Ile Asp Tyr Glu
        115                 120                 125

Glu Leu Arg Glu Gln Leu Ser Ser Val Ser Ser Phe Glu Arg Phe Glu
    130                 135                 140

Ile Phe Pro Lys Glu Ser Ser Trp Pro Asn His Asn Thr Asn Gly Val
145                 150                 155                 160

Thr Ala Ala Cys Ser His Glu Gly Lys Ser Ser Phe Tyr Arg Asn Leu
                165                 170                 175

Leu Trp Leu Thr Glu Lys Glu Gly Ser Tyr Pro Lys Leu Lys Asn Ser
            180                 185                 190

Tyr Val Asn Lys Lys Gly Lys Glu Val Leu Val Leu Trp Gly Ile His
        195                 200                 205

His Pro Ser Asn Ser Lys Glu Gln Gln Asn Leu Tyr Gln Asn Glu Asn
    210                 215                 220

Ala Tyr Val Ser Val Val Thr Ser Asn Tyr Asn Arg Arg Phe Thr Pro
225                 230                 235                 240

Glu Ile Ala Glu Arg Pro Lys Val Arg Asp Gln Ala Gly Arg Met Asn
                245                 250                 255

Tyr Tyr Trp Thr Leu Leu Lys Pro Gly Asp Thr Ile Ile Phe Glu Ala
            260                 265                 270

Asn Gly Asn Leu Ile Ala Pro Met Ser Ala Phe Ala Leu Ser Arg Gly
        275                 280                 285

Phe Gly Ser Gly Ile Ile Thr Ser Asn Ala Ser Met His Glu Cys Asn
    290                 295                 300

Thr Lys Cys Gln Thr Pro Leu Gly Ala Ile Asn Ser Ser Leu Pro Tyr
305                 310                 315                 320

Gln Asn Ile His Pro Val Thr Ile Gly Glu Arg Pro Lys Tyr Val Arg
                325                 330                 335

Ser Ala Lys Leu Arg Met Val Thr Gly Leu Arg Asn Ile Pro Ser Ile
            340                 345                 350

Gln Ser Arg Gly
        355

<210> SEQ ID NO 13
```

<211> LENGTH: 1836
<212> TYPE: DNA
<213> ORGANISM: Artificial
<220> FEATURE:
<223> OTHER INFORMATION: synthetic

<400> SEQUENCE: 13

| | | | | | |
|---|---|---|---|---|---|
| atgcagttac | ttcgctgttt | ttcaatattt | tctgttattg | cttcagtttt | agcacaggaa | 60 |
| ctgacaacta | tatgcgagca | atcccctca | ccaactttag | aatcgacgcc | gtactctttg | 120 |
| tcaacgacta | ctattttggc | caacgggaag | gcaatgcaag | gagttttga | atattacaaa | 180 |
| tcagtaacgt | ttgtcagtaa | ttgcggttct | caccctcaa | caactagcaa | aggcagcccc | 240 |
| ataaacacac | agtatgtttt | tactagtgat | cagatttgca | ttggttacca | tgcaaacaac | 300 |
| tcgacagagc | aggttgacac | aataatggaa | agaacgtta | ctgttacaca | tgcccaagac | 360 |
| atactggaaa | agaaacacaa | cgggaagctc | tgcgatctag | atggagtgaa | gcctctaatt | 420 |
| ttgagagatt | gtagcgtagc | tggatggctc | ctcggaaacc | caatgtgtga | cgaattcatc | 480 |
| aatgtgccgg | aatggtctta | catagtggag | aaggccaatc | cagtcaatga | cctctgttac | 540 |
| ccaggggatt | tcaatgacta | tgaagaattg | aaacacctat | tgagcagaat | aaaccatttt | 600 |
| gagaaaattc | agatcatccc | caaagttct | tggtccagtc | atgaggcctc | attagggtg | 660 |
| agctcagcat | gtccatatca | gggaaagtcc | tccttttca | gaaatgtggt | atggcttatc | 720 |
| aaaaagaaca | gtacataccc | aacaataaag | aggagctaca | ataataccaa | ccaagaagat | 780 |
| cttttggtac | tgtgggggat | tcaccatcct | aatgatgcgg | cagagcagac | aaagctctat | 840 |
| caaaacccaa | ccacctatat | ttccgttggg | acatcaacac | taaaccagag | attggtacca | 900 |
| agaatagcta | ctagatccaa | agtaaacggg | caaagtggaa | ggatggagtt | cttctggaca | 960 |
| attttaaagc | caaatgatgc | aatcaacttc | gagagtaatg | gaaatttcat | tgctccagaa | 1020 |
| tatgcataca | aaattgtcaa | gaaggggac | tcaacaatta | tgaaaagtga | actcgagtat | 1080 |
| ggtaactgca | acaccaagtg | tcaaactcca | atggggggcga | taaactctag | catgccattc | 1140 |
| cacaatatac | accctctcac | cattggggaa | tgccccaaat | atgtgaaatc | aaacagatta | 1200 |
| gtccttgcga | ctgggctcag | aaatagccct | caaagagaga | aagaagaaa | aagagagga | 1260 |
| ttatttggag | ctatagcagg | ttttatagag | ggaggatggc | agggaatggt | agatggttgg | 1320 |
| tatgggtacc | accatagcaa | tgagcagggg | agtgggtacg | ctgcagacaa | agaatccact | 1380 |
| caaaaggcaa | tagatggagt | caccaataag | gtcaactcga | tcattgacaa | aatgaacact | 1440 |
| cagtttgagg | ccgttggaag | ggaatttaac | aacttagaaa | ggagaataga | gaatttaaac | 1500 |
| aagaagatgg | aagacgggtt | tctagatgtc | tggacttata | atgctgaact | tctggttctc | 1560 |
| atggaaaatg | agagaactct | agactttcat | gactcaaatg | tcaagaacct | ttacgacaag | 1620 |
| gtccgactac | agcttaggga | caatgcaaag | gagctgggaa | atggatgttt | tgagttctac | 1680 |
| cacaagtgtg | acaatgaatg | catggaaagt | gtaagaaatg | gactatga | ttatccccag | 1740 |
| tattcagaag | aagcgagact | aaaaagagag | gaaataagtg | gagtaaaatt | ggaatcaata | 1800 |
| ggaatttacc | aacatcacca | tcaccatcac | tgatag | | | 1836 |

<210> SEQ ID NO 14
<211> LENGTH: 610
<212> TYPE: PRT
<213> ORGANISM: Artificial
<220> FEATURE:
<223> OTHER INFORMATION: synthetic

<400> SEQUENCE: 14

-continued

```
Met Gln Leu Leu Arg Cys Phe Ser Ile Phe Ser Val Ile Ala Ser Val
1               5                   10                  15

Leu Ala Gln Glu Leu Thr Thr Ile Cys Glu Gln Ile Pro Ser Pro Thr
            20                  25                  30

Leu Glu Ser Thr Pro Tyr Ser Leu Ser Thr Thr Thr Ile Leu Ala Asn
        35                  40                  45

Gly Lys Ala Met Gln Gly Val Phe Glu Tyr Tyr Lys Ser Val Thr Phe
    50                  55                  60

Val Ser Asn Cys Gly Ser His Pro Ser Thr Thr Ser Lys Gly Ser Pro
65                  70                  75                  80

Ile Asn Thr Gln Tyr Val Phe Thr Ser Asp Gln Ile Cys Ile Gly Tyr
                85                  90                  95

His Ala Asn Asn Ser Thr Glu Gln Val Asp Thr Ile Met Glu Lys Asn
                100                 105                 110

Val Thr Val Thr His Ala Gln Asp Ile Leu Glu Lys His Asn Gly
            115                 120                 125

Lys Leu Cys Asp Leu Asp Gly Val Lys Pro Leu Ile Leu Arg Asp Cys
130                 135                 140

Ser Val Ala Gly Trp Leu Leu Gly Asn Pro Met Cys Asp Glu Phe Ile
145                 150                 155                 160

Asn Val Pro Glu Trp Ser Tyr Ile Val Glu Lys Ala Asn Pro Val Asn
                165                 170                 175

Asp Leu Cys Tyr Pro Gly Asp Phe Asn Asp Tyr Glu Glu Leu Lys His
            180                 185                 190

Leu Leu Ser Arg Ile Asn His Phe Glu Lys Ile Gln Ile Ile Pro Lys
            195                 200                 205

Ser Ser Trp Ser Ser His Glu Ala Ser Leu Gly Val Ser Ser Ala Cys
            210                 215                 220

Pro Tyr Gln Gly Lys Ser Ser Phe Phe Arg Asn Val Val Trp Leu Ile
225                 230                 235                 240

Lys Lys Asn Ser Thr Tyr Pro Thr Ile Lys Arg Ser Tyr Asn Asn Thr
                245                 250                 255

Asn Gln Glu Asp Leu Leu Val Leu Trp Gly Ile His His Pro Asn Asp
            260                 265                 270

Ala Ala Glu Gln Thr Lys Leu Tyr Gln Asn Pro Thr Thr Tyr Ile Ser
            275                 280                 285

Val Gly Thr Ser Thr Leu Asn Gln Arg Leu Val Pro Arg Ile Ala Thr
            290                 295                 300

Arg Ser Lys Val Asn Gly Gln Ser Gly Arg Met Glu Phe Phe Trp Thr
305                 310                 315                 320

Ile Leu Lys Pro Asn Asp Ala Ile Asn Phe Glu Ser Asn Gly Asn Phe
            325                 330                 335

Ile Ala Pro Glu Tyr Ala Tyr Lys Ile Val Lys Lys Gly Asp Ser Thr
            340                 345                 350

Ile Met Lys Ser Glu Leu Glu Tyr Gly Asn Cys Asn Thr Lys Cys Gln
            355                 360                 365

Thr Pro Met Gly Ala Ile Asn Ser Ser Met Pro Phe His Asn Ile His
        370                 375                 380

Pro Leu Thr Ile Gly Glu Cys Pro Lys Tyr Val Lys Ser Asn Arg Leu
385                 390                 395                 400

Val Leu Ala Thr Gly Leu Arg Asn Ser Pro Gln Arg Glu Arg Arg
                405                 410                 415
```

```
Lys Lys Arg Gly Leu Phe Gly Ala Ile Ala Gly Phe Ile Glu Gly Gly
            420                 425                 430

Trp Gln Gly Met Val Asp Gly Trp Tyr Gly Tyr His His Ser Asn Glu
        435                 440                 445

Gln Gly Ser Gly Tyr Ala Ala Asp Lys Glu Ser Thr Gln Lys Ala Ile
    450                 455                 460

Asp Gly Val Thr Asn Lys Val Asn Ser Ile Ile Asp Lys Met Asn Thr
465                 470                 475                 480

Gln Phe Glu Ala Val Gly Arg Glu Phe Asn Asn Leu Glu Arg Arg Ile
                485                 490                 495

Glu Asn Leu Asn Lys Lys Met Glu Asp Gly Phe Leu Asp Val Trp Thr
            500                 505                 510

Tyr Asn Ala Glu Leu Leu Val Leu Met Glu Asn Glu Arg Thr Leu Asp
        515                 520                 525

Phe His Asp Ser Asn Val Lys Asn Leu Tyr Asp Lys Val Arg Leu Gln
    530                 535                 540

Leu Arg Asp Asn Ala Lys Glu Leu Gly Asn Gly Cys Phe Glu Phe Tyr
545                 550                 555                 560

His Lys Cys Asp Asn Glu Cys Met Glu Ser Val Arg Asn Gly Thr Tyr
                565                 570                 575

Asp Tyr Pro Gln Tyr Ser Glu Glu Ala Arg Leu Lys Arg Glu Glu Ile
            580                 585                 590

Ser Gly Val Lys Leu Glu Ser Ile Gly Ile Tyr Gln His His His His
        595                 600                 605

His His
    610

<210> SEQ ID NO 15
<211> LENGTH: 2610
<212> TYPE: DNA
<213> ORGANISM: Artificial
<220> FEATURE:
<223> OTHER INFORMATION: synthetic

<400> SEQUENCE: 15
atggccgacg aggcaccaag tcttctaacc gaggtcgaaa cgtacgtact ctctatcatc     60
ccgtcaggcc cctcaaagc cgagatcgca cagagacttg aagatgtctt tgcaggaag    120 aacaccgatc ttgaggttct catggaatgg ctaaagacaa gaccaatcct gtcacctctg    180
actaagggga ttttaggatt tgtgttcacg ctcaccgtgc ccagtgagcg aggactgcag    240
cgtagacgct ttgtccaaaa tgcccttaat gggaacgggg atccaaataa catggacaaa    300
gcagttaaac tgtataggaa gctcaagagg gagataacat ccatggggc caaagaaatc    360 tcactcagtt attctgctgg tgcacttgcc agttgtatgg cctcatata acaggatg      420 ggggctgtga ccactgaagt ggcatttggc ctggtatgtg caacctgtga acagattgct    480
gactcccagc atcggtctca taggcaaatg gtgacaacaa ccaatccact aatcagacat    540
gagaacagaa tggttttagc cagcactaca gctaaggcta tggagcaaat ggctggatcg    600
agtgagcaag cagcagaggc catggaggtt gctagtcagg ctagacaaat ggtgcaagcg    660
atgagaacca ttgggactca tcctagctcc agtgctggtc tgaaaaatga tcttcttgaa    720
aatttgcagg cctatcagaa acgaatgggg gtgcagatgc aacggttcaa gggtggcggg    780
ctcgagatgg cgtcccaagg caccaaacgg tcttacgaac agatggagac tgatggagaa    840
cgccagaatg ccactgaaat cagagcatcc gtcggaaaaa tgattggtgg aattggacga    900
```

-continued

```
ttctacatcc aaatgtgcac cgaactcaaa ctcagtgatt atgagggacg gttgatccaa      960
aacagcttaa caatagagag aatggtgctc tctgcttttg acgaaaggag aaataaatac     1020
ctggaagaac atcccagtgc ggggaaagat cctaagaaaa ctggaggacc tatatacagg     1080
agagtaaacg gaaagtggat gagagaactc atcctttatg acaaagaaga aataaggcga     1140
atctggcgcc aagctaataa tggtgacgat gcaacggctg gtctgactca catgatgatc     1200
tggcattcca atttgaatga tgcaacttat cagaggacaa gagctcttgt tcgcaccgga     1260
atggatccca ggatgtgctc tctgatgcaa ggttcaactc tccctaggag gtctggagcc     1320
gcaggtgctg cagtcaaagg agttggaaca atggtgatgg aattggtcag gatgatcaaa     1380
cgtgggatca atgatcggaa cttctggagg ggtgagaatg gacgaaaaac aagaattgct     1440
tatgaaagaa tgtgcaacat tctcaaaggg aaatttcaaa ctgctgcaca aaaagcaatg     1500
atggatcaag tgagagagag ccggaaccca gggaatgctg agttcgaaga tctcactttt     1560
ctagcacggt ctgcactcat attgagaggg tcggttgctc acaagtcctg cctgcctgcc     1620
tgtgtgtatg acctgccgt agccagtggg tacgactttg aaagagaggg atactctcta      1680
gtcggaatag accctttcag actgcttcaa aacagccaag tgtacagcct aatcagacca     1740
aatgagaatc cagcacacaa gagtcaactg gtgtggatgg catgccattc tgccgcattt     1800
gaagatctaa gagtattaag cttcatcaaa gggacgaagg tgctcccaag agggaagctt     1860
tccactagag gagttcaaat tgcttccaat gaaaatatgg agactatgga atcaagtaca     1920
cttgaactga gaagcaggta ctgggccata aggaccagaa gtggaggaaa caccaatcaa     1980
cagagggcat ctgcgggcca atcagcata caacctacgt tctcagtaca gagaaatctc     2040
ccttttgaca gaacaaccgt tatggcagca ttcagtggga atacagaggg agaacatct     2100
gacatgagga ccgaaatcat aaggatgatg gaaagtgcaa gaccagaaga tgtgtctttc     2160
caggggcggg gagtcttcga gctctcggac gaaaaggcag cgagcccgat cgtgccttcc     2220
tttgacatga gtaatgaagg atcttatttc ttcggagaca tgcagagga gtacgacaat     2280
actagtatga gcctcctgac agaagtagag actccgatcc gcaacgaatg gggctgtcgg     2340
tgcaacggat catcggaccc atcattattg acggaggtcg aaacaccaac aaggaatgag     2400
tgggagtgca gatgttctga cagcagtgat ccgcccggga tgagcctcct gacagaagta     2460
gagactccga tccgcaacga atgggctgt cggtgcaacg atcatcgga cccatcatta      2520
ttgacggagg tcgaaacacc aacaaggaat gaatgggagt gcagatgttc tgacagcagt     2580
gatccgcatc accatcacca tcactaatag                                      2610
```

<210> SEQ ID NO 16
<211> LENGTH: 868
<212> TYPE: PRT
<213> ORGANISM: Artificial
<220> FEATURE:
<223> OTHER INFORMATION: synthetic

<400> SEQUENCE: 16

Met Ala Asp Glu Ala Pro Ser Leu Leu Thr Glu Val Glu Thr Tyr Val
1               5                   10                  15

Leu Ser Ile Ile Pro Ser Gly Pro Leu Lys Ala Glu Ile Ala Gln Arg
            20                  25                  30

Leu Glu Asp Val Phe Ala Gly Lys Asn Thr Asp Leu Glu Val Leu Met
        35                  40                  45

Glu Trp Leu Lys Thr Arg Pro Ile Leu Ser Pro Leu Thr Lys Gly Ile
    50                  55                  60

-continued

```
Leu Gly Phe Val Phe Thr Leu Thr Val Pro Ser Glu Arg Gly Leu Gln
 65                  70                  75                  80

Arg Arg Arg Phe Val Gln Asn Ala Leu Asn Gly Asn Gly Asp Pro Asn
                 85                  90                  95

Asn Met Asp Lys Ala Val Lys Leu Tyr Arg Lys Leu Lys Arg Glu Ile
            100                 105                 110

Thr Phe His Gly Ala Lys Glu Ile Ser Leu Ser Tyr Ser Ala Gly Ala
        115                 120                 125

Leu Ala Ser Cys Met Gly Leu Ile Tyr Asn Arg Met Gly Ala Val Thr
    130                 135                 140

Thr Glu Val Ala Phe Gly Leu Val Cys Ala Thr Cys Glu Gln Ile Ala
145                 150                 155                 160

Asp Ser Gln His Arg Ser His Arg Gln Met Val Thr Thr Asn Pro
                165                 170                 175

Leu Ile Arg His Glu Asn Arg Met Val Leu Ala Ser Thr Thr Ala Lys
            180                 185                 190

Ala Met Glu Gln Met Ala Gly Ser Ser Glu Gln Ala Ala Glu Ala Met
        195                 200                 205

Glu Val Ala Ser Gln Ala Arg Gln Met Val Gln Ala Met Arg Thr Ile
    210                 215                 220

Gly Thr His Pro Ser Ser Ser Ala Gly Leu Lys Asn Asp Leu Leu Glu
225                 230                 235                 240

Asn Leu Gln Ala Tyr Gln Lys Arg Met Gly Val Gln Met Gln Arg Phe
                245                 250                 255

Lys Gly Gly Gly Leu Glu Met Ala Ser Gln Gly Thr Lys Arg Ser Tyr
            260                 265                 270

Glu Gln Met Glu Thr Asp Gly Glu Arg Gln Asn Ala Thr Glu Ile Arg
        275                 280                 285

Ala Ser Val Gly Lys Met Ile Gly Gly Ile Gly Arg Phe Tyr Ile Gln
    290                 295                 300

Met Cys Thr Glu Leu Lys Leu Ser Asp Tyr Glu Gly Arg Leu Ile Gln
305                 310                 315                 320

Asn Ser Leu Thr Ile Glu Arg Met Val Leu Ser Ala Phe Asp Glu Arg
                325                 330                 335

Arg Asn Lys Tyr Leu Glu Glu His Pro Ser Ala Gly Lys Asp Pro Lys
            340                 345                 350

Lys Thr Gly Gly Pro Ile Tyr Arg Arg Val Asn Gly Lys Trp Met Arg
        355                 360                 365

Glu Leu Ile Leu Tyr Asp Lys Glu Glu Ile Arg Arg Ile Trp Arg Gln
    370                 375                 380

Ala Asn Asn Gly Asp Asp Ala Thr Ala Gly Leu Thr His Met Met Ile
385                 390                 395                 400

Trp His Ser Asn Leu Asn Asp Ala Thr Tyr Gln Arg Thr Arg Ala Leu
                405                 410                 415

Val Arg Thr Gly Met Asp Pro Arg Met Cys Ser Leu Met Gln Gly Ser
            420                 425                 430

Thr Leu Pro Arg Arg Ser Gly Ala Ala Gly Ala Ala Val Lys Gly Val
        435                 440                 445

Gly Thr Met Val Met Glu Leu Val Arg Met Ile Lys Arg Gly Ile Asn
    450                 455                 460

Asp Arg Asn Phe Trp Arg Gly Glu Asn Gly Arg Lys Thr Arg Ile Ala
465                 470                 475                 480
```

-continued

```
Tyr Glu Arg Met Cys Asn Ile Leu Lys Gly Lys Phe Gln Thr Ala Ala
                485                 490                 495
Gln Lys Ala Met Met Asp Gln Val Arg Glu Ser Arg Asn Pro Gly Asn
            500                 505                 510
Ala Glu Phe Glu Asp Leu Thr Phe Leu Ala Arg Ser Ala Leu Ile Leu
        515                 520                 525
Arg Gly Ser Val Ala His Lys Ser Cys Leu Pro Ala Cys Val Tyr Gly
    530                 535                 540
Pro Ala Val Ala Ser Gly Tyr Asp Phe Glu Arg Glu Gly Tyr Ser Leu
545                 550                 555                 560
Val Gly Ile Asp Pro Phe Arg Leu Leu Gln Asn Ser Gln Val Tyr Ser
                565                 570                 575
Leu Ile Arg Pro Asn Glu Asn Pro Ala His Lys Ser Gln Leu Val Trp
            580                 585                 590
Met Ala Cys His Ser Ala Ala Phe Glu Asp Leu Arg Val Leu Ser Phe
        595                 600                 605
Ile Lys Gly Thr Lys Val Leu Pro Arg Gly Lys Leu Ser Thr Arg Gly
    610                 615                 620
Val Gln Ile Ala Ser Asn Glu Asn Met Glu Thr Met Glu Ser Ser Thr
625                 630                 635                 640
Leu Glu Leu Arg Ser Arg Tyr Trp Ala Ile Arg Thr Arg Ser Gly Gly
                645                 650                 655
Asn Thr Asn Gln Gln Arg Ala Ser Ala Gly Gln Ile Ser Ile Gln Pro
            660                 665                 670
Thr Phe Ser Val Gln Arg Asn Leu Pro Phe Asp Arg Thr Thr Val Met
        675                 680                 685
Ala Ala Phe Ser Gly Asn Thr Glu Gly Arg Thr Ser Asp Met Arg Thr
    690                 695                 700
Glu Ile Ile Arg Met Met Glu Ser Ala Arg Pro Glu Asp Val Ser Phe
705                 710                 715                 720
Gln Gly Arg Gly Val Phe Glu Leu Ser Asp Glu Lys Ala Ala Ser Pro
                725                 730                 735
Ile Val Pro Ser Phe Asp Met Ser Asn Glu Gly Ser Tyr Phe Phe Gly
            740                 745                 750
Asp Asn Ala Glu Glu Tyr Asp Asn Thr Ser Met Ser Leu Leu Thr Glu
        755                 760                 765
Val Glu Thr Pro Ile Arg Asn Glu Trp Gly Cys Arg Cys Asn Gly Ser
    770                 775                 780
Ser Asp Pro Ser Leu Leu Thr Glu Val Glu Thr Pro Thr Arg Asn Glu
785                 790                 795                 800
Trp Glu Cys Arg Cys Ser Asp Ser Ser Asp Pro Pro Gly Met Ser Leu
                805                 810                 815
Leu Thr Glu Val Glu Thr Pro Ile Arg Asn Glu Trp Gly Cys Arg Cys
            820                 825                 830
Asn Gly Ser Ser Asp Pro Ser Leu Leu Thr Glu Val Glu Thr Pro Thr
        835                 840                 845
Arg Asn Glu Trp Glu Cys Arg Cys Ser Asp Ser Ser Asp Pro His His
    850                 855                 860
His His His His
865

<210> SEQ ID NO 17
<211> LENGTH: 1706
<212> TYPE: DNA
```

<213> ORGANISM: Artificial
<220> FEATURE:
<223> OTHER INFORMATION: synthetic

<400> SEQUENCE: 17

| | | | | | |
|---|---|---|---|---|---|
| atggccgacg | aggcaccagc | gtcccaaggc | accaaacggt | cttacgaaca | gatggagact | 60 |
| gatggagaac | gccagaatgc | cactgaaatc | agagcatccg | tcggaaaaat | gattggtgga | 120 |
| attggacgat | tctacatcca | aatgtgcacc | gaactcaaac | tcagtgatta | tgagggacgg | 180 |
| ttgatccaaa | acagcttaac | aatagagaga | atggtgctct | ctgcttttga | cgaaaggaga | 240 |
| aataaatacc | tggaagaaca | tcccagtgcg | gggaaagatc | ctaagaaaac | tggaggacct | 300 |
| atatacagga | gagtaaacgg | aaagtggatg | agagaactca | tcctttatga | caaagaagaa | 360 |
| ataaggcgaa | tctggcgcca | agctaataat | ggtgacgatg | caacggctgg | tctgactcac | 420 |
| atgatgatct | ggcattccaa | tttgaatgat | gcaacttatc | agaggacaag | agctcttgtt | 480 |
| cgcaccggaa | tggatcccag | gatgtgctct | ctgatgcaag | gttcaactct | ccctaggagg | 540 |
| tctggagccg | caggtgctgc | agtcaaagga | gttggaacaa | tggtgatgga | attggtcagg | 600 |
| atgatcaaac | gtgggatcaa | tgatcggaac | ttctggaggg | gtgagaatgg | acgaaaaaca | 660 |
| agaattgctt | atgaaagaat | gtgcaacatt | ctcaaaggga | aatttcaaac | tgctgcacaa | 720 |
| aaagcaatga | tggatcaagt | gagagagagc | cggaacccag | ggatgctga | gttcgaagat | 780 |
| ctcactttc | tagcacggtc | tgcactcata | ttgagagggt | cggttgctca | caagtcctgc | 840 |
| ctgcctgcct | gtgtgtatgg | acctgccgta | gccagtgggt | acgactttga | aagagggga | 900 |
| tactctctag | tcggaataga | ccctttcaga | ctgcttcaaa | acagccaagt | gtacagccta | 960 |
| atcagaccaa | atgagaatcc | agcacacaag | agtcaactgg | tgtggatggc | atgccattct | 1020 |
| gccgcatttg | aagatctaag | agtattaagc | ttcatcaaag | gacgaaggt | gctcccaaga | 1080 |
| gggaagcttt | ccactagagg | agttcaaatt | gcttccaatg | aaaatatgga | gactatggaa | 1140 |
| tcaagtacac | ttgaactgag | aagcaggtac | tgggccataa | ggaccagaag | tggaggaaac | 1200 |
| accaatcaac | agagggcatc | tgcgggccaa | atcagcatac | aacctacgtt | ctcagtacag | 1260 |
| agaaatctcc | cttttgacag | aacaaccgtt | atggcagcat | tcagtgggaa | tacagagggg | 1320 |
| agaacatctg | acatgaggac | cgaaatcata | aggatgatgg | aaagtgcaag | accagaagat | 1380 |
| gtgtctttcc | aggggcgggg | agtcttcgag | ctctcggacg | aaaaggcagc | gagcccgatc | 1440 |
| gtgccttcct | ttgacatgag | taatgaagga | tcttatttct | tcggagacaa | tgcagaggag | 1500 |
| tacgacaata | ctagtatgag | cctcctgaca | gaagtagaga | ctccgatccg | caacgaatgg | 1560 |
| ggctgtcggt | gcaacggatc | atcggacccc | gggatgagcc | tcctgacaga | agtagagact | 1620 |
| ccgatccgca | acgaatgggg | ctgtcggtgc | aacggatcat | cggacggtgg | cgggcatcac | 1680 |
| catcaccatc | actaataggc | ggccgc | | | | 1706 |

<210> SEQ ID NO 18
<211> LENGTH: 564
<212> TYPE: PRT
<213> ORGANISM: Artificial
<220> FEATURE:
<223> OTHER INFORMATION: synthetic

<400> SEQUENCE: 18

Met Ala Asp Glu Ala Pro Ala Ser Gln Gly Thr Lys Arg Ser Tyr Glu
1               5                   10                  15

Gln Met Glu Thr Asp Gly Glu Arg Gln Asn Ala Thr Glu Ile Arg Ala
            20                  25                  30

```
Ser Val Gly Lys Met Ile Gly Ile Gly Arg Phe Tyr Ile Gln Met
         35                  40                  45
Cys Thr Glu Leu Lys Leu Ser Asp Tyr Glu Gly Arg Leu Ile Gln Asn
 50                  55                  60
Ser Leu Thr Ile Glu Arg Met Val Leu Ser Ala Phe Asp Glu Arg Arg
 65                  70                  75                  80
Asn Lys Tyr Leu Glu Glu His Pro Ser Ala Gly Lys Asp Pro Lys Lys
                 85                  90                  95
Thr Gly Gly Pro Ile Tyr Arg Arg Val Asn Gly Lys Trp Met Arg Glu
                100                 105                 110
Leu Ile Leu Tyr Asp Lys Glu Glu Ile Arg Arg Ile Trp Arg Gln Ala
            115                 120                 125
Asn Asn Gly Asp Asp Ala Thr Ala Gly Leu Thr His Met Met Ile Trp
130                 135                 140
His Ser Asn Leu Asn Asp Ala Thr Tyr Gln Arg Thr Arg Ala Leu Val
145                 150                 155                 160
Arg Thr Gly Met Asp Pro Arg Met Cys Ser Leu Met Gln Gly Ser Thr
                165                 170                 175
Leu Pro Arg Arg Ser Gly Ala Ala Gly Ala Ala Val Lys Gly Val Gly
            180                 185                 190
Thr Met Val Met Glu Leu Val Arg Met Ile Lys Arg Gly Ile Asn Asp
            195                 200                 205
Arg Asn Phe Trp Arg Gly Glu Asn Gly Arg Lys Thr Arg Ile Ala Tyr
210                 215                 220
Glu Arg Met Cys Asn Ile Leu Lys Gly Lys Phe Gln Thr Ala Ala Gln
225                 230                 235                 240
Lys Ala Met Met Asp Gln Val Arg Glu Ser Arg Asn Pro Gly Asn Ala
                245                 250                 255
Glu Phe Glu Asp Leu Thr Phe Leu Ala Arg Ser Ala Leu Ile Leu Arg
            260                 265                 270
Gly Ser Val Ala His Lys Ser Cys Leu Pro Ala Cys Val Tyr Gly Pro
            275                 280                 285
Ala Val Ala Ser Gly Tyr Asp Phe Glu Arg Glu Gly Tyr Ser Leu Val
290                 295                 300
Gly Ile Asp Pro Phe Arg Leu Leu Gln Asn Ser Gln Val Tyr Ser Leu
305                 310                 315                 320
Ile Arg Pro Asn Glu Asn Pro Ala His Lys Ser Gln Leu Val Trp Met
                325                 330                 335
Ala Cys His Ser Ala Ala Phe Glu Asp Leu Arg Val Leu Ser Phe Ile
                340                 345                 350
Lys Gly Thr Lys Val Leu Pro Arg Gly Lys Leu Ser Thr Arg Gly Val
            355                 360                 365
Gln Ile Ala Ser Asn Glu Asn Met Glu Thr Met Glu Ser Ser Thr Leu
            370                 375                 380
Glu Leu Arg Ser Arg Tyr Trp Ala Ile Arg Thr Arg Ser Gly Gly Asn
385                 390                 395                 400
Thr Asn Gln Gln Arg Ala Ser Ala Gly Gln Ile Ser Ile Gln Pro Thr
                405                 410                 415
Phe Ser Val Gln Arg Asn Leu Pro Phe Asp Arg Thr Thr Val Met Ala
            420                 425                 430
Ala Phe Ser Gly Asn Thr Glu Gly Arg Thr Ser Asp Met Arg Thr Glu
            435                 440                 445
```

```
Ile Ile Arg Met Met Glu Ser Ala Arg Pro Glu Asp Val Ser Phe Gln
    450                 455                 460

Gly Arg Gly Val Phe Glu Leu Ser Asp Glu Lys Ala Ala Ser Pro Ile
465                 470                 475                 480

Val Pro Ser Phe Asp Met Ser Asn Glu Gly Ser Tyr Phe Phe Gly Asp
                485                 490                 495

Asn Ala Glu Glu Tyr Asp Asn Thr Ser Met Ser Leu Leu Thr Glu Val
            500                 505                 510

Glu Thr Pro Ile Arg Asn Glu Trp Gly Cys Arg Cys Asn Gly Ser Ser
        515                 520                 525

Asp Pro Gly Met Ser Leu Leu Thr Glu Val Glu Thr Pro Ile Arg Asn
    530                 535                 540

Glu Trp Gly Cys Arg Cys Asn Gly Ser Ser Asp Gly Gly Gly His His
545                 550                 555                 560

His His His His
```

<210> SEQ ID NO 19
<211> LENGTH: 1884
<212> TYPE: DNA
<213> ORGANISM: Artificial
<220> FEATURE:
<223> OTHER INFORMATION: synthetic

<400> SEQUENCE: 19

| | | | | |
|---|---|---|---|---|
| atgcagttac | ttcgctgttt | ttcaatattt | tctgttattg | cttcagtttt | agcacaggaa | 60 |
| ctgacaacta | tatgcgagca | atcccctca | ccaactttag | aatcgacgcc | gtactctttg | 120 |
| tcaacgacta | ctattttggc | caacgggaag | gcaatgcaag | gagttttga | atattacaaa | 180 |
| tcagtaacgt | ttgtcagtaa | ttgcggttct | cacccctcaa | caactagcaa | aggcagcccc | 240 |
| ataaacacac | agtatgtttt | tactagtaag | gcaaacctac | tggtcctgtt | atgtgcactt | 300 |
| gcagctgcag | atgcagatca | gatttgcatt | ggttaccatg | caaacaactc | gacagagcag | 360 |
| gttgacacaa | taatggaaaa | gaacgttact | gttacacatg | cccaagacat | actggaaaag | 420 |
| aaacacaacg | ggaagctctg | cgatctagat | ggagtgaagc | ctctaatttt | gagagattgt | 480 |
| agcgtagctg | gatggctcct | cggaaaccca | atgtgtgacg | aattcatcaa | tgtgccggaa | 540 |
| tggtcttaca | tagtgagaa | ggccaatcca | gtcaatgacc | tctgttaccc | agggatttc | 600 |
| aatgactatg | aagaattgaa | acacctattg | agcagaataa | accattttga | gaaaattcag | 660 |
| atcatcccca | aaagttcttg | gtccagtcat | gaggcctcat | taggggtgag | ctcagcatgt | 720 |
| ccatatcagg | gaaagtcctc | cttttttcaga | aatgtggtat | ggcttatcaa | aagaacagt | 780 |
| acatacccaa | caataaagag | gagctacaat | aataccaacc | aagaagatct | tttggtactg | 840 |
| tgggggattc | accatcctaa | tgatgcggca | gagcagacaa | agctctatca | aaacccaacc | 900 |
| acctatattt | ccgttgggac | atcaacacta | accagagatt | ggtaccaag | aatagctact | 960 |
| agatccaaag | taaacgggca | agtggaagg | atggagttct | tctggacaat | tttaaagcca | 1020 |
| aatgatgcaa | tcaacttcga | gagtaatgga | aatttcattg | ctccagaata | tgcatacaaa | 1080 |
| attgtcaaga | aaggggactc | aacaattatg | aaaagtgaac | tcgagtatgg | taactgcaac | 1140 |
| accaagtgtc | aaactccaat | ggggcgata | aactctagca | tgccattcca | caatatacac | 1200 |
| cctctcacca | ttggggaatg | ccccaaatat | gtgaaatcaa | acagattagt | ccttgcgact | 1260 |
| gggctcagaa | atagccctca | agagagagaa | agaagaaaa | agagaggatt | atttggagct | 1320 |
| atagcaggtt | ttatagaggg | aggatggcag | ggaatggtag | atggttggta | tgggtaccac | 1380 |

```
catagcaatg agcaggggag tgggtacgct gcagacaaag aatccactca aaaggcaata    1440
gatggagtca ccaataaggt caactcgatc attgacaaaa tgaacactca gtttgaggcc    1500
gttggaaggg aatttaacaa cttagaaagg agaatagaga atttaaacaa gaagatggaa    1560
gacgggtttc tagatgtctg gacttataat gctgaacttc tggttctcat ggaaaatgag    1620
agaactctag actttcatga ctcaaatgtc aagaaccttt acgacaaggt ccgactacag    1680
cttagggaca atgcaaagga gctgggaaat ggatgttttg agttctacca caagtgtgac    1740
aatgaatgca tggaaagtgt aagaaatggg acttatgatt atccccagta ttcagaagaa    1800
gcgagactaa aaagagagga aataagtgga gtaaaattgg aatcaatagg aatttaccaa    1860
catcaccatc accatcactg atag                                          1884
```

```
<210> SEQ ID NO 20
<211> LENGTH: 626
<212> TYPE: PRT
<213> ORGANISM: Artificial
<220> FEATURE:
<223> OTHER INFORMATION: synthetic

<400> SEQUENCE: 20
```

Met Gln Leu Leu Arg Cys Phe Ser Ile Phe Ser Val Ile Ala Ser Val
1               5                   10                  15

Leu Ala Gln Glu Leu Thr Thr Ile Cys Glu Gln Ile Pro Ser Pro Thr
            20                  25                  30

Leu Glu Ser Thr Pro Tyr Ser Leu Ser Thr Thr Thr Ile Leu Ala Asn
        35                  40                  45

Gly Lys Ala Met Gln Gly Val Phe Glu Tyr Tyr Lys Ser Val Thr Phe
    50                  55                  60

Val Ser Asn Cys Gly Ser His Pro Ser Thr Thr Ser Lys Gly Ser Pro
65                  70                  75                  80

Ile Asn Thr Gln Tyr Val Phe Thr Ser Lys Ala Asn Leu Leu Val Leu
                85                  90                  95

Leu Cys Ala Leu Ala Ala Ala Asp Ala Asp Gln Ile Cys Ile Gly Tyr
            100                 105                 110

His Ala Asn Asn Ser Thr Glu Gln Val Asp Thr Ile Met Glu Lys Asn
        115                 120                 125

Val Thr Val Thr His Ala Gln Asp Ile Leu Glu Lys Lys His Asn Gly
    130                 135                 140

Lys Leu Cys Asp Leu Asp Gly Val Lys Pro Leu Ile Leu Arg Asp Cys
145                 150                 155                 160

Ser Val Ala Gly Trp Leu Leu Gly Asn Pro Met Cys Asp Glu Phe Ile
                165                 170                 175

Asn Val Pro Glu Trp Ser Tyr Ile Val Glu Lys Ala Asn Pro Val Asn
            180                 185                 190

Asp Leu Cys Tyr Pro Gly Asp Phe Asn Asp Tyr Glu Glu Leu Lys His
        195                 200                 205

Leu Leu Ser Arg Ile Asn His Phe Glu Lys Ile Gln Ile Ile Pro Lys
    210                 215                 220

Ser Ser Trp Ser Ser His Glu Ala Ser Leu Gly Val Ser Ser Ala Cys
225                 230                 235                 240

Pro Tyr Gln Gly Lys Ser Ser Phe Phe Arg Asn Val Val Trp Leu Ile
                245                 250                 255

Lys Lys Asn Ser Thr Tyr Pro Thr Ile Lys Arg Ser Tyr Asn Asn Thr
            260                 265                 270

Asn Gln Glu Asp Leu Leu Val Leu Trp Gly Ile His His Pro Asn Asp
            275                 280                 285

Ala Ala Glu Gln Thr Lys Leu Tyr Gln Asn Pro Thr Thr Tyr Ile Ser
        290                 295                 300

Val Gly Thr Ser Thr Leu Asn Gln Arg Leu Val Pro Arg Ile Ala Thr
305                 310                 315                 320

Arg Ser Lys Val Asn Gly Gln Ser Gly Arg Met Glu Phe Phe Trp Thr
                325                 330                 335

Ile Leu Lys Pro Asn Asp Ala Ile Asn Phe Glu Ser Asn Gly Asn Phe
            340                 345                 350

Ile Ala Pro Glu Tyr Ala Tyr Lys Ile Val Lys Lys Gly Asp Ser Thr
        355                 360                 365

Ile Met Lys Ser Glu Leu Glu Tyr Gly Asn Cys Asn Thr Lys Cys Gln
    370                 375                 380

Thr Pro Met Gly Ala Ile Asn Ser Ser Met Pro Phe His Asn Ile His
385                 390                 395                 400

Pro Leu Thr Ile Gly Glu Cys Pro Lys Tyr Val Lys Ser Asn Arg Leu
                405                 410                 415

Val Leu Ala Thr Gly Leu Arg Asn Ser Pro Gln Arg Glu Arg Arg Arg
            420                 425                 430

Lys Lys Arg Gly Leu Phe Gly Ala Ile Ala Gly Phe Ile Glu Gly Gly
        435                 440                 445

Trp Gln Gly Met Val Asp Gly Trp Tyr Gly Tyr His His Ser Asn Glu
    450                 455                 460

Gln Gly Ser Gly Tyr Ala Ala Asp Lys Glu Ser Thr Gln Lys Ala Ile
465                 470                 475                 480

Asp Gly Val Thr Asn Lys Val Asn Ser Ile Ile Asp Lys Met Asn Thr
                485                 490                 495

Gln Phe Glu Ala Val Gly Arg Glu Phe Asn Asn Leu Glu Arg Arg Ile
            500                 505                 510

Glu Asn Leu Asn Lys Lys Met Glu Asp Gly Phe Leu Asp Val Trp Thr
        515                 520                 525

Tyr Asn Ala Glu Leu Leu Val Leu Met Glu Asn Glu Arg Thr Leu Asp
    530                 535                 540

Phe His Asp Ser Asn Val Lys Asn Leu Tyr Asp Lys Val Arg Leu Gln
545                 550                 555                 560

Leu Arg Asp Asn Ala Lys Glu Leu Gly Asn Gly Cys Phe Glu Phe Tyr
                565                 570                 575

His Lys Cys Asp Asn Glu Cys Met Glu Ser Val Arg Asn Gly Thr Tyr
            580                 585                 590

Asp Tyr Pro Gln Tyr Ser Glu Glu Ala Arg Leu Lys Arg Glu Glu Ile
        595                 600                 605

Ser Gly Val Lys Leu Glu Ser Ile Gly Ile Tyr Gln His His His His
    610                 615                 620

His His
625

<210> SEQ ID NO 21
<211> LENGTH: 1851
<212> TYPE: DNA
<213> ORGANISM: Artificial
<220> FEATURE:
<223> OTHER INFORMATION: synthetic

<400> SEQUENCE: 21

```
atgcagttac ttcgctgttt ttcaatattt tctgttattg cttcagtttt agcacaggat    60
cagatttgca ttggttacca tgcaaacaac tcgacagagc aggttgacac aataatggaa   120
aagaacgtta ctgttacaca tgcccaagac atactggaaa agaaacacaa cgggaagctc   180
tgcgatctag atggagtgaa gcctctaatt ttgagagatt gtagcgtagc tggatggctc   240
ctcggaaacc caatgtgtga cgaattcatc aatgtgccgg aatggtctta catagtggag   300
aaggccaatc cagtcaatga cctctgttac ccagggggatt caatgacta tgaagaattg   360
aaacacctat tgagcagaat aaaccatttt gagaaaattc agatcatccc caaaagttct   420
tggtccagtc atgaggcctc attaggggtg agctcagcat gtccatatca gggaaagtcc   480
tcctttttca gaaatgtggt atggcttatc aaaagaaca gtacataccc aacaataaag   540
aggagctaca ataataccaa ccaagaagat cttttggtac tgtgggggat tcaccatcct   600
aatgatgcgg cagagcagac aaagctctat caaaacccaa ccacctatat ttccgttggg   660
acatcaacac taaccagag attggtacca agaatagcta ctagatccaa agtaaacggg   720
caaagtggaa ggatggagtt cttctggaca attttaaagc caatgatgc aatcaacttc   780
gagagtaatg gaaatttcat tgctccagaa tatgcataca aaattgtcaa gaaaggggac   840
tcaacaatta tgaaaagtga actcgagtat ggtaactgca acaccaagtg tcaaactcca   900
atgggggcga taaactctag catgccattc acaatatac accctctcac cattggggaa   960
tgccccaaat atgtgaaatc aaacagatta gtccttgcga ctgggctcag aaatagccct  1020
caaagagaga aagaagaaa aagagagga ttatttggag ctatagcagg ttttatagag  1080
ggaggatggc agggaatggt agatggttgg tatgggtacc accatagcaa tgagcagggg  1140
agtgggtacg ctgcggacaa agaatccact caaaaggcaa tagatggagt caccaataag  1200
gtcaactcga tcattgacaa aatgaacact cagtttgagg ccgttggaag ggaatttaac  1260
aacttagaaa ggagaataga gaatttaaac aagaagatgg aagacgggtt tctagatgtc  1320
tggacttata atgctgaact tctggttctc atggaaaatg agagaactct agactttcat  1380
gactcaaatg tcaagaacct ttacgacaag gtccgactac agcttaggga caatgcaaag  1440
gagctgggaa atggatgttt tgagttctac cacaagtgtg acaatgaatg catggaaagt  1500
gtaagaaatg gacttatga ttatcccag tattcagaag aagcgagact aaaaagagag  1560
gaaataagtg gagtaaaatt ggaatcaata ggaatttacc aaactagtca ccaccaccac  1620
caccacgacg acgacgacga caaagaactg caactatat gcgagcaaat cccctcacca  1680
actttagaat cgacgccgta ctctttgtca acgactacta ttttggccaa cgggaaggca  1740
atgcaaggag ttttttgaata ttacaaatca gtaacgtttg tcagtaattg cggttctcac  1800
ccctcaacaa ctagcaaagg cagccccata aacacacagt atgttttttg a           1851
```

<210> SEQ ID NO 22
<211> LENGTH: 616
<212> TYPE: PRT
<213> ORGANISM: Artificial
<220> FEATURE:
<223> OTHER INFORMATION: synthetic

<400> SEQUENCE: 22

Met Gln Leu Leu Arg Cys Phe Ser Ile Phe Ser Val Ile Ala Ser Val
1               5                   10                  15

Leu Ala Gln Asp Gln Ile Cys Ile Gly Tyr His Ala Asn Asn Ser Thr
            20                  25                  30

Glu Gln Val Asp Thr Ile Met Glu Lys Asn Val Thr Val Thr His Ala

```
                35                  40                  45
Gln Asp Ile Leu Glu Lys Lys His Asn Gly Lys Leu Cys Asp Leu Asp
 50                  55                  60
Gly Val Lys Pro Leu Ile Leu Arg Asp Cys Ser Val Ala Gly Trp Leu
 65                  70                  75                  80
Leu Gly Asn Pro Met Cys Asp Glu Phe Ile Asn Val Pro Glu Trp Ser
                 85                  90                  95
Tyr Ile Val Glu Lys Ala Asn Pro Val Asn Asp Leu Cys Tyr Pro Gly
                100                 105                 110
Asp Phe Asn Asp Tyr Glu Glu Leu Lys His Leu Leu Ser Arg Ile Asn
                115                 120                 125
His Phe Glu Lys Ile Gln Ile Ile Pro Lys Ser Ser Trp Ser Ser His
                130                 135                 140
Glu Ala Ser Leu Gly Val Ser Ser Ala Cys Pro Tyr Gln Gly Lys Ser
145                 150                 155                 160
Ser Phe Phe Arg Asn Val Val Trp Leu Ile Lys Lys Asn Ser Thr Tyr
                165                 170                 175
Pro Thr Ile Lys Arg Ser Tyr Asn Asn Thr Asn Gln Glu Asp Leu Leu
                180                 185                 190
Val Leu Trp Gly Ile His His Pro Asn Asp Ala Ala Glu Gln Thr Lys
                195                 200                 205
Leu Tyr Gln Asn Pro Thr Thr Tyr Ile Ser Val Gly Thr Ser Thr Leu
                210                 215                 220
Asn Gln Arg Leu Val Pro Arg Ile Ala Thr Arg Ser Lys Val Asn Gly
225                 230                 235                 240
Gln Ser Gly Arg Met Glu Phe Phe Trp Thr Ile Leu Lys Pro Asn Asp
                245                 250                 255
Ala Ile Asn Phe Glu Ser Asn Gly Asn Phe Ile Ala Pro Glu Tyr Ala
                260                 265                 270
Tyr Lys Ile Val Lys Lys Gly Asp Ser Thr Ile Met Lys Ser Glu Leu
                275                 280                 285
Glu Tyr Gly Asn Cys Asn Thr Lys Cys Gln Thr Pro Met Gly Ala Ile
                290                 295                 300
Asn Ser Ser Met Pro Phe His Asn Ile His Pro Leu Thr Ile Gly Glu
305                 310                 315                 320
Cys Pro Lys Tyr Val Lys Ser Asn Arg Leu Val Leu Ala Thr Gly Leu
                325                 330                 335
Arg Asn Ser Pro Gln Arg Glu Arg Arg Lys Lys Arg Gly Leu Phe
                340                 345                 350
Gly Ala Ile Ala Gly Phe Ile Glu Gly Gly Trp Gln Gly Met Val Asp
                355                 360                 365
Gly Trp Tyr Gly Tyr His His Ser Asn Glu Gln Gly Ser Gly Tyr Ala
                370                 375                 380
Ala Asp Lys Glu Ser Thr Gln Lys Ala Ile Asp Gly Val Thr Asn Lys
385                 390                 395                 400
Val Asn Ser Ile Ile Asp Lys Met Asn Thr Gln Phe Glu Ala Val Gly
                405                 410                 415
Arg Glu Phe Asn Asn Leu Glu Arg Arg Ile Glu Asn Leu Asn Lys Lys
                420                 425                 430
Met Glu Asp Gly Phe Leu Asp Val Trp Thr Tyr Asn Ala Glu Leu Leu
                435                 440                 445
Val Leu Met Glu Asn Glu Arg Thr Leu Asp Phe His Asp Ser Asn Val
450                 455                 460
```

```
Lys Asn Leu Tyr Asp Lys Val Arg Leu Gln Leu Arg Asp Asn Ala Lys
465                 470                 475                 480

Glu Leu Gly Asn Gly Cys Phe Glu Phe Tyr His Lys Cys Asp Asn Glu
            485                 490                 495

Cys Met Glu Ser Val Arg Asn Gly Thr Tyr Asp Tyr Pro Gln Tyr Ser
            500                 505                 510

Glu Glu Ala Arg Leu Lys Arg Glu Glu Ile Ser Gly Val Lys Leu Glu
            515                 520                 525

Ser Ile Gly Ile Tyr Gln Thr Ser His His His His His His Asp Asp
530                 535                 540

Asp Asp Asp Lys Glu Leu Thr Thr Ile Cys Glu Gln Ile Pro Ser Pro
545                 550                 555                 560

Thr Leu Glu Ser Thr Pro Tyr Ser Leu Ser Thr Thr Thr Ile Leu Ala
                565                 570                 575

Asn Gly Lys Ala Met Gln Gly Val Phe Glu Tyr Tyr Lys Ser Val Thr
            580                 585                 590

Phe Val Ser Asn Cys Gly Ser His Pro Ser Thr Thr Ser Lys Gly Ser
            595                 600                 605

Pro Ile Asn Thr Gln Tyr Val Phe
610                 615

<210> SEQ ID NO 23
<211> LENGTH: 1857
<212> TYPE: DNA
<213> ORGANISM: Artificial
<220> FEATURE:
<223> OTHER INFORMATION: synthetic

<400> SEQUENCE: 23
atgcttttgc aagctttcct tttccttttg gctggttttg cagccaaaat atctgcatca      60
atggatcaga tttgcattgg ttaccatgca acaactcga cagagcaggt tgacacaata     120
atggaaaaga acgttactgt tacacatgcc caagacatac tggaaaagaa acacaacggg     180
aagctctgcg atctagatgg agtgaagcct ctaattttga gagattgtag cgtagctgga     240
tggctcctcg gaaacccaat gtgtgacgaa ttcatcaatg tgccggaatg gtcttacata     300
gtggagaagg ccaatccagt caatgacctc tgttacccag gggatttcaa tgactatgaa     360
gaattgaaac ctattgag cagaataaac cattttgaga aaattcagat catccccaaa     420
agttcttggt ccagtcatga ggcctcatta ggggtgagct cagcatgtcc atatcaggga     480
aagtcctcct ttttcagaaa tgtggtatgg cttatcaaaa agaacagtac atacccaaca     540
ataaagagga gctacaataa taccaaccaa gaagatcttt tggtactgtg ggggattcac     600
catcctaatg atgcggcaga gcagacaaag ctctatcaaa acccaaccac ctatatttcc     660
gttgggacat caactctaaa ccagagattg gtaccaagaa tagctactag atccaaagta     720
aacgggcaaa gtggaaggat ggagttcttc tggacaattt taaagccaaa tgatgcaatc     780
aacttcgaga gtaatggaaa tttcattgct ccagaatatg catacaaaat tgtcaagaaa     840
ggggactcaa caattatgaa aagtgaactc gagtatggta actgcaacac caagtgtcaa     900
actccaatgg gggcgataaa ctctagcatg ccattccaca atatacaccc tctcaccatt     960
ggggaatgcc ccaaatatgt gaaatcaaac agattagtcc ttgcgactgg gctcagaaat    1020
agccctcaaa gagagagaag aagaaaaaag agaggattat ttggagctat agcaggtttt    1080
atagagggag gatggcaggg aatggtagat ggttggtatg gtaccaccca tagcaatgag    1140
```

-continued

```
caggggagtg ggtacgctgc ggacaaagaa tccactcaaa aggcaataga tggagtcacc    1200
aataaggtca actcgatcat tgacaaaatg aacactcagt tgaggccgt tggaagggaa     1260 tttaacaact tagaaaggag aatagagaat ttaaacaaga agatggaaga cgggtttcta    1320
gatgtctgga cttataatgc tgaacttctg gttctcatgg aaaatgagag aactctagac    1380
tttcatgact caaatgtcaa gaacctttac gacaaggtcc gactacagct tagggacaat    1440
gcaaaggagc tgggaaatgg atgttttgag ttctaccaca gtgtgacaa tgaatgcatg     1500 gaaagtgtaa gaaatgggac ttatgattat ccccagtatt cagaagaagc gagactaaaa    1560
agagaggaaa taagtggagt aaaattggaa tcaataggaa tttaccaaac tagtcaccac    1620
caccaccacc acgacgacga cgacgacaaa gccatttctc aaatcactga cggtcaaatc    1680
caagctacta ccactgctac caccgaagct accaccactg ctgccccatc ttccaccgtt    1740
gaaactgttt ctccatccag caccgaaact atctctcaac aaactgaaaa tggtgctgct    1800
aaggccgctg tcggtatggg tgccggtgct ctagctgctg ctgctatgtt gttataa       1857
```

<210> SEQ ID NO 24
<211> LENGTH: 618
<212> TYPE: PRT
<213> ORGANISM: Artificial
<220> FEATURE:
<223> OTHER INFORMATION: synthetic

<400> SEQUENCE: 24

```
Met Leu Leu Gln Ala Phe Leu Phe Leu Leu Ala Gly Phe Ala Ala Lys
1               5                   10                  15

Ile Ser Ala Ser Met Asp Gln Ile Cys Ile Gly Tyr His Ala Asn Asn
            20                  25                  30

Ser Thr Glu Gln Val Asp Thr Ile Met Glu Lys Asn Val Thr Val Thr
        35                  40                  45

His Ala Gln Asp Ile Leu Glu Lys Lys His Asn Gly Lys Leu Cys Asp
    50                  55                  60

Leu Asp Gly Val Lys Pro Leu Ile Leu Arg Asp Cys Ser Val Ala Gly
65                  70                  75                  80

Trp Leu Leu Gly Asn Pro Met Cys Asp Glu Phe Ile Asn Val Pro Glu
                85                  90                  95

Trp Ser Tyr Ile Val Glu Lys Ala Asn Pro Val Asn Asp Leu Cys Tyr
            100                 105                 110

Pro Gly Asp Phe Asn Asp Tyr Glu Glu Leu Lys His Leu Leu Ser Arg
        115                 120                 125

Ile Asn His Phe Glu Lys Ile Gln Ile Ile Pro Lys Ser Ser Trp Ser
    130                 135                 140

Ser His Glu Ala Ser Leu Gly Val Ser Ser Ala Cys Pro Tyr Gln Gly
145                 150                 155                 160

Lys Ser Ser Phe Phe Arg Asn Val Val Trp Leu Ile Lys Lys Asn Ser
                165                 170                 175

Thr Tyr Pro Thr Ile Lys Arg Ser Tyr Asn Asn Thr Asn Gln Glu Asp
            180                 185                 190

Leu Leu Val Leu Trp Gly Ile His His Pro Asn Asp Ala Ala Glu Gln
        195                 200                 205

Thr Lys Leu Tyr Gln Asn Pro Thr Thr Tyr Ile Ser Val Gly Thr Ser
    210                 215                 220

Thr Leu Asn Gln Arg Leu Val Pro Arg Ile Ala Thr Arg Ser Lys Val
225                 230                 235                 240
```

-continued

```
Asn Gly Gln Ser Gly Arg Met Glu Phe Phe Trp Thr Ile Leu Lys Pro
                245                 250                 255

Asn Asp Ala Ile Asn Phe Glu Ser Asn Gly Asn Phe Ile Ala Pro Glu
            260                 265                 270

Tyr Ala Tyr Lys Ile Val Lys Lys Gly Asp Ser Thr Ile Met Lys Ser
        275                 280                 285

Glu Leu Glu Tyr Gly Asn Cys Asn Thr Lys Cys Gln Thr Pro Met Gly
    290                 295                 300

Ala Ile Asn Ser Ser Met Pro Phe His Asn Ile His Pro Leu Thr Ile
305                 310                 315                 320

Gly Glu Cys Pro Lys Tyr Val Lys Ser Asn Arg Leu Val Leu Ala Thr
                325                 330                 335

Gly Leu Arg Asn Ser Pro Gln Arg Glu Arg Arg Lys Lys Arg Gly
            340                 345                 350

Leu Phe Gly Ala Ile Ala Gly Phe Ile Glu Gly Gly Trp Gln Gly Met
        355                 360                 365

Val Asp Gly Trp Tyr Gly Tyr His His Ser Asn Glu Gln Gly Ser Gly
    370                 375                 380

Tyr Ala Ala Asp Lys Glu Ser Thr Gln Lys Ala Ile Asp Gly Val Thr
385                 390                 395                 400

Asn Lys Val Asn Ser Ile Ile Asp Lys Met Asn Thr Gln Phe Glu Ala
                405                 410                 415

Val Gly Arg Glu Phe Asn Asn Leu Glu Arg Arg Ile Glu Asn Leu Asn
            420                 425                 430

Lys Lys Met Glu Asp Gly Phe Leu Asp Val Trp Thr Tyr Asn Ala Glu
        435                 440                 445

Leu Leu Val Leu Met Glu Asn Glu Arg Thr Leu Asp Phe His Asp Ser
    450                 455                 460

Asn Val Lys Asn Leu Tyr Asp Lys Val Arg Leu Gln Leu Arg Asp Asn
465                 470                 475                 480

Ala Lys Glu Leu Gly Asn Gly Cys Phe Glu Phe Tyr His Lys Cys Asp
                485                 490                 495

Asn Glu Cys Met Glu Ser Val Arg Asn Gly Thr Tyr Asp Tyr Pro Gln
            500                 505                 510

Tyr Ser Glu Glu Ala Arg Leu Lys Arg Glu Glu Ile Ser Gly Val Lys
        515                 520                 525

Leu Glu Ser Ile Gly Ile Tyr Gln Thr Ser His His His His His His
    530                 535                 540

Asp Asp Asp Asp Lys Ala Ile Ser Gln Ile Thr Asp Gly Gln Ile
545                 550                 555                 560

Gln Ala Thr Thr Thr Ala Thr Thr Glu Ala Thr Thr Ala Ala Pro
                565                 570                 575

Ser Ser Thr Val Glu Thr Val Ser Pro Ser Ser Thr Glu Thr Ile Ser
            580                 585                 590

Gln Gln Thr Glu Asn Gly Ala Ala Lys Ala Ala Val Gly Met Gly Ala
        595                 600                 605

Gly Ala Leu Ala Ala Ala Met Leu Leu
    610                 615
```

<210> SEQ ID NO 25
<211> LENGTH: 1865
<212> TYPE: DNA
<213> ORGANISM: Artificial
<220> FEATURE:
<223> OTHER INFORMATION: synthetic

<400> SEQUENCE: 25

```
ctgcaggcca ccatgcagtt acttcgctgt ttttcaatat tttctgttat tgcttcagtt      60
ttagcacagg acacaatatg tataggctac catgcgaaca attcaaccga cactgttgac     120
acagtactcg agaagaatgt gacagtgaca cactctgtta acctgctcga agacagccac     180
aacgaaaaac tatgtagatt aaaggaata gccccactac aattggggaa atgtaacatc      240
gccggatggc tcttggggaa tccagaatgc gacccactgc ttccagtgag atcatggtcc     300
tacattgtag aaacaccaaa ctctgagaat ggaatatgtt atccaggaga tttcatcgac     360
tatgaggagc tgagggagca attgagctca gtgtcatcat tcgaaagatt cgaaatattt     420
cccaaagaaa gctcatggcc caaccacaac acaaacggag taacggcagc atgctcccat     480
gaggggaaaa gcagttttta cagaaatttg ctatggctga cggagaagga gggctcatac     540
ccaaagctga aaaattctta tgtgaacaaa aagggaaag aagtccttgt actgtggggt     600
attcatcacc cgtctaacag taaggaacaa cagaatctct atcagaatga aaatgcttat     660
gtctctgtag tgacttcaaa ttataacagg agatttaccc cggaaatagc agaaagaccc     720
aaagtaagag atcaagctgg gaggatgaac tattactgga ccttgctaaa acccggagac     780
acaataatat ttgaggcaaa tggaaatcta atagcaccaa tgtatgcttt cgcactgagt     840
agaggctttg ggtccggcat catcacctca aacgcatcaa tgcatgagtg taacacgaag     900
tgtcaaacac ccctgggagc tataaacagc agtctccctt accagaatat acacccagtc     960
acaataggag agcgcccaaa atacgtcagg agtgccaaat gaggatggt tacaggacta    1020
aggaacattc cgtccattca atccagaggt ctatttggag ccattgccgg ttttattgaa    1080
gggggatgga ctggaatgat agatggatgg tatggttatc atcatcagaa tgaacaggga    1140
tcaggctatg cagcggatca aaaaagcaca caaaatgcca ttaacgggat tacaaacaag    1200
gtgaacactg ttatcgagaa aatgaacatt caattcacag ctgtgggtaa agaattcaac    1260
aaattagaaa aaaggatgga aaatttaaat aaaaaagttg atgatggatt tctggacatt    1320
tggacatata atgcagaatt gttagttcta ctggaaaatg aaaggactct ggacttccat    1380
gactcaaata tgaagaatct gtatgagaaa gtaaaaagcc aattaaagaa taatgccaaa    1440
gaaatcggaa atggatgttt tgagttctac cacaagtgtg acaatgaatg catggaaagt    1500
gtaagaaatg ggacttatga ttatcccaaa tattcagaag agtcaaagtt gaacagggaa    1560
aaggtagatg gagtgaaatt ggaatcaatg gggatctatc agggtggcgg gactagtcac    1620
caccaccacc accacgacga cgacgacgac aaagaactga aactatatg cgagcaaatc    1680
ccctcaccaa ctttagaatc gacgccgtac tctttgtcaa cgactactat tttggccaac    1740
gggaaggcaa tgcaaggagt ttttgaatat tacaaatcag taacgtttgt cagtaattgc    1800
ggttctcacc cctcaacaac tagcaaaggc agccccataa acacacagta tgtttaagcg    1860
gccgc                                                                1865
```

<210> SEQ ID NO 26
<211> LENGTH: 614
<212> TYPE: PRT
<213> ORGANISM: Artificial
<220> FEATURE:
<223> OTHER INFORMATION: synthetic

<400> SEQUENCE: 26

```
Met Gln Leu Leu Arg Cys Phe Ser Ile Phe Ser Val Ile Ala Ser Val
1               5                   10                  15
```

-continued

```
Leu Ala Gln Asp Thr Ile Cys Ile Gly Tyr His Ala Asn Asn Ser Thr
                20                  25                  30
Asp Thr Val Asp Thr Val Leu Glu Lys Asn Val Thr Val Thr His Ser
            35                  40                  45
Val Asn Leu Leu Glu Asp Ser His Asn Gly Lys Leu Cys Arg Leu Lys
 50                  55                  60
Gly Ile Ala Pro Leu Gln Leu Gly Lys Cys Asn Ile Ala Gly Trp Leu
 65                  70                  75                  80
Leu Gly Asn Pro Glu Cys Asp Pro Leu Leu Pro Val Arg Ser Trp Ser
                85                  90                  95
Tyr Ile Val Glu Thr Pro Asn Ser Glu Asn Gly Ile Cys Tyr Pro Gly
            100                 105                 110
Asp Phe Ile Asp Tyr Glu Glu Leu Arg Glu Gln Leu Ser Ser Val Ser
        115                 120                 125
Ser Phe Glu Arg Phe Glu Ile Phe Pro Lys Glu Ser Ser Trp Pro Asn
130                 135                 140
His Asn Thr Asn Gly Val Thr Ala Ala Cys Ser His Glu Gly Lys Ser
145                 150                 155                 160
Ser Phe Tyr Arg Asn Leu Leu Trp Leu Thr Glu Lys Glu Gly Ser Tyr
                165                 170                 175
Pro Lys Leu Lys Asn Ser Tyr Val Asn Lys Lys Gly Lys Glu Val Leu
            180                 185                 190
Val Leu Trp Gly Ile His His Pro Ser Asn Ser Lys Glu Gln Gln Asn
        195                 200                 205
Leu Tyr Gln Asn Glu Asn Ala Tyr Val Ser Val Val Thr Ser Asn Tyr
    210                 215                 220
Asn Arg Arg Phe Thr Pro Glu Ile Ala Glu Arg Pro Lys Val Arg Asp
225                 230                 235                 240
Gln Ala Gly Arg Met Asn Tyr Tyr Trp Thr Leu Leu Lys Pro Gly Asp
                245                 250                 255
Thr Ile Ile Phe Glu Ala Asn Gly Asn Leu Ile Ala Pro Met Tyr Ala
            260                 265                 270
Phe Ala Leu Ser Arg Gly Phe Gly Ser Gly Ile Ile Thr Ser Asn Ala
        275                 280                 285
Ser Met His Glu Cys Asn Thr Lys Cys Gln Thr Pro Leu Gly Ala Ile
    290                 295                 300
Asn Ser Ser Leu Pro Tyr Gln Asn Ile His Pro Val Thr Ile Gly Glu
305                 310                 315                 320
Arg Pro Lys Tyr Val Arg Ser Ala Lys Leu Arg Met Val Thr Gly Leu
                325                 330                 335
Arg Asn Ile Pro Ser Ile Gln Ser Arg Gly Leu Phe Gly Ala Ile Ala
            340                 345                 350
Gly Phe Ile Glu Gly Gly Trp Thr Gly Met Ile Asp Gly Trp Tyr Gly
        355                 360                 365
Tyr His His Gln Asn Glu Gln Gly Ser Gly Tyr Ala Ala Asp Gln Lys
    370                 375                 380
Ser Thr Gln Asn Ala Ile Asn Gly Ile Thr Asn Lys Val Asn Thr Val
385                 390                 395                 400
Ile Glu Lys Met Asn Ile Gln Phe Thr Ala Val Gly Lys Glu Phe Asn
                405                 410                 415
Lys Leu Glu Lys Arg Met Glu Asn Leu Asn Lys Lys Val Asp Asp Gly
            420                 425                 430
```

```
Phe Leu Asp Ile Trp Thr Tyr Asn Ala Glu Leu Leu Val Leu Leu Glu
        435                 440                 445
Asn Glu Arg Thr Leu Asp Phe His Asp Ser Asn Met Lys Asn Leu Tyr
    450                 455                 460
Glu Lys Val Lys Ser Gln Leu Lys Asn Asn Ala Lys Glu Ile Gly Asn
465                 470                 475                 480
Gly Cys Phe Glu Phe Tyr His Lys Cys Asp Asn Glu Cys Met Glu Ser
                485                 490                 495
Val Arg Asn Gly Thr Tyr Asp Tyr Pro Lys Tyr Ser Glu Glu Ser Lys
            500                 505                 510
Leu Asn Arg Glu Lys Val Asp Gly Val Lys Leu Glu Ser Met Gly Ile
        515                 520                 525
Tyr Gln Gly Gly Gly Thr Ser His His His His His Asp Asp Asp
    530                 535                 540
Asp Asp Lys Glu Leu Thr Thr Ile Cys Glu Gln Ile Pro Ser Pro Thr
545                 550                 555                 560
Leu Glu Ser Thr Pro Tyr Ser Leu Ser Thr Thr Thr Ile Leu Ala Asn
                565                 570                 575
Gly Lys Ala Met Gln Gly Val Phe Glu Tyr Tyr Lys Ser Val Thr Phe
            580                 585                 590
Val Ser Asn Cys Gly Ser His Pro Ser Thr Thr Ser Lys Gly Ser Pro
        595                 600                 605
Ile Asn Thr Gln Tyr Val
    610
```

<210> SEQ ID NO 27
<211> LENGTH: 1862
<212> TYPE: DNA
<213> ORGANISM: Artificial
<220> FEATURE:
<223> OTHER INFORMATION: synthetic

<400> SEQUENCE: 27

```
atgcttttgc aagctttcct tttccttttg gctggttttg cagccaaaat atctgcatca      60
atggacacaa tatgtatagg ctaccatgcg aacaattcaa ccgacactgt tgacacagta     120
ctcgagaaga atgtgacagt gacacactct gttaacctgc tcgaagacag ccacaacgga     180
aaactatgta gattaaaagg aatagcccca ctacaattgg ggaaatgtaa catcgccgga     240
tggctcttgg ggaatccaga atgcgaccca ctgcttccag tgagatcatg gtcctacatt     300
gtagaaacac caaactctga aatggaata tgttatccag agatttcat cgactatgag     360
gagctgaggg agcaattgag ctcagtgtca tcattcgaaa gattcgaaat atttcccaaa     420
gaaagctcat ggcccaacca caacacaaac ggagtaacgg cagcatgctc ccatgagggg     480
aaaagcagtt tttacagaaa tttgctatgg ctgacggaga aggagggctc atacccaaag     540
ctgaaaaatt cttatgtgaa caaaaaaggg aagaagtcc ttgtactgtg ggtattcat     600
cacccgtcta acagtaagga caacagaat ctctatcaga atgaaaatgc ttatgtctct     660
gtagtgactt caaattataa caggagattt acccgggaaa tagcagaaag acccaaagta     720
agagatcaag ctgggaggat gaactattac tggaccttgc taaacccgg agacacaata     780
atatttgagg caaatggaaa tctaatagca ccaatgtatg ctttcgcact gagtagaggc     840
tttgggtccg gcatcatcac ctcaaacgca tcaatgcatg agtgtaacac gaagtgtcaa     900
acacccctgg gagctataaa cagcagtctc ccttaccaga atatacaccc agtcacaata     960
ggagagcgcc caaaatacgt caggagtgcc aaattgagga tggttacagg actaaggaac    1020
```

```
attccgtcca ttcaatccag aggtctattt ggagccattg ccggttttat tgaaggggga    1080
tggactggaa tgatagatgg atggtatggt tatcatcatc agaatgaaca gggatcaggc    1140
tatgcagcgg atcaaaaaag cacacaaaat gccattaacg ggattacaaa caaggtgaac    1200
actgttatcg agaaaatgaa cattcaattc acagctgtgg gtaaagaatt caacaaatta    1260
gaaaaaagga tggaaaattt aaataaaaaa gttgatgatg gatttctgga catttggaca    1320
tataatgcag aattgttagt tctactggaa atgaaagga ctctggactt ccatgactca    1380
aatatgaaga atctgtatga gaaagtaaaa agccaattaa agaataatgc aaagaaatc    1440 ggaaatggat gttttgagtt ctaccacaag tgtgacaatg aatgcatgga agtgtaaga    1500 aatgggactt atgattatcc caaatattca gaagagtcaa agttgaacag ggaaaaggta    1560
gatggagtga aattggaatc aatggggatc tatcagggtg gcgggactag tcaccaccac    1620
caccaccacg acgacgacga cgacaaagcc atttctcaaa tcactgacgg tcaaatccaa    1680
gctactacca ctgctaccac cgaagctacc accactgctg ccccatcttc caccgttgaa    1740
actgtttctc catccagcac cgaaactatc tctcaacaaa ctgaaaatgg tgctgctaag    1800
gccgctgtcg gtatgggtgc cggtgctcta gctgctgctg ctatgttgtt ataagcggcc    1860
gc                                                                   1862
```

```
<210> SEQ ID NO 28
<211> LENGTH: 617
<212> TYPE: PRT
<213> ORGANISM: Artificial
<220> FEATURE:
<223> OTHER INFORMATION: synthetic

<400> SEQUENCE: 28

Met Leu Leu Gln Ala Phe Leu Phe Leu Leu Ala Gly Phe Ala Ala Lys
1               5                   10                  15

Ile Ser Ala Ser Met Asp Thr Ile Cys Ile Gly Tyr His Ala Asn Asn
                20                  25                  30

Ser Thr Asp Thr Val Asp Thr Val Leu Glu Lys Asn Val Thr Val Thr
            35                  40                  45

His Ser Val Asn Leu Leu Glu Asp Ser His Asn Gly Lys Leu Cys Arg
        50                  55                  60

Leu Lys Gly Ile Ala Pro Leu Gln Leu Gly Lys Cys Asn Ile Ala Gly
65                  70                  75                  80

Trp Leu Leu Gly Asn Pro Glu Cys Asp Pro Leu Leu Pro Val Arg Ser
                85                  90                  95

Trp Ser Tyr Ile Val Glu Thr Pro Asn Ser Glu Asn Gly Ile Cys Tyr
                100                 105                 110

Pro Gly Asp Phe Ile Asp Tyr Glu Glu Leu Arg Glu Gln Leu Ser Ser
            115                 120                 125

Val Ser Ser Phe Glu Arg Phe Glu Ile Phe Pro Lys Glu Ser Ser Trp
        130                 135                 140

Pro Asn His Asn Thr Asn Gly Val Thr Ala Ala Cys Ser His Glu Gly
145                 150                 155                 160

Lys Ser Ser Phe Tyr Arg Asn Leu Leu Trp Leu Thr Glu Lys Glu Gly
                165                 170                 175

Ser Tyr Pro Lys Leu Lys Asn Ser Tyr Val Asn Lys Lys Gly Lys Glu
            180                 185                 190

Val Leu Val Leu Trp Gly Ile His His Pro Ser Asn Ser Lys Glu Gln
        195                 200                 205
```

```
Gln Asn Leu Tyr Gln Asn Glu Asn Ala Tyr Val Ser Val Val Thr Ser
    210                 215                 220

Asn Tyr Asn Arg Arg Phe Thr Pro Glu Ile Ala Glu Arg Pro Lys Val
225                 230                 235                 240

Arg Asp Gln Ala Gly Arg Met Asn Tyr Tyr Trp Thr Leu Leu Lys Pro
                245                 250                 255

Gly Asp Thr Ile Ile Phe Glu Ala Asn Gly Asn Leu Ile Ala Pro Met
                260                 265                 270

Tyr Ala Phe Ala Leu Ser Arg Gly Phe Gly Ser Gly Ile Ile Thr Ser
            275                 280                 285

Asn Ala Ser Met His Glu Cys Asn Thr Lys Cys Gln Thr Pro Leu Gly
        290                 295                 300

Ala Ile Asn Ser Ser Leu Pro Tyr Gln Asn Ile His Pro Val Thr Ile
305                 310                 315                 320

Gly Glu Arg Pro Lys Tyr Val Arg Ser Ala Lys Leu Arg Met Val Thr
                325                 330                 335

Gly Leu Arg Asn Ile Pro Ser Ile Gln Ser Arg Gly Leu Phe Gly Ala
            340                 345                 350

Ile Ala Gly Phe Ile Glu Gly Gly Trp Thr Gly Met Ile Asp Gly Trp
        355                 360                 365

Tyr Gly Tyr His His Gln Asn Glu Gln Gly Ser Gly Tyr Ala Ala Asp
    370                 375                 380

Gln Lys Ser Thr Gln Asn Ala Ile Asn Gly Ile Thr Asn Lys Val Asn
385                 390                 395                 400

Thr Val Ile Glu Lys Met Asn Ile Gln Phe Thr Ala Val Gly Lys Glu
                405                 410                 415

Phe Asn Lys Leu Glu Lys Arg Met Glu Asn Leu Asn Lys Lys Val Asp
            420                 425                 430

Asp Gly Phe Leu Asp Ile Trp Thr Tyr Asn Ala Glu Leu Leu Val Leu
        435                 440                 445

Leu Glu Asn Glu Arg Thr Leu Asp Phe His Asp Ser Asn Met Lys Asn
    450                 455                 460

Leu Tyr Glu Lys Val Lys Ser Gln Leu Lys Asn Asn Ala Lys Glu Ile
465                 470                 475                 480

Gly Asn Gly Cys Phe Glu Phe Tyr His Lys Cys Asp Asn Glu Cys Met
                485                 490                 495

Glu Ser Val Arg Asn Gly Thr Tyr Asp Tyr Pro Lys Tyr Ser Glu Glu
            500                 505                 510

Ser Lys Leu Asn Arg Glu Lys Val Asp Gly Val Lys Leu Glu Ser Met
        515                 520                 525

Gly Ile Tyr Gln Gly Gly Gly Thr Ser His His His His His His Asp
    530                 535                 540

Asp Asp Asp Lys Ala Ile Ser Gln Ile Thr Asp Gly Gln Ile Gln
545                 550                 555                 560

Ala Thr Thr Thr Ala Thr Thr Glu Ala Thr Thr Ala Ala Pro Ser
                565                 570                 575

Ser Thr Val Glu Thr Val Ser Pro Ser Ser Thr Glu Thr Ile Ser Gln
            580                 585                 590

Gln Thr Glu Asn Gly Ala Ala Lys Ala Ala Val Gly Met Gly Ala Gly
        595                 600                 605

Ala Leu Ala Ala Ala Ala Met Leu Leu
    610                 615
```

<210> SEQ ID NO 29
<211> LENGTH: 1565
<212> TYPE: DNA
<213> ORGANISM: Influenza virus

<400> SEQUENCE: 29

| | | | | | |
|---|---|---|---|---|---|
| agcaaaagca | gggtagataa | tcactcactg | agtgacatca | aaatcatggc | gtctcaaggc | 60 |
| accaaacgat | cttacgaaca | gatggagact | gatggagaac | gccagaatgc | cactgaaatc | 120 |
| agagcatccg | tcggaaaaat | gattggtgga | attggacgat | tctacatcca | aatgtgcacc | 180 |
| gaactcaaac | tcagtgatta | tgagggacgg | ttgatccaaa | acagcttaac | aatagagaga | 240 |
| atggtgctct | ctgcttttga | cgaaaggaga | aataaatacc | ttgaagaaca | tcccagtgcg | 300 |
| gggaagatc | taagaaaac | tggaggacct | atatacagga | gagtaaacgg | aaagtggatg | 360 |
| agagaactca | tcctttatga | caaagaagaa | ataaggcgaa | tctggcgcca | agctaataat | 420 |
| ggtgacgatg | caacggctgg | tctgactcac | atgatgatct | ggcattccaa | tttgaatgat | 480 |
| gcaacttatc | agaggacaag | agctcttgtt | cgcaccggaa | tggatcccag | gatgtgctct | 540 |
| ctgatgcaag | gttcaactct | ccctaggagg | tctggagccg | caggtgctgc | agtcaaagga | 600 |
| gttggaacaa | tggtgatgga | attggtcaga | atgatcaaac | gtgggatcaa | tgatcggaac | 660 |
| ttctggaggg | gtgagaatgg | acgaaaaaca | agaattgctt | atgaaagaat | gtgcaacatt | 720 |
| ctcaaaggga | aatttcaaac | tgctgcacaa | aaagcaatga | tggatcaagt | gagagagagc | 780 |
| cggaacccag | ggaatgctga | gttcgaagat | ctcactttc | tagcacgtc | tgcactcata | 840 |
| ttgagagggt | cggttgctca | caagtcctgc | ctgcctgcct | gtgtgtatgg | acctgccgta | 900 |
| gccagtgggt | acgactttga | aagggaggga | tactctctag | tcggaataga | ccctttcaga | 960 |
| ctgcttcaaa | acagccaagt | gtacagccta | atcagaccaa | atgagaatcc | agcacacaag | 1020 |
| agtcaactgg | tgtggatggc | atgccattct | gccgcatttg | aagatctaag | agtattaagc | 1080 |
| ttcatcaaag | ggacgaaggt | gctcccaaga | gggaagcttt | ccactagagg | agttcaaatt | 1140 |
| gcttccaatg | aaaatatgga | gactatggaa | tcaagtacac | ttgaactgag | aagcaggtac | 1200 |
| tgggccataa | ggaccagaag | tggaggaaac | accaatcaac | agagggcatc | tgcgggccaa | 1260 |
| atcagcatac | aacctacgtt | ctcagtacag | agaaatctcc | cttttgacag | aacaaccgtt | 1320 |
| atggcagcat | tcagtgggaa | tacagagggg | agaacatctg | acatgaggac | cgaaatcata | 1380 |
| aggatgatgg | aaagtgcaag | accagaagat | gtgtctttcc | aggggcgggg | agtcttcgag | 1440 |
| ctctcggacg | aaaaggcagc | gagcccgatc | gtgccttcct | ttgacatgag | taatgaagga | 1500 |
| tcttatttct | tcggagacaa | tgcagaggaa | tacgataatt | aaagaaaaat | acccttgttt | 1560 |
| ctact | | | | | 1565 |

<210> SEQ ID NO 30
<211> LENGTH: 498
<212> TYPE: PRT
<213> ORGANISM: Influenza virus

<400> SEQUENCE: 30

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Gly Gly Ile Gly Arg Phe Tyr Ile Gln Met Cys Thr Glu Leu Lys
        35                  40                  45

-continued

```
Leu Ser Asp Tyr Glu Gly Arg Leu Ile Gln Asn Ser Leu Thr Ile Glu
 50                  55                  60

Arg Met Val Leu Ser Ala Phe Asp Glu Arg Asn Lys Tyr Leu Glu
 65                  70                  75                  80

Glu His Pro Ser Ala Gly Lys Asp Pro Lys Thr Gly Gly Pro Ile
                  85                  90                  95

Tyr Arg Arg Val Asn Gly Lys Trp Met Arg Glu Leu Ile Leu Tyr Asp
                 100                 105                 110

Lys Glu Glu Ile Arg Arg Ile Trp Arg Gln Ala Asn Asn Gly Asp Asp
                 115                 120                 125

Ala Thr Ala Gly Leu Thr His Met Met Ile Trp His Ser Asn Leu Asn
130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                 165                 170                 175

Gly Ala Ala Gly Ala Ala Val Lys Gly Val Gly Thr Met Val Met Glu
                 180                 185                 190

Leu Val Arg Met Ile Lys Arg Gly Ile Asn Asp Arg Asn Phe Trp Arg
                 195                 200                 205

Gly Glu Asn Gly Arg Lys Thr Arg Ile Ala Tyr Glu Arg Met Cys Asn
210                 215                 220

Ile Leu Lys Gly Lys Phe Gln Thr Ala Ala Gln Lys Ala Met Met Asp
225                 230                 235                 240

Gln Val Arg Glu Ser Arg Asn Pro Gly Asn Ala Glu Phe Glu Asp Leu
                 245                 250                 255

Thr Phe Leu Ala Arg Ser Ala Leu Ile Leu Arg Gly Ser Val Ala His
                 260                 265                 270

Lys Ser Cys Leu Pro Ala Cys Val Tyr Gly Pro Ala Val Ala Ser Gly
                 275                 280                 285

Tyr Asp Phe Glu Arg Glu Gly Tyr Ser Leu Val Gly Ile Asp Pro Phe
                 290                 295                 300

Arg Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                 325                 330                 335

Ala Phe Glu Asp Leu Arg Val Leu Ser Phe Ile Lys Gly Thr Lys Val
                 340                 345                 350

Leu Pro Arg Gly Lys Leu Ser Thr Arg Gly Val Gln Ile Ala Ser Asn
                 355                 360                 365

Glu Asn Met Glu Thr Met Glu Ser Ser Thr Leu Glu Leu Arg Ser Arg
                 370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Ile Gln Pro Thr Phe Ser Val Gln Arg
                 405                 410                 415

Asn Leu Pro Phe Asp Arg Thr Thr Val Met Ala Ala Phe Ser Gly Asn
                 420                 425                 430

Thr Glu Gly Arg Thr Ser Asp Met Arg Thr Glu Ile Ile Arg Met Met
                 435                 440                 445

Glu Ser Ala Arg Pro Glu Asp Val Ser Phe Gln Gly Arg Gly Val Phe
                 450                 455                 460

Glu Leu Ser Asp Glu Lys Ala Ala Ser Pro Ile Val Pro Ser Phe Asp
```

```
                465                 470                 475                 480
Met Ser Asn Glu Gly Ser Tyr Phe Phe Gly Asp Asn Ala Glu Glu Tyr
                    485                 490                 495

Asp Asn

<210> SEQ ID NO 31
<211> LENGTH: 1565
<212> TYPE: DNA
<213> ORGANISM: Influenza virus

<400> SEQUENCE: 31
agcaaaagca gggtagataa tcactcactg agtgacatca aaatcatggc gtcccaaggc      60
accaaacggt cttacgaaca gatggagact gatggagaac gccagaatgc cactgaaatc     120
agagcatccg tcggaaaaat gattggtgga attggacgat tctacatcca aatgtgcaca     180
gaacttaaac tcagtgatta tgagggacgg ttgatccaaa acagcttaac aatagagaga     240
atggtgctct ctgcttttga cgaaaggaga ataaatacc  tggaagaaca tcccagtgcg     300
gggaaggatc ctaagaaaac tggaggacct atatacagaa gagtaaacgg aaagtggatg     360
agagaactca tcctttatga caagaagaa  ataaggcgaa tctggcgcca agctaataat     420
ggtgacgatg caacggctgg tctgactcac atgatgatct ggcattccaa tttgaatgat     480
gcaacttatc agaggacaag ggctcttgtt cgcaccggaa tggatccag  gatgtgctct     540 ctgatgcaag gttcaactct ccctaggagg tctggagccg caggtgctgc agtcaaagga     600
gttggaacaa tggtgatgga attggtcagg atgatcaaac gtgggatcaa tgatcggaac     660
ttctggaggg gtgagaatgg acgaaaaaca agaattgctt atgaaagaat gtgcaacatt     720
ctcaaaggga aatttcaaac tgctgcacaa aagcaatga  tggatcaagt gagagagagc     780
cgggacccag ggaatgctga gttcgaagat ctcactttc  tagcacggtc tgcactcata     840
ttgagagggt cggttgctca caagtcctgc ctgcctgcct gtgtgtatgg acctgccgta     900
gccagtgggt acgactttga aagagggga  tactctctag tcggaataga cccctttcaga     960 ctgcttcaaa acagccaagt gtacagccta atcagaccaa atgagaatcc agcacacaag    1020
agtcaactgg tgtggatggc atgccattct gccgcatttg aagatctaag agtattgagc    1080
ttcatcaaag gacgaaggt  ggtcccaaga gggaagcttt ccactagagg agttcaaatt    1140
gcttccaatg aaaatatgga gactatggaa tcaagtacac ttgaactgag aagcaggtac    1200
tgggccataa ggaccagaag tggaggaaac accaatcaac agagggcatc tgcgggccaa    1260
atcagcatac aacctacgtt ctcagtacag agaaatctcc cttttgacag aacaaccgtt    1320
atggcagcat tcactgggaa tacagagggg agaaacatctg acatgaggac cgaaatcata    1380
aggatgatgg aaagtgcaag accagaagat gtgtctttcc aggggcgggg agtcttcgag    1440
ctctcggacg aaaaggcagc gagcccgatc gtgccttcct ttgacatgag taatgaagga    1500 tcttattct  tcggagacaa tgcagaggag tacgacaatt aaagaaaaat accttgttt    1560 ctact                                                              1565

<210> SEQ ID NO 32
<211> LENGTH: 498
<212> TYPE: PRT
<213> ORGANISM: Influenza virus

<400> SEQUENCE: 32

Met Ala Ser Gln Gly Thr Lys Arg Ser Tyr Glu Gln Met Glu Thr Asp
1               5                   10                  15
```

```
Gly Glu Arg Gln Asn Ala Thr Glu Ile Arg Ala Ser Val Gly Lys Met
            20                  25                  30

Ile Gly Gly Ile Gly Arg Phe Tyr Ile Gln Met Cys Thr Glu Leu Lys
            35                  40                  45

Leu Ser Asp Tyr Glu Gly Arg Leu Ile Gln Asn Ser Leu Thr Ile Glu
            50                  55                  60

Arg Met Val Leu Ser Ala Phe Asp Glu Arg Asn Lys Tyr Leu Glu
 65              70                  75                  80

Glu His Pro Ser Ala Gly Lys Asp Pro Lys Lys Thr Gly Gly Pro Ile
                 85                  90                  95

Tyr Arg Arg Val Asn Gly Lys Trp Met Arg Glu Leu Ile Leu Tyr Asp
             100                 105                 110

Lys Glu Glu Ile Arg Arg Ile Trp Arg Gln Ala Asn Asn Gly Asp Asp
             115                 120                 125

Ala Thr Ala Gly Leu Thr His Met Met Ile Trp His Ser Asn Leu Asn
 130                 135                 140

Asp Ala Thr Tyr Gln Arg Thr Arg Ala Leu Val Arg Thr Gly Met Asp
 145                 150                 155                 160

Pro Arg Met Cys Ser Leu Met Gln Gly Ser Thr Leu Pro Arg Arg Ser
                 165                 170                 175

Gly Ala Ala Gly Ala Ala Val Lys Gly Val Gly Thr Met Val Met Glu
                 180                 185                 190

Leu Val Arg Met Ile Lys Arg Gly Ile Asn Asp Arg Asn Phe Trp Arg
                 195                 200                 205

Gly Glu Asn Gly Arg Lys Thr Arg Ile Ala Tyr Glu Arg Met Cys Asn
 210                 215                 220

Ile Leu Lys Gly Lys Phe Gln Thr Ala Ala Gln Lys Ala Met Met Asp
 225                 230                 235                 240

Gln Val Arg Glu Ser Arg Asp Pro Gly Asn Ala Glu Phe Glu Asp Leu
                 245                 250                 255

Thr Phe Leu Ala Arg Ser Ala Leu Ile Leu Arg Gly Ser Val Ala His
                 260                 265                 270

Lys Ser Cys Leu Pro Ala Cys Val Tyr Gly Pro Ala Val Ala Ser Gly
                 275                 280                 285

Tyr Asp Phe Glu Arg Glu Gly Tyr Ser Leu Val Gly Ile Asp Pro Phe
                 290                 295                 300

Arg Leu Leu Gln Asn Ser Gln Val Tyr Ser Leu Ile Arg Pro Asn Glu
 305                 310                 315                 320

Asn Pro Ala His Lys Ser Gln Leu Val Trp Met Ala Cys His Ser Ala
                 325                 330                 335

Ala Phe Glu Asp Leu Arg Val Leu Ser Phe Ile Lys Gly Thr Lys Val
                 340                 345                 350

Val Pro Arg Gly Lys Leu Ser Thr Arg Gly Val Gln Ile Ala Ser Asn
                 355                 360                 365

Glu Asn Met Glu Thr Met Glu Ser Ser Thr Leu Glu Leu Arg Ser Arg
                 370                 375                 380

Tyr Trp Ala Ile Arg Thr Arg Ser Gly Gly Asn Thr Asn Gln Gln Arg
 385                 390                 395                 400

Ala Ser Ala Gly Gln Ile Ser Ile Gln Pro Thr Phe Ser Val Gln Arg
                 405                 410                 415

Asn Leu Pro Phe Asp Arg Thr Thr Val Met Ala Ala Phe Thr Gly Asn
                 420                 425                 430
```

```
Thr Glu Gly Arg Thr Ser Asp Met Arg Thr Glu Ile Ile Arg Met Met
            435                 440                 445
Glu Ser Ala Arg Pro Glu Asp Val Ser Phe Gln Gly Arg Gly Val Phe
        450                 455                 460
Glu Leu Ser Asp Glu Lys Ala Ala Ser Pro Ile Val Pro Ser Phe Asp
465                 470                 475                 480
Met Ser Asn Glu Gly Ser Tyr Phe Phe Gly Asp Asn Ala Glu Glu Tyr
                485                 490                 495
Asp Asn

<210> SEQ ID NO 33
<211> LENGTH: 1707
<212> TYPE: DNA
<213> ORGANISM: Influenza virus

<400> SEQUENCE: 33
atggagaaaa tagtgcttct ttttgcaata gtcagtcttg ttaaaagtga tcagatttgc      60
attggttacc atgcaaacaa ctcgacagag caggttgaca caataatgga aaagaacgtt     120
actgttacac atgcccaaga catactggaa agaaacacac acgggaagct ctgcgatcta     180
gatggagtga agcctctaat tttgagagat tgtagcgtag ctggatggct cctcggaaac     240
ccaatgtgtg acgaattcat caatgtgccg aatggtcttc atagtggaga aggccaat      300
ccagtcaatg acctctgtta cccaggggat tcaatgact atgaagaatt gaaacaccta     360
ttgagcagaa taaccatttt tgagaaaatt cagatcatcc ccaaaagttc ttggtccagt     420
catgaagcct cattaggggt gagctcagca tgtccatacc agggaaagtc ctcctttttc     480
agaaatgtgg tatggcttat caaaaagaac agtacatacc caacaataaa gaggagctac     540
aataatacca accaagaaga tctttttggta ctgtggggga ttcaccatcc taatgatgcg     600
gcagagcaga caaagctcta tcaaaaccca accacctata tttccgttgg gacatcaaca     660
ctaaaccaga gattggtacc aagaatagct actagatcca agtaaacgg gcaaagtgga     720
aggatggagt tcttctggac aatttttaaag ccgaatgatg caatcaactt cgagagtaat     780
ggaaatttca ttgctccaga atatgcatac aaaattgtca gaaaggggga ctcaacaatt     840
atgaaaagtg aattggaata tggtaactgc aacaccaagt gtcaaactcc aatgggggcg     900
ataaactcta gcatgccatt ccacaatata caccctctca ccattgggga tgccccaaa      960
tatgtgaaat caaacagatt agtccttgcg actgggctca gaaatagccc tcaaagagag    1020
agaagaagaa aaagagagg attatttgga gctatagcag gttttataga gggaggatgg    1080
cagggaatgg tagatggttg gtatgggtac caccatagca atgagcaggg gagtgggtac    1140
gctgcagaca agaatccac tcaaaaggca atagatggag tcaccaataa ggtcaactcg    1200
atcattgaca aaatgaacac tcagtttgag gccgttggaa gggaatttaa caacttagaa    1260
aggagaatag agaattaaa caagaagatg gaagacgggg tcctagatgt ctggacttat    1320
aatgctgaac ttctggttct catggaaaat gagagaactc tagactttca tgactcaaat    1380
gtcaagaacc tttacgacaa ggtccgacta cagcttaggg ataatgcaaa ggagctgggt    1440
aacggttgtt tcgagttcta tcataaatgt gataatgaat gtatggaaag tgtaagaaat    1500
ggaacgtatg actacccgca gtattcagaa gaagcgagac taaaaagaga ggaaataagt    1560
ggagtaaaat tggaatcaat aggaatttac caaatactgt caatttattc tacagtggcg    1620
agttccctag cactgcaat catggtagct ggtctatcct tatggatgtg ctccaatgga    1680
tcgttacaat gcagaatttg catttaa                                         1707
```

<210> SEQ ID NO 34
<211> LENGTH: 568
<212> TYPE: PRT
<213> ORGANISM: Influenza virus

<400> SEQUENCE: 34

```
Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Lys His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Ser His Glu Ala Ser
    130                 135                 140

Leu Gly Val Ser Ser Ala Cys Pro Tyr Gln Gly Lys Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Arg Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
```

```
                370             375             380
Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
                500                 505                 510

Arg Leu Lys Arg Glu Glu Ile Ser Gly Val Lys Leu Glu Ser Ile Gly
            515                 520                 525

Ile Tyr Gln Ile Leu Ser Ile Tyr Ser Thr Val Ala Ser Ser Leu Ala
        530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565
```

<210> SEQ ID NO 35
<211> LENGTH: 1833
<212> TYPE: DNA
<213> ORGANISM: Artificial
<220> FEATURE:
<223> OTHER INFORMATION: synthetic

<400> SEQUENCE: 35

```
atgcagttac ttcgctgttt ttcaatattt tctgttattg cttcagtttt agcacaggaa    60
ctgacaacta tatgcgagca atcccctca ccaactttag aatcgacgcc gtactctttg   120
tcaacgacta ctattttggc caacgggaag gcaatgcaag gagttttga atattacaaa   180
tcagtaacgt ttgtcagtaa ttgcggttct caccccctcaa caactagcaa aggcagcccc   240
ataaacacac agtatgtttt tactagtgac acaatatgta taggctacca tgcgaacaat   300
tcaaccgaca ctgttgacac agtactcgag aagaatgtga cagtgacaca ctctgttaac   360
ctgctcgaag acagccacaa cggaaaacta tgtagattaa aaggaatagc cccactacaa   420
ttggggaaat gtaacatcgc cggatggctc ttggggaatc cagaatgcga cccactgctt   480
ccagtgagat catggtccta cattgtagaa acaccaaact tgagaatgg aatatgttat   540
ccaggagatt tcatcgacta tgaggagctg agggagcaat tgagctcagt gtcatcattc   600
gaaagattcg aaatatttcc caagaaaagc tcatggccca accacaacac aaacggagta   660
acggcagcat gctcccatga ggggaaaagc agttttttaca gaaatttgct atggctgacg   720
gagaaggagg gctcataccc aaagctgaaa aattcttatg tgaacaaaaa agggaaagaa   780
gtccttgtac tgtggggtat tcatcacccg tctaacagta ggaacaaca gaatctctat   840
cagaatgaaa atgcttatgt ctctgtagtg acttcaaatt ataacaggag atttacccg   900
gaaatagcag aaagacccaa agtaagagat caagctggga ggatgaacta ttactggacc   960
```

```
ttgctaaaac ccggagacac aataatattt gaggcaaatg gaaatctaat agcaccaatg    1020
tatgctttcg cactgagtag aggctttggg tccggcatca tcacctcaaa cgcatcaatg    1080
catgagtgta acacgaagtg tcaaacaccc ctgggagcta taaacagcag tctcccttac    1140
cagaatatac acccagtcac aataggagag cgcccaaaat acgtcaggag tgccaaattg    1200
aggatggtta caggactaag gaacattccg tccattcaat ccagaggtct atttggagcc    1260
attgccggtt ttattgaagg gggatggact ggaatgatag atggatggta tggttatcat    1320
catcagaatg aacagggatc aggctatgca gcggatcaaa aaagcacaca aaatgccatt    1380
aacgggatta caaacaaggt gaacactgtt atcgagaaaa tgaacattca attcacagct    1440
gtgggtaaag aattcaacaa attagaaaaa aggatgaaaa atttaaataa aaagttgat     1500 gatggatttc tggacatttg gacatataat gcagaattgt tagttctact ggaaaatgaa    1560
aggactctgg acttccatga ctcaaatatg aagaatctgt atgagaaagt aaaaagccaa    1620
ttaaagaata atgccaaaga atcggaaat ggatgttttg agttctacca caagtgtgac     1680
aatgaatgca tggaaagtgt aagaaatggg acttatgatt atcccaaata ttcagaagag    1740
tcaaagttga acaggaaaa ggtagatgga gtgaaattgg aatcaatggg gatctatcag     1800
ggtggcgggc atcaccatca ccatcactag tga                                 1833
```

<210> SEQ ID NO 36
<211> LENGTH: 609
<212> TYPE: PRT
<213> ORGANISM: Artificial
<220> FEATURE:
<223> OTHER INFORMATION: synthetic

<400> SEQUENCE: 36

```
Met Gln Leu Leu Arg Cys Phe Ser Ile Phe Ser Val Ile Ala Ser Val
1               5                   10                  15

Leu Ala Gln Glu Leu Thr Thr Ile Cys Glu Gln Ile Pro Ser Pro Thr
            20                  25                  30

Leu Glu Ser Thr Pro Tyr Ser Leu Ser Thr Thr Thr Ile Leu Ala Asn
        35                  40                  45

Gly Lys Ala Met Gln Gly Val Phe Glu Tyr Tyr Lys Ser Val Thr Phe
    50                  55                  60

Val Ser Asn Cys Gly Ser His Pro Ser Thr Thr Ser Lys Gly Ser Pro
65                  70                  75                  80

Ile Asn Thr Gln Tyr Val Phe Ser Asp Thr Ile Cys Ile Gly Tyr
            85                  90                  95

His Ala Asn Asn Ser Thr Asp Thr Val Asp Thr Val Leu Glu Lys Asn
            100                 105                 110

Val Thr Val Thr His Ser Val Asn Leu Leu Glu Asp Ser His Asn Gly
        115                 120                 125

Lys Leu Cys Arg Leu Lys Gly Ile Ala Pro Leu Gln Leu Gly Lys Cys
    130                 135                 140

Asn Ile Ala Gly Trp Leu Leu Gly Asn Pro Glu Cys Asp Pro Leu Leu
145                 150                 155                 160

Pro Val Arg Ser Trp Ser Tyr Ile Val Glu Thr Pro Asn Ser Glu Asn
                165                 170                 175

Gly Ile Cys Tyr Pro Gly Asp Phe Ile Asp Tyr Glu Glu Leu Arg Glu
            180                 185                 190

Gln Leu Ser Ser Val Ser Ser Phe Glu Arg Phe Glu Ile Phe Pro Lys
        195                 200                 205
```

-continued

```
Glu Ser Ser Trp Pro Asn His Asn Thr Asn Gly Val Thr Ala Ala Cys
    210                 215                 220
Ser His Glu Gly Lys Ser Ser Phe Tyr Arg Asn Leu Leu Trp Leu Thr
225                 230                 235                 240
Glu Lys Glu Gly Ser Tyr Pro Lys Leu Lys Asn Ser Tyr Val Asn Lys
                245                 250                 255
Lys Gly Lys Glu Val Leu Val Leu Trp Gly Ile His His Pro Ser Asn
                260                 265                 270
Ser Lys Glu Gln Gln Asn Leu Tyr Gln Asn Glu Asn Ala Tyr Val Ser
            275                 280                 285
Val Val Thr Ser Asn Tyr Asn Arg Arg Phe Thr Pro Glu Ile Ala Glu
    290                 295                 300
Arg Pro Lys Val Arg Asp Gln Ala Gly Arg Met Asn Tyr Tyr Trp Thr
305                 310                 315                 320
Leu Leu Lys Pro Gly Asp Thr Ile Ile Phe Glu Ala Asn Gly Asn Leu
                325                 330                 335
Ile Ala Pro Met Tyr Ala Phe Ala Leu Ser Arg Gly Phe Gly Ser Gly
                340                 345                 350
Ile Ile Thr Ser Asn Ala Ser Met His Glu Cys Asn Thr Lys Cys Gln
            355                 360                 365
Thr Pro Leu Gly Ala Ile Asn Ser Ser Leu Pro Tyr Gln Asn Ile His
    370                 375                 380
Pro Val Thr Ile Gly Glu Arg Pro Lys Tyr Val Arg Ser Ala Lys Leu
385                 390                 395                 400
Arg Met Val Thr Gly Leu Arg Asn Ile Pro Ser Ile Gln Ser Arg Gly
                405                 410                 415
Leu Phe Gly Ala Ile Ala Gly Phe Ile Glu Gly Gly Trp Thr Gly Met
                420                 425                 430
Ile Asp Gly Trp Tyr Gly Tyr His His Gln Asn Glu Gln Gly Ser Gly
            435                 440                 445
Tyr Ala Ala Asp Gln Lys Ser Thr Gln Asn Ala Ile Asn Gly Ile Thr
    450                 455                 460
Asn Lys Val Asn Thr Val Ile Glu Lys Met Asn Ile Gln Phe Thr Ala
465                 470                 475                 480
Val Gly Lys Glu Phe Asn Lys Leu Glu Lys Arg Met Glu Asn Leu Asn
                485                 490                 495
Lys Lys Val Asp Asp Gly Phe Leu Asp Ile Trp Thr Tyr Asn Ala Glu
                500                 505                 510
Leu Leu Val Leu Leu Glu Asn Glu Arg Thr Leu Asp Phe His Asp Ser
            515                 520                 525
Asn Met Lys Asn Leu Tyr Glu Lys Val Lys Ser Gln Leu Lys Asn Asn
    530                 535                 540
Ala Lys Glu Ile Gly Asn Gly Cys Phe Glu Phe Tyr His Lys Cys Asp
545                 550                 555                 560
Asn Glu Cys Met Glu Ser Val Arg Asn Gly Thr Tyr Asp Tyr Pro Lys
                565                 570                 575
Tyr Ser Glu Glu Ser Lys Leu Asn Arg Glu Lys Val Asp Gly Val Lys
                580                 585                 590
Leu Glu Ser Met Gly Ile Tyr Gln Gly Gly Gly His His His His
            595                 600                 605
His
```